US011203787B2

(12) United States Patent
Abate et al.

(10) Patent No.: US 11,203,787 B2
(45) Date of Patent: Dec. 21, 2021

(54) METHODS AND SYSTEMS FOR DETECTING BIOLOGICAL COMPONENTS

(71) Applicant: The Regents of the University of California, Oakland, CA (US)

(72) Inventors: Adam R. Abate, Daly City, CA (US); Dennis Jay Eastburn, Burlingame, CA (US); Adam R. Sciambi, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 388 days.

(21) Appl. No.: 16/164,707

(22) Filed: Oct. 18, 2018

(65) Prior Publication Data

US 2019/0241965 A1 Aug. 8, 2019

Related U.S. Application Data

(63) Continuation of application No. 14/420,646, filed as application No. PCT/US2013/054517 on Aug. 12, 2013, now Pat. No. 10,161,007.

(60) Provisional application No. 61/682,707, filed on Aug. 13, 2012, provisional application No. 61/784,754, filed on Mar. 14, 2013.

(51) Int. Cl.
| | |
|---|---|
| *C12P 19/34* | (2006.01) |
| *C12Q 1/6886* | (2018.01) |
| *C12Q 1/6806* | (2018.01) |
| *B01L 3/00* | (2006.01) |
| *B01L 7/00* | (2006.01) |
| *B01F 5/06* | (2006.01) |
| *B01F 13/00* | (2006.01) |
| *B01F 3/08* | (2006.01) |
| *C12Q 1/686* | (2018.01) |
| *C12Q 1/6844* | (2018.01) |

(52) U.S. Cl.
CPC .......... *C12Q 1/6886* (2013.01); *B01F 3/0807* (2013.01); *B01F 5/0652* (2013.01); *B01F 13/0062* (2013.01); *B01F 13/0076* (2013.01); *B01L 3/502784* (2013.01); *B01L 7/52* (2013.01); *C12Q 1/6806* (2013.01); *C12Q 1/686* (2013.01); *C12Q 1/6844* (2013.01); *B01L 2200/0652* (2013.01); *B01L 2300/0816* (2013.01); *B01L 2300/0864* (2013.01); *B01L 2300/0867* (2013.01); *B01L 2300/0883* (2013.01); *B01L 2300/1822* (2013.01); *B01L 2400/0415* (2013.01); *B01L 2400/0487* (2013.01); *C12Q 2600/118* (2013.01); *C12Q 2600/158* (2013.01); *C12Q 2600/16* (2013.01)

(58) Field of Classification Search
CPC .................................................. C12Q 1/6806
See application file for complete search history.

(56) References Cited

U.S. PATENT DOCUMENTS

| | | | |
|---|---|---|---|
| 7,638,276 B2 | 12/2009 | Griffiths et al. | |
| RE41,780 E | 9/2010 | Anderson et al. | |
| 8,067,159 B2 | 11/2011 | Brown et al. | |
| 8,257,925 B2 | 9/2012 | Brown et al. | |
| 8,765,485 B2 | 7/2014 | Link et al. | |
| 9,150,852 B2 | 10/2015 | Samuels et al. | |
| 10,161,007 B2 | 12/2018 | Abate et al. | |
| 10,745,762 B2 | 8/2020 | Abate et al. | |
| 2002/0086042 A1 | 7/2002 | Delrieu et al. | |
| 2003/0156993 A1 | 8/2003 | Staats | |
| 2003/0180737 A1 | 9/2003 | Gu et al. | |
| 2005/0019902 A1 | 1/2005 | Mathies et al. | |
| 2005/0112639 A1 | 5/2005 | Wang et al. | |
| 2005/0172476 A1 | 8/2005 | Stone et al. | |
| 2007/0039866 A1 | 2/2007 | Schroeder et al. | |
| 2007/0077572 A1 | 4/2007 | Tawfik et al. | |
| 2007/0141593 A1 | 6/2007 | Lee et al. | |
| 2007/0231880 A1 | 10/2007 | Chang-Yen et al. | |
| 2008/0014589 A1 | 1/2008 | Link et al. | |
| 2009/0045064 A1 | 2/2009 | Simmons et al. | |
| 2009/0098555 A1 | 4/2009 | Roth et al. | |
| 2010/0015614 A1 | 1/2010 | Beer et al. | |
| 2010/0028915 A1 | 2/2010 | Gualberto et al. | |
| 2010/0055677 A1 | 3/2010 | Colston, Jr. et al. | |
| 2010/0137163 A1 | 6/2010 | Link et al. | |
| 2010/0173394 A1 | 7/2010 | Colston, Jr. et al. | |
| 2010/0248237 A1 | 9/2010 | Froehlich et al. | |
| 2010/0285975 A1 | 11/2010 | Mathies et al. | |
| 2011/0053798 A1 | 3/2011 | Hindson et al. | |
| 2011/0056575 A1 | 3/2011 | Hong et al. | |
| 2011/0059556 A1 | 3/2011 | Strey et al. | |

(Continued)

FOREIGN PATENT DOCUMENTS

| | | |
|---|---|---|
| AU | 2013203624 | 5/2013 |
| AU | 2013302867 A1 | 2/2015 |

(Continued)

OTHER PUBLICATIONS

International Search Report and Written Opinion received for PCT Application Serial No. PCT/US2017/68006 dated Mar. 26, 2018, 9 pages.

(Continued)

*Primary Examiner* — Kenneth R Horlick

(74) *Attorney, Agent, or Firm* — Edward J. Baba; Bozicevic, Field & Francis LLP

(57) ABSTRACT

Methods for the detection of components from biological samples are provided. In certain aspects, the methods may be used to detect and/or quantify specific components in a biological sample, such as tumor cells (e.g., circulating tumor cells). Systems and devices for practicing the subject methods are also provided.

9 Claims, 61 Drawing Sheets

Specification includes a Sequence Listing.

(56) References Cited

U.S. PATENT DOCUMENTS

| | | |
|---|---|---|
| 2011/0086352 A1 | 4/2011 | Bashir et al. |
| 2011/0103176 A1 | 5/2011 | Van Dam et al. |
| 2011/0104816 A1 | 5/2011 | Pollack et al. |
| 2011/0118151 A1 | 5/2011 | Eshoo et al. |
| 2011/0160078 A1 | 6/2011 | Fodor et al. |
| 2011/0217736 A1 | 9/2011 | Hindson |
| 2011/0311978 A1 | 12/2011 | Makarewicz et al. |
| 2012/0010086 A1 | 1/2012 | Froehlich et al. |
| 2012/0045765 A1 | 2/2012 | Curran et al. |
| 2012/0122714 A1 | 5/2012 | Samuels et al. |
| 2012/0132288 A1 | 5/2012 | Weitz et al. |
| 2012/0309002 A1 | 6/2012 | Link |
| 2012/0190032 A1 | 7/2012 | Ness et al. |
| 2012/0190033 A1 | 7/2012 | Ness et al. |
| 2012/0196288 A1 | 8/2012 | Beer |
| 2012/0219947 A1 | 8/2012 | Yurkovetsky et al. |
| 2012/0220494 A1 | 8/2012 | Samuels et al. |
| 2012/0258870 A1 | 10/2012 | Schwartz et al. |
| 2012/0264646 A1 | 10/2012 | Link et al. |
| 2012/0270739 A1 | 10/2012 | Rava et al. |
| 2012/0316074 A1 | 12/2012 | Saxonov et al. |
| 2013/0032235 A1 | 2/2013 | Johnstone et al. |
| 2013/0046030 A1 | 2/2013 | Rotem et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0236901 A1 | 9/2013 | Potier et al. |
| 2013/0295567 A1 | 11/2013 | Link et al. |
| 2013/0295587 A1 | 11/2013 | Sjobom |
| 2014/0057799 A1 | 2/2014 | Johnson et al. |
| 2014/0154695 A1 | 6/2014 | Raindance |
| 2014/0155295 A1 | 6/2014 | Hindson et al. |
| 2014/0179544 A1 | 6/2014 | Steenblock et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378345 A1 | 12/2014 | Hindson et al. |
| 2014/0378349 A1 | 12/2014 | Hindson et al. |
| 2015/0232942 A1 | 2/2015 | Abate et al. |
| 2015/0298091 A1 | 10/2015 | Weitz et al. |
| 2016/0177375 A1 | 6/2016 | Abate et al. |
| 2016/0265043 A1 | 9/2016 | Geng et al. |
| 2017/0009274 A1 | 1/2017 | Abate et al. |
| 2017/0022538 A1 | 1/2017 | Abate et al. |
| 2017/0121756 A1 | 5/2017 | Abate et al. |
| 2018/0056288 A1 | 3/2018 | Abate et al. |
| 2018/0216160 A1 | 8/2018 | Abate et al. |
| 2018/0237836 A1 | 8/2018 | Abate et al. |
| 2019/0127789 A1 | 5/2019 | Weitz et al. |
| 2019/0169700 A1 | 6/2019 | Abate et al. |
| 2019/0218594 A1 | 7/2019 | Abate et al. |
| 2019/0330701 A1 | 10/2019 | Abate et al. |

FOREIGN PATENT DOCUMENTS

| | | |
|---|---|---|
| AU | 2016215298 A1 | 8/2017 |
| AU | 2016215304 A1 | 8/2017 |
| AU | 2017382905 A1 | 7/2019 |
| AU | 2019226236 A1 | 9/2019 |
| CA | 2 881 783 A1 | 2/2014 |
| CA | 3 001 986 A1 | 4/2016 |
| CA | 2 974 299 A1 | 8/2016 |
| CA | 2 974 306 A1 | 8/2016 |
| CA | 3047328 A1 | 6/2018 |
| CN | 1693478 | 11/2005 |
| CN | 104736725 A | 6/2015 |
| CN | 107107058 A | 8/2017 |
| CN | 107429426 A | 12/2017 |
| CN | 107530654 A | 1/2018 |
| CN | 108350488 A | 7/2018 |
| CN | 110088290 A | 8/2019 |
| CN | 110462053 A | 11/2019 |
| DE | 10339452 | 3/2005 |
| EP | 1547677 | 6/2005 |
| EP | 2145955 | 2/2012 |
| EP | 2565650 | 3/2013 |
| EP | 2 882 872 A2 | 6/2015 |
| EP | 3 160 654 A2 | 5/2017 |
| EP | 3 209 419 A1 | 8/2017 |
| EP | 3 253 479 A2 | 12/2017 |
| EP | 3 253 910 A1 | 12/2017 |
| EP | 3 337 907 A1 | 6/2018 |
| EP | 3 497 228 A1 | 6/2019 |
| EP | 3571308 A1 | 11/2019 |
| GB | 2 519 906 A | 5/2015 |
| GB | 2 539 836 A | 12/2016 |
| JP | 2013503630 A | 2/2013 |
| JP | 2014521334 A | 8/2014 |
| JP | 2015-533079 A | 11/2015 |
| JP | 2018-505671 A | 3/2018 |
| JP | 2018-525004 A | 9/2018 |
| JP | 2018-508198 A | 11/2018 |
| WO | WO 1994012216 | 6/1994 |
| WO | WO 2007140015 | 12/2007 |
| WO | WO 2009050512 | 4/2009 |
| WO | WO 2009054870 | 4/2009 |
| WO | WO 2009111014 | 9/2009 |
| WO | WO 2010148039 | 12/2010 |
| WO | WO 2011047307 | 4/2011 |
| WO | WO 2012011091 | 1/2012 |
| WO | WO 2012048341 | 4/2012 |
| WO | WO 2012162267 | 5/2012 |
| WO | WO 2012083225 | 6/2012 |
| WO | 2012106385 A2 | 8/2012 |
| WO | WO 2012109600 | 8/2012 |
| WO | WO 2012142213 | 10/2012 |
| WO | 2013015793 A1 | 1/2013 |
| WO | 2013095469 A1 | 6/2013 |
| WO | WO 2013119753 | 8/2013 |
| WO | WO 2013126741 | 8/2013 |
| WO | WO 2013130512 | 9/2013 |
| WO | WO 2013134261 | 9/2013 |
| WO | WO 2013173394 | 11/2013 |
| WO | WO 2014028378 | 2/2014 |
| WO | WO 2014028537 | 2/2014 |
| WO | WO 2014047556 | 3/2014 |
| WO | WO 2014083435 | 6/2014 |
| WO | WO 2014093676 | 6/2014 |
| WO | WO 2014108323 | 7/2014 |
| WO | WO 2014138132 | 9/2014 |
| WO | WO 2014151658 | 9/2014 |
| WO | WO 2014153071 | 9/2014 |
| WO | WO 2015120398 | 2/2015 |
| WO | WO 2015031691 | 3/2015 |
| WO | 2015/069798 A1 | 5/2015 |
| WO | WO 2015200717 | 6/2015 |
| WO | WO 2015157369 | 10/2015 |
| WO | WO2015179848 A1 | 11/2015 |
| WO | 2015189336 A1 | 12/2015 |
| WO | WO 2016064755 | 4/2016 |
| WO | WO 2016065056 | 4/2016 |
| WO | WO 2016126865 | 8/2016 |
| WO | WO 2016126871 | 8/2016 |
| WO | 2017/031125 A1 | 2/2017 |
| WO | 2018031691 A1 | 2/2018 |
| WO | 2018/119301 A1 | 6/2018 |
| WO | WO2019099908 A1 | 5/2019 |

OTHER PUBLICATIONS

International Preliminary Report on Patentability received for PCT Application Serial No. PCT/US2017/68006 dated Jul. 4, 2019, 7 pages.

EmPCR-amplificationmanual for GS-FLX series (May 2011); 454 Life Science Corp; 12 pages.

Sciambi Adam and Abate Adam R., (2015) "Accurate microfluidic sorting of droplets at 30 kHz"; Lab Chip 15(1); pp. 47-51.

(56) References Cited

OTHER PUBLICATIONS

Abate Adam. R, et al; (2010) "Microfluidic sorting with high-speed single-layer membrane valves"; *Applied Physics Letters* 96; pp. 203509-1-203509-3.
Abate Adam. R., et al; "High-throughput injection with microfluidics using picoinjectors"; *PNAS* vol. 107 1 No. 45; Nov. 9, 2010; pp. 19163-19166.
Abate AR, et al; (2011) "Efficient encapsulation with plug-triggered drop formation"; *Physical Review E.*;84(3):031502.
Abate AR and Weitz DA; (2011) "Faster multiple emulsification with drop splitting". *Lab on a Chip*; 11(11); pp. 1911-1915.
Abate AR, et al; (2011) "One-step formation of multiple emulsions in microfluidics"; *Lab on a Chip* 11 (2); pp. 253-258.
Abate AR, et al; (2008) "Photoreactive coating for high-contrast spatial patterning of microfluidic device wettability"; *Lab on a Chip* 8(12); pp. 2157-2160.
Ali et al. "Rolling circle amplification: a versatile tool for chemical biology, materials science and medicine"; *Chem Soc Rev.* vol. 43; Mar. 18, 2014; pp. 3324-3341.
Agresti JJ, et al; "Ultrahigh-throughput screening in drop-based microfluidics for directed evolution"; *PNAS* vol. 107, No. 9; Mar. 2, 2010; pp. 4004-4009.
Agresti J., et al; (2010) "Correction for Ultrahigh-throughput screening in drop-based microfluidics for directed evolution"; *Proc. Nat.l Acad. Sci. USA*, 107; pp. 6550-6551.
Ahn K, et al; (2006) "Electrocoalescence of drops synchronized by size-dependent flow in microfluidic channels"; *Appl Phys Lett* 88; pp. 264105-1-264105-3.
Allen LZ, et al; (2011) "Single virus genomics: a new tool for virus discovery"; *PLoS One* 6(3):e17722.
Arriaga LR, et al. (2014) "Ultrathin Shell Double Emulsion Templated Giant Unilamellar Lipid Vesicles with Controlled Microdomain Formation"; *Small* 10(5); pp. 950-956; Epub Oct. 22, 2013.
Atten P; (1993) "Electrocoalescence of Water Droplets in an Insulating Liquid"; *J Electrostat* 30; pp. 259-269.
Barenholz Y, et al; (1977) "A simple method for the preparation of homogeneous phospholipid vesicles" *Biochemistry* 16(12); pp. 2806-2810.
Baret J-C, et al. (2009) "Fluorescence-activated droplet sorting (FADS): efficient microfluidic cell sorting based on enzymatic activity"; *Lab on a Chip*;9(13); pp. 1850-1858.
Battaglia G, et al; (2006) "Polymeric vesicle permeability: a facile chemical assay"; *Langmuir* 22(11); pp. 4910-4913.
Beer NR, et al; (2008) "On-chip single-copy real-time reverse-transcription PCR in isolated picoliter droplets"; *Anal Chem* 80; pp. 1854-1858.
Bernath, et al; (2004) "In vitro compartmentalization by double emulsions: sorting and gene enrichment by fluorescence activated cell sorting"; *Analytical Biochemistry* 325; pp. 151-157.
Bird et al., (1988) "Single-chain antigen-binding proteins"; *Science* 242; pp. 423-426.
Blainey PC. (2013) "The future is now: single-cell genomics of bacteria and archaea"; *FEMS microbiology reviews* 37(3); pp. 407-427.
Brouzes E, et al; "Droplet microfluidic technology for single-cell high-throughput screening"; *PNAS* vol. 106, No. 34; Aug. 25, 2009; pp. 14195-14200.
Brown, R. B. et al: (2008) "Current techniques for single-cell lysis"; *J. R. Soc. Interface* 5; pp. S131-S138.
Caron G.; (1998) "Assessment of bacterial viability status by flow cytometry and single cell sorting"; *Journal of applied microbiology* 84(6): pp. 988-998.
Chaffer C. L. and Weinberg R. A.; "A Perspective on Cancer Cell Metastasis"; *Science*, vol. 331; Mar. 25, 2011; pp. 1559-1564.
Chabert M, et al; (2005) "Droplet fusion by alternating current (AC) field electrocoalescence in microchannels"; *Electrophoresis* 26; pp. 3706-3715.

Chen C-M, et al; (2000) "Influence of pH on the stability of oil-in-water emulsions stabilized by a splittable surfactant"; *Colloids and Surfaces A: Physicochemical and Engineering Aspects* 170(2); pp. 173-179.
Chung, C. et al; (2010) "Droplet dynamics passing through obstructions in confined microchannel flow"; *Microfluidics Nanofluidics*, 9(6), pp. 1151-1163.
Clausell-Tormos, Jennifer, et al; "Droplet-based microfluidic platforms for the encapsulation and screening of Mammalian cells and multicellular organisms"; *Chemistry and Biology* 15; (May 2008); pp. 427-437.
Dejournette CJ, et al; (2013) "Creating Biocompatible Oil—Water Interfaces without Synthesis: Direct Interactions between Primary Amines and Carboxylated Perfluorocarbon Surfactants"; *Analytical chemistry*.;85(21); pp. 10556-10564.
Dietrich et al; "Effects of UV irradiation and hydrogen peroxide on DNA fragmentation, motility and fertilizing ability of rainbow trout (*Oncorhynchus mykiss*) spermatozoa"; *Theriogenology.* vol. 64; (Nov. 2005) pp. 1809-1822.
Duffy DC, et al; (1998) "Rapid Prototyping of Microfluidic Systems in Poly (dimethylsiloxane)"; *Anal. Chem.* 70; pp. 4974-4984.
Eastburn Dennis J., et al; (2013) "Ultrahigh-Throughput Mammalian Single-Cell Reverse-Transcriptase Polymerase Chain Reaction in Microfluidic Drops"; *Anal. Chem.* 85; pp. 8016-8021.
Eastburn DJ, et al; (2013) "Picoinjection Enables Digital Detection of RNA with Droplet RT-PCR"; *PloS one.*;8(4):e62961.
Edd et al., (2008) Controlled encapsulation of single cells into monodisperse picoliter drop *Lab on a Chip*, 8(8); pp. 1262-1264.
European search report and opinion dated Feb. 8, 2016 for EP Application No. 13829925.
Frenz L, et al; (2009) "Reliable microfluidic on-chip incubation of droplets in delay-lines"; *Lab on a Chip* 9(10); pp. 1344-1348.
Garstecki P. et al; "Formation of droplets and bubbles in a microfluidic T-junction-scaling and mechanism of break-up"; *Lab Chip* 6; (2006); pp. 437-446.
Gevensleben H, et al; (2013) "Noninvasive Detection of HER2 Amplification with Plasma DNA Digital PCR"; *Clinical Cancer Research.*; 19(12); pp. 3276-3284.
Gribskov, et al; (1986) "Sigma factors from *E. coli*, B. subtilis, phage SP01, and phage T4 are homologous proteins"; *Nucl. Acids Res.* 14(6):6745-6763.
Hayward RC, et al; (2006) "Dewetting instability during the formation of polymersomes from block-copolymer-stabilized double emulsions"; *Langmuir* 22(10); pp. 4457-4461.
Herminghaus S, "Dynamical Instability of Thin Liquid Films Between Conducting Media"; *Physical Review Letter*, vol. 83, No. 12; Sep. 20, 1999; pp. 2359-2361.
Holland, et al; (1991) "Detection of specific polymerase chain reaction product by utilizing the 5'—3' exonuclease activity of Thermus aquaticus DNA polymerase"; *PNAS*, 88 (16); 7276-7280.
Holtze C., et al; (2008) "Biocompatible surfactants for water-in-fluorocarbon emulsions"; *Lab Chip* 8; pp. 1632-1639.
Horton et al; "Gene splicing by overlap extension: tailor-made genes using the polymerase chain reaction"; *Biotechniques*, vol. 54; Mar. 1, 2013; pp. 129-133.
Hu, Hoa et al; (2009) "Mutation screening in 86 known X-linked mental retardation genes by droplet-based multiplex PCR and massive parallel sequencing"; *HUGO J.*3; pp. 41-49.
Huebner et al; (2008) "Microdroplets: A sea of applications?"; *Lab on a Chip*, 8; pp. 1244-1254.
Hunkapiller and Hood, (1986) "Immunology: The growing immunoglobulin gene superfamily"; *Nature*, 323; pp. 15-16.
Hunt JA, et al; (1994) "Effect of pH on the stability and surface composition of emulsions made with whey protein isolate"; *Journal of Agricultural and Food Chemistry.*;42(10); pp. 2131-2135.
Huston et al; (1988) "Protein engineering of antibody binding sites: recovery of specific activity in an anti-digoxin single-chain Fv analogue produced in *Escherichia coli*"; *Proc. Natl. Acad. Sci. U.S.A.*, 85; pp. 5879-5883.
International Search Report and Written Opinion dated Feb. 21, 2014 for PCT/US2013/054517.
Kawasaki (1990) "Sample Preparation From Blood, Cells, and Other Fluids"; Chapter 18; pp. 146-152 in *PCR protocols: A guide*

(56) References Cited

OTHER PUBLICATIONS

*to methods and Applications*, edited by Michael A. Innis, David H. Gelfand, John J. Sninsky, Thomas J. White.
Ki, JS., et al. (2005) "Integrated method for single-cell DNA extraction, PCR amplification, and sequencing of ribosomal DNA from harmful Dinoflagellates Cochlodium polykrikoides and Alexandrium catenella"; Marine Biotechnology, vol. 6; pp. 587-593.
Kiss MM, et al.(2008) "High-Throughput Quantitative Polymerase Chain Reaction in Picoliter Droplets"; *Anal Chem* 80(23); pp. 8975-8981.
Kritikou Ekat; "It's cheaper in the Picolab"; *Nat Rev Genet*, 6; (Sep. 2005); pp. 668.
Lagally ET, et al; (2001) "Single-Molecule DNA Amplification and Analysis in an Integrated Microfluidic Device"; *Analytical Chemistry.*;73(3); pp. 565-570.
Lanzavecchia et al; (1987) "The use of hybrid hybridomas to target human cytotoxic T lymphocytes"; *Eur. J. Immunol.* 17(1); pp. 105-111.
Leary JF. (1994) "Strategies for rare cell detection and isolation"; *Methods Cell Biol.*;42(Pt B); pp. 331-358.
Lim, Shuan and Abate Adam, (2013) "Ultrahigh-throughput sorting of microfluidic drops with flow cytometry"; *Lab Chip*13; pp. 4563-4572.
Link, et al; (2004) "Geometrically mediated breakup of drops in microfluidic devices"; *Phys Rev Lett.* 92(5):054503.
Livak KJ and Schmittgen TD; (2001) "Analysis of Relative Gene Expression Data Using Real-Time Quantitative PCR and the $2^{-\Delta\Delta CT}$ Method"; *methods.*;25(4); pp. 402-408.
Longo MC, et al; (1990) "Use of uracil DNA glycosylase to control carry-over contamination in polymerase chain reactions"; *Gene.*;93(1); pp. 125-128.
Malloggi F, et al; "Electrowetting-controlled droplet generation in a microfluidic flow-focusing device"; *J. Phys.: Condens. Matter* 19; (2007); 462101; 7 pages.
Markou Athina,et al; (2011) "Molecular Characterization of Circulating Tumor Cells in Breast Cancer by a Liquid Bead Array Hybridization Assay"; *Clinical Chemistry* 57:3; pp. 421-430.
Marcus et al., "Parallel Picoliter RT-PCR Assays Using Microfluidics"; *Analytical Chemistry*, 78(3); (2006); pp. 956-958.
Mary P Pascaline, et al; "Controlling droplet incubation using close-packed plug flow"; *Biomicrofluidics* 5; (2011); pp. 024101-1-024101-6.
Mazutis L, et al; (2013) "Single-cell analysis and sorting using droplet-based microfluidics"; *Nature protocols.*8(5); pp. 870-891.
McDonald, et al; (2000) "Fabrication of microfluidic systems in poly(dimethylsiloxane"; *Electrophoresis*, 21(1); pp. 27-40.
Medkova, Martina et al; "Analyzing Cancer at Single Cell Resolution with Droplet Technology"; *American Association of Cancer Research (AACR)*; Apr. 19, 2010; 1 page.
Metzker, Michael L. "Sequencing technologies—the next generation"; *Nature Reviews Genetics*, vol. 11 (Jan. 2010); pp. 31-46.
Miyazaki, K; (2002) "Random DNA fragmentation with endonuclease V: application to DNA shuffling"; *Nucleic Acids Res.* 30(24); e139.
Miyazaki et al. (2013) "A new large-DNA-fragment delivery system based on integrase activity from an integrative and conjugative element"; *Appl Environ Microbiol* 79(14); pp. 4440-4447.
Moon Sangjun, et al; "Drop-on-Demand Single Cell Isolation and Total RNA Analysis"; *PloS ONE*, vol. 6, Issue 3; e17455 (Mar. 2011); pp. 1-10.
Morton et al; (2008) "Crossing microfluidic streamlines to lyse, label and wash cells†"; *Lab on a Chip*, 8(9); pp. 1448-1453.
Mui B, et al; (1993) "Osmotic properties of large unilamellar vesicles prepared by extrusion"; *Biophysical journal* 64(2); pp. 443-453.
Nagrath Sunitha, et al; "Isolation of rare circulating tumour cells in cancer patients by microchip technology"; *Nature* 450(7173); Dec. 20; 2007; pp. 1235-1239.

Nakano M, et al. (2005) "Single-molecule reverse transcription polymerase chain reaction using water-in-oil emulsion"; *J Biosci Bioeng* 99; pp. 293-295.
Nikolova AN and Jones MN; (1996) "Effect of grafted PEG-2000 on the size and permeability of vesicles"; *Biochimica et Biophysica Acta (BBA)-Lipids and Lipid Metabolism.*; 1304(2); pp. 120-128.
Novak, et al; (2011) "Single-cell multiplex gene detection and sequencing with microfluidically generated agarose emulsions"; *Angew Chem Int Ed Engl.* 50(2):390-395.
Oberholzer,Thomas, et al; (1995) "Polymerase chain reaction in liposomes"; *Chemistry & Biology* vol. 2 No. 10; pp. 677-682.
O'Donovan B, et al; (2012) "Electrode-free picoinjection of microfluidic drops"; *Lab Chip* 12; pp. 4029-4032.
Okochi M et al; (2010) "Droplet-based gene expression analysis using a device with magnetic force-based-droplet-handling system"; *J Biosci Bioeng.* 109(2); pp. 193-197.
Perry DJ; (1999) "Solid-Phase Sequencing of Biotinylated PCR Products with Streptavidin-Coated Magnetic Beads"; *Hemostasis and Thrombosis Protocols: Springer*;. p. 49-54.
Piatek AS, et al; (1998) "Molecular beacon sequence analysis for detecting drug resistance in Mycobacterium tuberculosis";. *Nat Biotechnol.* 16(4); pp. 359-363.
Priest Craig, et al; (2006) "Controlled electrocoalescence in microfluidics: Targeting a single lamella"; *Appl Phys Lett*, 89; p. 134101-1-134101-3.
Sciambi et al. (2013) "Adding reagent to droplets with controlled rupture of encapsulated double emulsions"; Biomicrofluidics 7(4); pp. 1-6.
Scott S. H, et al; (2011) "Microfluidic immuno magnetic multitarget sorting—a model for controlling deflection of paramagnetic beads"; *Lab Chip* 11; pp. 2577-2582.
Seemann R, et al; (2012) "Droplet based microfluidics"; *Rep Prog Phys* 75; pp. 016601.
Shui et al; (2011) "Microfluidic DNA fragmentation for on-chip genomic analysis" *Nanotechnology* 22(49): 494013. 7 pages.
Siegel Adam C,et al; (2007) "Microsolidics: Fabrication of Three-Dimensional Metallic Microstructures inPoly( dimethylsiloxane )"; *Adv Mater* 19; pp. 727-733.
Song H, et al; (2006) "Reactions in droplets in microfluidic channels" *Angew Chem Int Ed Engl* 45; pp. 7336-7356.
Squires Tom M.; "Microfluidics: Fluid physics at the nanoliter scale"; *Reviews of modern physics.*;77(3); (Jul. 2005) pp. 977-1026.
Stone HA, et al; (2004) "Engineering flows in small devices: microfluidics toward a lab-on-a-chip";*Annu Rev Fluid Mech.*;36; pp. 381-411.
Stott Shannon L.; et al; "Isolation of circulating tumor cells using a microvortex-generating herringbone-chip"; *PNAS* vol. 107, No. 43; Oct. 26, 2010; pp. 18392-18397.
Syed et al. (2009) "Next-generation sequencing library preparation: simultaneous fragmentation and tagging using in vitro transposition"; *Nature Methods* vol. 6; pp. 1-2.
Tadmor AD, et al; (2011) "Probing individual environmental bacteria for viruses by using microfluidic digital PCR"; *Science.*;333(6038); pp. 58-62.
Takagi et al. (2005) "Continuous particle separation in a microchannel having asymmetrically arranged multiple branches" *Lab Chip*, 5(7); pp. 778-784.
Teh SY,et al; (2008) "Droplet microfluidics"; *Lab Chip* 8; pp. 198-220.
Tewhey Ryan, et al; "Microdroplet-based PCR enrichment for large-scale targeted sequencing"; *Nature Biotechnology*, vol. 27 No. 11; (Nov. 2009); pp. 1025-1035.
Thomann Y, et al; (2005) "PMMA Gradient Materials and in situ Nanocoating via Self-Assembly of Semifluorinated Hyperbranched Amphiphiles"; *Macromolecular Chemistry and Physics.*;206(1); pp. 135-141.
Thorsen T, et al; (2001) "Dynamic pattern formation in a vesicle-generating microfluidic device"; *Phys Rev Lett* 86; pp. 4163-4166.
Tsai Scott S. H., et al; (2011) "Microfluidic immunomagnetic multi-target sorting—a model for controlling deflection of paramagnetic beads"; *Lab Chip* 11; pp. 2577-2582.

(56) References Cited

OTHER PUBLICATIONS

Ullal, et al; (2014) "Cancer cell profiling by barcoding allows multiplexed protein analysis in fine needle aspirates"; *Sci Transl Med.* 6(219):219ra9; pp. 1-22.
Utada, et al; (2007) "Dripping to jetting transitions in coflowing liquid streams"; *Phys Rev Lett.* Aug. 31, 2007;99(9; pp. :094502-1-094502-4.
Vanapalli SA, et al; "Hydrodynamic resistance of single confined moving drops in rectangular microchannels"; *Lab Chip* 9 (2009); pp. 982-990.
Vickers, et al., (2006) "Generation of Hydrophilic Poly(dimethylsiloxane) for High-Performance Microchip Electrophoresis"; *Anal. Chem*, 78(21); pp. 7446-7452.
Wang C, et al; (2012) "Amphiphilic building blocks for self-assembly: from amphiphiles to supra-amphiphiles"; *Accounts of Chemical Research* 45(4); pp. 608-618.
Whitcombe D, et al; (1999) "Detection of PCR products using self-probing amplicons and fluorescence"; *Nature biotechnology* 17(8); pp. 804-807.
Whitesides GM. (2006) The origins and the future of microfluidics. *Nature* 442(7101); pp. 368-373.
Xia Yn, et al; (1998) "Soft lithography"; *Angew Chem Int Edit* 37; pp. 551-575.
Zeng Yong, et al; "High-Performance Single Cell Genetic Analysis Using Microfluidic Emulsion Generator Arrays"; *Anal Chem.* 82(8); Apr. 15; 2010; pp. 3183-3190.
Zheng B, et al; (2004) "Formation of droplets of in microfluidic channels alternating composition and applications to indexing of concentrations in droplet-based assays"; *Anal Chem* 76; pp. 4977-4982.
Zhong Qun, et al; (2011) "Multiplex digital PCR: breaking the one target per color barrier of quantitative PCR"; *Lab Chip* 11; pp. 2167-2174.
Zhu et al., (2001) "Reverse transcriptase template switching: a SMART approach for full-length cDNA library construction"; *BioTechniques* 30: pp. 892-897.
Zhu Z, et al (2012) "Highly sensitive and quantitative detection of rare pathogens through agarose droplet microfluidic emulsion PCR at the single-cell level"; *Lab on a Chip* 12(20); pp. 3907-3913.
Zien TF; (1969) "Hydrodynamics of bolus flow—an analytical approach to blood flow in capillaries"; *Math Biophys*, 31; pp. 681-694.
U.S. Appl. No. 16/324,532, filed Feb. 8, 2019, Abate, Adam et al.
U.S. Appl. No. 16/382,080, filed Apr. 11, 2019, Abate, Adam et al.
Fu, Yusi et al (2015) "Uniform and accurate single-cell sequencing based on emulsion whole-genome amplification"; Proc Natl Acad Sci U S A. 112(38); pp. 11923-11928.
Grover, et al (2009) "Multiple displacement amplification as a pre-polymerase chain reaction (pre-PCR) to detect ultra low population of Ralstonia solanacearum (Smith 1896) Yabuchi et al. (1996)" Lett Appl Microbiol. 49(5); pp. 539-543.
Küster, et al (2013) "Interfacing droplet microfluidics with matrix-assisted laser desorption/ionization mass spectrometry: label-free content analysis of single droplets"; *Anal Chem.* 5;85(3); pp. 1285-1289.
Nishikawa, Yohei et al (2015) "Monodisperse Picoliter Droplets for Low-Bias and Contamination-Free Reactions in Single-Cell Whole Genome Amplification" PLoS One 10(9); pp. e0138733.
Nunes et al. (2013) "Dripping and jetting in microfluidic multiphase flows applied to particle and fiber synthesis"; *J Phys D Appl Phys.* 46(11); pii: 114002.
Sidore, et al (2016) "Enhanced sequencing coverage with digital droplet multiple displacement amplification"; Nucleic Acids Res. 44(7):e66.; pp. 1-9.
Tamminen, et al (2015) "Single gene-based distinction of individual microbial genomes from a mixed population of microbial cells"; Front Microbiol. 6:195; pp. 1-10.
Wheeler et al, (2005) "Digital micro fluidics with in-line sample purification for proteomics analyses with MALDI-MS"; *Anal Chem.* 77(2); 534-40.
Yu, et al (2014) "Mung bean nuclease treatment increases capture specificity of microdroplet-PCR based targeted DNA enrichment"; PLoS One 9(7): e103491; pp. 1-7.
Extended European Search Report received for European Patent Application Serial No. 16/747,229 9 dated Sep. 10, 2019, 8 pages.
International Search Report and Written Opinion received for PCT Application Serial No. PCT/US2016/016444 dated Jul. 27, 2016, 43 pages.
International Preliminary Report on Patentability received for PCT Application Serial No. PCT/US2016/016444 dated Aug. 17, 2017, 40 pages.
Extended European Search Report received for European Patent Application Serial No. 16747224.0 dated May 24, 2018, 9 pages.
International Search Report and Written Opinion received for PCT Application Serial No. PCT/US2016/016438 dated Jun. 10, 2016, 14 pages.
International Preliminary Report on Patentability received for PCT Application Serial No. PCT/US2016/016438 dated Aug. 17, 2017, 10 pages.
Rolando et al. (Cell host & microbe 13.4 (2013): 395-405.). (Year: 2013).
Extended European Search Report received for European Patent Application Serial No. 15812857.9 dated Oct. 17, 2017, 7 pages.
International Search Report and Written Opinion received for PCT Application Serial No. PCT/US2015/037822 dated Feb. 2, 2016, 9 pages.
International Preliminary Report on Patentability received for PCT Application Serial No. PCT/US2015/037822 dated Jan. 5, 2017, 7 pages.
First search received for Chinese Patent Application Serial No. 2015800704110 dated Dec. 13, 2018, 2 pages.
Extended European Search Report received for European Patent Application Serial No. 15853268.9 dated Sep. 3, 2018, 12 pages.
International Search Report and Written Opinion received for PCT Application Serial No. PCT/US2015/56743 dated Mar. 3, 2016, 12 pages.
International Preliminary Report on Patentability received for PCT Application Serial No. PCT/US2015/56743 dated May 4, 2017, 9 pages.
First search received for Chinese Patent Application Serial No. 2013800532581 dated Feb. 22, 2016, 2 pages.
International Preliminary Report on Patentability received for PCT Application Serial No. PCT/US2013/054517 dated Feb. 26, 2015, 14 pages.
Extended European Search Report received for European Patent Application Serial No. 16837703.4 dated Nov. 29, 2018, 9 pages.
International Search Report and Written Opinion received for PCT Application Serial No. PCT/US2016/47199 dated Dec. 12, 2016, 10 pages.
International Preliminary Report on Patentability received for PCT Application Serial No. PCT/US2016/47199 dated Mar. 1, 2018, 8 pages.
International Search Report and Written Opinion received for PCT Application Serial No. PCT/US2017/046159 dated Nov. 21, 2017, 12 pages.
International Preliminary Report on Patentability received for PCT Application Serial No. PCT/US2017/046159 dated Feb. 21, 2019, 9 pages.
Demaree, Benjamin , et al., "An Ultrahigh-throughput Microfluidic Platform for Single-cell Genome Sequencing", Journal of Visualized Experiments 135 (e57598), 2018, 1-13.
Gong, Jian , et al., "Characterization and Design of Digitizing Processes for Uniform and Controllable Droplet Volume in EWOD Digital Microfluidics", Solid-State Sensors, Actuators, and Microsystems Workshop, 2006, 159-162.
Ichii, Teisuo , et al., "Amplification of RNA in Growing and Dividing Micro-Droplets", 14th International Conf on Miniaturized Systems for Chemistry and Life Sciences, 2010, 2089-2091.
Kumaresan, Palani, et al., "High-Throughput Single Copy DNA Amplification and Cell Analysis in Engineered Nanoliter Droplets", Anal. Chem. 80, 2008, 3522-3529.

(56) References Cited

OTHER PUBLICATIONS

Lan, Freeman, et al., "Single-cell genome sequencing at ultra-high-throughput with microfluidic droplet barcoding", Nature Biotechnology 35(7), 2017, 640-646.
Lim, Shaun W., et al., "Ultrahigh-throughput sorting of microfluidic drops with flow cytometry", Lab Chip, 2013, vol. 13, pp. 4563-4572.
Pekin, Deniz, et al., "Quantitative and sensitive detection of rare mutations using droplet-based microfluidics", Lab Chip 11, 2011, 2156-2166.
Rakszewska, Agata, et al., "One drop at a time: toward droplet microfluidics as a versatile tool for single-cell analysis", NPG Asia Materials 6(10), 2014, 1-11.
Shembekar, Nachiket, et al., "Droplet-based microfluidics in drug discovery, transcriptomics and high-throughput molecular genetics", Lab on a Chip 16(8), 2016, 1314-1331.
Extended European Search Report received for European Patent Application Serial No. 17885180.4 dated Jul. 20, 2020, 11 pages.
Extended European Search Report received for European Patent Application Serial No. 17840230.1 dated Apr. 30, 2020, 12 pages.
Integrated DNA Technologies "Molecular Facts and Figures", 2011, 1-9.
Caruccio, et al., (2011) "Preparation of next-generation sequencing libraries using Nextera™ technology: simultaneous DNA fragmentation and adaptor tagging by in vitro transposition", Methods in Molecular Biology, vol. 733, pp. 241-255.
Hindson, et al., (2011) "High-throughput droplet digital PCR system for Absolute Quatitation of DNA copy number", Analytical chemistry, 83(22), pp. 8604-8610.
Lage, J. M., et al., (2003) "Whole Genome Analysis of Genetic Alterations in Small DNA Samples Using Hyperbranched Strand Displacement Amplification and Array-CGH", Genome Res., pp. 294-307.
Le Goff, Gaelle C, et al., (2015) "Hydrogel microparticles for biosensing", Eur Polym J., vol. 72, pp. 385-412.
Spencer, Sarah J., et al., (2016) "Massively parallel sequencing of single cells by epioPCR links functional genes with phylogenetic markers", The ISME Journal 10, pp. 427-436.
Abate, Adam R., et al., (2013) "DNA sequence analysis with droplet-based microfluids", Lab Chip, vol. 13(24), pp. 4864-4869.
Abate, Adam R., et al., (2009) "Beating Poisson encapsulation statistics using close-packed ordering", Lab Chip, vol. 9, pp. 2628-2631.
Abbaspourrad, et al., (2015) "Label-free single-cell protein quantification using a dropbased mix-and-read system", Sci. Rep., 5, p. 12756.
Agargel, (2019) "Agar-Agar", retrieved on Jun. 6, 2019 from https://web.archive.org/web/20170527222040/http://www.agargel.com.br/agar-tecen. html, 3 pages.
Autour, et al., (2017) "Ultrahigh-throughput improvement and discovery of enzymes using droplet-based microfluidic screening" Micromachines, vol. 8(128), pp. 1-21.
Baker, (2012) "Digital PCR hits its stride", Nat. Methods, vol. 9(6), pp. 541-544.
Bjork, et al., (2012) "Metabolite profiling of microfluidic cell culture conditions for droplet based screening", Biomicrojluidics, vol. 9, p. 044128.
Blainey, et al., (2014) "Dissecting genomic diversity, one cell at a time" Nat. Methods, vol. 11(1), pp. 19-21.
Chang, et al., (2012) "Single Molecule Enzyme-Linked Immunosorbent Assays: Theoretical Considerations", J Immunol Methods, vol. 378(1-2), pp. 102-115.
Chen et al., (2017) "Centrifugal micro-channel array droplet generation for highly parallel digital PCR", Lab Chip, 17, pp. 235-240.
Chen et al., (2016) "Spinning micropipette liquid emulsion generator for single cell whole genome amplification", Lab Chip, 16, pp. 4512-4516.
Civelek et al., (2014) "Systems genetics approaches to understand complex traits", Nat. Rev. Genet., 15(1), pp. 34-48.
Collins et al., (2015) "The Poisson distribution and beyond: methods for microfluidic droplet production and single cell encapsulation", Lab on a Chip, 15, pp. 3439-3459.
Costa et al., (2008) "Complex networks: The key to systems biology", Genet. Mol. Biol., 31(3), pp. 591-601.
Elnifro, et al., (2000) "Multiplex PCR: Optimization and Application in Diagnostic Virology", Clin. Microbial. Rev., 13, pp. 559-570.
Fritzsch et al., (2012), "Single-Cell Analysis in Biotechnology, Systems Biology, and Biocatalysis", Annu. Rev. Chem. Biomol. Eng. 3, pp. 129-155.
Gielen, et al., (2016) "Ultrahigh-throughput-directed enzyme evolution by absorbance activated droplet sorting (AADS)", PNAS, pp. E7383-E7389.
Griffiths, et al., (2006) "Miniaturising the laboratory in emulsion droplets Trends" Biotechnol., 24, pp. 395-402.
Guo, et al., (2012) "Droplet microfluidics for highthroughput biological assays.", Lab Chip, pp. 2146-2155.
Halldorsson et al., (2015) "Advantages and challenges of microfluidic cell culture in polydimethylsiloxane devices", Biosens. Bioelectron., 63, pp. 218-231.
Huang, et al., (2017) "Collective generation of milliemulsions by step-emulsification", RSC Advances, 7, pp. 14932-14938.
Joanicot, et al., (2005) "Droplet control for microfluidics", Science, 309(5736), pp. 887-888.
Katepalli, et al., (2014) "Bose, A. Response of Surfactant Stabilized Oil-in-Water Emulsions to the Addition of Particles in an Aqueous Suspension", Langmuir, 30(43), pp. 12736-12742.
Kim, et al., (2017) "Measurement of copy number variation in single cancer cells using rapid-emulsification digital droplet MPA", Microsystems & Nanoengineering 3:17018, pp. 1-7.
Kim, et al., (2014) "Droplet Microfluidics for Producing Functional Microparticles", Langmuir, 30, pp. 1473-1488.
Kimmerling et al., (2016) "A microfluidic platform enabling single-cell RNA-seq of multigenerational lineages", Nature Commun., 7, p. 10220.
Kolodziejczyk, et al., (2015) "The Technology and Biology of Single-Cell RNA Sequencing", Mol. Cell, 58(4), pp. 610-620.
Lance, et al., (2016) "Peering below the diffraction limit: robust and specific sorting of viruses with flow cytometry", Viral J, 13, p. 201.
Macosko, et al., (2015) "Highly parallel genome-wide expression profiling of individual cells using nanoliter droplets" Cell, 161, pp. 1202-1214.
Margulies, et al., (2005) "Genome sequencing in microfabricated high-density picolitre reactors", Nature, 437, pp. 376-380.
Mashaghi, et al., (2016) "Droplet microfluidics: A tool for biology, chemistry and nanotechnology", TrAC—Trends Anal. Chem., 82, pp. 118-125.
Morimoto, et al., (2013) "Three-dimensional cell culture based on microfluidic techniques to mimic living tissues", Biomaterials Science, vol. 1, No. 3, pp. 257-264.
Morimoto, et al., (2009) "Reconstruction of 3D Hierarchic Micro-Tissues using Monodisperse Collagen Microbeads", Micro Electro Mechanical Systems, IEEE 22nd International Conference, pp. 56-59.
Pinheiro, et al., (2012) Evaluation of a droplet digital polymerase chain reaction format for DNA copy number quantification, Anal. Chem., 84, pp. 1003-1011.
Romero, et al., (2015) "Dissecting enzyme function with microfluidic-based deep mutational scanning", PNAS, 112(23), pp. 7159-7164.
Sandberg, et al., (2009) "Flow cytometry for enrichment and titration in massively parallel DNA sequencing", Nucleic Acids Res, 37(8), p. e63.
Song, et al., (2006) "On-Chip Titration of an Anticoagulant Argatroban and Determination of the Clotting Time within Whole Blood or Plasma Using a Plug-Based Microfluidic System", Anal. Chem., 78(14), pp. 4839-4849.
Soon, et al., (2013) "High-throughput sequencing for biology and medicine", Mol. Syst. Biol., 9(64), pp. 1-14.
Spies, et al., (2017) "Genome-wide reconstruction of complex structural variants using read clouds", Nat. Methods, 14(9), pp. 915-920.
Sukovich, et al., (2017) "Sequence specific sorting of DNA molecules with FACS using 3dPCR", Sci. Rep., 7, p. 39385.

(56) References Cited

OTHER PUBLICATIONS

Taly, et al., (2013) "Multiplex picodroplet digital PCR to detect KRAS mutations in circulating DNA from the plasma of colorectal cancer patients", Clin. Chem., 59, pp. 1722-1731.
Tran, et al., (2013) "From tubes to drops: dropletbased biology microfluidics for ultrahigh-throughput", J Phys. D. Appl. Phys., 46, p. 114004.
Weaver, et al., (2014) "Advances in high-throughput single-cell microtechnologies", Curr. Opin. Biotechnol., 0, pp. 114-123.
Yan, et al., (2017) "Intestinal Enteroendocrine Lineage Cells Possess Homeostatic and Injury-Inducible Stem Cell Activity", Cell Stem Cell, 21, pp. 78-90.
Zhu, et al., (2017) "Hydrogel Droplet Microfluidics for High-Throughput Single Molecule/Cell Analysis", Ace. Chern. Res., 50(1), pp. 22-31.
Zilionis, et al., (2017) "Single-cell barcoding and sequencing using droplet microfluidics", Nat. Protoc., 12(1), pp. 44-73.

FIG. 12 (Cont.)
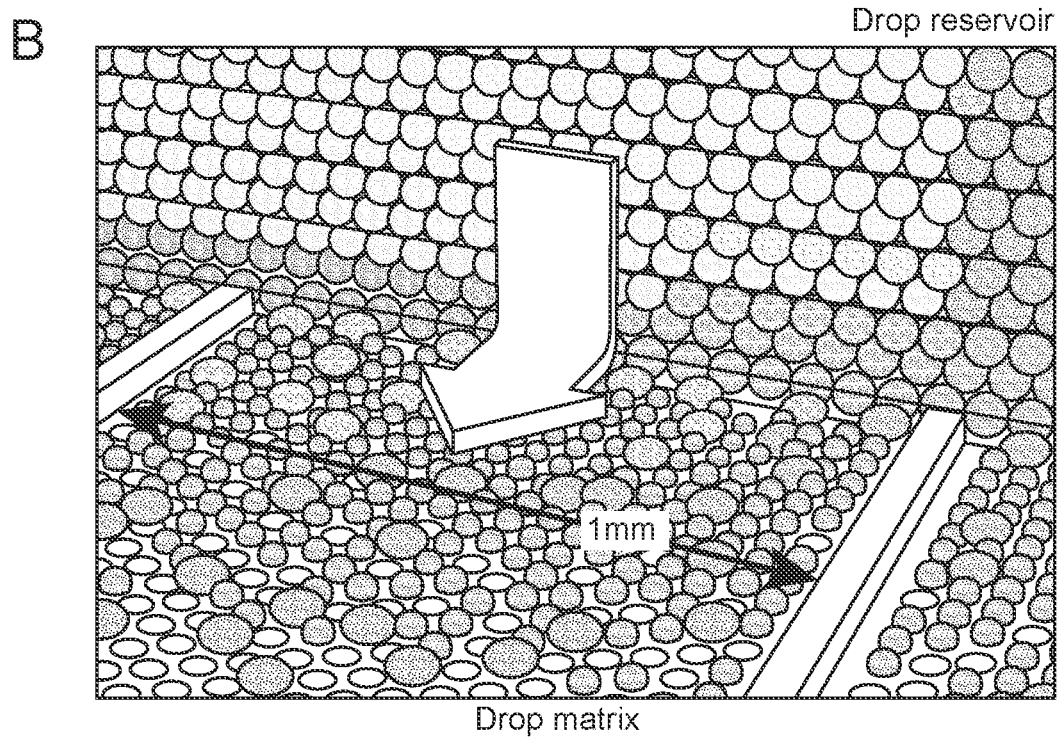
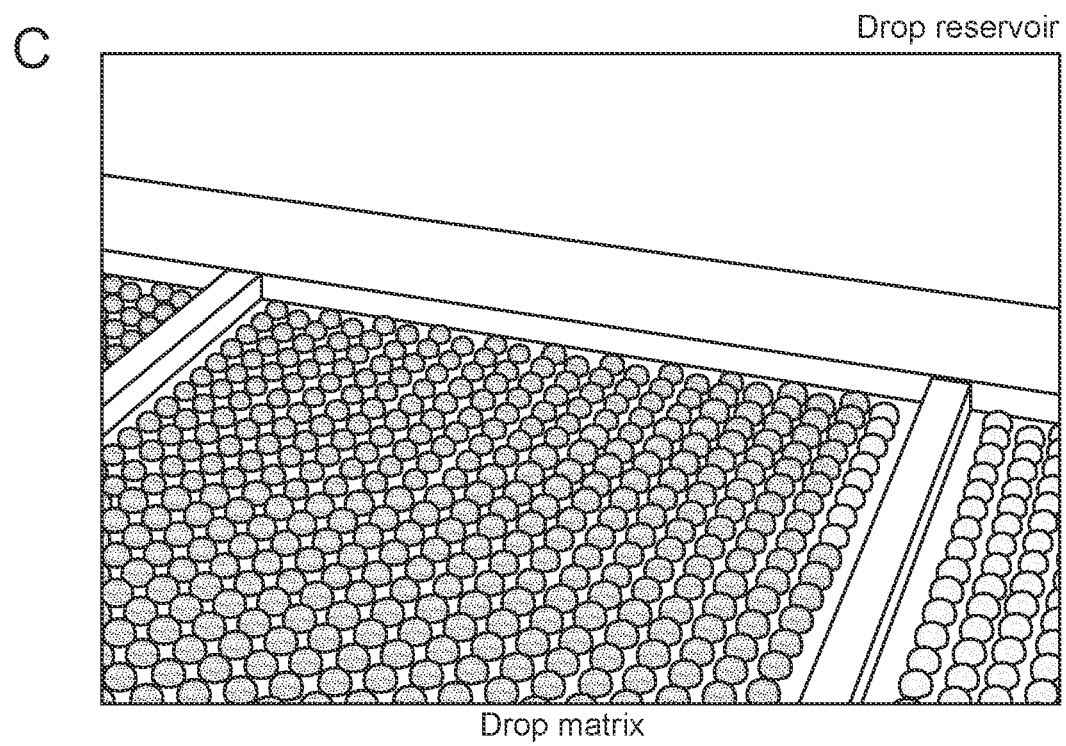

FIG. 14
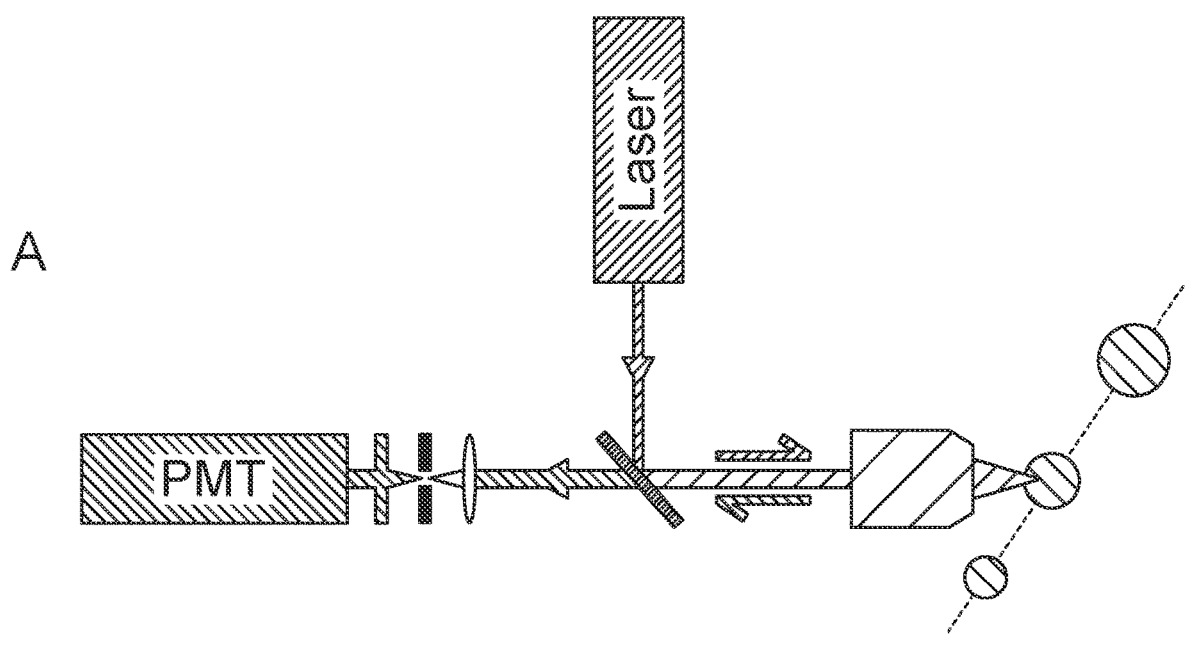
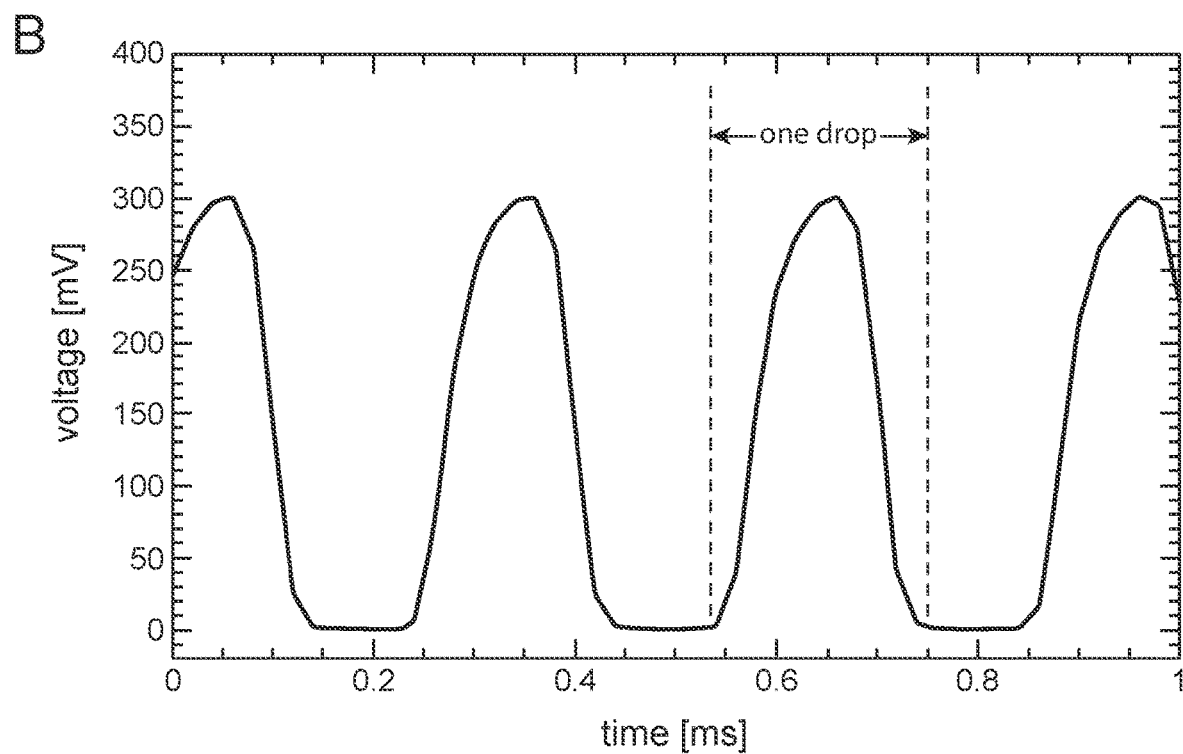

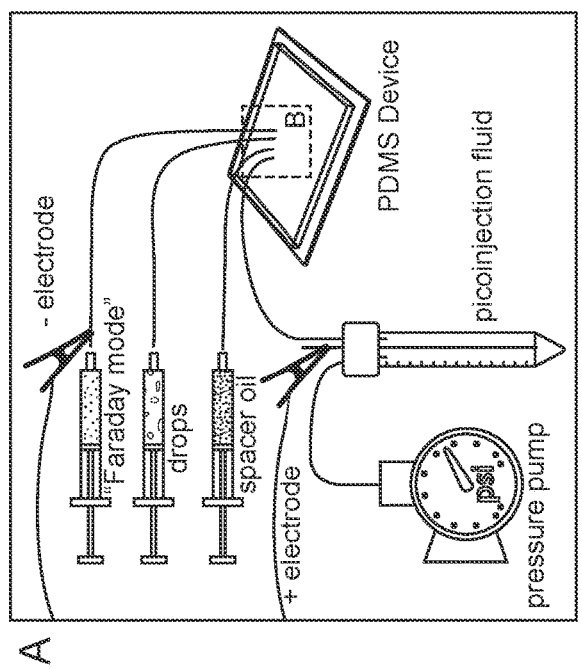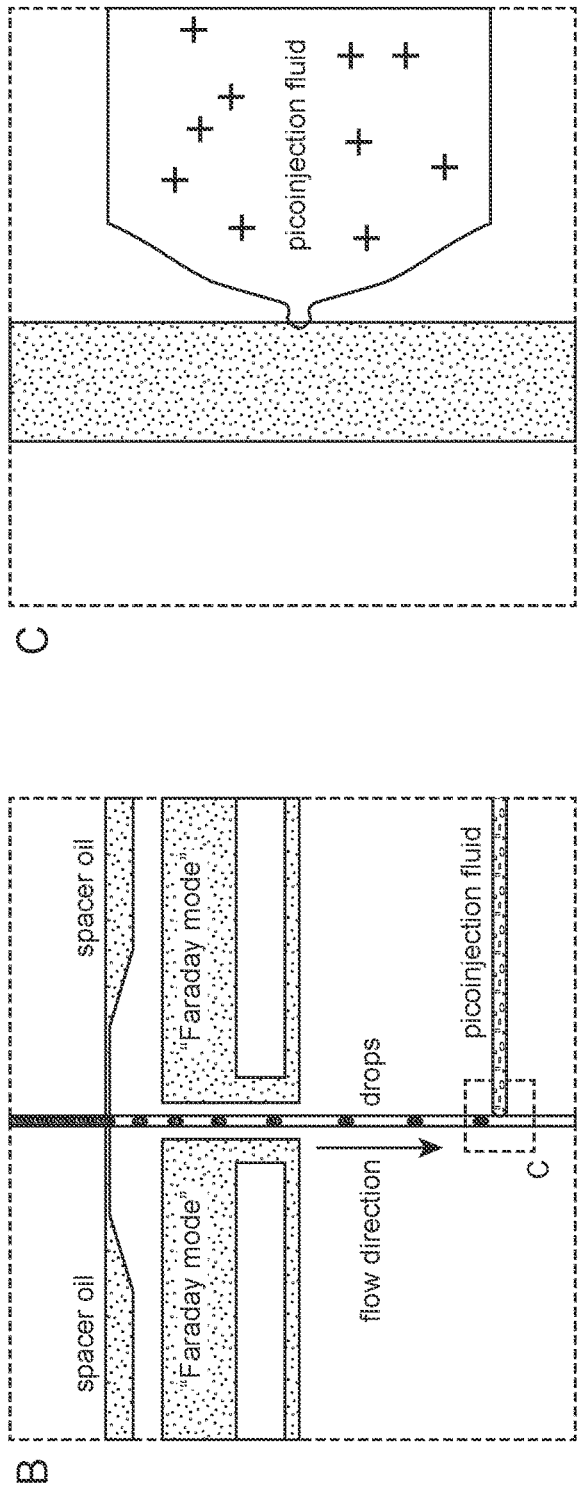
FIG. 15

FIG. 16
A 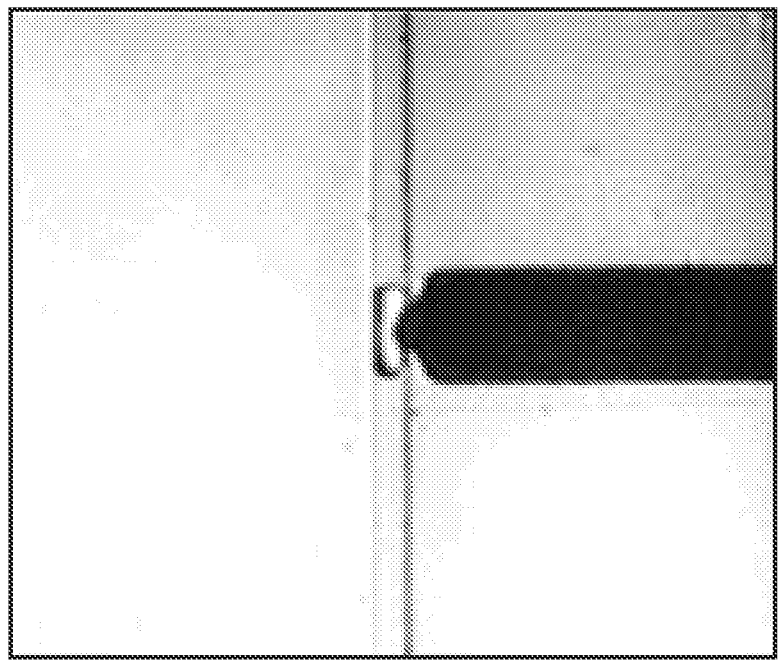
B 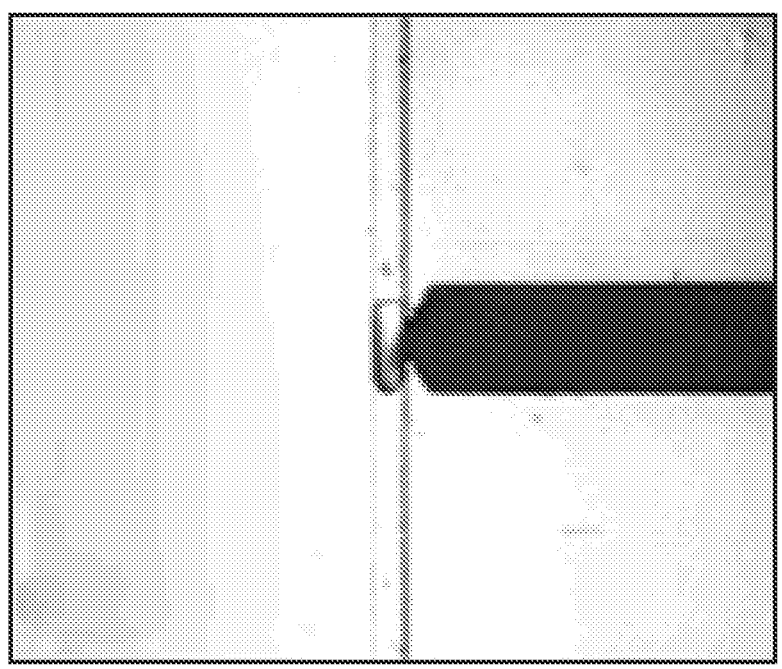

FIG. 20
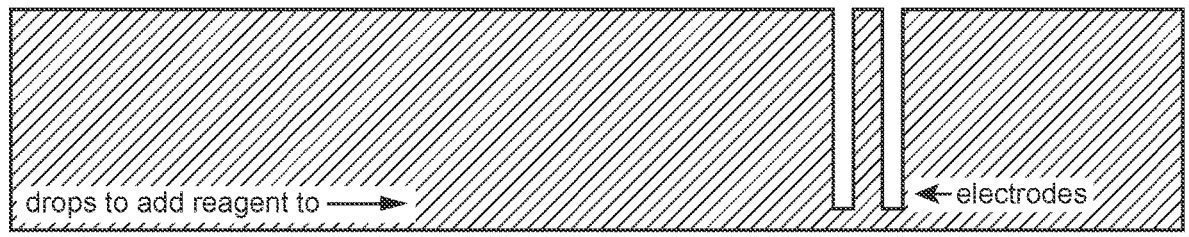
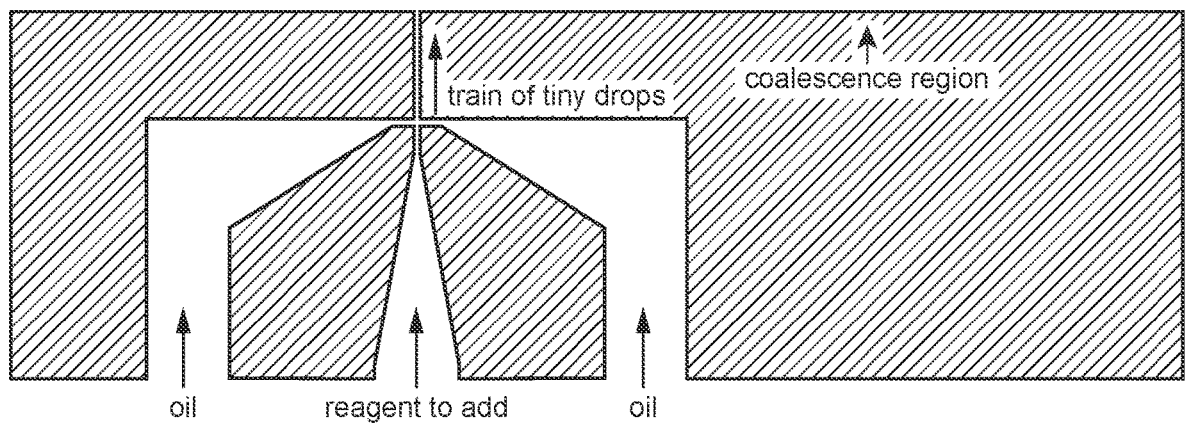
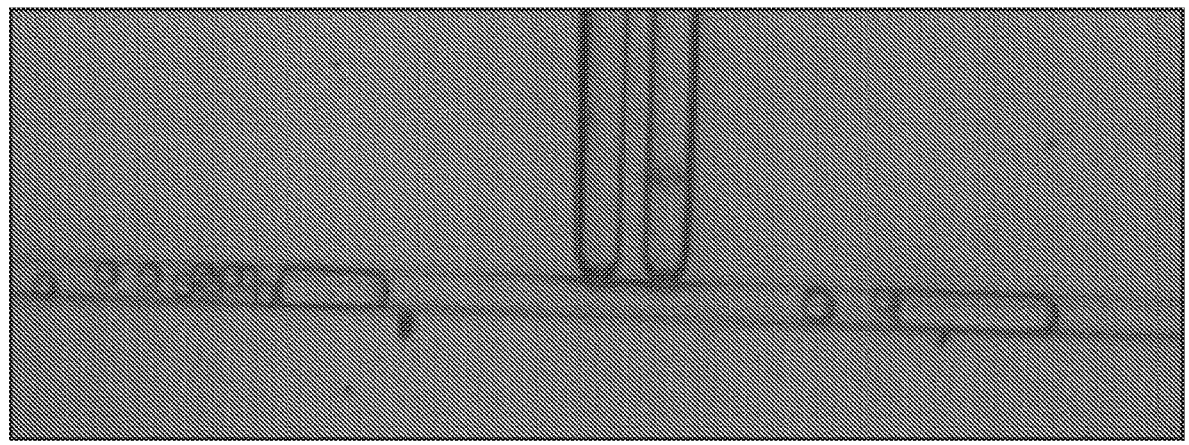

FIG. 22
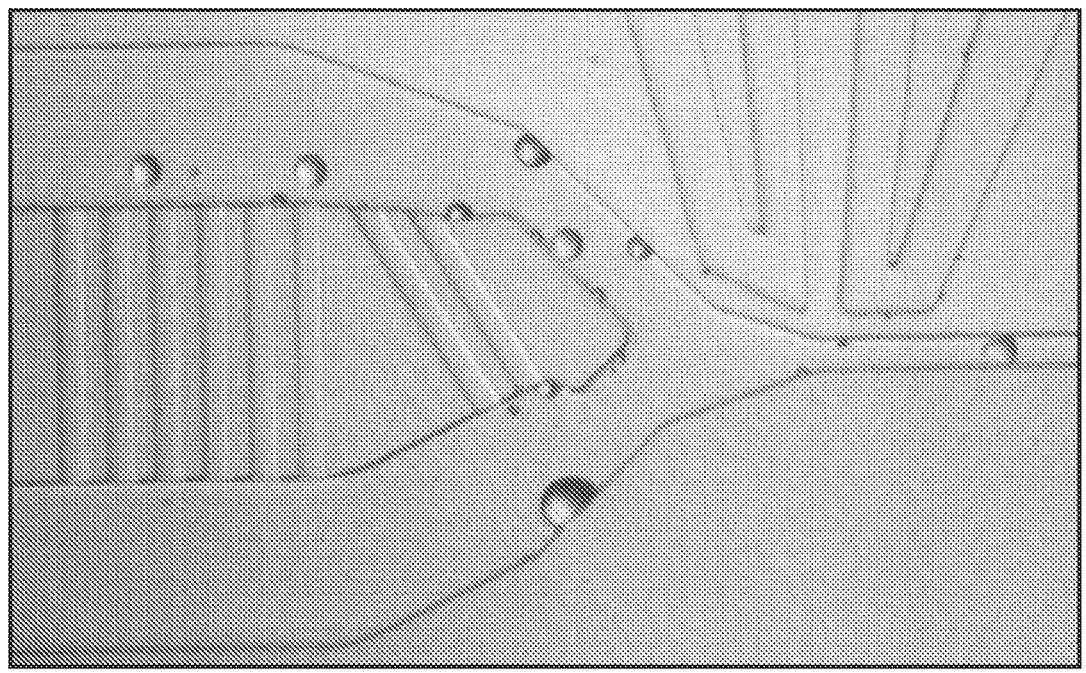
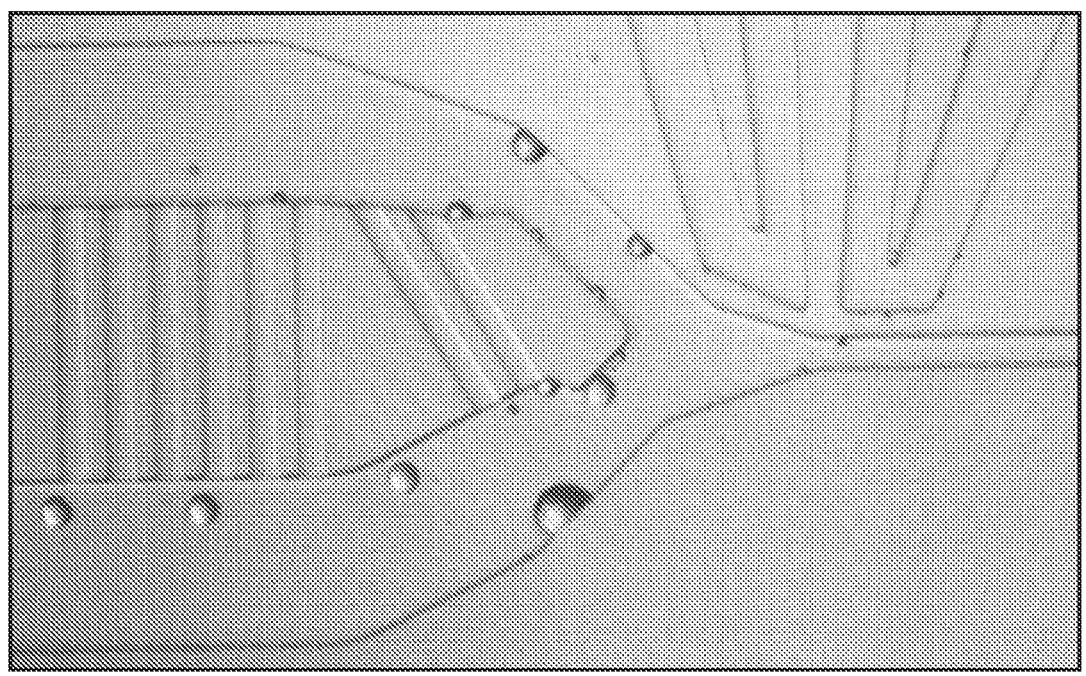

FIG. 26
A
Encapsulate Mix into Drops
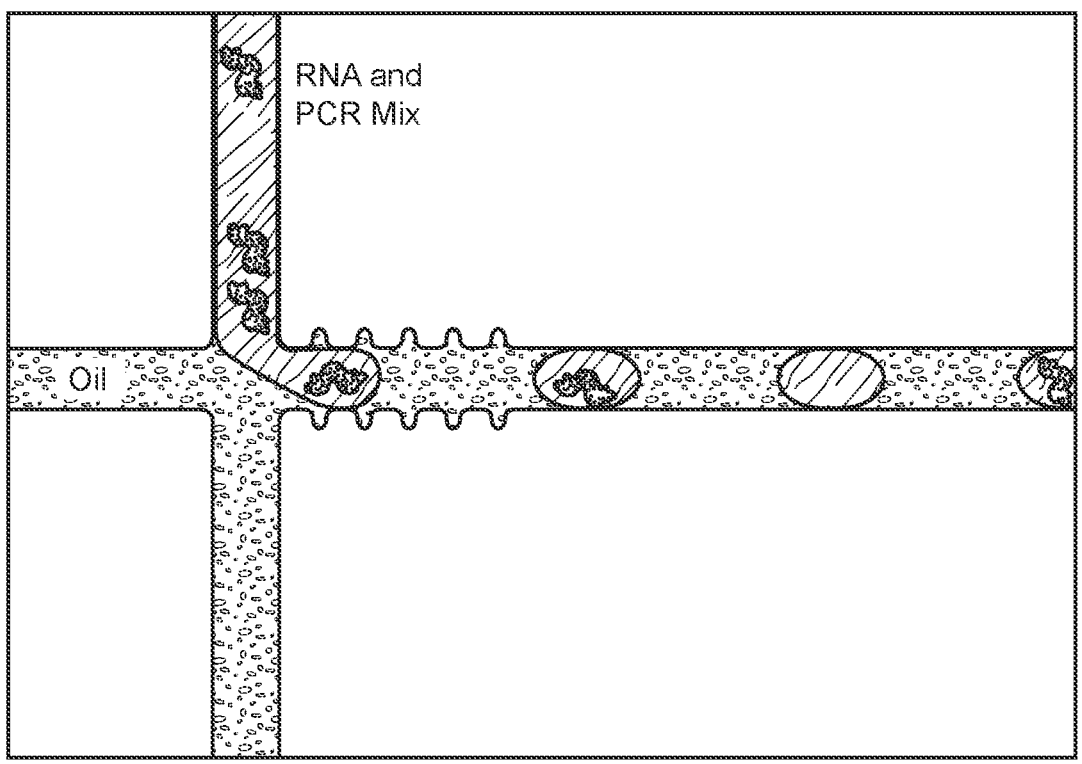
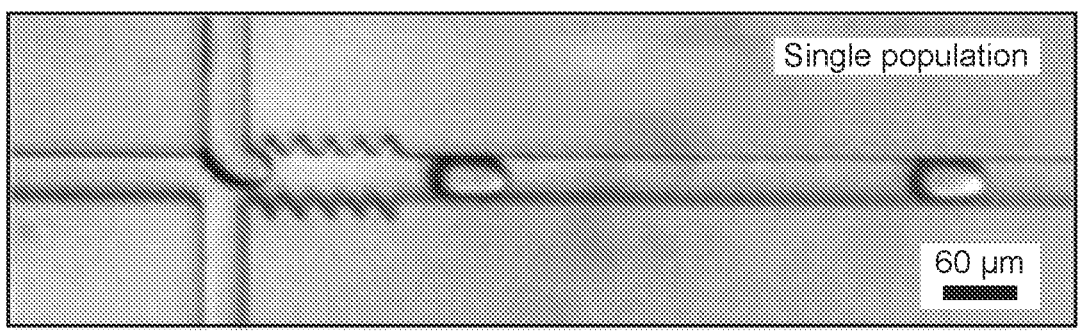
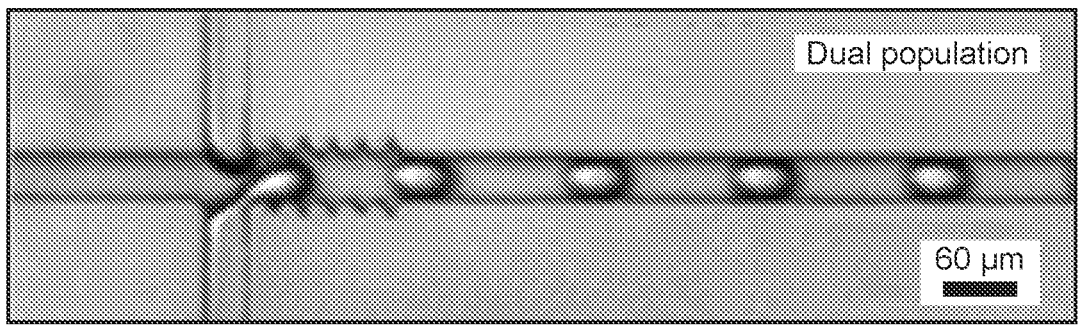

FIG. 26 (Cont.)
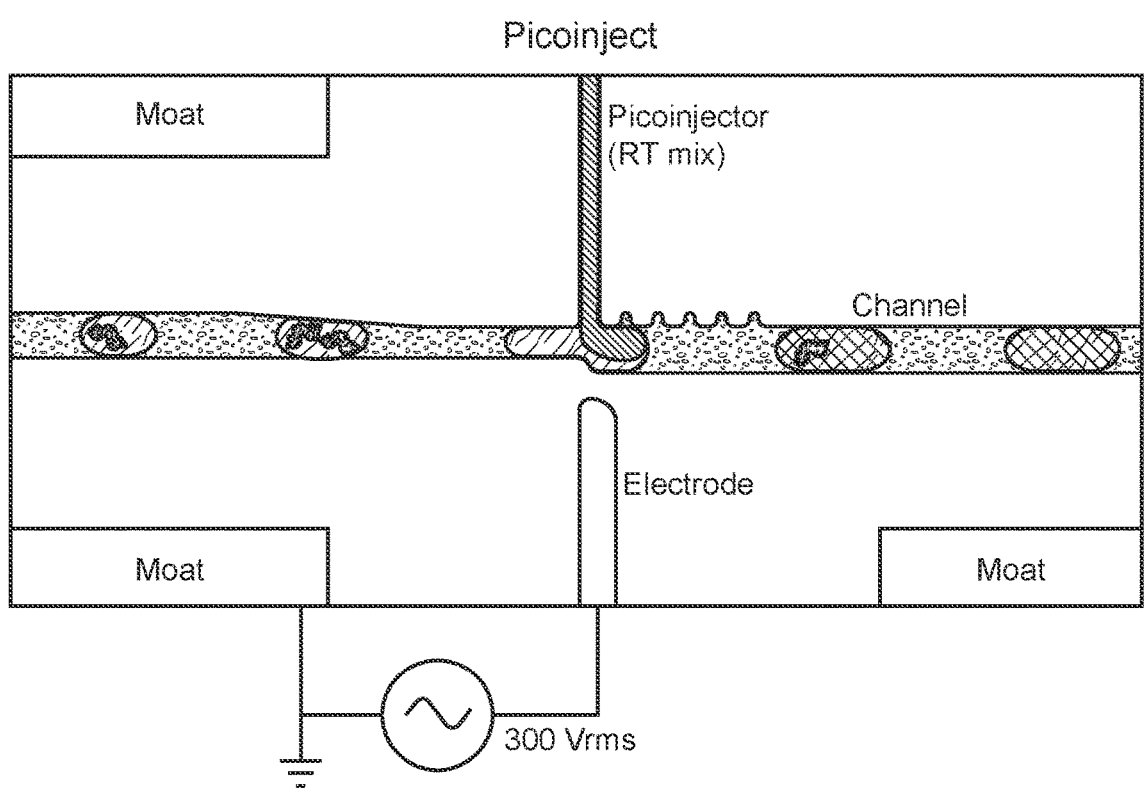
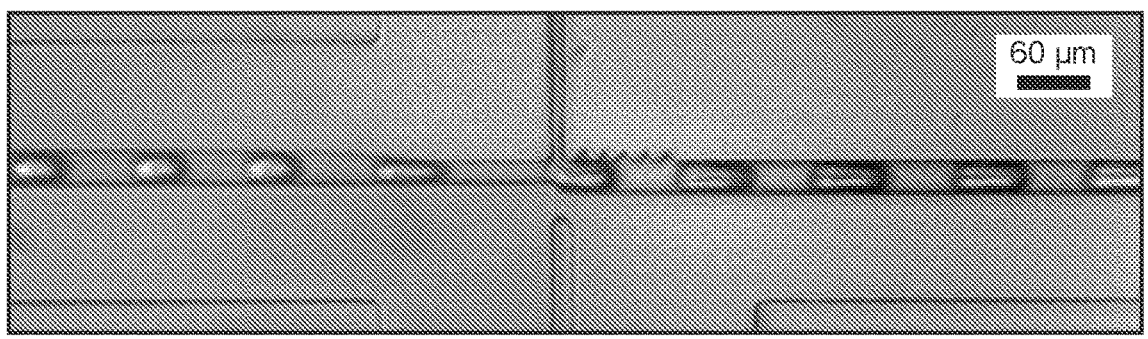

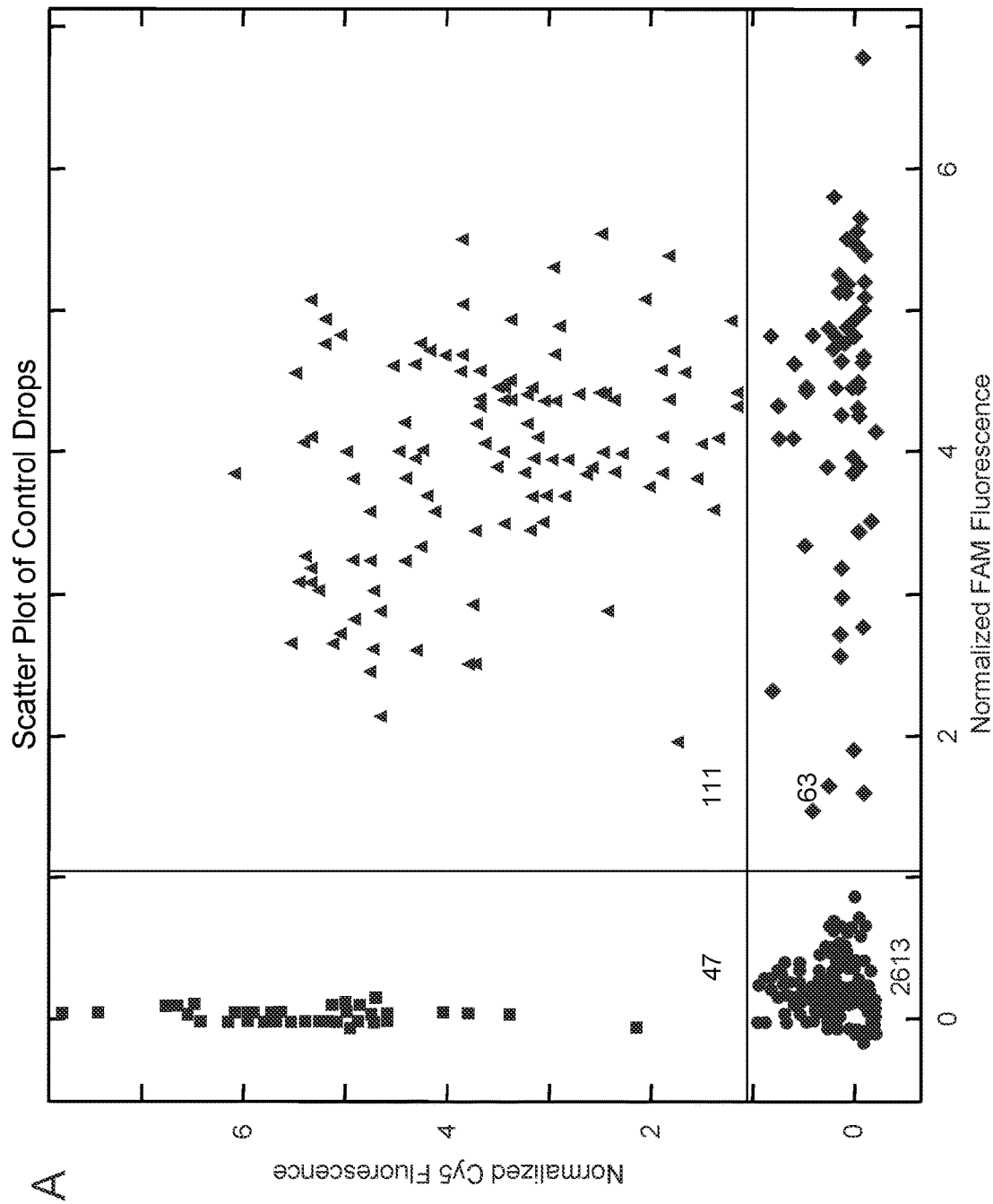

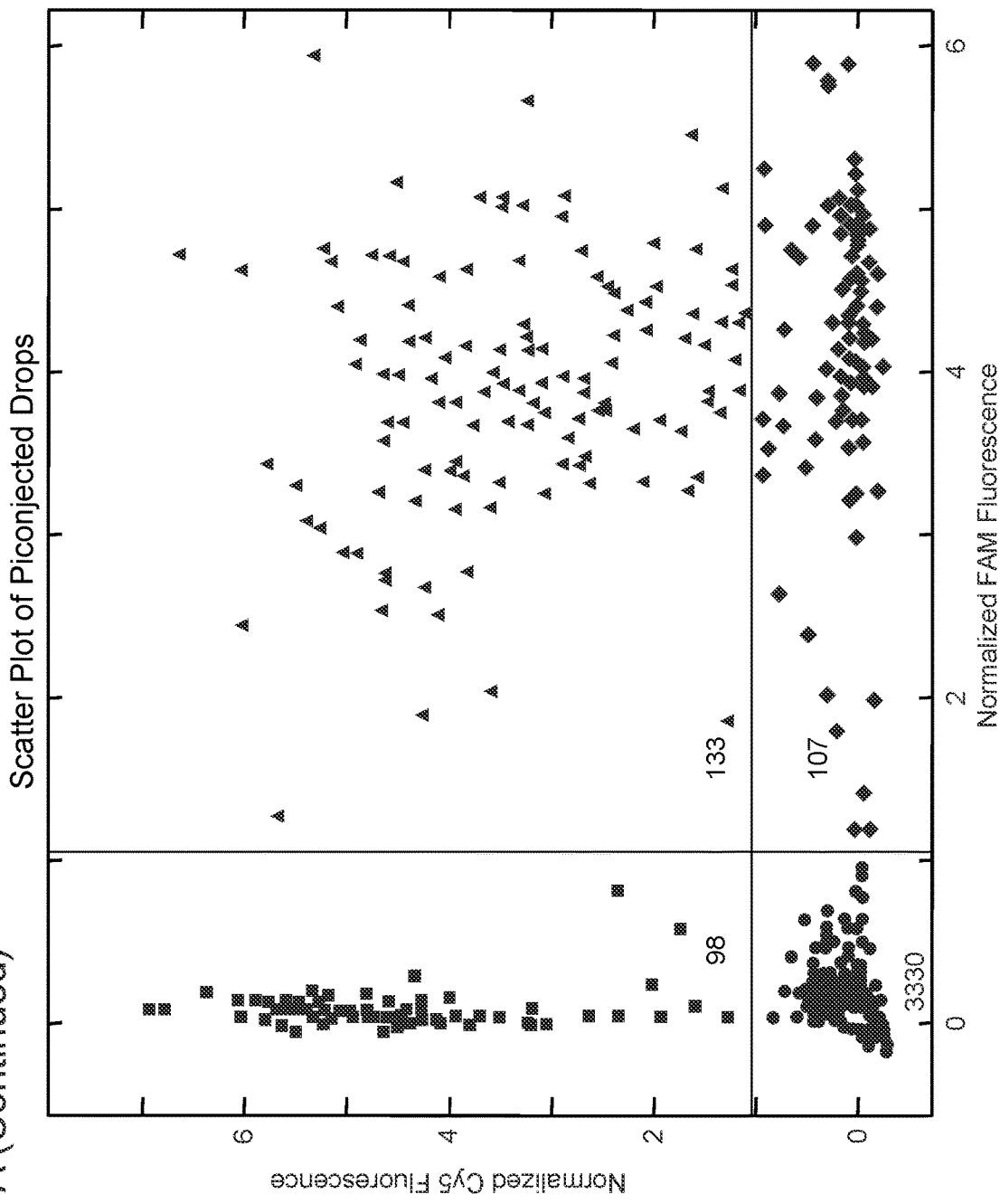

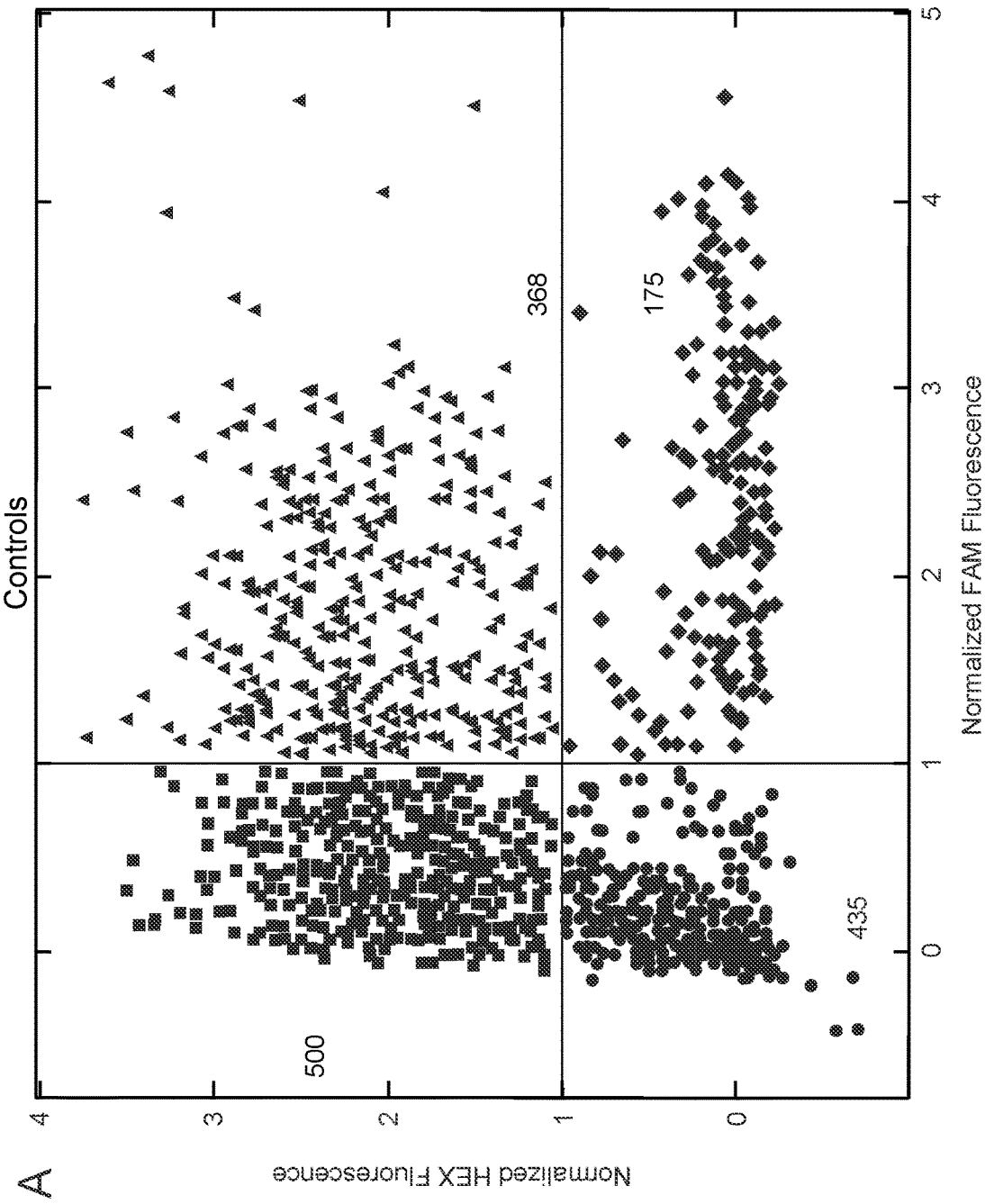

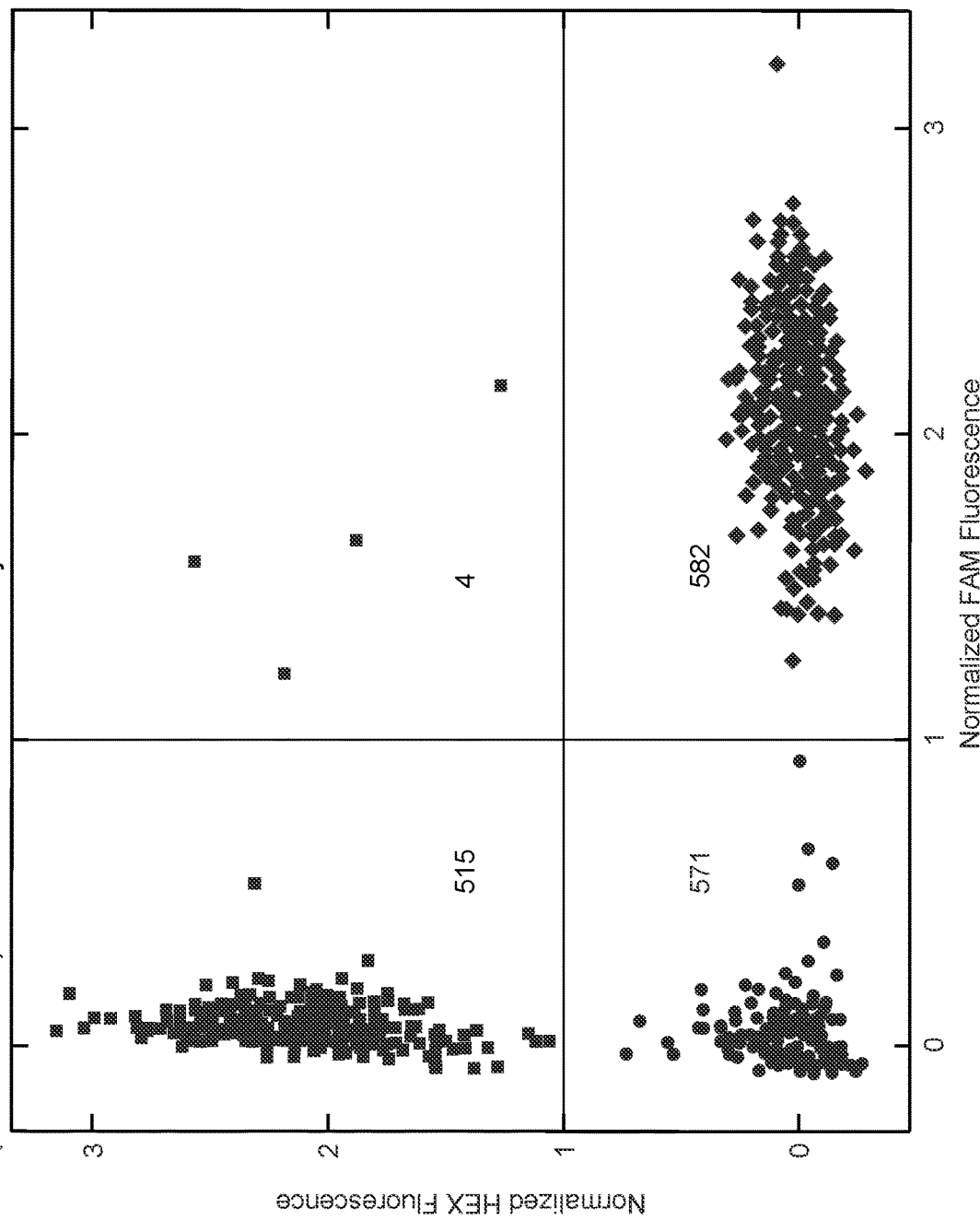
FIG. 30 (Cont.) A (Continued)

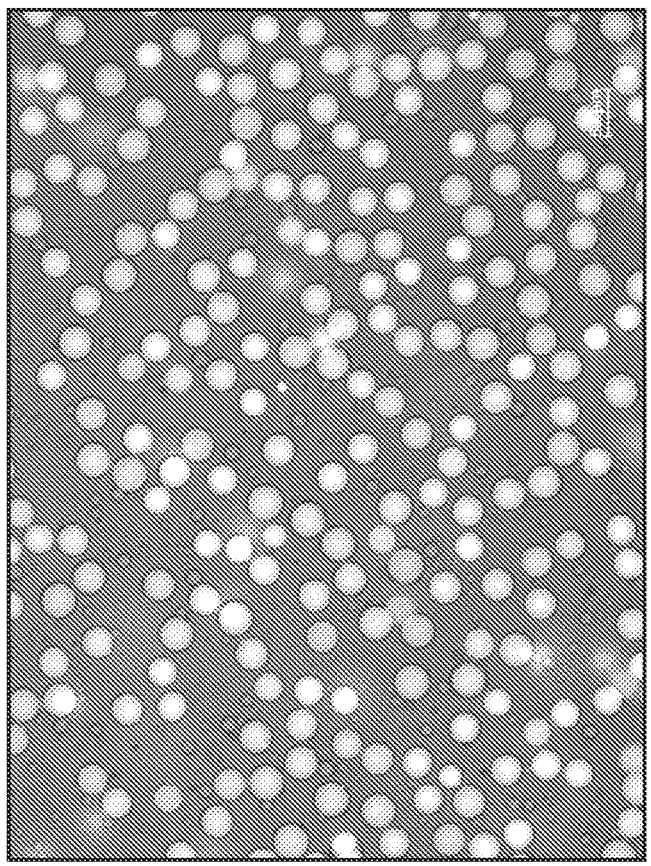
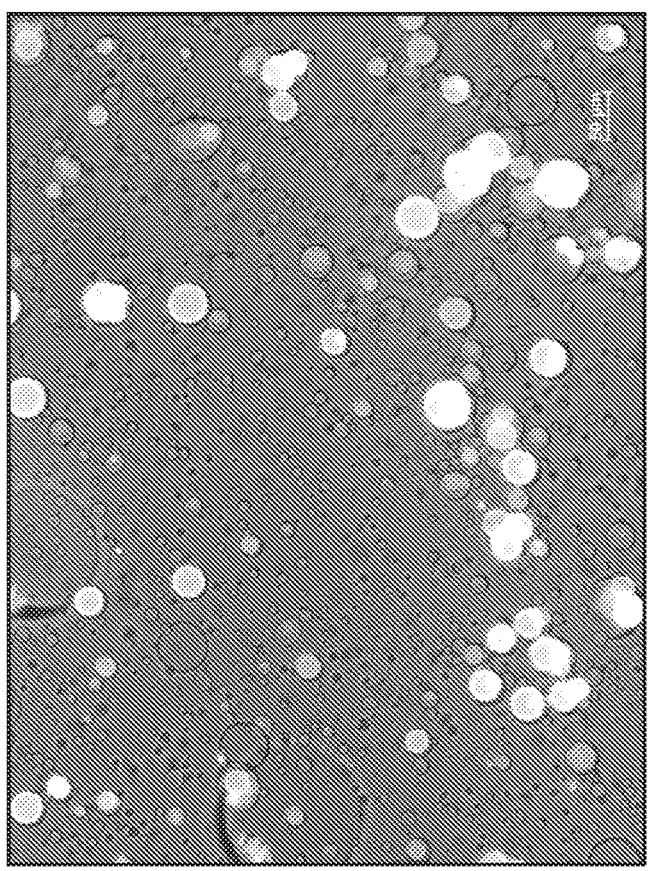
FIG. 41

FIG. 47
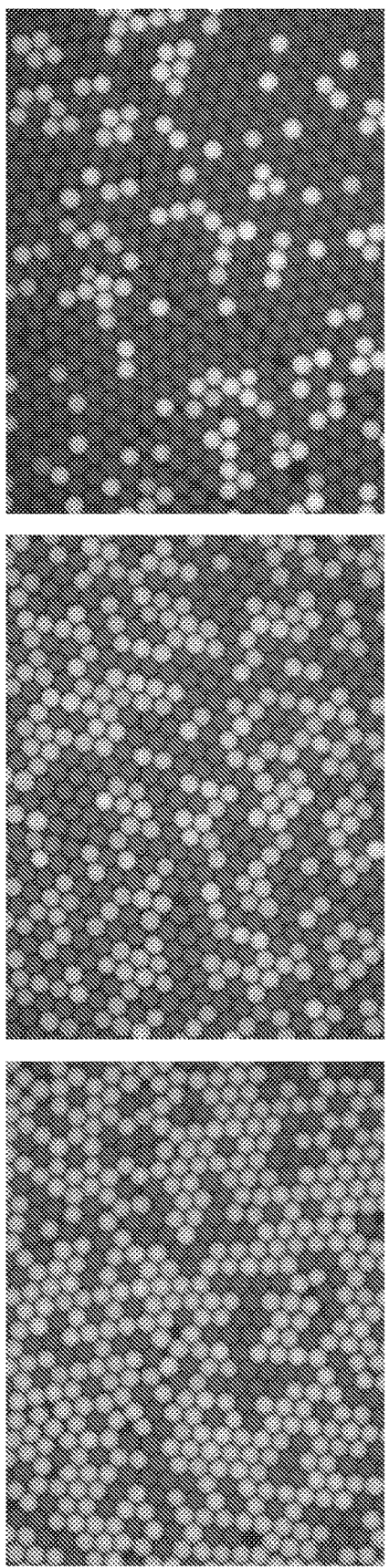
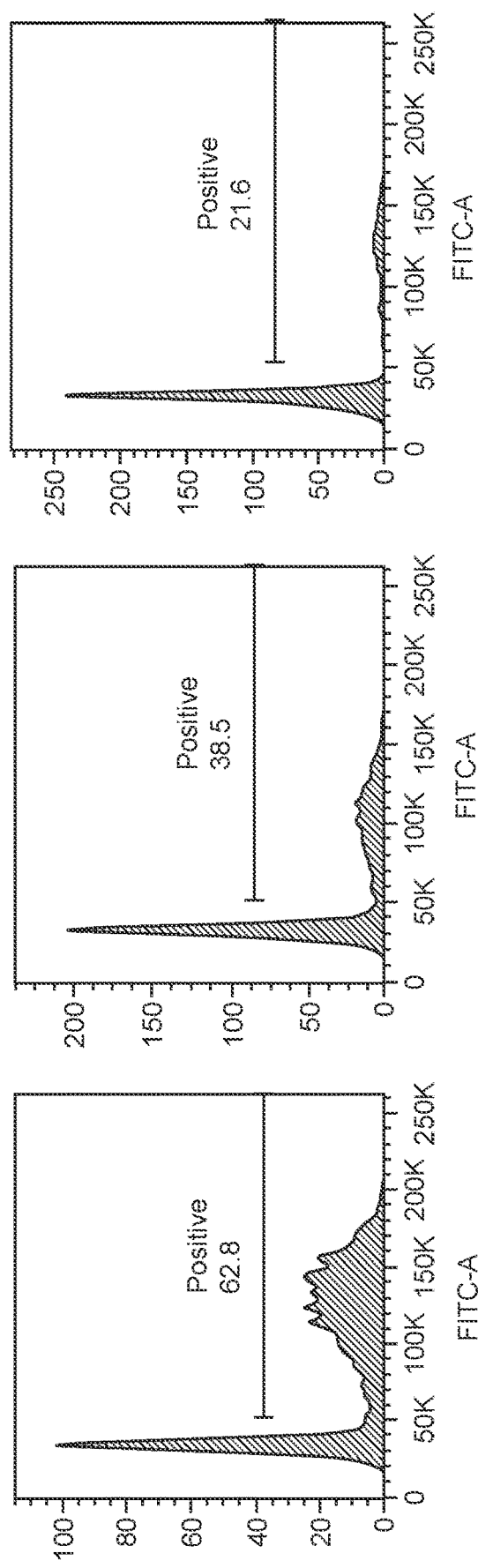

FIG. 48
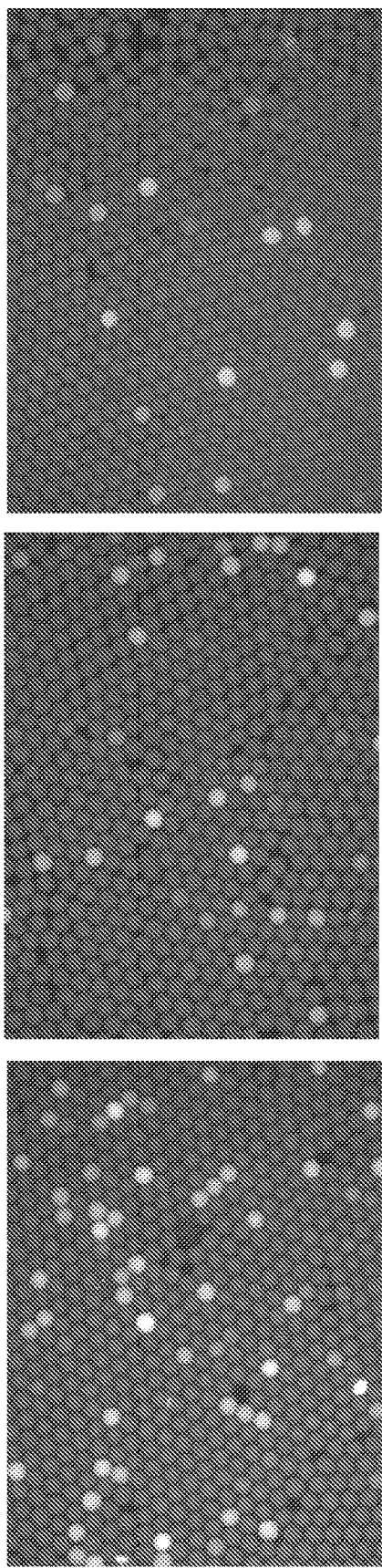
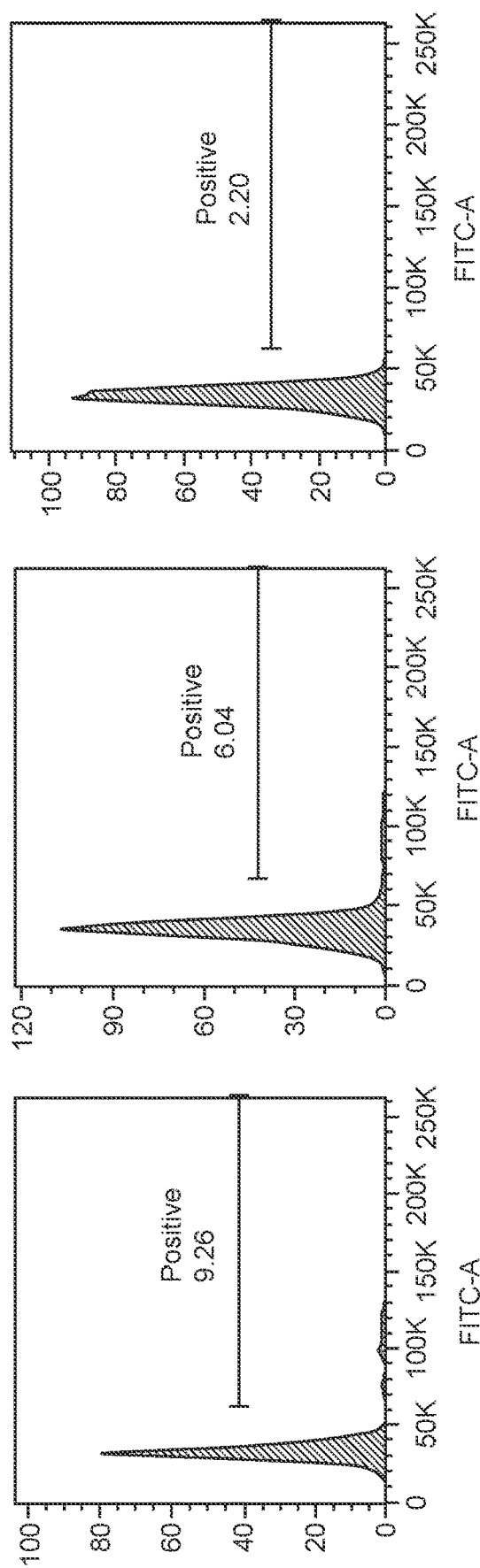

FIG. 49
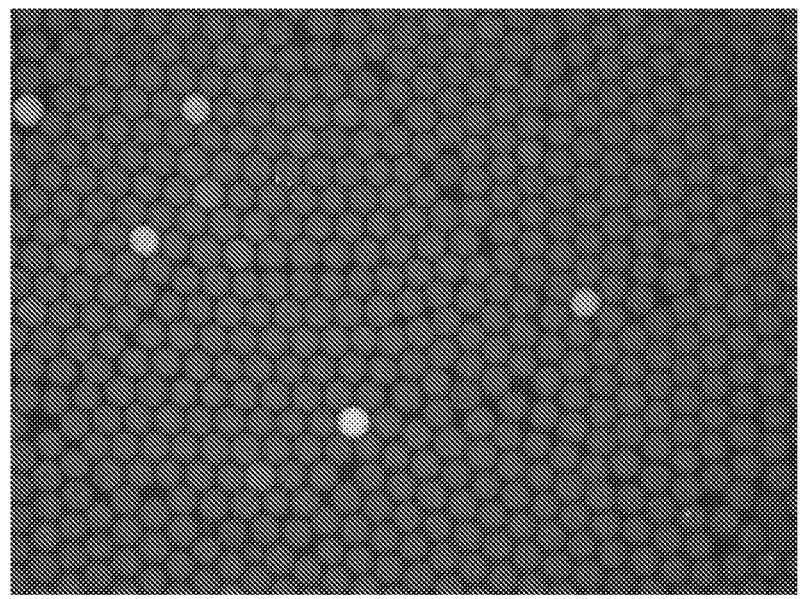
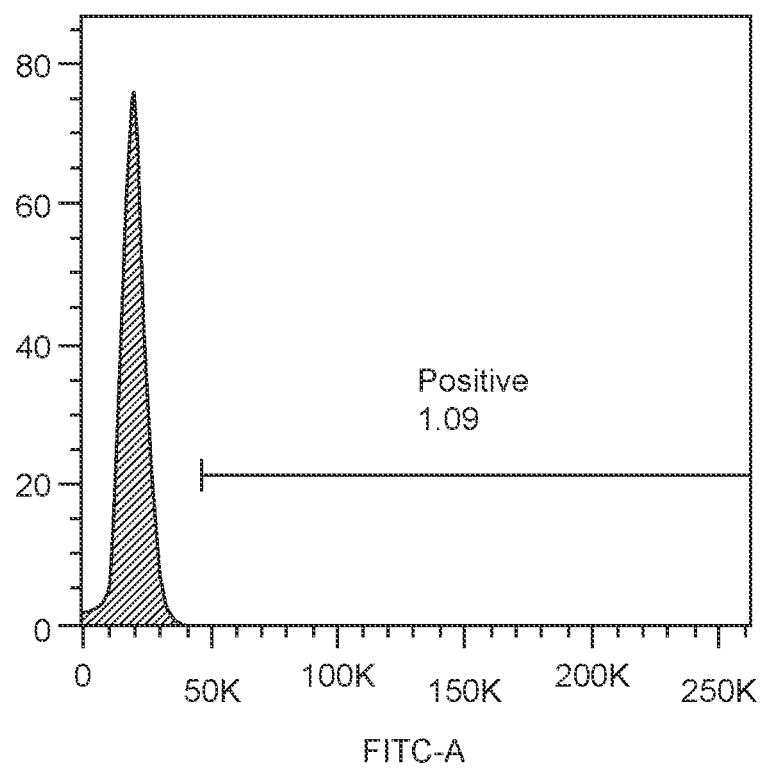

FIG. 55
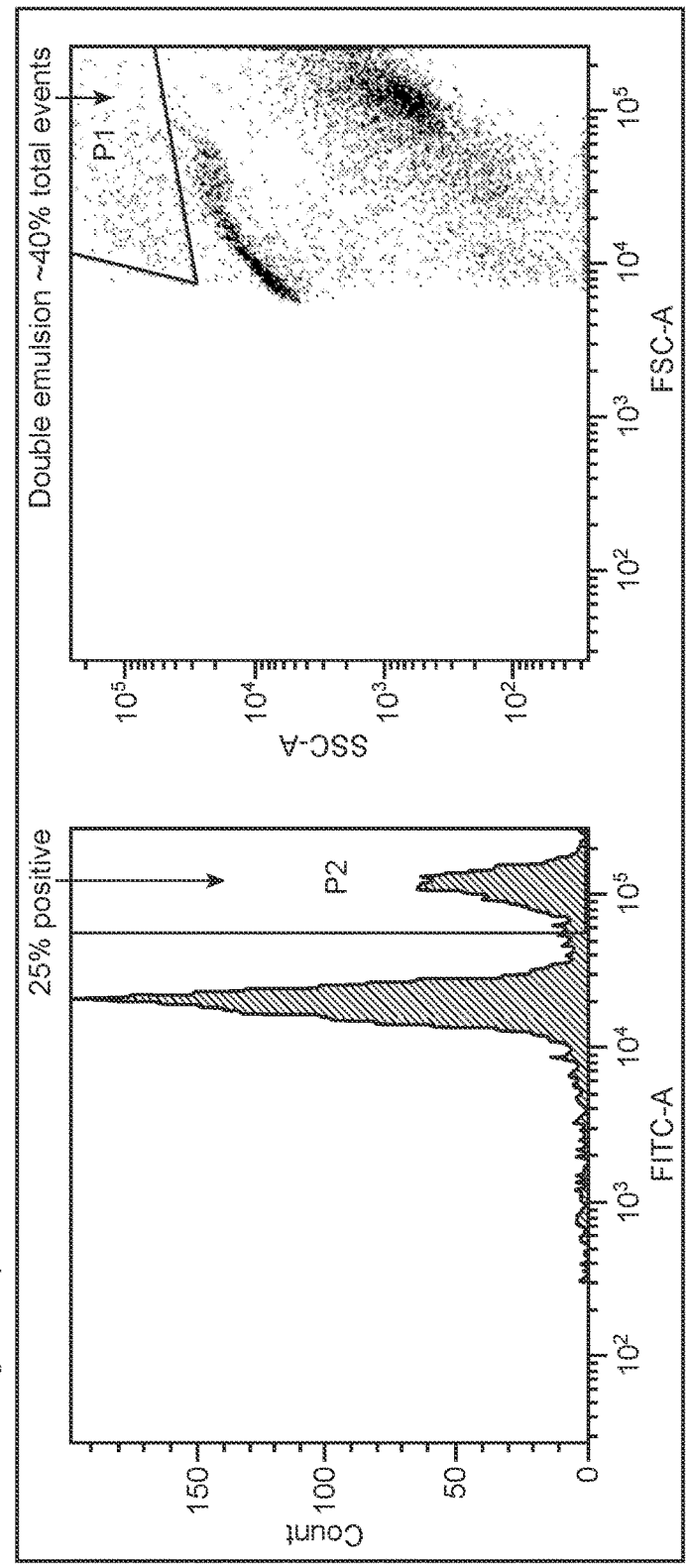
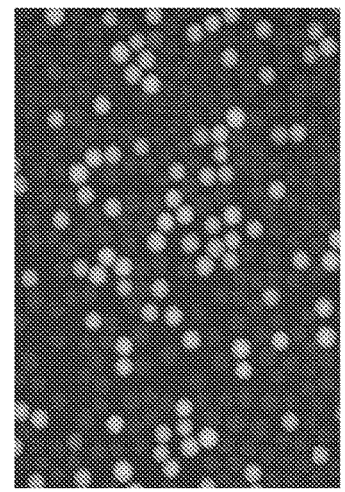

METHODS AND SYSTEMS FOR DETECTING BIOLOGICAL COMPONENTS

CROSS-REFERENCE TO RELATED APPLICATIONS

This application is a continuation of U.S. patent application Ser. No. 14/420,646, now U.S. Pat. No. 10,161,007, which application is a 35 U.S.C. § 371 national stage entry of International Application No. PCT/US2013/054517, filed Aug. 12, 2013, which application claims priority to U.S. Provisional Application No. 61/682,707, filed Aug. 13, 2012; and to U.S. Provisional Application No. 61/784,754, filed Mar. 14, 2013; which applications are incorporated by reference herein in their entireties and for all purposes.

GOVERNMENT RIGHTS

This invention was made with government support under grant nos. HG007233 and AR068129, awarded by the National Institutes of Health, and grant no. DBI1253293, awarded by the National Science Foundation. The government has certain rights in the invention.

INTRODUCTION

Biological samples from a subject often contain a large number of different components. For example, a sample of a subject's blood may contain free floating DNA and RNA, circulating cells, and many other components. The number and diversity of such components in a biological sample often complicates or prevents the accurate identification and/or quantification of specific components of interest within the sample, which would enable the diagnosis or monitoring of a condition in the subject, such as cancer.

For instance, circulating tumor cells (CTCs) are cells shed from tumors that enter into a subject's blood stream. Once in the blood, these cells can circulate through the subject's body, where they can invade other tissues and grow new tumors. CTCs are thus implicated in metastasis, which is the primary cause of death in subjects with cancer. Efforts to count CTCs have been hampered by the fact that CTCs are extremely difficult to detect: they are exceptionally rare, and may be difficult to distinguish from healthy cells. Current approaches for detecting CTCs rely on immunoassays, in which antibodies are used to target specific biomarkers on the surfaces of the CTCs. However, such approaches have limitations in sensitivity and/or specificity, leading to many healthy cells being mischaracterized as cancerous, and many cancer cells being missed in the analysis.

SUMMARY

Methods for the detection of components from biological samples are provided. In certain aspects, the methods may be used to detect and/or quantify specific components in a biological sample, such as tumor cells (e.g., circulating tumor cells, or CTCs). Systems and devices for use in practicing methods of the invention are also provided.

Methods of the present disclosure include methods for the detection of cells in a biological sample, such as tumor cells. Using microfluidics, components of the biological sample may be encapsulated into microdroplets, which are tiny spheres of solution generally ranging from 0.1 to 1000 µm in diameter, which may be used to encapsulate cells, polynucleotides, polypeptides, and other components. The components encapsulated in each microdroplet may be assayed, as described more fully herein.

Aspects of the methods may include encapsulating in a microdroplet a cell obtained from a subject's blood sample, wherein at least one cell is present in the microdroplet; lysing the cell; introducing polymerase chain reaction (PCR) reagents, a detection component, and a plurality of PCR primers into the microdroplet and incubating the microdroplet under conditions allowing for PCR amplification to produce PCR amplification products, wherein the plurality of PCR primers include one or more primers that hybridizes to one or more oligonucleotides (e.g., oncogenes); and detecting the presence or absence of the PCR amplification products by detection of the detection component, wherein detection of the detection component indicates the presence of PCR amplification products. In certain aspects, the step of lysing the cell involves introducing a lysing agent into the microdroplet and incubating the microdroplet under conditions effective for cell lysis. The methods may include determining the number of circulating tumor cells (CTCs) present in a sample of the subject's blood, based at least in part on the number of microdroplets in which PCR products were detected. In other aspects, the methods may include determining the number of tumor cells present in a solid tissue sample from the subject, based at least in part on the number of microdroplets in which PCR products were detected.

In other aspects, the methods for the detection of cells include encapsulating a plurality of cells in a plurality of microdroplets under conditions in which a majority of microdroplets contain zero or one cell, wherein the plurality of cells are obtained from a subject's blood sample; enriching the plurality of microdroplets for microdroplets containing one cell; lysing the cell; introducing polymerase chain reaction (PCR) reagents, a detection component, and a plurality of PCR primers into the plurality of microdroplets and incubating the plurality of microdroplets under conditions allowing for PCR amplification to produce PCR amplification products, wherein the plurality of PCR primers include one or more primers that each hybridize to one or more oligonucleotides (e.g., oncogenes); detecting the presence or absence of the PCR amplification products by detection of the detection component, wherein detection of the detection component indicates the presence of the PCR amplification products; and determining the number of cells present in the sample of the subject's blood based at least in part on the number of microdroplets in which the PCR amplification products were detected; wherein one or more steps are performed under microfluidic control. In certain aspects, the cells are tumor cells, and the plurality of PCR primers include one or more primers that each hybridize to one or more oncogenes. The step of lysing the cell may involve introducing a lysing agent into the microdroplet and incubating the microdroplet under conditions effective for cell lysis.

Methods of the present disclosure also include methods for genotyping cells, including tumor cells. In certain aspects, the methods for genotyping cells include encapsulating in a microdroplet a cell obtained from a biological sample from the subject, wherein one cell is present in the microdroplet; introducing a lysing agent into the microdroplet and incubating the microdroplet under conditions effective for cell lysis; introducing polymerase chain reaction (PCR) reagents and a plurality PCR primers into the microdroplet, and incubating the microdroplet under conditions allowing for PCR amplification to produce PCR amplification products; introducing a plurality of probes into the microdroplet, wherein the probes hybridize to one or more mutations of interest and fluoresce at different wavelengths; and detecting the presence or absence of specific PCR amplification products by detection of fluorescence of a probe, wherein detection of fluorescence indicates the presence of the PCR amplification products; wherein one or more of steps are performed under microfluidic control. The plurality of probes may include one or more TaqMan® probes.

Methods of the present disclosure also include methods for the detection of cancer, the methods including encapsulating in a microdroplet oligonucleotides obtained from a biological sample from the subject, wherein at least one oligonucleotide is present in the microdroplet; introducing polymerase chain reaction (PCR) reagents, a detection component, and a plurality of PCR primers into the microdroplet and incubating the microdroplet under conditions allowing for PCR amplification to produce PCR amplification products, wherein the plurality of PCR primers include one or more primers that each hybridize to one or more oncogenes; and detecting the presence or absence of the PCR amplification products by detection of the detection component, wherein detection of the detection component indicates the presence of the PCR amplification products. The detection of cancer in the subject may be based upon the presence of PCR amplification products for one or more oncogenes.

In other aspects, the methods of the present disclosure include encapsulating in a microdroplet an oligonucleotide obtained from a biological sample obtained from a subject, wherein at least one oligonucleotide is present in the microdroplet; introducing polymerase chain reaction (PCR) reagents, a detection component, and a plurality of PCR primers into the microdroplet and incubating the microdroplet under conditions allowing for PCR amplification to produce PCR amplification products; and detecting the presence or absence of the PCR amplification products by detection of the detection component, wherein detection of the detection component indicates the presence of PCR amplification products; wherein one or more steps are performed under microfluidic control.

In practicing the subject methods, several variations may be employed. For example, a wide range of different PCR-based assays may be employed, such as quantitative PCR (qPCR). The number and nature of primers used in such assays may vary, based at least in part on the type of assay being performed, the nature of the biological sample, and/or other factors. In certain aspects, the number of primers that may be added to a microdroplet may be 1 to 100 or more, and/or may include primers to detect from about 1 to 100 or more different genes (e.g., oncogenes). In addition to, or instead of, such primers, one or more probes (e.g., TaqMan® probes) may be employed in practicing the subject methods.

The microdroplets themselves may vary, including in size, composition, contents, and the like. Microdroplets may generally have an internal volume of about 0.001 to 1000 picoliters or more. Further, microdroplets may or may not be stabilized by surfactants and/or particles.

The means by which reagents are added to a microdroplet may vary greatly. Reagents may be added in one step or in multiple steps, such as 2 or more steps, 4 or more steps, or 10 or more steps. In certain aspects, reagents may be added using techniques including droplet coalescence, picoinjection, multiple droplet coalescence, and the like, as shall be described more fully herein. In certain embodiments, reagents are added by a method in which the injection fluid itself acts as an electrode. The injection fluid may contain one or more types of dissolved electrolytes that permit it to be used as such. Where the injection fluid itself acts as the electrode, the need for metal electrodes in the microfluidic chip for the purpose of adding reagents to a droplet may be obviated. In certain embodiments, the injection fluid does not act as an electrode, but one or more liquid electrodes are utilized in place of metal electrodes.

Various ways of detecting the absence or presence of PCR products may be employed, using a variety of different detection components. Detection components of interest include, but are not limited to, fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Detection components may include beads (e.g., magnetic or fluorescent beads, such as Luminex beads) and the like. In certain aspects, detection may involve holding a microdroplet at a fixed position during thermal cycling so it can be repeatedly imaged. Such repeated imaging may involve the use of a Megadroplet Array, as shall be described more fully herein. In certain aspects, detection may involve fixing and/or permeabilizing one or more cells in one or more microdroplets.

Suitable subjects for the methods disclosed herein include mammals, e.g., humans. The subject may be one that exhibits clinical presentations of a disease condition, or has been diagnosed with a disease. In certain aspects, the subject may be one that has been diagnosed with cancer, exhibits clinical presentations of cancer, or is determined to be at risk of developing cancer due to one or more factors such as family history, environmental exposure, genetic mutation(s), lifestyle (e.g., diet and/or smoking), the presence of one or more other disease conditions, and the like.

Microfluidic systems and devices are also provided by the present disclosure. In certain aspects, the microfluidic devices include a cell loading region to encapsulate a cell to be analyzed in a microdroplet; a first chamber in fluidic communication with the cell loading region, the first chamber having a means for adding a first reagent to the microdroplet, and a heating element; a second chamber in fluidic communication with the first chamber, the second chamber having a means for adding a second reagent to the microdroplet, and a heating element, wherein the heating element may heat the microdroplet at one or more temperatures; and a detection region, in fluidic communication with the second chamber, which detects the presence or absence of reaction products from the first or second chamber.

BRIEF DESCRIPTION OF THE DRAWINGS

The invention may be best understood from the following detailed description when read in conjunction with the accompanying drawings. Included in the drawings are the following figures:

FIG. 14, Panels A-B depict the use of a one-color flow-cytometer used to detect PCR amplification products in drops, via fluorescence. Panel A: Schematic of detector, consisting of a 488 nm laser directed into the back of an objective, and focused onto a microfluidic channel through which the droplets flow. The laser excites fluorescent dyes within the drops, and any emitted light is captured by the objective and imaged onto a photomultiplier tube (PMT) after it is filtered through a dichroic mirror and 520±5 nm band pass filter. Panel B: The drops appear as peaks in intensity as a function of time, as shown by the output voltage of a PMT, which is proportional to the intensity of the emitted light, as a function of time for detected fluorescent drops.

FIG. 15, Panels A-C show a schematic of device setup. Panel A: Drops, spacer oil, and 1 M NaCl are introduced to the PDMS device via syringe pumps. The picoinjection fluid is introduced using an air pressure control pump. Electrodes from the high voltage amplifier are connected to a wire submerged in the picoinjection fluid and to the metal needle of the syringe containing the 1 M NaCl "Faraday Mote." Panel B: A magnified view of the droplet spacer and picoinjection site. Panel C: Further magnified view of the picoinjection site showing the fluid bulge at the injection orifice.

FIG. 16, Panels A-B show bright field microscopy images of the picoinjection site. In the absence of an electric field (Panel A), surfactants prevent coalescence with the injection fluid and a distinct boundary is visible at the droplet/injection fluid interface. When the electric field is applied, the boundary disappears and reagent is injected as the droplet passes (Panel B).

FIG. 20, Panels A-B show adding reagents via multiple droplet coalescence. Panel A: A schematic of a microfluidic device for adding reagents via multiple droplet coalescence. The reagent to add is introduced from below, along with oil, into a very small drop maker. This leads to the production of a train of very small drops at a high frequency. The drops to which the reagent is to be added are injected, spaced by oil, from the left and then the streams combine where the channel intersects with the outlet of the tiny drop maker. Because the reagent drops are much smaller than the target drops, they are introduced at a high rate frequency, and so many (tens or more) of these drops are injected for every one target drop. Due to their small size they flow faster than the larger drops and collect behind them so that, by the time the reach the electrode channels they are in contact and can be coalesced by the electric field. Panel B: Close-up of the coalescence region in such a microfluidic device. Drops flow from left to the right. A train of tiny droplets form behind the droplet to which they are to be added. Once the tiny droplets and the droplet pass through the coalescence region, the electrodes cause the tiny droplets to merge into the droplet. The resulting output on the right is a droplet that contains the reagent(s) that were present in the tiny droplets.

FIG. 22, Panels A-B show sorting. Droplets enter from the right and flow to the left, passing by the electrodes. The drops are thus sorted on the presence (Panel A; droplets flow into the top output) or absence of a particular property (Panel B; droplets flow into the bottom output).

FIG. 41 provides fluorescent microscope images of fluorescent double emulsions. The image on the left shows double emulsions formed by shaking the fluids, which results in a large amount of polydispersity and a small number of drops of the appropriate size for FACS sorting. The image on the right shows double emulsions made with the microfluidic process disclosed herein, which are much more monodisperse.

FIG. 47 shows emulsions containing three different concentrations of DNA. All drops contain TaqMan® probes for the DNA target, but the target is encapsulated at limiting concentration, so that only the drops that get a target undergo amplification. When the target concentration is reduced, the fraction of fluorescent drops goes down. The lower plots show the drops after being encapsulated in double emulsions and screed on FACS.

FIG. 48 shows emulsions containing three concentrations of DNA lower than those in the previous Figure. All drops contain TaqMan® probes for the DNA target, but the target is encapsulated at limiting concentration, so that only the drops that get a target undergo amplification. When the target concentration is reduced, the fraction of fluorescent drops goes down. The lower plots show the drops after being encapsulated in double emulsions and screed on FACS.

FIG. 49 shows emulsions as for FIGS. 47 and 48 at the lowest DNA concentration of the three Figures. The lower plot shows the drops after being encapsulated in double emulsions and screed on FACS.

FIG. 55 shows results for the PCR amplification of *Azospira* amplicons (left) and FACS analysis of *Azospira* containing double emulsions (right).

DETAILED DESCRIPTION

Figure 1:
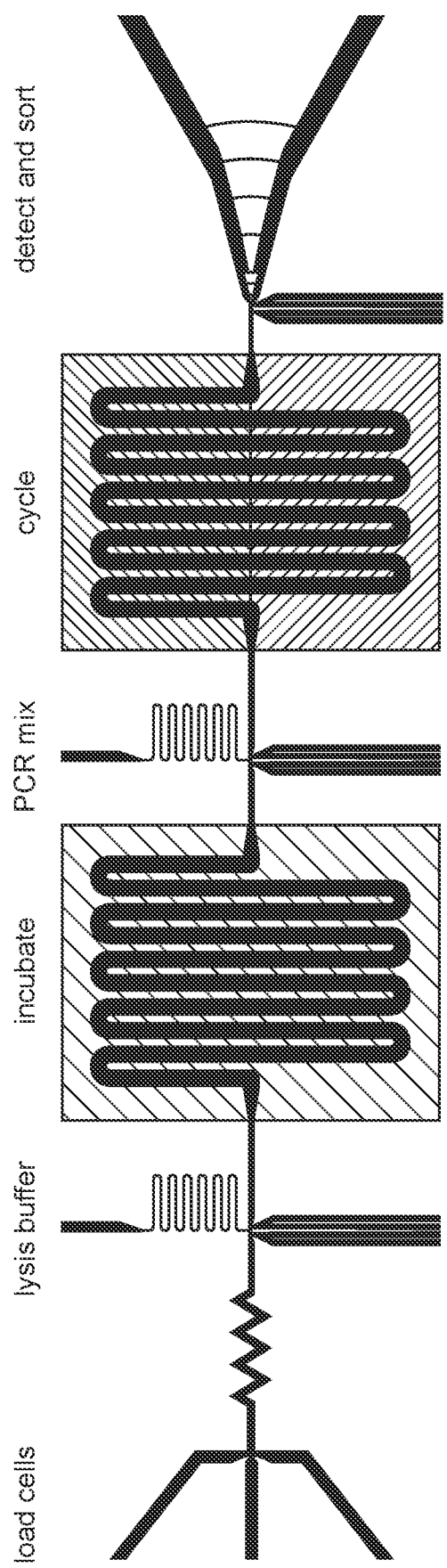
FIG. 1 is a simplified depiction of a microfluidic system of the instant disclosure. In the depicted system, the microfluidic system may be used for detecting and/or genotyping a component of a biological sample. As applied to the detection of tumor cells in this particular system, nucleated blood cells are encapsulated into individual droplets using an encapsulation device (left). The droplets are injected with a lysis buffer and incubated at 37° C. to accelerate cell lysis. They are injected with PCR mix containing primers targeting characteristic oncogenic mutations (center). The droplets are flowed through a channel snaking over zones maintained at 65° C. and 95° C. As the droplets move through the zones, their temperature cycles, as needed for PCR. During this PCR reaction, if a droplet contains a genome of a tumor cell with a mutation for which the primers are designed to detect, amplification will be initiated, producing a fluorescent output that turns the droplet fluorescent. The droplets are then optically scanned using flow cytometry and sorted using droplet sorting to recover them (right). The droplets may be stored or used for further analysis, such as being subjected to sequencing (e.g., used as input for a next-gen sequencer, or provided to a sequencing facility).

Methods for the detection of components from biological samples are provided. In certain aspects, the methods may be used to detect and/or quantify specific components in a biological sample, such as tumor cells (e.g., circulating tumor cells). Systems and devices for use in practicing methods of the invention are also provided.

The subject methods and devices may find use in a wide variety of applications, such as the detection of cancer, detection of aneuploidy from DNA circulating in a mother's blood stream, monitoring disease progression, analyzing the DNA or RNA content of cells, and a variety of other applications in which it is desired to detect and/or quantify specific components in a biological sample.

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a microdroplet" includes a plurality of such microdroplets and reference to "the microdroplet" includes reference to one or more microdroplets, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods for the detection of components from biological samples. Aspects include methods for the detection, quantification, and/or genotyping of cells, e.g. normal cells (i.e., non-tumor cells), tumor cells or CTCs.

As used herein, the phrase "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, cells, serum, plasma, biological fluid, and tissue samples. "Biological sample" includes cells; biological fluids such as blood, cerebrospinal fluid, semen, saliva, and the like; bile; bone marrow; skin (e.g., skin biopsy); and antibodies obtained from an individual.

As described more fully herein, in various aspects the subject methods may be used to detect a variety of components from such biological samples. Components of interest include, but are not necessarily limited to, cells (e.g., circulating cells and/or circulating tumor cells), polynucleotides (e.g., DNA and/or RNA), polypeptides (e.g., peptides and/or proteins), and many other components that may be present in a biological sample.

"Polynucleotides" or "oligonucleotides" as used herein refer to linear polymers of nucleotide monomers, and may be used interchangeably. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, *Human Molecular Genetics* 2 (Wiley-Liss, New York, 1999).

The terms "polypeptide," "peptide," and "protein," used interchangeably herein, refer to a polymeric form of amino acids of any length. $NH_2$ refers to the free amino group present at the amino terminus of a polypeptide. COOH refers to the free carboxyl group present at the carboxyl terminus of a polypeptide. In keeping with standard polypeptide nomenclature, *J. Biol. Chem.*, 243 (1969), 3552-3559 is used.

In certain aspects, methods are provided for counting and/or genotyping cells, including normal cells or tumor cells, such as CTCs. A feature of such methods is the use of microfluidics.

Figure 3:
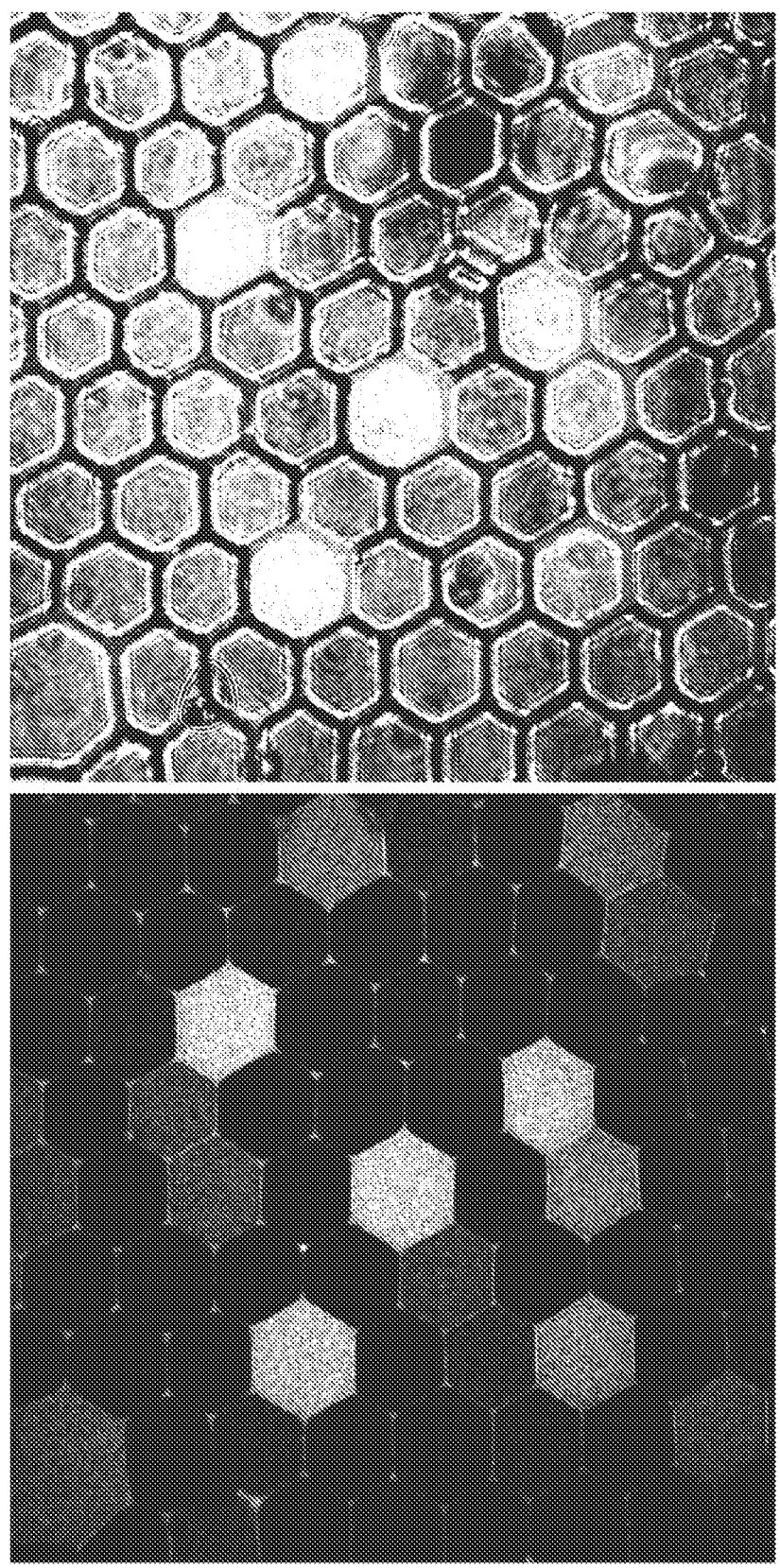
FIG. 3 depicts digital detection of BRAF using a TaqMan® PCR probe labeled with the fluorophore FAM that is complementary to an amplicon from a portion of the human BRAF gene. Fluorescent drops indicate amplification of the BRAF gene from purified human genomic DNA, while non-fluorescent drops were devoid of the gene.
Figure 4:
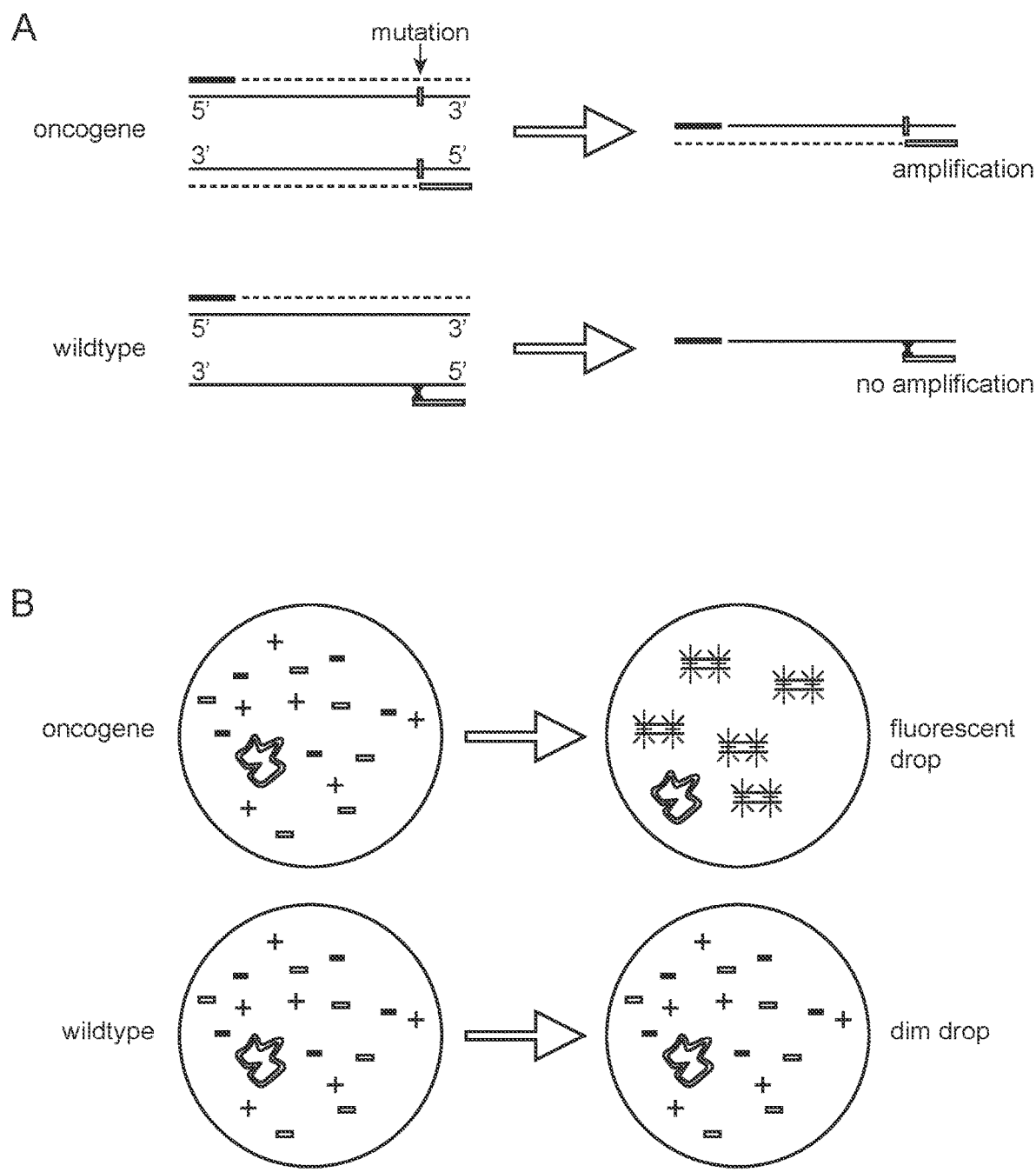
FIG. 4, Panels A-B depict a binary PCR reaction to detect CTCs. Panel A: Forward and reverse primers are encapsulated in the drops that target an oncogenic sequence. If the oncogenic sequence is present, the PCR reaction produces double-stranded PCR products (Panel A, upper), whereas, if it is not, no products are produced (Panel A, lower). An intercalating stain (e.g., SybrGreen) may also be present in the drop. Panel B: If double-stranded products are produced, the dye intercalates into them, becoming fluorescent, and turning the drop fluorescent (Panel B, upper); by contrast, if no double-stranded products are produced, the dye remains non-fluorescent, producing a dim drop (Panel B, lower).

FIG. 1 presents a non-limiting, simplified representation of one type of a microfluidics system and method of the present disclosure. The particular application depicted in FIG. 1 is the detection and/or genotyping of cells, e.g., tumor cells, from a biological sample. In one such method, nucleated blood cells may be obtained from a biological sample from a subject. The nucleated blood cells are encapsulated into individual drops using an encapsulation device (left). The drops may then be injected with a lysis buffer and incubated at conditions that accelerate cell lysis (e.g., at 37° C.). The drops may be injected with a PCR mix that includes one or more primers targeting characteristic oncogenic mutations (center). The drops containing the PCR mix may be flowed through a channel that incubates the droplets under conditions effective for PCR. In the figure, this is achieved by flowing the drops through a channel that snakes over various zones maintained at 65° C. and 95° C. As the drops move through the zones, their temperature cycles, as needed for PCR. During the PCR reaction, if a droplet contains a genome of a cell with a mutation for which the primer(s) are designed to detect, amplification is initiated. The presence of these particular PCR products may be detected by, for example, a fluorescent output that turns the drop fluorescent (FIGS. 3-4). The drops may thus be scanned, such as by using flow cytometry, to detect the presence of fluorescent drops (FIG. 14, Panels A-B). In certain aspects, the drops may also be sorted using, for example, droplet sorting to recover drops of interest (right). Using the nomenclature of the current disclosure, the steps described above are thus performed "under microfluidic control." That is, the steps are performed on one or more microfluidics devices.

Figure 2:
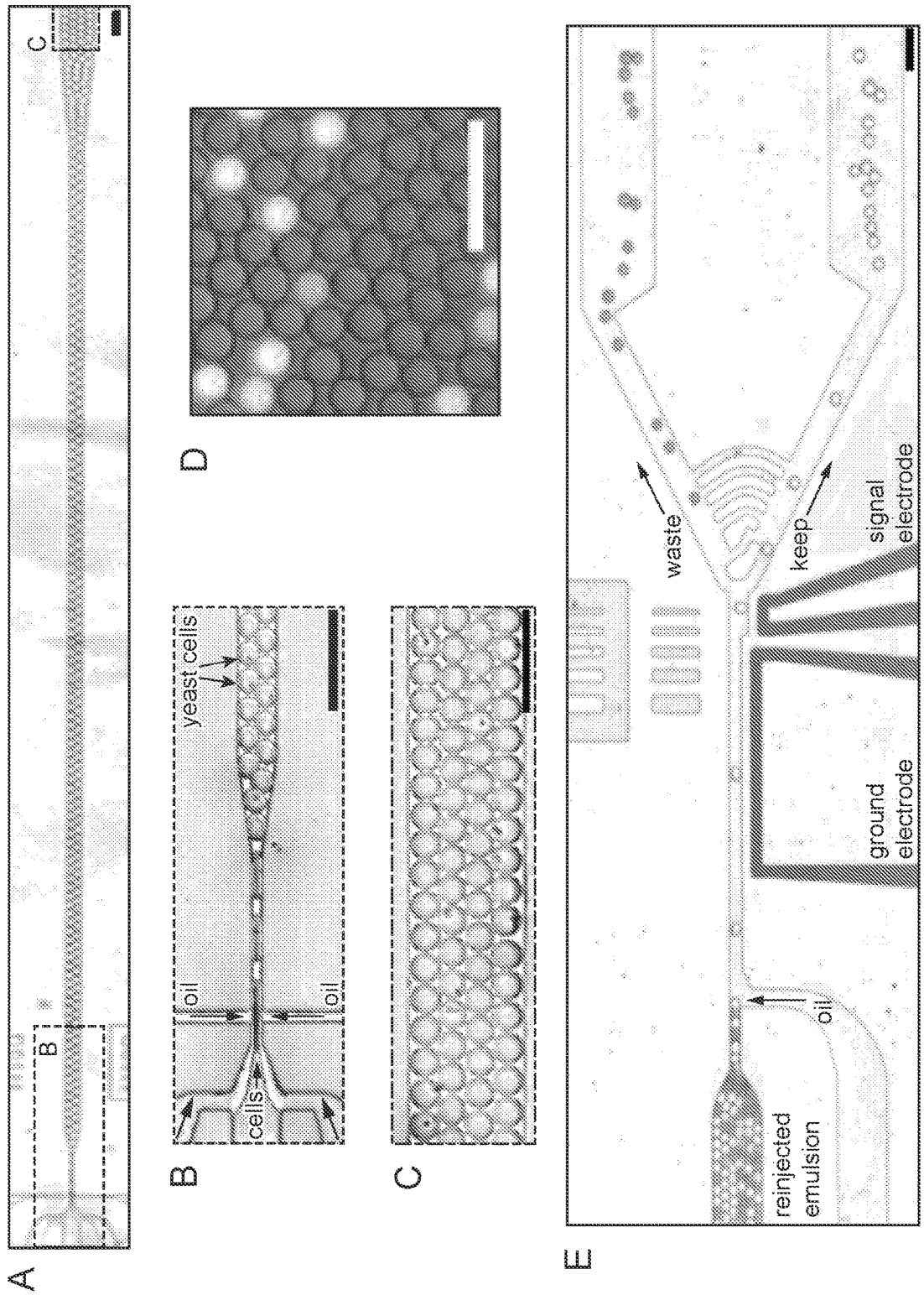
FIG. 2, Panels A-E depict single cells enclosed in microdroplets, using a fluorescence assay. Yeast cells (black specks) enter from the far left and are encapsulated into drops, shown at low (4× objective; Panel A) and high magnification (10× objective; Panel B). The drops are incubated to allowing the yeast to secrete their product (Panel C); this produces a fluorescent compound in the drops, so that drops containing efficient producers quickly become fluorescent (Panel D). The drops are then sorted to extract the most efficient yeast using a microfluidic sorter (Panel E). The scale bars denote 80 mm.

FIG. 2, Panels A-E depict a microfluidics system involving many of the general principles and steps described above. Here, yeast cells (black specks) enter from the far left and are encapsulated into drops, shown at low (4× objective; Panel A) and high magnification (10× objective; Panel B). The drops are incubated to allowing the yeast to secrete their product (Panel C); this produces a fluorescent compound in the drops, so that drops containing efficient producers quickly become fluorescent (Panel D). The drops are then sorted to extract the most efficient yeast using a microfluidic sorter (Panel E).

Figure 5:
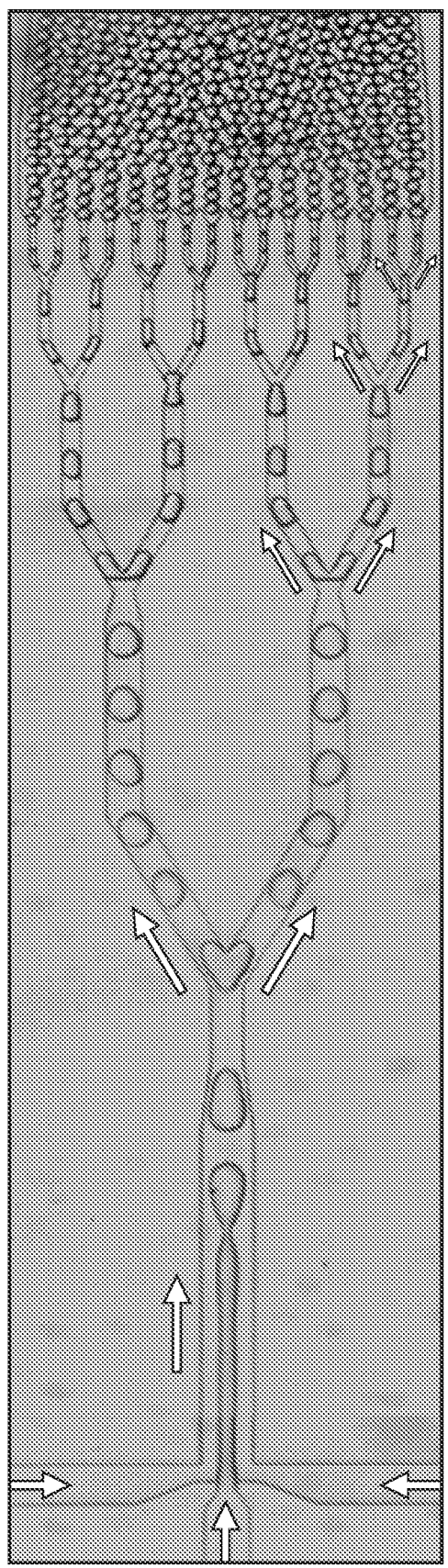
FIG. 5 is an optical microscopy image of massively parallel drop formation in a serial bisection device. DI water that does not contain cells is injected from the left. The solution flowing in along the top and bottom arrows is HFE-7500 fluorocarbon oil with a fluorocarbon surfactant at 2% by weight. After serial bisection, the resulting drops shown to the far right are 25 µm in diameter.

Encapsulating a component from a biological sample may be achieved by any convenient means. FIG. 5 presents but one possible example, in which droplets are formed in a massively parallel fashion a serial bisection device. For instance, cell-containing solution may be injected from the left and formed into large drops, which flow into the serial bisection array and are split into small drops; drops shown to the far right are 25 mm in diameter. Encapsulation approaches of interest also include, but are not limited to, hydrodynamically-triggered drop formation and those described by Link, et al., *Phys. Rev. Lett.* 92, 054503 (2004), the disclosure of which is incorporated herein by reference.

Figure 6:
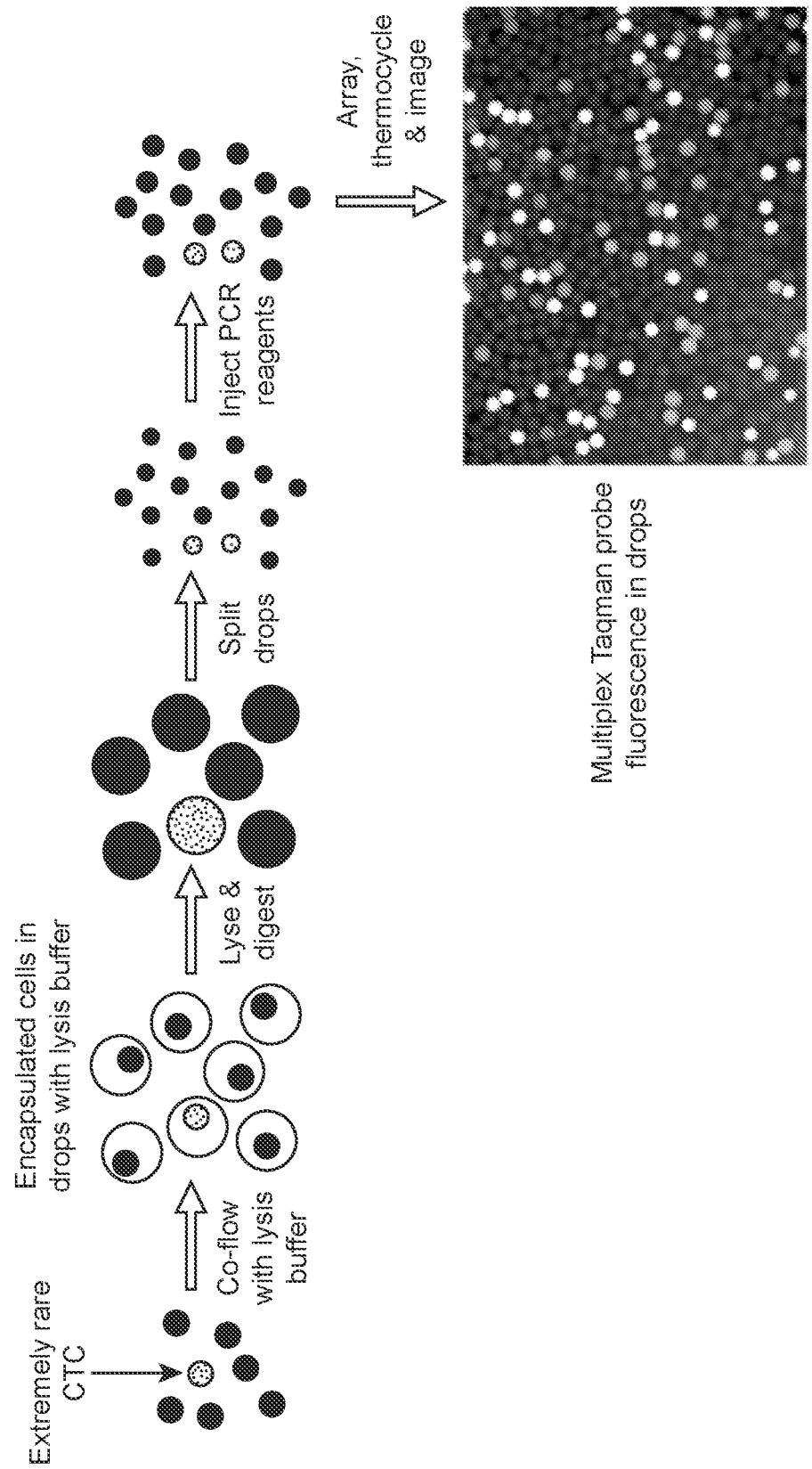
FIG. 6 is a schematic microfluidic device and data showing procedure for droplet-based detection of CTCs. Blood cells and rare CTCs are encapsulated in microdrops with lysis buffer containing Proteinase K. The drops are incubated at 55° C. to lyse cells and digest cellular proteins. Drops are then split to a size optimal for imaging, and the Proteinase K is heat-inactivated. The drops are then picoinjected with PCR reagents and TaqMan® probes, followed by thermocycling and imaging on a Megadroplet Array. CTCs are identified based on the presence of CTC-specific transcripts, detected by multiplexed TaqMan® probe fluorescence.

As evidenced by FIGS. 1, 4, and 6, a feature of certain methods of the present disclosure is the use of a polymerase chain reaction (PCR)-based assay to detect the presence of certain oligonucleotides and/or oncogene(s) present in cells. Examples of PCR-based assays of interest include, but are not limited to, quantitative PCR (qPCR), quantitative fluorescent PCR (QF-PCR), multiplex fluorescent PCR (MF-PCR), real time PCR (RT-PCR), single cell PCR, PCR-RFLP/RT-PCR-RFLP, hot start PCR, nested PCR, in situ polony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA).

A PCR-based assay may be used to detect the presence of certain gene(s), such as certain oncogene(s). FIG. 4, Panels A-B depict a PCR-based assay to detect oncogenes. In this assay, one or more primers specific to each oncogene of interest are reacted with the genome of each cell. These primers have sequences specific to the particular oncogene, so that they will only hybridize and initiate PCR when they are complimentary to the genome of the cell. If an oncogene is present and the primer is a match, large many copies of the oncogene are created. To determine whether an oncogene is present, the PCR products may be detected through an assay probing the liquid of the drop, such as by staining the solution with an intercalating dye, like SybrGreen or ethidium bromide, hybridizing the PCR products to a solid substrate, such as a bead (e.g., magnetic or fluorescent beads, such as Luminex beads), or detecting them through an intermolecular reaction, such as FRET. These dyes, beads, and the like are each examples of a "detection component," a term that is used broadly and generically herein to refer to any component that is used to detect the presence or absence of PCR product(s).

A great number of variations of these basic approaches will now be outlined in greater detail below.

Detecting Rare Cells (e.g., Tumor Cells)

Aspects of the subject methods involve detecting the presence of one or more subset of cells (e.g., tumor cells) in a biological sample. Such a scheme is depicted in FIG. 6. To use this approach for the detection of tumor cells, a biological sample (e.g., whole blood) may be recovered from a subject using any convenient means. The biological sample may be processed to remove components other than cells using, for example, processing steps such as centrifugation, filtration, and the like.

Each cell in the biological sample is then encapsulated into a droplet using a microfluidic device, such as that shown in FIGS. 5 and/or 8. Using the example from FIG. 5, the cell-containing solution is injected from the left and formed into large drops, which flow into the serial bisection array and are split into smaller droplets. Other methods of encapsulating cells into droplets are known in the art. Where desired, the cells may be stained with one or more antibodies and/or probes prior to encapsulating them into drops. As used herein, the terms "drop," "droplet," and "microdroplet" may be used interchangeably, to refer to tiny spheres containing an aqueous phase, e.g., water, generally ranging from 0.1 to 1000 μm in diameter, which may be used to encapsulate cells, DNA, enzymes, and other components. Accordingly, the terms may be used to refer to a droplet produced in, on, or by a microfluidics device.

One or more lysing agents may also be added to the droplets containing a cell, under conditions in which the cell(s) may be caused to burst, thereby releasing their genomes. The lysing agents may be added after the cells are encapsulated into microdroplets. Any convenient lysing agent may be employed, such as proteinase K or cytotoxins. In particular embodiments, cells may be co-encapsulated in drops with lysis buffer containing detergents such as Triton X100 and/or proteinase K. The specific conditions in which the cell(s) may be caused to burst will vary depending on the specific lysing agent used. For example, if proteinase K is incorporated as a lysing agent, the microdroplets may be heated to about 37-60° C. for about 20 min to lyse the cells and to allow the proteinase K to digest cellular proteins, after which they may be heated to about 95° C. for about 5-10 min to deactivate the proteinase K.

In certain aspects, cell lysis may also, or instead, rely on techniques that do not involve addition of lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient means of effecting cell lysis may be employed in the methods described herein.

Primers may be introduced into the droplet, for each of the genes, e.g., oncogenes, to be detected. Hence, in certain aspects, primers for all oncogenes may be present in the droplet at the same time, thereby providing a multiplexed assay. The droplets are temperature-cycled so that droplets containing cancerous cells, for example, will undergo PCR. During this time, only the primers corresponding to oncogenes present in the genome will induce amplification, creating many copies of these oncogenes in the droplet. Detecting the presence of these PCR products may be achieved by a variety of ways, such as by using FRET, staining with an intercalating dye, or attaching them to a bead. For more information on the different options for this, see the section describing variations of the technique. The droplet may be optically probed to detect the PCR products (FIG. 14). Optically probing the droplet may involve counting the number of tumor cells present in the initial population, and/or to allow for the identification the oncogenes present in each tumor cell.

The subject methods may be used to determine whether a biological sample contains particular cells of interest, e.g., tumor cells, or not. In certain aspects, the subject methods may include quantifying the number of cells of interest, e.g., tumor cells, present in a biological sample. Quantifying the number of cells of interest, e.g., tumor cells, present in a biological sample may be based at least in part on the number of microdroplets in which PCR amplification products were detected. For example, microdroplets may be produced under conditions in which the majority of droplets are expected to contain zero or one cells. Those droplets that do not contain any cells may be removed, using techniques described more fully herein. After performing the PCR steps outlined above, the total number of microdroplets that are detected to contain PCR products may be counted, so as to quantify the number of cells of interest, e.g., tumor cells, in the biological sample. In certain aspects, the methods may also include counting the total number of microdroplets, so as to determine the fraction or percentage of cells from the biological sample that are cells of interest, e.g., tumor cells.
PCR As summarized above, in practicing methods of the invention a PCR-based assay may be used to detect the presence of certain genes of interest, e.g., oncogene(s), present in cells. The conditions of such PCR-based assays may vary in one or more ways.

For instance, the number of PCR primers that may be added to a microdroplet may vary. The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The number of PCR primers that may be added to a microdroplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

These primers may contain primers for one or more gene of interest, e.g. oncogenes. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more. Genes and oncogenes of interest include, but are not limited to, BAX, BCL2L1, CASP8, CDK4, ELK1, ETS1, HGF, JAK2, JUNB, JUND, KIT, KITLG, MCL1, MET, MOS, MYB, NFKBIA, EGFR, Myc, EpCAM, NRAS, PIK3CA, PML, PRKCA, RAF1, RARA, REL, ROS1, RUNX1, SRC, STAT3, CD45, cytokeratins, CEA, CD133, HER2, CD44, CD49f, CD146, MUC1/2, and ZHX2.

Such primers and/or reagents may be added to a microdroplet in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent.

Once primers have been added to a microdroplet, the microdroplet may be incubated under conditions allowing for PCR. The microdroplet may be incubated on the same microfluidic device as was used to add the primer(s), or may be incubated on a separate device. In certain embodiments, incubating the microdroplet under conditions allowing for PCR amplification is performed on the same microfluidic device used to encapsulate the cells and lyse the cells. Incubating the microdroplets may take a variety of forms. In certain aspects, the drops containing the PCR mix may be flowed through a channel that incubates the droplets under conditions effective for PCR. Flowing the microdroplets through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the drops move through such zones, their temperature cycles, as needed for PCR. The precise number of zones, and the respective temperature of each zone, may be readily determined by those of skill in the art to achieve the desired PCR amplification.

Figure 12:
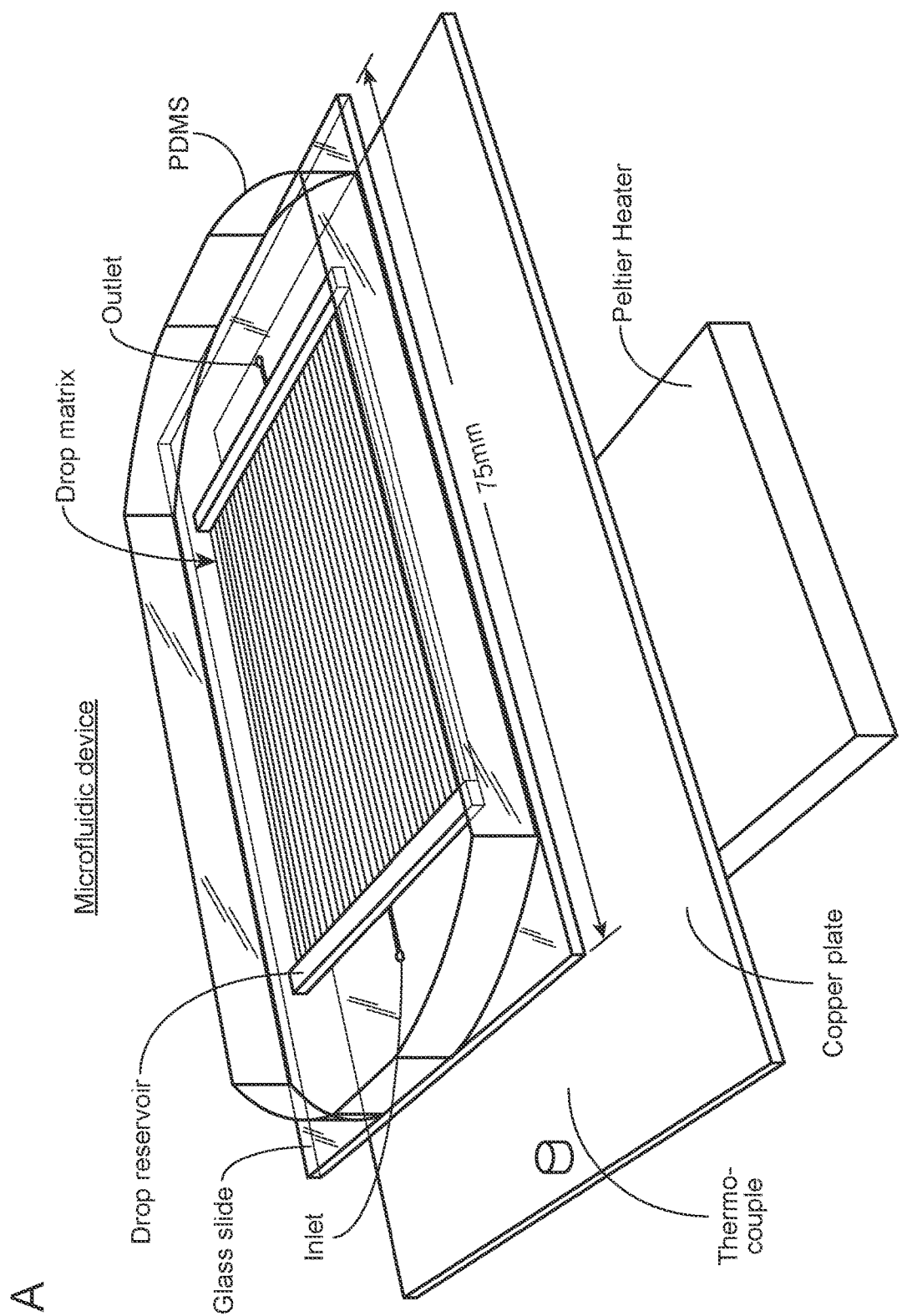
FIG. 12, Panels A-C show a schematic illustration of a device for performing multiplexed qPCR analysis on cells individually. The device consists of an array of about 10 million traps indented into a PDMS channel that sits above a thermal system (Panel A). The height of the microfluidic channel is smaller than the diameter of the drops, causing drops to adopt a flattened pancake shape. When a drop flows over an unoccupied indentation, it adopts a lower, more energetically favorable, radius of curvature, leading to a force that pulls the drop entirely into the trap (Panel B). By flowing drops as a close pack, it is ensured that all traps on the array are occupied, as illustrated in Panel C. The entire device is thermal cycled and imaged between cycles using a microarray scanner.
Figure 13:
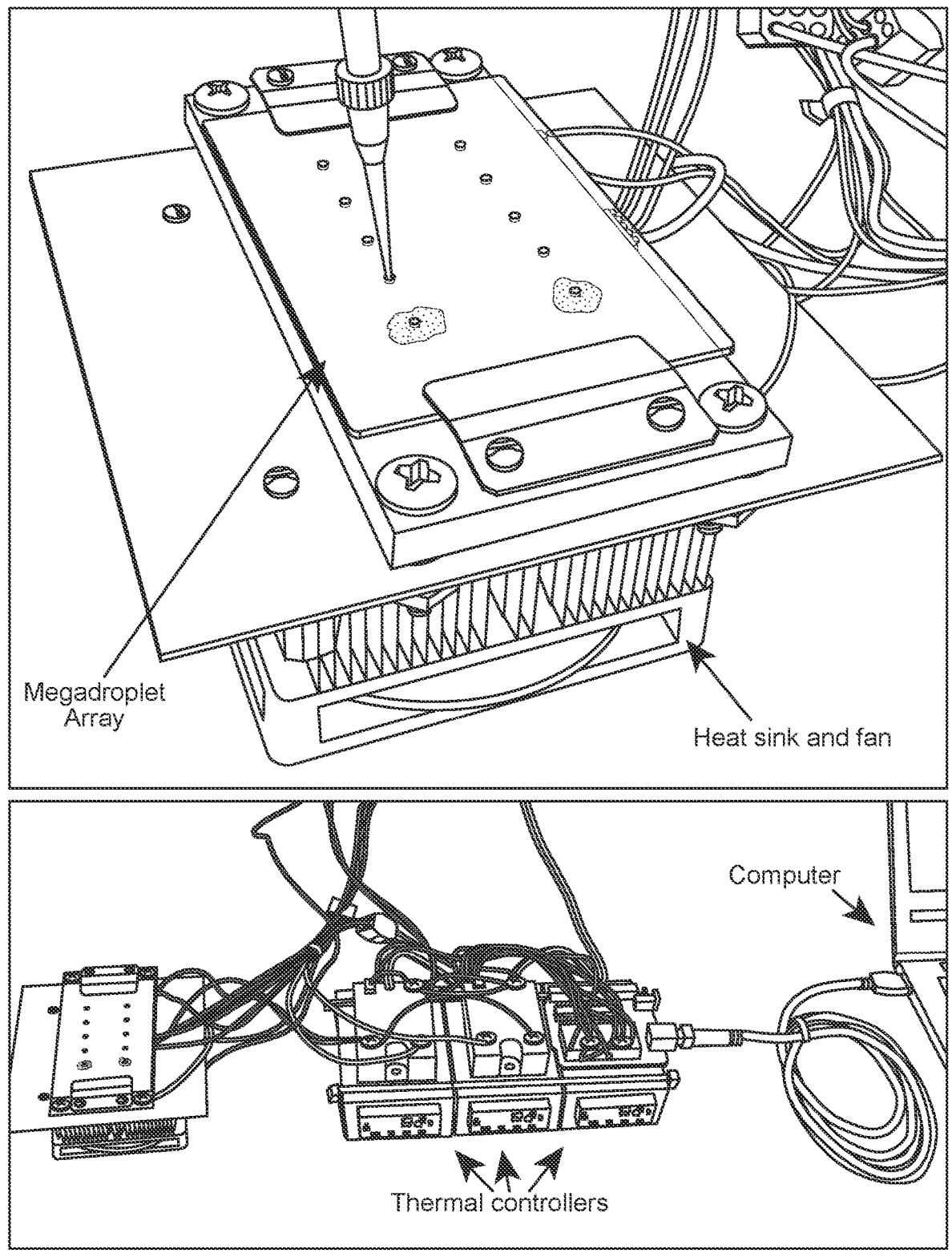
FIG. 13 depicts a Megadroplet Array for multiplexed qPCR analysis, of the type depicted in FIG. 12, Panels A-C. Drops are pipetted and sealed in a clear glass/epoxy chamber and fixed in place using a microfabricated well array (top). The entire chip is clamped to a metal block and thermocycled using Peltier heaters under the copper blocks. Thermometers, a heat sink, a fan (top), and digital controllers are used to regulate and cycle the temperature (bottom). Amplification is monitored in real time by imaging the array through the transparent plates that make up the top of the device.

In other embodiments, incubating the microdroplets may involve the use of a device of the general types depicted in FIG. 12, Panels A-C, and FIG. 13; a device of this general type may be referred to herein as a "Megadroplet Array." In such a device, an array of hundreds, thousands, or millions of traps indented into a channel (e.g., a PDMS channel) sit above a thermal system (FIG. 12, Panel A). The channel may be pressurized, thereby preventing gas from escaping. The height of the microfluidic channel is smaller than the diameter of the drops, causing drops to adopt a flattened pancake shape. When a drop flows over an unoccupied indentation, it adopts a lower, more energetically favorable, radius of curvature, leading to a force that pulls the drop entirely into the trap (FIG. 12, Panel B). By flowing drops as a close pack, it is ensured that all traps on the array are occupied, as illustrated in FIG. 12, Panel C. The entire device may be thermal cycled using a heater.

In certain aspects, the heater includes a Peltier plate, heat sink, and control computer. The Peltier plate allows for the heating or cooling of the chip above or below room temperature by controlling the applied current. To ensure controlled and reproducible temperature, a computer may monitor the temperature of the array using integrated temperature probes, and may adjust the applied current to heat and cool as needed. A metallic (e.g. copper) plate allows for uniform application of heat and dissipation of excess heat during cooling cycles, enabling cooling from about 95° C. to about 60° C. In under about one minute.

Methods of the invention may also include introducing one or more probes to the microdroplet. As used herein with respect to nucleic acids, the term "probe" refers to a labeled oligonucleotide which forms a duplex structure with a sequence in the target nucleic acid, due to complementarity of at least one sequence in the probe with a sequence in the target region. The probe, preferably, does not contain a sequence complementary to sequence(s) used to prime the polymerase chain reaction. The number of probes that are added may be from about one to 500, e.g., about 1 to 10 probes, about 10 to 20 probes, about 20 to 30 probes, about 30 to 40 probes, about 40 to 50 probes, about 50 to 60 probes, about 60 to 70 probes, about 70 to 80 probes, about 80 to 90 probes, about 90 to 100 probes, about 100 to 150 probes, about 150 to 200 probes, about 200 to 250 probes, about 250 to 300 probes, about 300 to 350 probes, about 350 to 400 probes, about 400 to 450 probes, about 450 to 500 probes, or about 500 probes or more. The probe(s) may be introduced into the microdroplet prior to, subsequent with, or after the addition of the one or more primer(s). Probes of interest include, but are not limited to, TaqMan® probes (e.g., as described in Holland, P. M.; Abramson, R. D.; Watson, R.; Gelfand, D. H. (1991). "Detection of specific polymerase chain reaction product by utilizing the 5'—3' exonuclease activity of Thermus aquaticus DNA polymerase". PNAS, 88 (16): 7276-7280).

In certain embodiments, an RT-PCR based assay may be used to detect the presence of certain transcripts of interest, e.g., oncogene(s), present in cells. In such embodiments, reverse transcriptase and any other reagents necessary for cDNA synthesis are added to the microdroplet in addition to the reagents used to carry out PCR described herein (collectively referred to as the "RT-PCR reagents"). The RT-PCR reagents are added to the microdroplet using any of the methods described herein. Once reagents for RT-PCR have been added to a microdroplet, the microdroplet may be incubated under conditions allowing for reverse transcription followed by conditions allowing for PCR as described herein. The microdroplet may be incubated on the same microfluidic device as was used to add the RT-PCR reagents, or may be incubated on a separate device. In certain embodiments, incubating the microdroplet under conditions allowing for RT-PCR is performed on the same microfluidic device used to encapsulate the cells and lyse the cells.

In certain embodiments, the reagents added to the microdroplet for RT-PCR or PCR further includes a fluorescent DNA probe capable of detecting real-time RT-PCR or PCR products. Any suitable fluorescent DNA probe can be used including, but not limited to SYBR Green, TaqMan®, Molecular Beacons and Scorpion probes. In certain embodiments, the reagents added to the microdroplet include more than one DNA probe, e.g., two fluorescent DNA probes, three fluorescent DNA probes, or four fluorescent DNA probes. The use of multiple fluorescent DNA probes allows for the concurrent measurement of RT-PCR or PCR products in a single reaction.

Double PCR

To amplify rare transcripts, a microdroplet that has undergone a first-step RT-PCR or PCR reaction as described herein may be further subjected to a second step PCR reaction. In some embodiments, a portion of a microdroplet that has undergone a first-step RT-PCR or PCR reaction is extracted from the microdroplet and coalesced with a droplet containing additional PCR reagents, including, but not limited to enzymes (e.g. DNA polymerase), DNA probes (e.g. fluorescent DNA probes) and primers. In certain embodiments, the droplet containing the additional PCR reagents is larger than the microdroplet that has undergone the first step RT-PCR or PCR reaction. This may be beneficial, for example, because it allows for the dilution of cellular components that may be inhibitory to the second step PCR. The second step PCR reaction may be carried out on the same microfluidic device used to carry out the first-step reaction or on a different microfluidic device.

In some embodiments, the primers used in the second step PCR reaction are the same primers used in the first step RT-PCR or PCR reaction. In other embodiments, the primers used in the second step PCR reaction are different than the primers used in the first step reaction.

Multiplexing

In certain embodiments of the subject methods, multiple biomarkers may be detected and analyzed for a particular cell. Biomarkers detected may include, but are not limited to, one or more proteins, transcripts and/or genetic signatures in the cell's genome or combinations thereof. With standard fluorescence based detection, the number of biomarkers that can be simultaneously interrogated may be limited to the number of fluorescent dyes that can be independently visualized within each microdrop. In certain embodiments, the number of biomarkers that can be individually detected within a particular microdroplet can be increased. For example, this may be accomplished by segregation of dyes to different parts of the microdroplet. In particular embodiments, beads (e.g. LUMINEX® beads) conjugated with dyes and probes (e.g., nucleic acid or antibody probes) may be encapsulated in the microdroplet to increase the number of biomarkers analyzed. In another embodiment, fluorescence polarization may be used to achieve a greater number of detectable signals for different biomarkers for a single cell. For example, fluorescent dyes may be attached to various probes and the microdroplet may be visualized under different polarization conditions. In this way, the same colored dye can be utilized to provide a signal for different probe targets for a single cell. The use of fixed and/or permeabilized cells (as discussed in greater detail below) also allows for increased levels of multiplexing. For example, labeled antibodies may be used to target protein targets localized to cellular components while labeled PCR and/or RT-PCR products are free within a microdroplet. This allows for dyes of the same color to be used for antibodies and for amplicons produced by RT-PCR.

Types of Microdroplets

In practicing the methods of the present invention, the composition and nature of the microdroplets may vary. For instance, in certain aspects, a surfactant may be used to stabilize the microdroplets. Accordingly, a microdroplet may involve a surfactant stabilized emulsion. Any convenient surfactant that allows for the desired reactions to be performed in the drops may be used. In other aspects, a microdroplet is not stabilized by surfactants or particles.

The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox FSH). If, however, the oil was switched to be a hydrocarbon oil, for example, the surfactant would instead be chosen so that it had a hydrophobic hydrocarbon block, like the surfactant ABIL EM90. In selecting a surfactant, desirable properties that may be considered in choosing the surfactant may include one or more of the following: (1) the surfactant has low viscosity; (2) the surfactant is immiscible with the polymer used to construct the device, and thus it doesn't swell the device; (3) biocompatibility; (4) the assay reagents are not soluble in the surfactant; (5) the surfactant exhibits favorable gas solubility, in that it allows gases to come in and out; (6) the surfactant has a boiling point higher than the temperature used for PCR (e.g., 95 C); (7) the emulsion stability; (8) that the surfactant stabilizes drops of the desired size; (9) that the surfactant is soluble in the carrier phase and not in the droplet phase; (10) that the surfactant has limited fluorescence properties; and (11) that the surfactant remains soluble in the carrier phase over a range of temperatures.

Other surfactants can also be envisioned, including ionic surfactants. Other additives can also be included in the oil to stabilize the drops, including polymers that increase droplet stability at temperatures above 35° C.

Adding Reagents to Microdroplets

In practicing the subject methods, a number of reagents may need to be added to the microdroplets, in one or more steps (e.g., about 2, about 3, about 4, or about 5 or more steps). The means of adding reagents to the microdroplets may vary in a number of ways. Approaches of interest include, but are not limited to, those described by Ahn, et al., Appl. Phys. Lett. 88, 264105 (2006); Priest, et al., Appl. Phys. Lett. 89, 134101 (2006); Abate, et al., PNAS, Nov. 9, 2010 vol. 107 no. 45 19163-19166; and Song, et al., Anal. Chem., 2006, 78 (14), pp 4839-4849; the disclosures of which are incorporated herein by reference.

For instance, a reagent may be added to a microdroplet by a method involving merging a microdroplet with a second microdroplet that contains the reagent(s). The reagent(s) that are contained in the second microdroplet may be added by any convenient means, specifically including those described herein. This droplet may be merged with the first microdroplet to create a microdroplet that includes the contents of both the first microdroplet and the second microdroplet.

One or more reagents may also, or instead, be added using techniques such as droplet coalescence, or picoinjection. In droplet coalescence, a target drop (i.e., the microdroplet) may be flowed alongside a microdroplet containing the reagent(s) to be added to the microdroplet. The two microdroplets may be flowed such that they are in contact with each other, but not touching other microdroplets. These drops may then be passed through electrodes or other means of applying an electrical field, wherein the electric field may destabilize the microdroplets such that they are merged together.

Reagents may also, or instead, be added using picoinjection. In this approach, a target drop (i.e., the microdroplet) may be flowed past a channel containing the reagent(s) to be added, wherein the reagent(s) are at an elevated pressure. Due to the presence of the surfactants, however, in the absence of an electric field, the microdroplet will flow past without being injected, because surfactants coating the microdroplet may prevent the fluid(s) from entering. However, if an electric field is applied to the microdroplet as it passes the injector, fluid containing the reagent(s) will be injected into the microdroplet. The amount of reagent added to the microdroplet may be controlled by several different parameters, such as by adjusting the injection pressure and the velocity of the flowing drops, by switching the electric field on and off, and the like.

In other aspects, one or more reagents may also, or instead, be added to a microdroplet by a method that does not rely on merging two droplets together or on injecting liquid into a drop. Rather, one or more reagents may be added to a microdroplet by a method involving the steps of emulsifying a reagent into a stream of very small drops, and merging these small drops with a target microdroplet (FIG. 20, Panels A-B). Such methods shall be referred to herein as "reagent addition through multiple-drop coalescence." These methods take advantage of the fact that due to the small size of the drops to be added compared to that of the target drops, the small drops will flow faster than the target drops and collect behind them. The collection can then be merged by, for example, applying an electric field. This approach can also, or instead, be used to add multiple reagents to a microdroplet by using several co-flowing streams of small drops of different fluids. To enable effective merger of the tiny and target drops, it is important to make the tiny drops smaller than the channel containing the target drops, and also to make the distance between the channel injecting the target drops from the electrodes applying the electric field sufficiently long so as to give the tiny drops time to "catch up" to the target drops. If this channel is too short, not all tiny drops will merge with the target drop and adding less reagent than desired. To a certain degree, this can be compensated for by increasing the magnitude of the electric field, which tends to allow drops that are farther apart to merge. In addition to making the tiny drops on the same microfluidic device, as is shown in FIG. 20, Panels A-B, they can also, or instead, be made offline using another microfluidic drop maker or through homogenization and then injecting them into the device containing the target drops.

Accordingly, in certain aspects a reagent is added to a microdroplet by a method involving emulsifying the reagent into a stream of droplets, wherein the droplets are smaller than the size of the microdroplet; flowing the droplets together with the microdroplet; and merging a droplet with the microdroplet. The diameter of the droplets contained in the stream of droplets may vary ranging from about 75% or less than that of the diameter of the microdroplet, e.g., the diameter of the flowing droplets is about 75% or less than that of the diameter of the microdroplet, about 50% or less than that of the diameter of the microdroplet, about 25% or less than that of the diameter of the microdroplet, about 15% or less than that of the diameter of the microdroplet, about 10% or less than that of the diameter of the microdroplet, about 5% or less than that of the diameter of the microdroplet, or about 2% or less than that of the diameter of the microdroplet. In certain aspects, a plurality of flowing droplets may be merged with the microdroplet, such as 2 or more droplets, 3 or more, 4 or more, or 5 or more. Such merging may be achieved by any convenient means, including but not limited to by applying an electric field, wherein the electric field is effective to merge the flowing droplet with the microdroplet.

As a variation of the above-described methods, the fluids may be jetting. That is, rather than emulsifying the fluid to be added into flowing droplets, a long jet of this fluid can be formed and flowed alongside the target microdroplet. These two fluids can then be merged by, for example, applying an electric field. The result is a jet with bulges where the microdroplets are, which may naturally break apart into microdroplets of roughly the size of the target microdroplets before the merger, due to the Rayleigh plateau instability. A number of variants are contemplated. For instance, one or more agents may be added to the jetting fluid to make it easier to jet, such as gelling agents and/or surfactants. Moreover, the viscosity of the continuous fluid could also be adjusted to enable jetting, such as that described by Utada, et al., *Phys. Rev. Lett.* 99, 094502 (2007), the disclosure of which is incorporated herein by reference.

In other aspects, one or more reagents may be added using a method that uses the injection fluid itself as an electrode, by exploiting dissolved electrolytes in solution (FIGS. 15-19). Methods of this general type are described more fully herein in Example 3.

In another aspect, a reagent is added to a drop (e.g., a microdroplet) formed at an earlier time by enveloping the drop to which the reagent is be added (i.e., the "target drop") inside a drop containing the reagent to be added (the "target reagent"). In certain embodiments such a method is carried out by first encapsulating the target drop in a shell of a suitable hydrophobic phase, e.g., oil, to form a double emulsion. The double emulsion is then encapsulated by a drop containing the target reagent to form a triple emulsion. To combine the target drop with the drop containing the target reagent, the double emulsion is then burst open using any suitable method, including, but not limited to, applying an electric field, adding chemicals that destabilizes the droplet interface, flowing the triple emulsion through constrictions and other microfluidic geometries, applying mechanical agitation or ultrasound, increasing or reducing temperature, or by encapsulating magnetic particles in the drops that can rupture the double emulsion interface when pulled by a magnetic field. Methods of making a triple emulsion and combining a target drop with a target reagent are described in Example 4 provided herein.

Detecting PCR Products

In practicing the subject methods, the manner in which PCR products may be detected may vary. For example, if the goal is simply to count the number of a particular cell type, e.g., tumor cells, present in a population, this may be achieved by using a simple binary assay in which SybrGreen, or any other stain and/or intercalating stain, is added to each microdroplet so that in the event a characterizing gene, e.g., an oncogene, is present and PCR products are produced, the drop will become fluorescent. The change in fluorescence may be due to fluorescence polarization. The detection component may include the use of an intercalating stain (e.g., SybrGreen).

A variety of different detection components may be used in practicing the subject methods, including using fluorescent dyes known in the art. Fluorescent dyes may typically be divided into families, such as fluorescein and its derivatives; rhodamine and its derivatives; cyanine and its derivatives; coumarin and its derivatives; Cascade Blue and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va.

FIG. 14, Panels A-B depict the use of a one-color flow-cytometer, which can be used, for example, to detect tumor cell containing drops. Panel A presents a schematic of a detector, consisting of a 488 nm laser directed into the back of an objective, and focused onto a microfluidic channel through which the droplets flow. The laser may excite fluorescent dyes within the drops, and any emitted light is captured by the objective and imaged onto a PMT after it is filtered through a dichroic minor and 520±5 nm band pass filter. Turning to Panel B, drops appear as peaks in intensity as a function of time, as shown by the output voltage of a PMT, which is proportional to the intensity of the emitted light, as a function of time for detected fluorescent drops.

FIGS. 3 and 4, Panels A-B further illustrate such a concept. FIG. 3, for example, is a non-limiting example that depicts digital detection of BRAF using TaqMan® PCR assays in arrayed microdrops. Fluorescent drops indicate amplification of the BRAF gene from human genomic DNA, while non-fluorescent drops were devoid of the gene. Turning to FIG. 4, Panels A-B, this scheme is generalized. In FIG. 4, Panel A, a schematic is presented showing forward and reverse primers being encapsulated in the microdroplets that target an oncogenic sequence. If the oncogenic sequence is present, the PCR reaction produces double-stranded PCR products (Panel A, upper), whereas, if it is not, no products are produced (Panel A, lower). SybrGreen, or any other type of intercalating stain, is also present in the drop. The results are depicted by the images in FIG. 4, Panel B, in that if double-stranded products are produced, the dye intercalates into them, becoming fluorescent, and turning the drop fluorescent (FIG. 4, Panel B, upper); by contrast, if no double-stranded products are produced, the dye remains non-fluorescent, producing a dim drop (FIG. 4, Panel B, lower).

In other aspects, particularly if a goal is to further characterize the oncogenes present, additional testing may be needed. For instance, in the case of the multiplex assays described more fully herein (Example 2), this may be achieved by having optical outputs that relate which of the gene(s) amplified in the drop. An alternative approach would be to use a binary output, for example, with an intercalated stain, to simply determine which droplets have any oncogenes. These can then be sorted to recover these drops so that they could be analyzed in greater detail to determine which oncogenes they contain. To determine the oncogenes present in such a drop, microfluidic techniques or nonmicrofluidic techniques could be used. Using non-microfluidic techniques, a droplet identified as containing an oncogene can be placed into a well on a wellplate where will be diluted into a larger volume, releasing all of the PCR products that were created during the multiplexed PCR reaction. Samples from this well can then be transferred into other wells, into each of which would be added primers for one of the oncogenes. These wells would then be temperature-cycled to initiate PCR, at which point an intercalating stain would be added to cause wells that have matching oncogenes and primers to light up.

In practicing the subject methods, therefore, a component may be detected based upon, for example, a change in fluorescence. In certain aspects, the change in fluorescence is due to fluorescence resonance energy transfer (FRET). In this approach, a special set of primers may be used in which the 5' primer has a quencher dye and the 3' primer has a fluorescent dye. These dyes can be arranged anywhere on the primers, either on the ends or in the middles. Because the primers are complementary, they will exist as duplexes in solution, so that the emission of the fluorescent dye will be quenched by the quencher dye, since they will be in close proximity to one another, causing the solution to appear dark. After PCR, these primers will be incorporated into the long PCR products, and will therefore be far apart from one another. This will allow the fluorescent dye to emit light, causing the solution to become fluorescent. Hence, to detect if a particular oncogene is present, one may measure the intensity of the droplet at the wavelength of the fluorescent dye. To detect if different oncogenes are present, this would be done with different colored dyes for the different primers. This would cause the droplet to become fluorescent at all wavelengths corresponding to the primers of the oncogenes present in the cell.

Sorting

In practicing the methods of the present disclosure, one or more sorting steps may be employed. Sorting approaches of interest include, by are not necessarily limited to, approaches that involve the use of membrane valves, bifurcating channels, surface acoustic waves, and/or dielectrophoresis. Sorting approaches of interest further include those depicted in FIGS. 2 and 22, Panels A-B, and those described by Agresti, et al., PNAS vol. 107, no 9, 4004-4009; the disclosure of which is incorporated herein by reference. A population may be enriched by sorting, in that a population containing a mix of members having or not having a desired property may be enriched by removing those members that do not have the desired property, thereby producing an enriched population having the desired property.

Sorting may be applied before or after any of the steps described herein. Moreover, two or more sorting steps may be applied to a population of microdroplets, e.g., about 2 or more sorting steps, about 3 or more, about 4 or more, or about 5 or more, etc. When a plurality of sorting steps is applied, the steps may be substantially identical or different in one or more ways (e.g., sorting based upon a different property, sorting using a different technique, and the like).

Figure 21:
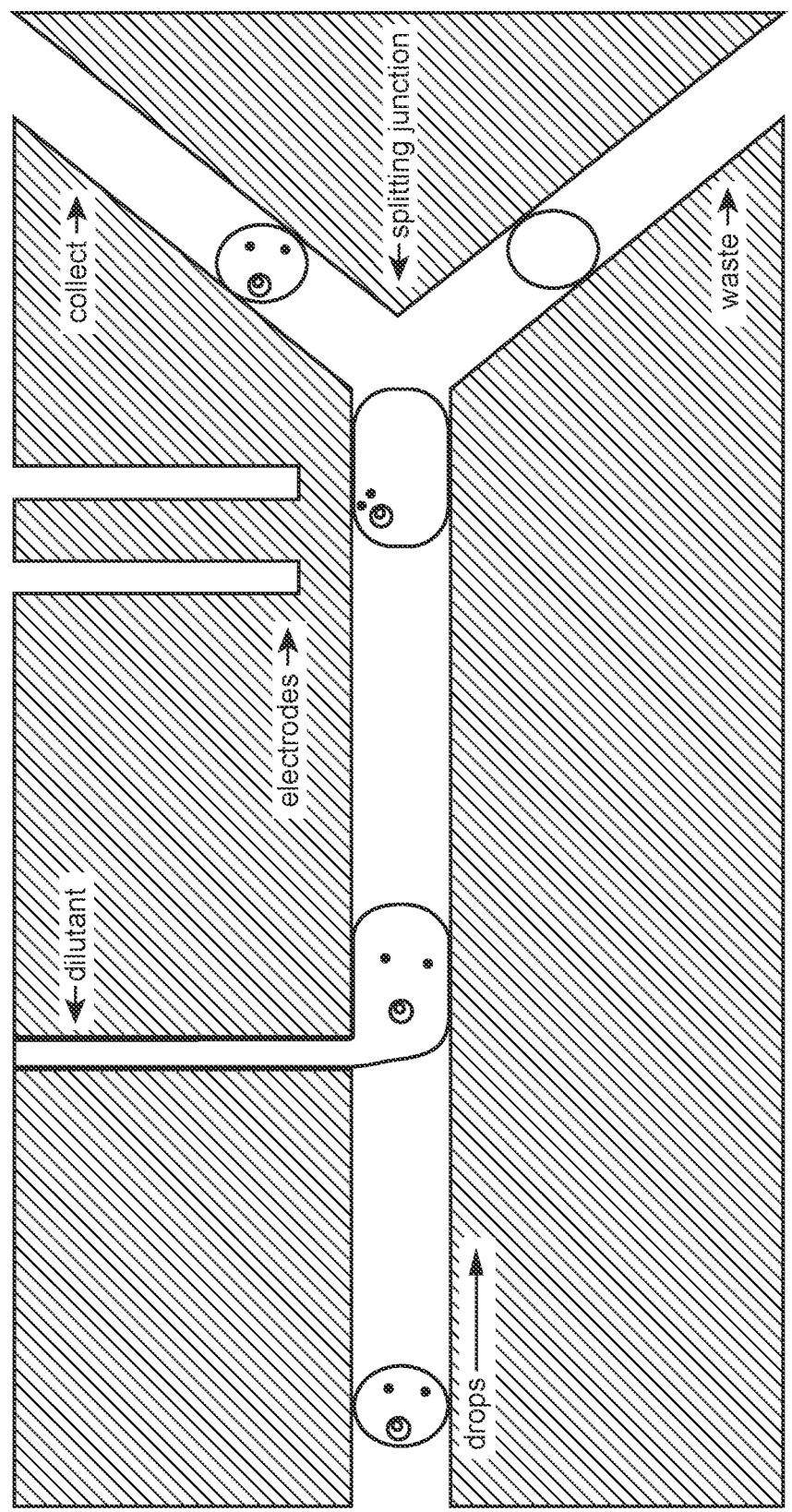
FIG. 21 shows a schematic of a microfluidic device whereby a microdroplet may be purified. That is, a majority of the fluid in the drop is replaced it with a purified solution, without removing any discrete reagents that may be encapsulated in the drop, such a cells or beads. The microdroplet is first injected with a solution to dilute any impurities within it. The diluted microdroplet is then flowed through a microfluidic channel on which an electric field is being applied using electrodes. Due to the dielectrophoretic forces generated by the field, as the cells or other discrete reagents pass through the field they will be displaced in the flow. The drops are then split, so that all the objects end up in one microdroplet. Accordingly, the initial microdroplet has been washed, in that the contaminants may be removed while the presence and/or concentration of discrete reagents, such as beads or cells, that may be encapsulated within the droplet are maintained in the resulting microdroplet.

Moreover, droplets may be purified prior to, or after, any sorting step. FIG. 21 presents a schematic of a microfluidic device whereby a microdroplet may be purified. That is, a majority of the fluid in the drop is replaced it with a purified solution, without removing any discrete reagents that may be encapsulated in the drop, such a cells or beads. The microdroplet is first injected with a solution to dilute any impurities within it. The diluted microdroplet is then flowed through a microfluidic channel on which an electric field is being applied using electrodes. Due to the dielectrophoretic forces generated by the field, as the cells or other discrete reagents pass through the field they will be displaced in the flow. The drops are then split, so that all the objects end up in one microdroplet. Accordingly, the initial microdroplet has been purified, in that the contaminants may be removed while the presence and/or concentration of discrete reagents, such as beads or cells, that may be encapsulated within the droplet are maintained in the resulting microdroplet.

Microdroplets may be sorted based on one or more properties. Properties of interest include, but are not limited to, the size, viscosity, mass, buoyancy, surface tension, electrical conductivity, charge, magnetism, and/or presence or absence of one or more components. In certain aspects, sorting may be based at least in part upon the presence or absence of a cell in the microdroplet. In certain aspects, sorting may be based at least in part based upon the detection of the presence or absence of PCR amplification products.

Microdroplet sorting may be employed, for example, to remove microdroplets in which no cells are present. Encapsulation may result in one or more microdroplets, including a majority of the microdroplets, in which no cell is present. If such empty drops were left in the system, they would be processed as any other drop, during which reagents and time would be wasted. To achieve the highest speed and efficiency, these empty drops may be removed with droplet sorting. For example, as described in Example 1, a drop maker may operate close to the dripping-to-jetting transition such that, in the absence of a cell, 8 µm drops are formed; by contrast, when a cell is present the disturbance created in the flow will trigger the breakup of the jet, forming drops 25 µm in diameter. The device may thus produce a bi-disperse population of empty 8 µm drops and single-cell containing 25 µm drops, which may then be sorted by size using, e.g., a hydrodynamic sorter to recover only the larger, single-cell containing drops.

Passive sorters of interest include hydrodynamic sorters, which sort microdroplets into different channels according to size, based on the different ways in which small and large drops travel through the microfluidic channels. Also of interest are bulk sorters, a simple example of which is a tube containing drops of different mass in a gravitational field. By centrifuging, agitating, and/or shaking the tube, lighter drops that are more buoyant will naturally migrate to the top of the container. Drops that have magnetic properties could be sorted in a similar process, except by applying a magnetic field to the container, towards which drops with magnetic properties will naturally migrate according to the magnitude of those properties. A passive sorter as used in the subject methods may also involve relatively large channels that will sort large numbers of drops simultaneously based on their flow properties.

Picoinjection can also be used to change the electrical properties of the drops. This could be used, for example, to change the conductivity of the drops by adding ions, which could then be used to sort them, for example, using dielectrophoresis. Alternatively, picoinjection can also be used to charge the drops. This could be achieved by injecting a fluid into the drops that is charged, so that after injection, the drops would be charged. This would produce a collection of drops in which some were charged and others not, and the charged drops could then be extracted by flowing them through a region of electric field, which will deflect them based on their charge amount. By injecting different amounts of liquid by modulating the piocoinjection, or by modulating the voltage to inject different charges for affixed injection volume, the final charge on the drops could be adjusted, to produce drops with different charge. These would then be deflected by different amounts in the electric field region, allowing them to be sorted into different containers.

Suitable Subjects

The subject methods may be applied to biological samples taken from a variety of different subjects. In many embodiments the subjects are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans. The subject methods may be applied to human subjects of both genders and at any stage of development (i.e., neonates, infant, juvenile, adolescent, adult), where in certain embodiments the human subject is a juvenile, adolescent or adult. While the present invention may be applied to a human subject, it is to be understood that the subject methods may also be carried-out on other animal subjects (that is, in "non-human subjects") such as, but not limited to, birds, mice, rats, dogs, cats, livestock and horses. Accordingly, it is to be understood that any subject in need of assessment according to the present disclosure is suitable.

Moreover, suitable subjects include those who have and those who have not been diagnosed with a condition, such as cancer. Suitable subjects include those that are and are not displaying clinical presentations of one or more cancers. In certain aspects, a subject may one that may be at risk of developing cancer, due to one or more factors such as family history, chemical and/or environmental exposure, genetic mutation(s) (e.g., BRCA1 and/or BRCA2 mutation), hormones, infectious agents, radiation exposure, lifestyle (e.g., diet and/or smoking), presence of one or more other disease conditions, and the like.

As described more fully above, a variety of different types of biological samples may be obtained from such subjects. In certain embodiments, whole blood is extracted from a subject. When desired, whole blood may be treated prior to practicing the subject methods, such as by centrifugation, fractionation, purification, and the like. The volume of the whole blood sample that is extracted from a subject may be 100 mL or less, e.g., about 100 mL or less, about 50 mL or less, about 30 mL or less, about 15 mL or less, about 10 mL or less, about 5 mL or less, or about 1 mL or less.

The subject methods and devices provided herein are compatible with both fixed and live cells. In certain embodiments, the subject methods and devices are practiced with live cells. In other embodiments, the subject methods and devices are practiced with fixed cells. Fixing a cellular sample allows for the sample to be washed to extract small molecules and lipids that may interfere with downstream analysis. Further, fixing and permeabilizing cells allows the cells to be stained with antibodies for surface proteins as well as intracellular proteins. Combined with the RT-PCR methods described herein, such staining can be used to achieve high levels of multiplexing because the antibodies are localized to the cell sample, while RT-PCR products are free within a microdroplet. Such a configuration allows for dyes of the same color to be used for antibodies and for amplicons produced by RT-PCR. Any suitable method can be used to fix cells, including but not limited to, fixing using formaldehyde, methanol and/or acetone.

RT-PCR carried out on a fixed cell encapsulated in a microdroplet can be carried out by first diluting the microdroplet and performing the RT-PCR reaction on a sample of the diluted microdroplet. Such dilution of the cellular sample can help to limit any cellular compounds that would interfere with RT-PCR. In other embodiments, the RT-PCR reagents are added directly to the microdroplet containing the fixed cell in a "one pot" reaction without any dilution of sample. In certain embodiments, fixed cells are solubilized prior to the RT-PCR using proteases and deteregents.

Genotyping Cells

As summarized above, aspects of the invention also include methods for genotyping components from biological samples. By "genotyping" it is meant the detection of two or more oligonucleotides (e.g., oncogenes) in a particular cell. Aspects include methods for genotyping cells, e.g., tumor cells, including CTCs.

In certain such aspects, the methods involve encapsulating in a microdroplet a cell obtained from a subject's blood sample, wherein one cell is present in the microdroplet; introducing a lysing agent into the microdroplet and incubating the microdroplet under conditions effective for cell lysis; introducing polymerase chain reaction (PCR) reagents and a plurality PCR primers into the microdroplet, and incubating the microdroplet under conditions allowing for PCR amplification to produce PCR amplification products, wherein the plurality of PCR primers include one or more primers that each hybridize to one or more oncogenes; introducing a plurality of probes into the microdroplet, wherein the probes hybridize to one or more mutations of interest and fluoresce at different wavelengths; and detecting the presence or absence of specific PCR amplification products by detection of fluorescence of a probe, wherein detection of fluorescence indicates the presence of the PCR amplification products; wherein one or more of steps are performed under microfluidic control.

In other aspects, the methods may involve encapsulating in a microdroplet a cell obtained from a subject's blood sample, wherein one cell is present in the microdroplet; introducing a lysing agent into the microdroplet and incubating the microdroplet under conditions effective for cell lysis; introducing polymerase chain reaction (PCR) reagents and a plurality PCR primers into the microdroplet, and incubating the microdroplet under conditions allowing for PCR amplification to produce PCR amplification products, wherein the plurality of PCR primers include one or more primers that each hybridize to one or more oncogenes, said primers comprising forward primers comprising a label, and reverse primers comprising a capture sequence; introducing a fluorescent bead into the microdroplet, wherein the bead includes a nucleotide sequence complementary to a capture sequence; and detecting the presence or absence of the PCR amplification products by detection of fluorescence of the bead and fluorescence of a primer, wherein detection of fluorescence indicates the presence of the PCR amplification products; wherein one or more of steps are performed under microfluidic control.

In practicing the methods for genotyping cells, any variants to the general steps described herein, such as the number of primers that may be added, the manner in which reagents are added, suitable subjects, and the like, may be made.

Detecting Cancer

Methods according to the present invention also involve methods for detecting cancer. Such methods may include encapsulating in a microdroplet oligonucleotides obtained from a biological sample from the subject, wherein at least one oligonucleotide is present in the microdroplet; introducing polymerase chain reaction (PCR) reagents, a detection component, and a plurality of PCR primers into the microdroplet and incubating the microdroplet under conditions allowing for PCR amplification to produce PCR amplification products, wherein the plurality of PCR primers include one or more primers that each hybridize to one or more oncogenes; and detecting the presence or absence of the PCR amplification products by detection of the detection component, wherein detection of the detection component indicates the presence of the PCR amplification products.

Detection of one or more PCR amplification products corresponding to one or more oncogenes may be indicative that the subject has cancer. The specific oncogenes that are added to the microdroplet may vary. In certain aspects, the oncogene(s) may be specific for a particular type of cancer, e.g., breast cancer, colon cancer, and the like.

Moreover, in practicing the subject methods the biological sample from which the components are to be detected may vary, and may be based at least in part on the particular type of cancer for which detection is sought. For instance, breast tissue may be used as the biological sample in certain instances, if it is desired to determine whether the subject has breast cancer, and the like.

In practicing the methods for detecting cancer, any variants to the general steps described herein, such as the number of primers that may be added, the manner in which reagents are added, suitable subjects, and the like, may be made.

Devices

As indicated above, embodiments of the invention employ microfluidics devices. Microfluidics devices of this invention may be characterized in various ways. In certain embodiments, for example, microfluidics devices have at least one "micro" channel. Such channels may have at least one cross-sectional dimension on the order of a millimeter or smaller (e.g., less than or equal to about 1 millimeter). Obviously for certain applications, this dimension may be adjusted; in some embodiments the at least one cross-sectional dimension is about 500 micrometers or less. In some embodiments, again as applications permit, the cross-sectional dimension is about 100 micrometers or less (or even about 10 micrometers or less—sometimes even about 1 micrometer or less). A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that micro-channels employed in this invention may have two dimensions that are grossly disproportionate—e.g., a rectangular cross-section having a height of about 100-200 micrometers and a width on the order or a centimeter or more. Of course, certain devices may employ channels in which the two or more axes are very similar or even identical in size (e.g., channels having a square or circular cross-section).

In some embodiments, microfluidic devices of this invention are fabricated using microfabrication technology. Such technology is commonly employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. A microfluidics "system" may include one or more microfluidic devices and associated fluidic connections, electrical connections, control/logic features, etc. Aspects of microfluidic devices include the presence of one or more fluid flow paths, e.g., channels, having dimensions as discussed herein.

In certain embodiments, microfluidic devices of this invention provide a continuous flow of a fluid medium. Fluid flowing through a channel in a microfluidic device exhibits many interesting properties. Typically, the dimensionless Reynolds number is extremely low, resulting in flow that always remains laminar. Further, in this regime, two fluids joining will not easily mix, and diffusion alone may drive the mixing of two compounds.

Various features and examples of microfluidic device components suitable for use with this invention will now be described.

Substrate

Substrates used in microfluidic systems are the supports in which the necessary elements for fluid transport are provided. The basic structure may be monolithic, laminated, or otherwise sectioned. Commonly, substrates include one or more microchannels serving as conduits for molecular libraries and reagents (if necessary). They may also include input ports, output ports, and/or features to assist in flow control.

In certain embodiments, the substrate choice may be dependent on the application and design of the device. Substrate materials are generally chosen for their compatibility with a variety of operating conditions. Limitations in microfabrication processes for a given material are also relevant considerations in choosing a suitable substrate. Useful substrate materials include, e.g., glass, polymers, silicon, metal, and ceramics.

Polymers are standard materials for microfluidic devices because they are amenable to both cost effective and high volume production. Polymers can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated device of this invention are polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidics devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Surface Treatments and Coatings

Surface modification may be useful for controlling the functional mechanics (e.g., flow control) of a microfluidic device. For example, it may be advantageous to keep fluidic species from adsorbing to channel walls or for attaching antibodies to the surface for detection of biological components.

Polymer devices in particular tend to be hydrophobic, and thus loading of the channels may be difficult. The hydrophobic nature of polymer surfaces also make it difficult to control electroosmotic flow (EOF). One technique for coating polymer surface is the application of polyelectrolyte multilayers (PEM) to channel surfaces. PEM involves filling the channel successively with alternating solutions of positive and negative polyelectrolytes allowing for multilayers to form electrostatic bonds. Although the layers typically do not bond to the channel surfaces, they may completely cover the channels even after long-term storage. Another technique for applying a hydrophilic layer on polymer surfaces involves the UV grafting of polymers to the surface of the channels. First grafting sites, radicals, are created at the surface by exposing the surface to UV irradiation while simultaneously exposing the device to a monomer solution. The monomers react to form a polymer covalently bonded at the reaction site.

Glass channels generally have high levels of surface charge, thereby causing proteins to adsorb and possibly hindering separation processes. In some situations, it may be advantageous to apply a polydimethylsiloxane (PDMS) and/or surfactant coating to the glass channels. Other polymers that may be employed to retard surface adsorption include polyacrylamide, glycol groups, polysiloxanes, glyceroglycidoxypropyl, poly(ethyleneglycol) and hydroxyethylated poly(ethyleneimine) Furthermore, for electroosmotic devices it is advantageous to have a coating bearing a charge that is adjustable in magnitude by manipulating conditions inside of the device (e.g. pH). The direction of the flow can also be selected based on the coating since the coating can either be positively or negatively charged.

Specialized coatings can also be applied to immobilize certain species on the channel surface—this process is known by those skilled in the art as "functionalizing the surface." For example, a polymethylmethacrylate (PMMA) surface may be coated with amines to facilitate attachment of a variety of functional groups or targets. Alternatively, PMMA surfaces can be rendered hydrophilic through an oxygen plasma treatment process.

Microfluidic Elements

Microfluidic systems can contain a number of microchannels, valves, pumps, reactors, mixers and other components. Some of these components and their general structures and dimensions are discussed below.

Various types of valves can be used for flow control in microfluidic devices of this invention. These include, but are not limited to passive valves and check valves (membrane, flap, bivalvular, leakage, etc.). Flow rate through these valves are dependent on various physical features of the valve such as surface area, size of flow channel, valve material, etc. Valves also have associated operational and manufacturing advantages/disadvantages that should be taken into consideration during design of a microfluidic device.

Micropumps as with other microfluidic components are subjected to manufacturing constraints. Typical considerations in pump design include treatment of bubbles, clogs, and durability. Micropumps currently available include, but are not limited to electric equivalent pumps, fixed-stroke microdisplacement, peristaltic micromembrane and pumps with integrated check valves.

Macrodevices rely on turbulent forces such as shaking and stirring to mix reagents. In comparison, such turbulent forces are not practically attainable in microdevices, mixing in microfluidic devices is generally accomplished through diffusion. Since mixing through diffusion can be slow and inefficient, microstructures are often designed to enhance the mixing process. These structures manipulate fluids in a way that increases interfacial surface area between the fluid regions, thereby speeding up diffusion. In certain embodiments, microfluidic mixers are employed. Such mixers may be provide upstream from (and in some cases integrated with) a microfluidic separation device of this invention.

Micromixers may be classified into two general categories: active mixers and passive mixers. Active mixers work by exerting active control over flow regions (e.g. varying pressure gradients, electric charges, etc.). Passive mixers do not require inputted energy and use only "fluid dynamics" (e.g. pressure) to drive fluid flow at a constant rate. One example of a passive mixer involves stacking two flow streams on top of one another separated by a plate. The flow streams are contacted with each other once the separation plate is removed. The stacking of the two liquids increases contact area and decreases diffusion length, thereby enhancing the diffusion process. Mixing and reaction devices can be connected to heat transfer systems if heat management is needed. As with macro-heat exchangers, micro-heat exchanges can either have co-current, counter-current, or cross-flow flow schemes. Microfluidic devices frequently have channel widths and depths between about 10 μm and about 10 cm. A common channel structure includes a long main separation channel, and three shorter "offshoot" side channels terminating in either a buffer, sample, or waste reservoir. The separation channel can be several centimeters long, and the three side channels usually are only a few millimeters in length. Of course, the actual length, cross-sectional area, shape, and branch design of a microfluidic device depends on the application as well other design considerations such as throughput (which depends on flow resistance), velocity profile, residence time, etc.

Microfluidic devices described herein may include electric field generators to perform certain steps of the methods described herein, including, but not limited to, picoinjection, droplet coalescence, selective droplet fusion, and droplet sorting. In certain embodiments, the electric fields are generated using metal electrodes. In particular embodiments, electric fields are generated using liquid electrodes. In certain embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel. In particular embodiments, the liquid electrodes are used in picoinjection, droplet coalescence, selective droplet fusion, and/or droplet sorting aspects of a microfluidic device described herein. Liquid electrodes may find use, for example, where a material to be injected via application of an electric field is not charged.

Liquid electrodes as described herein also have applicability outside of the specific microfluidic device applications discussed herein. For example, liquid electrodes may be utilized in a variety of devices in which metal electrodes are generally used. In addition, liquid electrodes may be particularly well suited for use in flexible devices, such as devices that are designed to be worn on the body and/or devices that must flex as a result of their operation.

In certain embodiments, one or more walls of a microfluidic device channel immediately down-stream of a junction with one or more of an input microchannel, pairing microchannel and/or picoinjection microchannel includes one or more ridges. Such ridges in the walls of the microchannel are configured to trap a layer of a suitable phase, e.g., a suitable hydrophobic phase (e.g., oil) and thereby prevent an immiscible phase, e.g., an aqueous phase, from touching the walls of the microchannel, which can cause wetting of the channel walls. Such wetting may be undesirable as it may lead to unpredictable drop formation and/or allow fluids to transfer between drops, leading to contamination. In certain embodiments, the ridges allow for the formation of drops at higher flow rate ratios R ($Q_{aq}/Q_{sum}$).

In certain embodiments, the width of one or more of the microchannels of the microfluidic device (e.g., input microchanel, pairing microchannel, pioinjection microchannel, and/or a flow channel upstream or downstream of one or more of these channels) is 100 microns or less, e.g., 90 microns or less, 80 microns or less, 70 microns or less, 60 microns or less, 50 microns or less, 45 microns or less, 40 microns or less, 39 microns or less, 38 microns or less, 37 microns or less, 36 microns or less, 35 microns or less, 34 microns or less, 33 microns or less, 32 microns or less, 31 microns or less, 30 microns or less, 29 microns or less, 28 microns or less, 27 microns or less, 26 microns or less, 25 microns or less, 20 microns or less. 15 microns or less, or 10 microns or less. In some embodiments, the width of one or more of the above microchannels is from about 10 microns to about 15 microns, from about 15 microns to about 20 microns, from about 20 microns to about 25 microns, from about 25 microns to about 30 microns, from about 30 microns to about 35 microns, from about 35 microns to about 40 microns, from about 40 microns to about 45 microns, or from about 45 microns to about 50 microns, from about 50 microns to about 60 microns, from about 60 microns to about 70 microns, from about 70 microns to about 80 microns, from about 80 microns to about 90 microns, or from about 90 microns to about 100 microns.

In certain embodiments, the base of each of the one or more ridges is from about 10 microns to about 20 microns in length, e.g., from about 11 to about 19 microns in length, from about 12 to about 18 microns in length, from about 13 to about 17 microns in length, from about 14 to about 16 microns in length, or about 15 microns in length.

In certain embodiments, the peak of each of the one or more ridges has a width of about 1 to about 10 microns, e.g., from about 1 to about 9 microns, from about 2 to about 8 microns, from about 3 to about 7 microns, from about 4 to about 6 microns, or about 5 microns. In certain embodiments, the peak of each of the one or more ridges has a width of from about 1 micron to about 2 microns, from about 2 microns to about 3 microns, from about 3 microns to about 4 microns, from about 4 microns to about 5 microns, from about 5 microns to about 6 microns, from about 6 microns to about 7 microns, from about 7 microns to about 8 microns, from about 8 microns to about 9 microns, or from about 9 microns to about 10 microns.

In certain embodiments, the height of each of the one or more ridges is from about 5 microns to about 15 microns, e.g., about 6 microns to about 14 microns, about 7 microns to about 13 microns, about 8 microns to about 12 microns, about 9 microns to about 11 microns, or about 10 microns.

In certain embodiments, the ratio of the base of each of the one or more ridges to the height of each of the one or more ridges is from about 1.0:0.75 to about 0.75:1.0. In certain embodiments, the ratio of the base of each of the one or more ridges to the width of the peak of each of the one or more ridges is about 1.0:0.5 to about 1.0:0.1, e.g, from about 1.0:0.2, from about 1.0:0.3, or from about 1.0:0.4.

In certain embodiments, the ratio of the base of each of the one or more ridges to the height of each of the one or more ridges to the width of the peak of the one or more ridges is about 1:0.75:0.5.

In certain embodiments, a channel as described herein is provided with a plurality of ridges which extend for a distance along the channel wall. This distance may be, for example, from about 50 microns to about 500 microns, e.g., from about 50 microns to about 450 microns, from about 100 microns to about 400 microns, from about 150 microns to about 350 microns, from about 200 microns to about 300 microns, or about 250 microns. In certain embodiments, a plurality of ridges may be provided which extend for a distance along the channel wall, wherein the ratio between the distance along the channel wall and the width of the channel is from about 10:1 to about 1:2, e.g., about 10:1, about 9:1, about 8:1, about 7:1, about 6:1 about 5:1, about 4:1, about 3:1, about 2:1, about 1:1, or about 1:2.

It should be noted that one or more of the various dimensions discussed above may be scaled up or down as appropriate for a particular application, for example each of the above dimensions may be scaled up or down by a factor of 2, 5, 10 or more as appropriate.

In some embodiments, one or more channel junctions, e.g., one or more droplet forming junctions, such as a picoinjector junction, include a "step-down" structure. This is depicted, for example, in FIG. 26, wherein the portion of the flow channel at the picoinjector junction and downstream of the picoinjector junction is wider than the portion of the flow channel upstream of the picoinjector junction. This step-down structure facilitates the pinching-off of droplets and thus facilitates droplet formation. The step size may be chosen based on the desired size of the droplet to be formed, with larger steps creating larger droplets. Such structures may also help to avoid dripping of material from the picoinjector following injection from the picoinjector into a droplet. In some embodiments, the width of the flow channel at the picoinjector junction and downstream of the picoinjector junction is from about 5% to about 50% wider than the width of the flow channel immediately upstream of the picoinjector junction, e.g., about 5 to about 10% wider, about 10 to about 20% wider, about 20 to about 30% wider, about 30 to about 40% wider or about 40 to about 50% wider.

Methods of Fabrication

Microfabrication processes differ depending on the type of materials used in the substrate and the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition)

The combination of lithography, etching and deposition techniques may be used to make microcanals and microcavities out of glass, silicon and other "hard" materials. Technologies based on the above techniques are commonly applied in for fabrication of devices in the scale of 0.1-500 micrometers.

Microfabrication techniques based on current semiconductor fabrication processes are generally carried out in a clean room. The quality of the clean room is classified by the number of particles<4 μm in size in a cubic inch. Typical clean room classes for MEMS microfabrication are 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 μm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate—area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physicochemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 μm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features are usually sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used should ideally have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100° C.

Polymers/Plastics

A number of techniques may be employed for micromachining plastic substrates in accordance with embodiments of this invention. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In micro-injection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is well suited for microchannels between about 5 and 500 μm. Specific properties of PDMS make it particularly suitable for microfluidic purposes:

1) It is optically clear which allows for visualization of the flows;
2) PDMS when mixed with a proper amount of reticulating agent has elastomeric qualities that facilitates keeping microfluidic connections "watertight;"
3) Valves and pumps using membranes can be made with PDMS because of its elasticity;
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. But it's also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180° C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials such as stainless steel make very durable mold inserts and can be micromachined to form structures down to the 10-μm range. Various other micromachining techniques for microfabrication exist including μ-Electro Discharge Machining (μ-EDM), μ-milling, focused ion beam milling. μ-EDM allows the fabrication of 3-dimensional structures in conducting materials. In μ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices must be closed up before they can become functional. Common problems in the bonding process for microfluidic devices include the blocking of channels and changes in the physical parameters of the channels. Lamination is one method used to seal plastic microfluidic devices. In one lamination process, a PET foil (about 30 µm) coated with a melting adhesive layer (typically 5-10 µm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65° C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

The nucleic acid amplification technique described here is a polymerase chain reaction (PCR). However, in certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA).

Regarding PCR amplification modules, it will be necessary to provide to such modules at least the building blocks for amplifying nucleic acids (e.g., ample concentrations of four nucleotides), primers, polymerase (e.g., Taq), and appropriate temperature control programs). The polymerase and nucleotide building blocks may be provided in a buffer solution provided via an external port to the amplification module or from an upstream source. In certain embodiments, the buffer stream provided to the sorting module contains some of all the raw materials for nucleic acid amplification. For PCR in particular, precise temperature control of the reacting mixture is extremely important in order to achieve high reaction efficiency. One method of on-chip thermal control is Joule heating in which electrodes are used to heat the fluid inside the module at defined locations. The fluid conductivity may be used as a temperature feedback for power control.

In certain aspects, the drops containing the PCR mix may be flowed through a channel that incubates the droplets under conditions effective for PCR. Flowing the microdroplets through a channel may involve a channel that snakes over various temperature zones maintained at temperatures effective for PCR. Such channels may, for example, cycle over two or more temperature zones, wherein at least one zone is maintained at about 65° C. and at least one zone maintained at about 95° C. As the drops move through such zones, their temperature cycles, as needed for PCR. The precise number of zones, and the respective temperature of each zone, may be readily determined by those of skill in the art to achieve the desired PCR amplification.

In other embodiments, incubating the microdroplets may involve the use of a Megadroplet Array. In such a device, an array consists of channels in which the channel ceilings are indented with millions of circular traps that are about 25 µm in diameter. Drops are distributed into the trapping channels using distribution plates—large channels connecting the inlets of the trapping channels (FIG. 12, Panel A). Due to the large size of the distribution channels compared to the trapping channels—the distribution channels are about 100× 500 µm in height and width, compared to only about 15×100 µm for the droplet trapping channels—the hydrodynamic resistance of the distribution channels is ~1500 times lower than that of the trapping channels; this ensures that the distribution channel fills with drops before the trapping channels begin to fill, allowing even distribution of the drops into the trapping channels. When the drops flow into the trapping channels, they are slightly pancaked in shape because the vertical height of the channel is 15 µm, or 10 µm shorter than the drops, as illustrated in FIG. 12, Panel B. When a drop nears a trap, its interface adopts a larger, more energetically favorable radius of curvature. To minimize its surface energy, the drop entirely fills the trap, allowing it to adopt the lowest, most energetically favorable, average radius of curvature. After a trap is occupied by a drop, no other drops are able to enter because the trap is large enough to fit only one drop; additional drops are diverted downstream, to occupy the first vacant trap they encounter. Because the array is filled using a close-packed emulsion, every trap will be occupied by a drop, since this is the most energetically favorable state under low flow conditions. After the droplet array is filled, oil is injected to remove excess drops and the array is thermal cycled and imaged.

A variety of different ways can be used to fill the traps of the device. For instance, buoyancy effects and centrifugation can also be used to fill and empty the traps by flipping the device with respect to the earth's gravitational field, since the droplet density is 63% that of the fluorocarbon carrier oil. That is, if the drops were heavier than the oil phase, then the wells could be imprinted into the "floor" of the device so that when the emulsion was flowed over it, the drops would sink into the wells. The flow rate of the emulsion could be adjusted to optimize this and the drop size would be made to be approximately the same size as the well so that the well could only fit a single drop at a time. In other aspects, the drops could also, or instead, be stored in a large chamber with no wells.

The device may achieve thermal cycling using a heater consisting of a Peltier plate, heat sink, and control computer (FIG. 12, Panel A; FIG. 13). The Peltier plate allows heating and/or cooling the chip above or below room temperature by controlling the applied current. To ensure controlled and reproducible temperature, a computer monitors the temperature of the array using integrated temperature probes, and adjusts the applied current to heat and cool as needed. A metallic (e.g., copper) plate allows uniform application of heat and dissipation of excess heat during cooling cycles, enabling cooling from 95° C. to 60° C. In under 1 min execution. In order to image microdroplets, certain embodiments may incorporate a scanner bed. In certain aspects, the scanner bed is a Canoscan 9000F scanner bed.

In order to effectively amplify nucleic acids from target components, the microfluidics system may include a cell lysing or viral protein coat-disrupting module to free nucleic acids prior to providing the sample to an amplification module. Cell lysing modules may rely on chemical, thermal, and/or mechanical means to effect cell lysis. Because the cell membrane consists of a lipid double-layer, lysis buffers containing surfactants can solubilize the lipid membranes. Typically, the lysis buffer will be introduced directly to a lysis chamber via an external port so that the cells are not prematurely lysed during sorting or other upstream process. In cases where organelle integrity is necessary, chemical lysis methods may be inappropriate. Mechanical breakdown of the cell membrane by shear and wear is appropriate in certain applications. Lysis modules relying mechanical techniques may employ various geometric features to effect piercing, shearing, abrading, etc. of cells entering the module. Other types of mechanical breakage such as acoustic techniques may also yield appropriate lysate. Further, thermal energy can also be used to lyse cells such as bacteria, yeasts, and spores. Heating disrupts the cell membrane and the intracellular materials are released. In order to enable subcellular fractionation in microfluidic systems a lysis module may also employ an electrokinetic technique or electroporation. Electroporation creates transient or permanent holes in the cell membranes by application of an external electric field that induces changes in the plasma membrane and disrupts the transmembrane potential. In microfluidic electroporation devices, the membrane may be permanently disrupted, and holes on the cell membranes sustained to release desired intracellular materials released.

Single Cell RT-PCR Microfluidic Device

Figure 32:
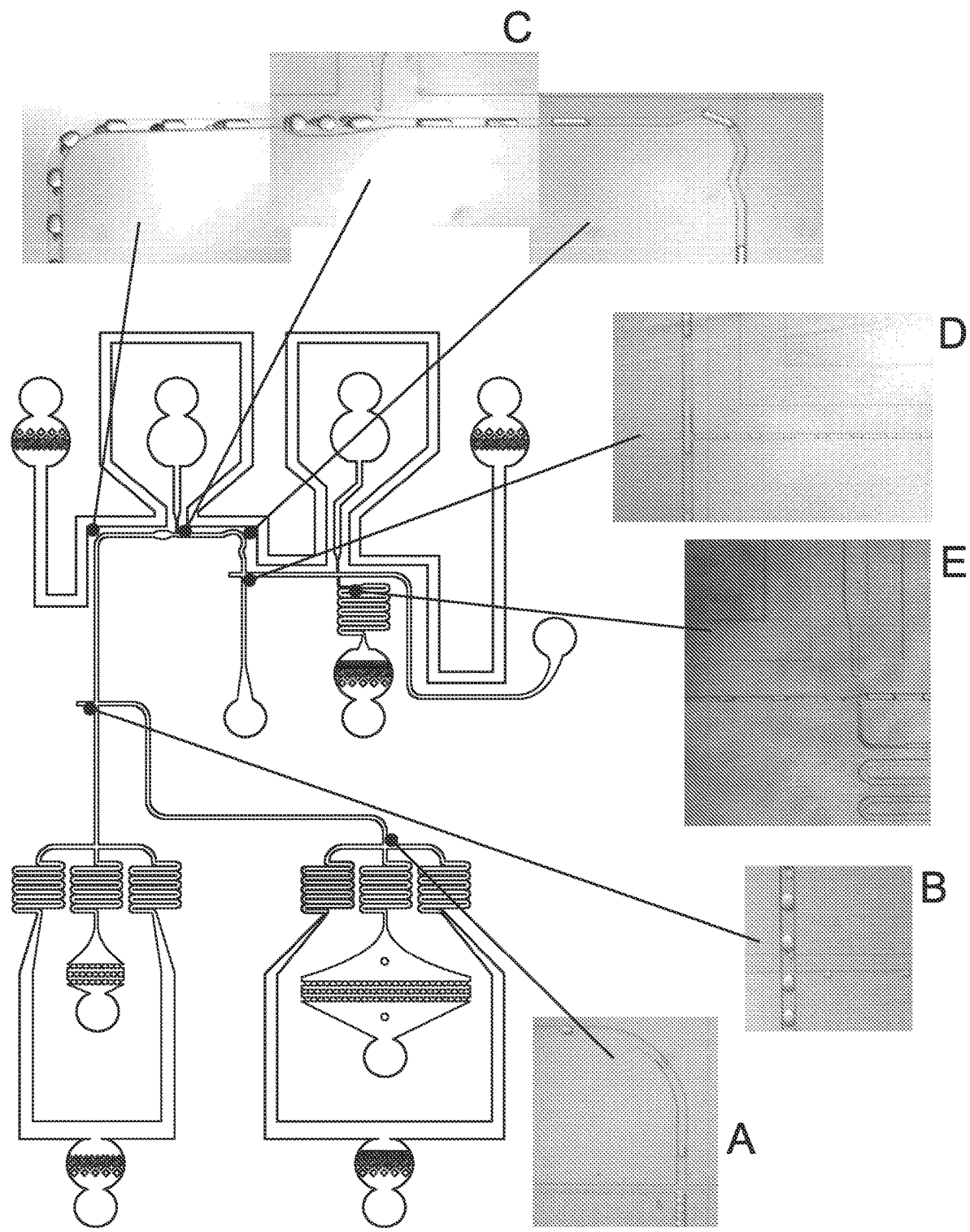
FIG. 32 shows an embodiment of a single cell RT-PCR microfluidic device as described herein.

In another aspect, provided herein is a single cell RT-PCR microfluidic device, described in greater detail below with reference to FIG. 32. In certain embodiments, the single cell RT-PCR microfluidic device includes an input microchannel, which may be coupled to a flow focus drop maker, for introducing microdroplets into the microfluidic device, wherein the flow focus drop maker spaces the microdroplets in the input microchannel, e.g., by a volume of a suitable hydrophobic phase, e.g., oil, whereineach microdroplet may include a cell lysate sample. An exemplary embodiment is shown in FIG. 32 (Panel A).

The microfluidic device may further include a pairing microchannel in fluidic communication with the input microchannel and a dilution buffer drop maker in fluidic communication with the pairing microchannel. In such embodiments, a microdroplet from the input microchannel flows into the pairing microchannel where the dilution buffer drop maker produces a drop of dilution buffer that is larger than and paired with each microdroplet. In certain embodiments, the dilution buffer drop maker is a T-junction drop maker. An exemplary embodiment is shown in FIG. 32 (Panel B).

The microfluidic device may also include a merging microchannel in fluidic communication with the pairing microchannel, the merging microchannel including an electric field generator positioned in proximity thereto. In such embodiments, the paired microdroplet and drop of dilution buffer enter the merging microchannel from the pairing microchannel and are merged upon passing through an electric field produced by the electric field generator to produce a diluted microdroplet. Any suitable electric field generator can be used to produce the diluted microdroplet. In certain embodiments, the electric field is created by metal electrodes. In other embodiments, the electric field is created by liquid electrodes as discussed herein. An exemplary embodiment is shown in FIG. 32 (Panel C).

The microfluidic device may also include a series of mixing microchannels in fluidic communication with the merging microchannel. Such mixing microchannels allow for the mixing of the contents of the diluted microdroplet.

The microfluidic device may also include a drop sampler in fluidic communication with the mixing microchannels. Such a drop sampler is capable of taking a sample of the diluted microdroplet, e.g., to be used in a subsequent RT-PCR reaction carried out in the microfluidic device. An exemplary embodiment is shown in FIG. 32 (Panel D).

The microfluidic may also include a picoinjection microchannel comprising a picoinjector, wherein the picoinjection microchannel may be a pressurized microchannel capable of receiving the sample of the diluted microdroplet produced by the drop sampler and allowing the picoinejctor to picoinject RT-PCR reagents into the sample. In certain embodiments the picoinjection is assisted by an electric field applied to the picoinjection microchannel. Any electric field generator can be used to create an electric field for picoinjection. In certain embodiments, the electric field is created by metal electrodes. In other embodiments, the electric field is created by liquid electrodes as discussed herein. An exemplary embodiment is shown in FIG. 32 (Panel E).

Samples of the diluted microdroplet that have been picoinjected with RT-PCR reagents can then be subjected to conditions for RT-PCR using any of the approaches described herein. The single cell RT-PCR microfluidic device advantageously allows for the dilution of the cell lysate sample prior to addition of RT-PCR agents. Such dilution helps in prevent inhibition of RT-PCR that may be caused by components of the cell lysate. In certain embodiments, the microfluidic device also includes an encapsulating chamber in fluidic communication with the input microchannel, for encapsulating a cell and lysis regeant into a microdroplet. In such embodiments, the input microchannel is capable of receiving the microdroplet from the encapsulating chamber.

Certain non-limiting aspects of the disclosure are provided below:

1. A method for the detection of cells, the method including:
   encapsulating in a microdroplet a cell obtained from a biological sample from a subject, wherein at least one cell is present in the microdroplet;
   incubating the microdroplet under conditions effective for cell lysis;
   introducing polymerase chain reaction (PCR) reagents, a detection component, and a plurality of PCR primers into the microdroplet and incubating the microdroplet under conditions allowing for PCR amplification to produce PCR amplification products, wherein the plurality of PCR primers include one or more primers that each hybridize to one or more oligonucleotides; and
   detecting the presence or absence of the PCR amplification products by detection of the detection component, wherein detection of the detection component indicates the presence of PCR amplification products;
   wherein one or more steps are performed under microfluidic control.
2. The method according to 1, wherein incubating the microdroplet under conditions effective for cell lysis includes introducing a lysing agent into the microdroplet.
3. The method according to 1 or 2, wherein the one or more oligonucleotides are oncogenes.
4. The method according to any of 1-3, wherein the biological sample is blood and the method includes determining the number of circulating tumor cells (CTCs) present in the sample of the subject's blood based at least in part on the number of microdroplets in which PCR amplification products were detected.
5. The method according to any of 1-4, wherein all steps are performed under microfluidic control.
6. The method according to 5, wherein all steps are performed on the same microfluidic device.
7. The method according to any of the above, wherein the plurality of PCR primers includes 10 or more primers.
8. The method according to any of the above, wherein the plurality of PCR primers includes 20 to 100 primers.
9. The method according to any of the above, wherein the plurality of PCR primers includes primers for 10 or more oncogenes.
10. The method according to any of the above, wherein incubating the microdroplet under conditions allowing for PCR amplification is performed on the same microfluidic device used to encapsulate the cells and lyse the cells.
11. The method according to any of the above, wherein the PCR reagents and PCR primers are added at the same time as the lysing agent.
12. The method according to any of the above, wherein the PCR reagents are added in two steps or more.
13. The method according to any of the above, further including introducing a probe into the microdroplet.
14. The method according to 13, wherein the probe is introduced prior to incubating the microdroplet under conditions allowing for PCR amplification.
15. The method according to 13 or 14, wherein the probe is a TaqMan® probe.
16. The method according to any of the above, wherein a reagent is added to the microdroplet by merging the microdroplet with a second microdroplet including the reagent.
17. The method according to any of the above, wherein a reagent is added to the microdroplet using either droplet coalescence or picoinjection.
18. The method according to any of the above, wherein a reagent is added to the microdroplet by a method including:
   a) emulsifying the reagent into a stream of droplets, wherein the droplets are smaller than the size of the microdroplet;
   b) flowing the droplets together with the microdroplet; and
   c) merging a droplet with the microdroplet.
19. The method according to 18, wherein the diameter of the droplets is 25% or less than that of the diameter of the microdroplet, and a plurality of droplets are merged with the microdroplet.
20. The method according to 18 or 19, wherein the merging includes applying an electric field.
21. The method according to any of the above, wherein a reagent is added to the microdroplet by a method including:
   a) jetting the reagent into a fluid jet;
   b) flowing the fluid jet alongside the microdroplet; and
   c) merging a droplet with the microdroplet.
22. The method according to 21, wherein merging includes applying an electric field.
23. The method according to 21 or 22, wherein jetting the reagent includes adding a viscosity-increasing agent or surfactant.
24. The method according to any of the above, wherein a reagent is added to the microdroplet by a method including using a fluid injected into the microdroplet as an electrode.
25. The method according to any of the above, wherein the detection component is detected based on a change in fluorescence.
26. The method according to 25, where in the change in fluorescence is due to fluorescence resonance energy transfer (FRET).
27. The method according to 25, where in the change in fluorescence is due to fluorescence polarization.
28. The method according to 25 or 27, wherein the detection component is an intercalating stain.
29. The method according to any of the above, wherein detecting the presence or absence of the PCR amplification products includes repeatedly imaging the microdroplet.
30. The method according to 29, wherein the microdroplet is repeatedly imaged while the microdroplet is subjected to conditions allowing for PCR amplification to produce the PCR amplification products.
31. The method according to any of the above, wherein incubating the microdroplet under conditions allowing for PCR amplification and detecting the presence or absence of the PCR amplification products are performed on a Megadroplet Array.
32. The method according to any of the above, including sorting a microdroplet.
33. The method according to 32, wherein the sorting includes using membrane valves, bifurcating channels, surface acoustic waves, or dielectrophoresis.
34. The method according to 32 or 33, wherein the microdroplet is sorted based on a property including size, viscosity, mass, buoyancy, surface tension, electrical conductivity, charge, or magnetism.
35. The method according to any of 32-34, including sorting based at least in part based upon the detection of the presence or absence of PCR amplification products.
36. The method according to any of 32-35, wherein the microdroplet is sorted prior to the introduction of a PCR reagent.
37. The method according to any of 32-36, wherein the microdroplet is sorted prior to the introduction of a lysing agent.
38. The method according to any of the above, further including:
   injecting a diluent into the microdroplet; and
   flowing the microdroplet through a microfluidic channel on which an electric field is being applied, under conditions in which the microdroplet is split.
39. The method according to any of the above, wherein the subject is mammalian.
40. The method according to any of the above, wherein the subject is human.
41. The method according to any of the above, wherein the subject has been diagnosed with cancer.
42. The method according to any of the above, wherein the biological sample is a blood sample.
43. The method of 42, wherein the blood sample is whole blood.
44. The method of 42 or 43, including fractionating the blood sample.
45. The method of any one of 42-44, including drawing 30 mL or less of the subject's blood.
46. The method of 45, wherein the blood sample is 15 mL or less.
47. The method of any one of the above, including fixing and/or permeabilizing the cell.

48. The method of any one of the above, including introducing a plurality of different detection components, and detecting the presence or absence of the PCR amplification products by detection of the plurality of detection components, wherein detection of the detection components indicates the presence of PCR amplification products.

49. The method of any one of the above, including contacting the cell or a component thereof with a detectably labeled antibody.

50. A method for the detection of tumor cells, the method including:
    encapsulating a plurality of cells in a plurality of microdroplets under conditions in which a majority of microdroplets include zero or one cell, wherein the plurality of cells are obtained from a subject's blood sample suspected of containing circulating tumor cells (CTCs);
    enriching the plurality of microdroplets for microdroplets containing one cell;
    introducing a lysing agent into the plurality of microdroplets and incubating under conditions effective for cell lysis;
    introducing polymerase chain reaction (PCR) reagents, a detection component, and a plurality of PCR primers into the plurality of microdroplets and incubating the plurality of microdroplets under conditions allowing for PCR amplification to produce PCR amplification products, wherein the plurality of PCR primers include one or more primers that each hybridize to one or more oncogenes;
    detecting the presence or absence of the PCR amplification products by detection of the detection component, wherein detection of the detection component indicates the presence of the PCR amplification products; and determining the number of CTCs present in a sample of the subject's blood based at least in part on the number of microdroplets in which the PCR amplification products were detected;
    wherein one or more steps are performed under microfluidic control.

51. The method according to 50, wherein all steps are all performed under microfluidic control.

52. The method according to 50 or 51, wherein all steps are performed on the same microfluidic device.

53. The method according to any of 50-52, wherein the plurality of PCR primers includes 10 or more primers.

54. The method according to any of 50-53, wherein the plurality of PCR primers includes primers for 10 or more oncogenes.

55. The method according to any of 50-54, wherein the plurality of PCR primers includes a plurality of probes.

56. The method according to 55, wherein the probes include TaqMan® probes.

57. The method according to any of 50-56, wherein the PCR reagents are added in two steps or more.

58. The method according to any of 50-57, further including introducing a probe into the microdroplet.

59. The method according to any of 50-58, wherein a reagent is added to the plurality of microdroplets by merging a microdroplet with a second microdroplet including the reagent.

60. The method according to any of 50-59, wherein a reagent is added to the plurality of microdroplets using either droplet coalescence or picoinjection.

61. The method according to any of 50-60, wherein a reagent is added to the plurality of microdroplets by a method including:
    a) emulsifying the reagent into a stream of droplets, wherein the droplets are smaller than the size of a microdroplet;
    b) flowing the droplets together with the microdroplet; and
    c) merging a droplet with the microdroplet.

62. The method according to 58, wherein the merging includes applying an electric field.

63. The method according to any of 50-62, wherein a reagent is added to the plurality of microdroplets by a method including:
    a) jetting the reagent into a fluid jet;
    b) flowing the fluid jet alongside a microdroplet; and
    c) merging a droplet with the microdroplet.

64. The method according to any of 50-63, wherein a reagent is added to the microdroplet by a method including using a fluid injected into the microdroplet as an electrode.

65. The method according to any of 50-64, including sorting a microdroplet.

66. The method according to 65, wherein the plurality of microdroplets is sorted based on a property including size, viscosity, mass, buoyancy, surface tension, electrical conductivity, charge, or magnetism.

67. The method according to any of 65-66, wherein the plurality of microdroplets is sorted prior to the introduction of a PCR reagent.

68. The method according to any of 50-67, wherein detecting the presence or absence of the PCR amplification products includes repeatedly imaging the plurality of microdroplets.

69. The method according to 68, wherein the plurality of microdroplets is repeatedly imaged while the plurality of microdroplets is subjected to conditions allowing for PCR amplification to produce the PCR amplification products.

70. The method according to any of 50-69, wherein incubating the plurality of microdroplets under conditions allowing for PCR amplification and detecting the presence or absence of the PCR amplification products are performed on a Megadroplet Array.

71. The method according to any of 50-70, wherein the subject is mammalian.

72. The method according to any of 50-71, wherein the subject is human.

73. The method according to any of 50-72, wherein the subject has been diagnosed with cancer.

74. A method for genotyping of cells, the method including:
    encapsulating in a microdroplet a cell obtained from a biological sample from a subject, wherein one cell is present in the microdroplet;
    introducing a lysing agent into the microdroplet and incubating the microdroplet under conditions effective for cell lysis;
    introducing polymerase chain reaction (PCR) reagents and a plurality PCR primers into the microdroplet, and incubating the microdroplet under conditions allowing for PCR amplification to produce PCR amplification products, wherein the plurality of PCR primers include one or more primers that each hybridize to one or more oncogenes;

introducing a plurality of probes into the microdroplet, wherein the probes hybridize to one or more mutations of interest and fluoresce at different wavelengths; and detecting the presence or absence of specific PCR amplification products by detection of fluorescence of a probe, wherein detection of fluorescence indicates the presence of the PCR amplification products;

wherein one or more of steps are performed under microfluidic control.

75. The method according to 74, wherein the probes include TaqMan® probes.

76. The method according to 74 or 75, wherein detecting the presence or absence of specific PCR amplification products by detection of fluorescence of a probe includes repeatedly imaging the microdroplet while the microdroplet is subjected to conditions allowing for PCR amplification to produce PCR amplification products.

77. The method according to 76, including obtaining time-dependent fluorescence information.

78. The method according to any of 74-77, wherein a reagent is added to the microdroplet by merging the microdroplet with a second microdroplet including the reagent.

79. The method according to any of 74-78, wherein a reagent is added to the microdroplet using either droplet coalescence or picoinjection.

80. The method according to any of 74-79, wherein a reagent is added to the microdroplet by a method including:
a) emulsifying the reagent into a stream of droplets, wherein the droplets are smaller than the size of the microdroplet;
b) flowing the droplets together with the microdroplet; and
c) merging a droplet with the microdroplet.

81. The method according to any of 74-80, wherein a reagent is added to the microdroplet by a method including:
a) jetting the reagent into a fluid jet;
b) flowing the fluid jet alongside the microdroplet; and
c) merging a droplet with the microdroplet.

82. The method according to any of 74-81, wherein a reagent is added to the microdroplet by a method including using a fluid injected into the microdroplet as an electrode.

83. The method according to any of 74-82, including sorting a microdroplet.

84. The method according to 83, wherein the microdroplet is sorted based on a property including size, viscosity, mass, buoyancy, surface tension, electrical conductivity, charge, or magnetism.

85. The method according to any of 74-84, wherein the subject is mammalian.

86. The method according to any of 74-85, wherein the subject is human.

87. The method according to any of 74-86, wherein the subject has been diagnosed with cancer.

88. A method for the detection of cancer in a subject, the method including:
encapsulating in a microdroplet oligonucleotides obtained from a biological sample from the subject, wherein at least one oligonucleotide is present in the microdroplet;

introducing polymerase chain reaction (PCR) reagents, a detection component, and a plurality of PCR primers into the microdroplet and incubating the microdroplet under conditions allowing for PCR amplification to produce PCR amplification products, wherein the plurality of PCR primers include one or more primers that each hybridize to one or more oncogenes;

detecting the presence or absence of the PCR amplification products by detection of the detection component, wherein detection of the detection component indicates the presence of the PCR amplification products; and diagnosing the subject as having cancer or not based at least in part on the presence or absence of the PCR amplification products;

wherein one or more steps are performed under microfluidic control.

89. The method according to 88, wherein the plurality of PCR primers includes 10 or more primers.

90. The method according to any of 88-89, wherein the plurality of PCR primers includes primers for 10 or more oncogenes.

91. The method according to any of 88-90, further including introducing a probe into the microdroplet.

92. The method according to 91, wherein the probe is introduced prior to incubating the microdroplet under conditions allowing for PCR amplification.

93. The method according to 91 or 92, wherein the probe is a TaqMan® probe.

94. The method according to any of 88-93, wherein a reagent is added to the microdroplet by merging the microdroplet with a second microdroplet including the reagent.

95. The method according to any of 88-94, wherein a reagent is added to the microdroplet using either droplet coalescence or picoinjection.

96. The method according to any of 88-95, wherein a reagent is added to the microdroplet by a method including:
a) emulsifying the reagent into a stream of droplets, wherein the droplets are smaller than the size of the microdroplet;
b) flowing the droplets together with the microdroplet; and
c) merging a droplet with the microdroplet.

97. The method according to any of 88-96, wherein a reagent is added to the microdroplet by a method including:
a) jetting the reagent into a fluid jet;
b) flowing the fluid jet alongside the microdroplet; and
c) merging a droplet with the microdroplet.

98. The method according to any of 88-97, wherein a reagent is added to the microdroplet by a method including using a fluid injected into the microdroplet as an electrode.

99. The method according to any of 88-98, wherein the detection component is detected based on a change in fluorescence.

100. The method according to any of 88-99, wherein detecting the presence or absence of the PCR amplification products includes repeatedly imaging the microdroplet.

101. The method according to 100, wherein the microdroplet is repeatedly imaged while the microdroplet is subjected to conditions allowing for PCR amplification to produce the PCR amplification products.

102. The method according to any of 88-101, including sorting a microdroplet.
103. The method according to 102, wherein the microdroplet is sorted based on a property including size, viscosity, mass, buoyancy, surface tension, electrical conductivity, charge, or magnetism.
104. The method according to any of 88-103, including sorting based at least in part based upon the detection of the presence or absence of PCR amplification products.
105. The method according to any of 88-104, further including:
  injecting a diluent into the microdroplet; and
  flowing the microdroplet through a microfluidic channel on which an electric field is being applied, under conditions in which the microdroplet is split.
106. The method according to any of 88-105, wherein the subject is mammalian.
107. The method according to any of 88-106, wherein the subject is human.
108. The method according to any of 88-107, wherein the subject has been diagnosed with cancer.
109. A microfluidic device including:
  a cell encapsulation device for encapsulating a cell obtained from a subject's blood sample in a microdroplet;
  a first chamber in fluidic communication with the cell encapsulation device, the first chamber including a first reagent injector element for adding a first reagent to the microdroplet, and a heating element;
  a second chamber in fluidic communication with the first chamber, the second chamber including a second reagent injector element for adding a second reagent to the microdroplet, and a heating element, wherein the heating element is configured to heat the microdroplet at two or more temperatures; and
  a detection region, in fluidic communication with the second chamber, which detects the presence or absence of reaction products from the second chamber.
110. The microfluidic device as set forth in 109, wherein the heating element of the second chamber includes a Peltier plate, heat sink, and control computer.
111. The microfluidic device as set forth in 109, wherein the microfluidic device includes one or more liquid electrodes.
112. A single cell RT-PCR microfluidic device including:
  an input microchannel coupled to a drop maker for introducing microdroplets into the microfluidic device;
  a pairing microchannel in fluidic communication with the input microchannel;
  a dilution buffer drop maker in fluidic communication with the pairing microchannel, for producing drops of dilution buffer that are larger in volume than the microdroplets and for pairing a single drop of dilution buffer with a single microdroplet;
  a merging microchannel in fluidic communication with the pairing microchannel, for accepting a paired drop of dilution buffer and microdroplet from the pairing microchannel;
  a first electric field generator positioned along the merging microchannel for producing an electric field that is capable of merging a paired drop of dilution buffer and microdroplet in the merging microchannel to form a diluted microdroplet;
  a mixing microchannel in fluidic communication with the merging microchannel, for receiving the diluted microdroplet from the merging channel and mixing the contents of the diluted microdroplet;
  a drop sampler in fluidic communication with the mixing microchannel, for extracting a sample of the diluted microdroplet,
  a picoinjection microchannel in fluidic communication with the drop sampler, wherein the picoinjection microchannel includes a picoinjector and is for receiving the sample of the diluted microdroplet and picoinjecting RT-PCR reagents into the sample;
  a second electric field generator, wherein the second electric field generator is positioned along the picoinjection microchannel to create an electric field sufficient to allow for the picoinjection of the RT-PCR reagents into the sample;
  a thermocycler heating element in fluidic communication with the picoinjection microchannel for carrying out an RT-PCR reaction on the sample picoinjected with the RT-PCR reagents.
113. The microfluidic device of 112, further including an encapsulating chamber in fluidic communication with the input microchannel, for encapsulating a cell and lysis regeant into a microdroplet.
114. The microfluidic device of 112, wherein the first and/or second electric field generators are liquid electrodes connected to a power supply or high voltage amplifier.
115. The microfluidic device of 112, including ridges in one or more walls of a microfluidic flow channel downstream of the input microchannel, wherein the ridges are configured to trap a layer of oil and prevent wetting of the one or more walls of the flow channel.
116. The microfluidic device of 112, including ridges in one or more walls of a microfluidic flow channel downstream of the pairing microchannel, wherein the ridges are configured to trap a layer of oil and prevent wetting of the one or more walls of the flow channel.
117. The microfluidic device of 112, including ridges in one or more walls of a microfluidic flow channel downstream of the picoinjection microchannel, wherein the ridges are configured to trap a layer of oil and prevent wetting of the one or more walls of the flow channel.
118. The microfluidic device of 112, wherein the pioinjection microchannel is configured to receive a sample that has undergone an RT-PCR reaction in the sampler and picoinject the sample with PCR reagents.
119. The microfluidic device of 118, wherein the thermocycler is configured for performing a PCR reaction on a sample picoinjected with the PCR reagents.
120. The microfluidic device of 118, wherein the PCR reagents and the RT-PCR reagents include the same primers.
121. The microfluidic device of 118, wherein the PCR reagents and the RT-PCR reagents include different primers.
122. The microfluidic device of 112, wherein the RT-PCR reagents includes a bead conjugated with a fluorescent dye and a nucleic acid probe.
123. The microfluidic device of 112, wherein the RT-PCR reagents includes a fluorescent DNA probe.
124. A single cell RT-PCR microfluidic device including:
  an input microchannel coupled to a flow focus drop maker for introducing microdroplets into the microfluidic device, wherein the flow focus drop maker spaces the microdroplets in the input microchannel by a volume of oil and wherein each microdroplet including a cell lysate sample;

a pairing microchannel in fluidic communication with the input microchannel;

a dilution buffer drop maker in fluidic communication with the pairing microchannel, for producing a drop of dilution buffer that is larger in volume than a microdroplet and for pairing a single drop of dilution buffer with a single microdroplet;

a merging microchannel in fluidic communication with the pairing microchannel, for accepting a paired drop of dilution buffer and microdroplet from the pairing microchannel;

a first electric field generator positioned along the merging microchannel for producing an electric field across the merging channel that is capable of merging a paired drop of dilution buffer and microdroplet in the merging microchannel to form a diluted microdroplet;

a mixing microchannel in fluidic communication with the merging microchannel, for receiving the diluted microdroplet from the merging channel and mixing the contents of the diluted microdroplet;

a drop sampler in fluidic communication with the mixing microchannel, for extracting a sample of the diluted microdroplet, a picoinjection microchannel in fluidic communication with the drop sampler, wherein the picoinjection microchannel includes a picoinjector and is for receiving the sample of the diluted microdroplet and picoinjecting RT-PCR reagents into the sample;

a second electric field generator, wherein the second electric field generator is positioned along the picoinjection microchannel to create an electric field across the picoinjection microchannel sufficient to allow for the picoinjection of the RT-PCR reagents into the sample;

a thermocycler heating element in fluidic communication with the picoinjection microchannel for carrying out an RT-PCR reaction on the sample picoinjected with the RT-PCR reagents.

125. The microfluidic device of 124, further including an encapsulating chamber in fluidic communication with the input microchannel, for encapsulating a cell and lysis regeant into a microdroplet.

126. The microfluidic device of 124, wherein the first and/or second electric field generators are liquid electrodes connected to a power supply or high voltage amplifier.

127. The microfluidic device of 124, including ridges in one or more walls of a microfluidic flow channel downstream of the input microchannel, wherein the ridges are configured to trap a layer of oil and prevent wetting of the one or more walls of the flow channel.

128. The microfluidic device of 124, including ridges in one or more walls of a microfluidic flow channel downstream of the pairing microchannel, wherein the ridges are configured to trap a layer of oil and prevent wetting of the one or more walls of the flow channel.

129. The microfluidic device of 124, including ridges in one or more walls of a microfluidic flow channel downstream of the picoinjection microchannel, wherein the ridges are configured to trap a layer of oil and prevent wetting of the one or more walls of the flow channel.

130. The microfluidic device of 124, wherein the pioinjection microchannel is configured to receive a sample that has undergone an RT-PCR reaction in the sampler and picoinject the sample with PCR reagents.

131. The microfluidic device of 130, wherein the thermocycler is configured for performing a PCR reaction on a sample picoinjected with the PCR reagents.

132. The microfluidic device of 130, wherein the PCR reagents and the RT-PCR reagents include the same primers.

133. The microfluidic device of 130, wherein the PCR reagents and the RT-PCR reagents include different primers.

134. The microfluidic device of 124, wherein the RT-PCR reagents includes a bead conjugated with a fluorescent dye and a nucleic acid probe.

135. The microfluidic device of 124, wherein the RT-PCR reagents includes a fluorescent DNA probe.

136. The method of any one of 1-20, wherein a reagent is added to the microdroplet by:
   contacting the microdroplet with oil so that the oil encapsulates the microdroplet to form a double emulsion;
   contacting the double emulsion with a drop containing the reagent so that the drop containing the reagent encapsulates the double emulsion to form a triple emulsion;
   applying an electrical field to the triple emulsion so that the fluid interfaces of the triple emulsion are ruptured and allow the microdroplet and reagent to mix.

137. The method of 136, wherein the electric field is applied by one or more liquid electrodes.

138. A microfluidic device including: a flow channel, a microfluidic junction fluidically connected to the flow channel, and ridges in one or more walls of the microfluidic flow channel immediately downstream of the microfluidic junction.

139. The microfluidic device of 138, wherein the ridges trap a layer of oil and prevent wetting of the one or more walls of the flow channel.

140. The microfluidic device of 138, wherein the base of each of the one or more ridges is from about 10 microns to about 20 microns in length.

141. The microfluidic device of 138, wherein, the peak of each of the one or more ridges has a width of about 1 to about 10 microns.

142. The microfluidic device of 138, wherein the height of each of the one or more ridges is from about 5 microns to about 15 microns.

143. The microfluidic device of 138, wherein the ratio of the base of each of the one or more ridges to the height of each of the one or more ridges is from about 1.0:0.75 to about 0.75:1.0.

144. The microfluidic device of 138, wherein the base of each of the one or more ridges to the height of each of the one or more ridges to the width of the peak of the one or more ridges is about 1:0.75:0.5.

145. The microfluidic device of 138, wherein the ridges extend for a distance along the channel wall of from about 50 microns to about 500 microns.

146. The microfluidic device of 138, wherein the ridges extend for a distance along the channel wall, wherein the ratio between the distance along the channel wall and the width of the channel is from about 10:1 to about 1:2.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Example 1: Microfluidic System for Performing Single-Cell PCR Reactions

Device manufacturing: The chips were made using the same photolithographic processes in polydimethylsiloxane as the other devices described above. A general schematic of the chips is shown in FIG. 1. The general approach carried out by such chips is depicted in FIG. 6.

Sample preparation: 5-25 mL whole blood samples were extracted from a subject via syringe. Nucleated cells were separated using on-chip pinched-flow fractionation, as generally described in Lab on a Chip, 2005, 5, 778-784; the disclosure of which is incorporated herein by reference. Nucleated cells were collected for subsequent analysis.

Figure 7:
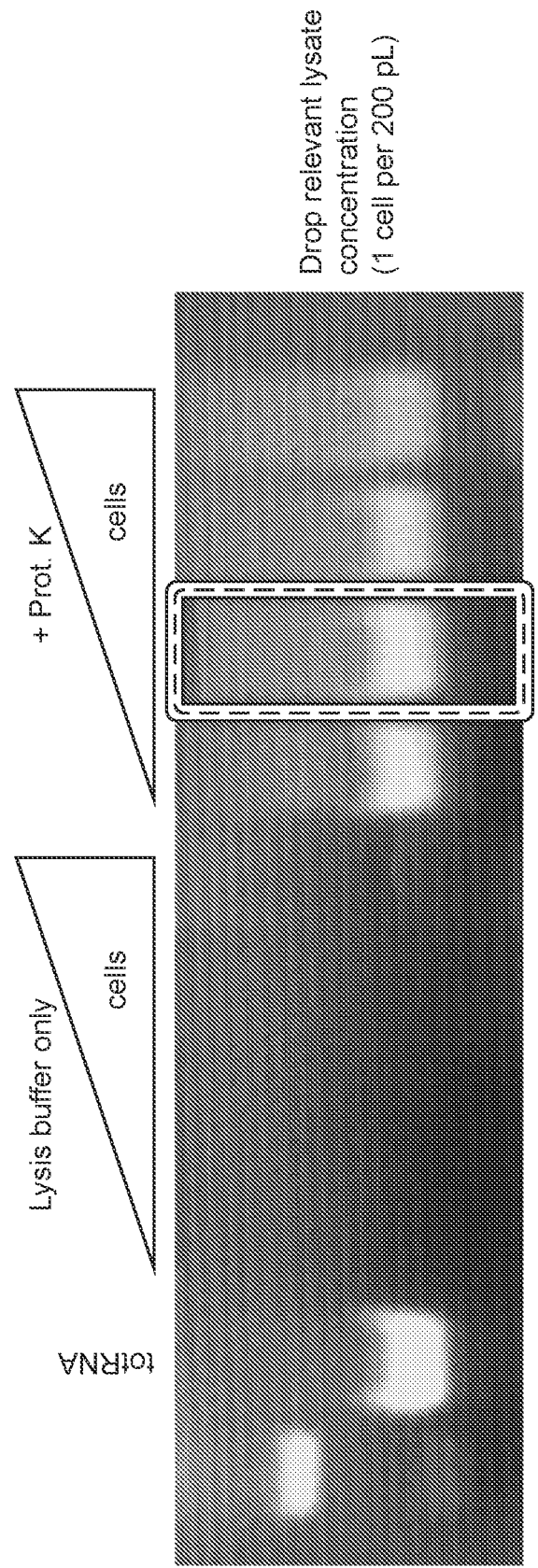
FIG. 7 shows relief of cell lysate-mediated inhibition of RT-PCR by proteinase K treatment. Increasing concentrations of cells were either treated with proteinase K and lysis buffer or lysis buffer only. Cells were then incubated at 55° C. followed by 95° C. Whole cell lysates were added directly to RT-PCR reactions at several drop relevant concentrations. Strong relief of lysate inhibition on PCR was seen at final cell concentrations of 1 cell per 200 pL in Proteinase K treated lysates but not in lysis buffer only lysates. PCR products are visualized on an ethidium bromide stained agarose gel.

PCR Reactions: The assay requires the execution of an RT-PCR reaction in drops containing concentrated cell lysates; however, cell lysates inhibit RT-PCR (FIG. 7). To overcome this inhibition, a protocol has been developed that utilizes proteinase K to digest inhibitory proteins in cell lysates. Using proteinase K allows efficient amplification in lysates at concentrations as high as 1 cell in 50 pL, with optimal amplification occurring at 1 cell in 200 pL (FIG. 7). Thus, the system operates at this concentration.

Figure 8:
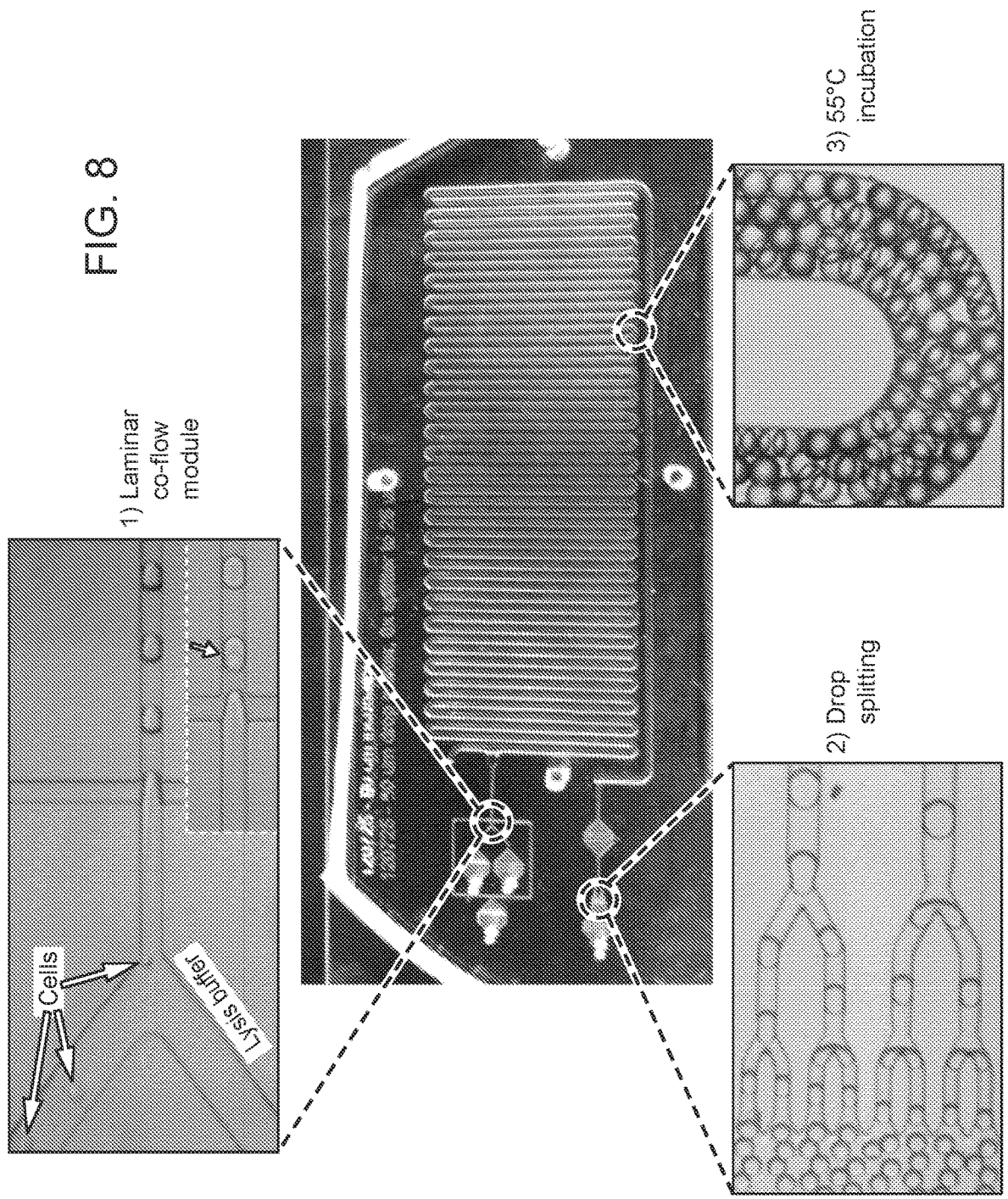
FIG. 8, Panels 1-3 show an integrated microfluidic system for cell encapsulation/dilution, lysis and drop splitting (center image). Panel 1: Co-flow module relies on laminar flow of Proteinase K containing lysis buffer and cell suspension solutions to encapsulate cells in drops without premature lysis or mixing of cells prior to drop formation; a laminar flow boundary is just visible between the cell and lysis buffer streams. Panel 2: Drops containing cells flow through a 55° C. Incubation channel for 20 minutes to lyse cells and digest inhibitory proteins. Panel 3: Drops are split to allow for efficient picoinjection of 2× RT-PCR reagents and imaging on the droplet array FIG. 9, Panels A-C show TaqMan® RT-PCR in drops following picoinjection. Drops containing a limiting dilution of total RNA from the prostate cancer cell line PC3 were injected with an equal volume of 2× RT-PCR reagents and a TaqMan® probe targeting EpCAM, (Panel A). Following picoinjection, drops were thermocycled and imaged for fluorescence, (Panel B). The number of fluorescent drops was found to be in agreement with the prediction of a Poisson distribution, demonstrating adequate sensitivity to detect single transcript molecules in drops. Panel C: To further confirm the results, the drops from Panel B were chemically ruptured and their contents run on an agarose gel to observe the presence of PCR products in negative control drops that were injected without RT-PCR enzymes (−) and experimental drops that received both RT and Taq (+). Both control reactions performed in a tube with no picoinjection and picoinjected reactions produced bands of similar intensity, demonstrating that the reaction efficiency was comparable. White stars mark picoinjected drops.

Cell encapsulation, lysis, and proteinase K digestion are accomplished using an integrated microfluidic system (FIG. 8, Panels 1-3). Cells are co-encapsulated in 70 μm drops (200 pL) with lysis buffer containing non-ionic detergents and proteinase K using a 30×30 μm flow focus device. Importantly, the cells are not exposed to lysis buffer until they are encapsulated in drops, ensuring that no lysis occurs prior to encapsulation. This is enabled by the laminar flow conditions in the microfluidic channels, which ensure that diffusive mixing is negligible compared to the convection of the fluids. Following encapsulation, the close-packed drops move through a 55° C. Incubation channel for 20 min, to allow the cells to lyse and the proteinase K to digest inhibitory proteins. The drops are then split into equally-sized drops using a hierarchical splitter (FIG. 5; FIG. 8, Panel 3), producing drops of the ideal small size for picoinjection and Megadroplet Array imaging (FIGS. 12-13).

Figure 9:
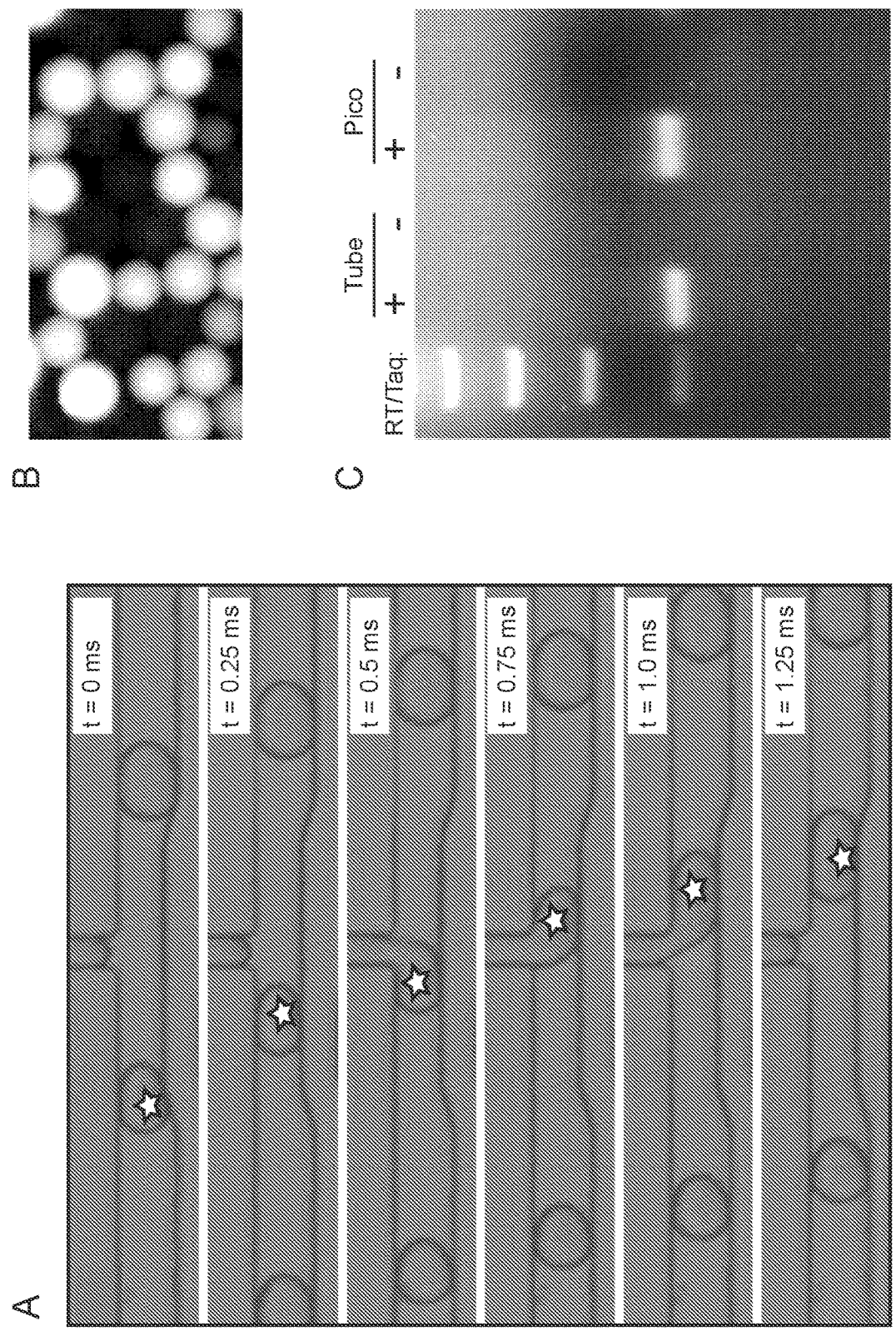
Figure 10:
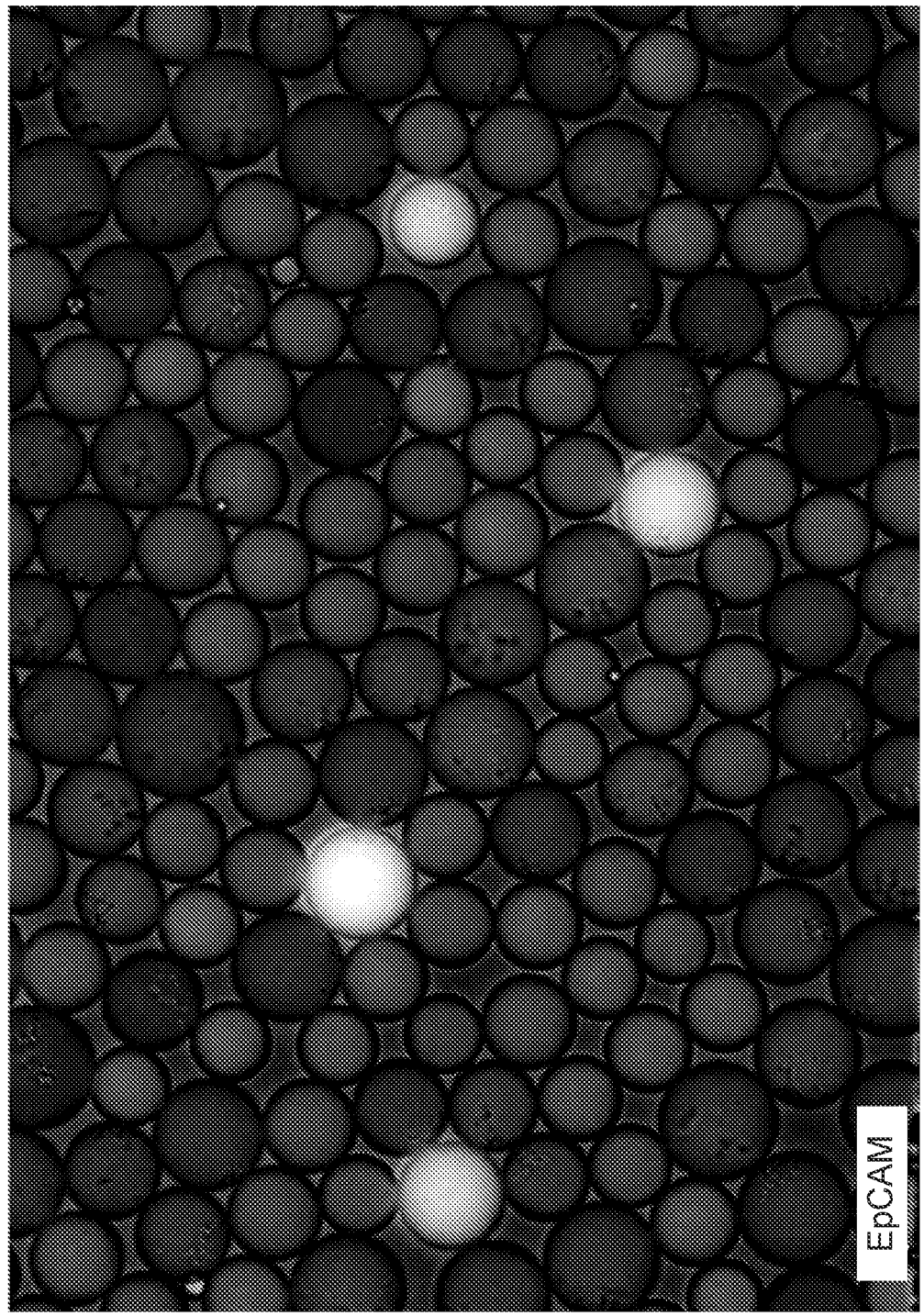
FIG. 10 shows detection of EpCAM transcripts from droplet encapsulated MCF7 breast cancer cells. Using the device depicted in FIG. 8, Panels 1-3, MCF7 cells were encapsulated in drops, lysed and drops were split. Lysate containing drops were then picoinjected with RT-PCR reagents and TaqMan® probes. Drops were then thermocycled and imaged for fluorescence. Brightfield and fluorescent channels are shown merged.

Prior to injection of the RT-PCR reagents and enzymes, the proteinase K is inactivated by heating the drops to 95° C. for 10 min. The drops are then injected with an equal volume of 2× primers and RT-PCR reagents (FIG. 9, Panel A). After picoinjection, the emulsion is collected into a PCR tube and thermal cycled. To determine whether a drop contains a cancer cell, TaqMan® probes are also included that hybridize to the EpCAM amplicons; this allows the probes to be hydrolyzed by the 5'-3' nuclease activity of Taq DNA polymerase, liberating the 5' fluorophore from the quenching 3' end modification making the drop fluorescent. By contrast, drops not containing cancer cells do not have EpCAM amplicons, so that the TaqMan® probes remain quenched and non-fluorescent (FIG. 4, Panels A-B). Hence, a bright drop relates the presence of an EpCAM positive cancer cell (FIG. 9, Panels B-C; FIG. 10). The thermocycled drops are injected into a flow cell 30 μm in height and 54 cm² in area; the narrow vertical gap of the flow cell forces the emulsion into a monolayer, allowing unobstructed epi-fluorescence visualization of every drop. For the fluorescence imaging, an automated microscope captures a mosaic of the entire flow cell and stores the images on a hard drive. The images are processed with custom Matlab code to identify fluorescent drops and measure their brightness. All data is stored digitally and analyzed using custom algorithms.

Example 2: Quantitative Multiplexed Assay

Figure 11:
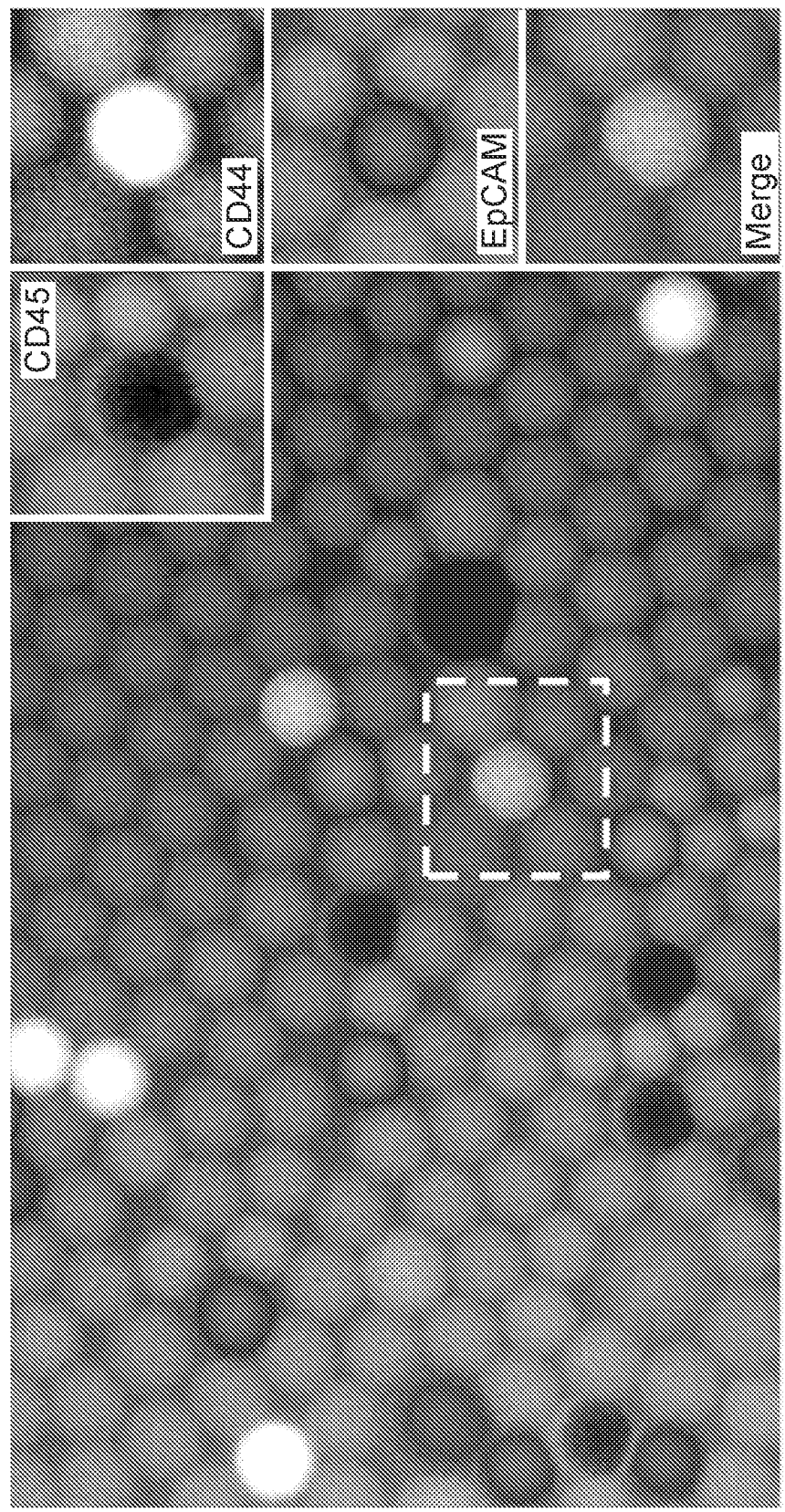
FIG. 11 depicts digital droplet RT-PCR multiplexing with TaqMan® probes. Limiting dilutions of total RNA from both Raji cells (B-lymphocytes) and PC3 prostate cancer cells were encapsulated in drops together with RT-PCR reagents and TaqMan® probes specific to CD45 (blue), CD44 (red) and EpCAM (green). Orange drops indicate the presence of both CD44 and EpCAM transcripts detected by a multiplex reaction. Other probe multiplexing combinations have also been seen (data not shown). Fluorescent channels are shown individually as a magnified inset for the dashed box region.

To screen more than one gene simultaneously, a multiplexed qPCR reaction may be utilized. Reactions were initially performed in bulk with PCR tubes to optimize reaction conditions. Using these methods, successful multiplexing was achieved during digital droplet RT-PCR for three TaqMan® probes, EpCAM, CD44 and CD45. An example of this multiplexing is shown in FIG. 11, where EpCAM and CD44 probes were multiplexed in drops containing both target transcripts. All PCR primer sets were designed to span large introns, making these larger genomic PCR products highly unlikely in multiplex reactions. Additionally, all TaqMan® probes are designed to hybridize to exon-exon junctions. The current probe sets do not recognize gDNA.

Single-cell qPCR with Megadroplet Arrays: To perform qPCR analysis on single cells, the drops are imaged as they are thermal cycled. This requires that the drops be held at fixed positions during thermal cycling so they can be repeatedly imaged. The microfluidic system used to prepare the drops was prepared as described above and in Example 1. After the drops are formed and loaded with cells and qPCR reagents, they are introduced into a Megadroplet Array (FIG. 12, Panels A-C; FIG. 13). The array consists of channels in which the channel ceilings are indented with millions of circular traps 25 μm in diameter. When the drops flow into the array, they are slightly pancaked in shape because the vertical height of the flow channel is 15 μm, or 10 mm shorter than the drops. When a drop nears a trap, its interface adopts a larger, more energetically favorable radius of curvature. To minimize its surface energy, the drop will entirely fill the trap, allowing it to adopt the lowest, most energetically favorable, average radius of curvature. The capillary pressure of the drop is several orders of magnitude larger than the shear exerted by the flow, ensuring that the drops remain intact and confined in the traps. After a trap is occupied by a drop, no other drops are able to enter because the trap will be large enough to fit only one drop; additional drops are diverted downstream, to occupy the first vacant trap they encounter. The array is filled using a close-packed emulsion, and thus every trap is occupied by a drop. After the droplet array is filled, oil is injected to remove excess drops and the array is thermal cycled and imaged.

Thermal system for temperature cycling and imaging: Once the array is filled with drops and cells, the device is thermal cycled while simultaneously imaging the drops, to obtain the time-dependent information necessary for qPCR.

The thermal cycling is accomplished using a custom heater consisting of a Peltier plate, heat sink, and control computer (FIG. 13). The Peltier plate permits heating or cooling the chip above or below room temperature by controlling the applied current. To ensure controlled and reproducible temperature, a computer monitors the temperature of the array using integrated temperature probes, and adjusts the applied current to heat and cool as needed. A copper-plate allows uniform application of heat and dissipation of excess heat during cooling cycles, enabling cooling from 95° C. to 60° C. in under 1 min execution of the qPCR assay in under two hours. To image the droplets during temperature cycling, a customized Canoscan 9000F scanner bed having a resolution of 9600 dpi by 9600 dpi is utilized. For 10 million hexagonally-packed 25 µm drops (54 cm$^2$), 800 million pixels are required at highest resolution. With a resolution of 20 pixels per drop, the full image may be captured in 3 s. The array is imaged several times per cycle with different excitation and emission filters to visualize the different dyes for the multiplexed TaqMan® probes.

Example 3: Electrode-Free Picoinjection of Drops of Microfluidic Drops

Microfluidic devices were fabricated in poly(dimethylsiloxane) (PDMS) using soft photolithographic techniques. The devices had channel heights of 30 µm, optimal for the picoinjection of water-in-oil droplets that are 50 µm in diameter. The device design is similar to those described previously by Abate, et al. *Proc. Natl. Acad. Sci. U.S.A.*, 2010, 107, 19163; the disclosure of which is incorporated herein by reference. An important difference, however, is that the channels for the metal solder electrodes are removed. Further, a "Faraday Mote"—an empty channel filled with a conducting aqueous solution—is implemented that runs between the injection site and the droplet spacer, as shown in FIG. 15, Panel B. The mote electrically isolates re-injected drops upstream of the picoinjection site from electric fields emanating from the picoinjector, preventing unintended merging. The emulsion that was picoinjected consists of monodisperse droplets of 3.8 mM fluorescein sodium salt ($C_{20}H_{10}Na_2O_5$) dissolved in Milli-Q $H_2O$. The droplets are suspended in a carrier oil of Novec HFE-7500 fluorinated oil with 2% (wt/wt) dissolved biocompatible surfactant. The picoinjection fluids consist of a dilution series of NaCl ranging from 0 to 500 mM, each containing 3.8 mM fluorescein sodium salt. This range of concentrations reflects the molarities of dissolved ions present in most biological buffers and reagents. Thus, since in most applications the fluids will already contain the requisite ions, the technique can be used without adding additional reagents to the solutions.

Droplets and carrier oil were introduced via syringe pumps (New Era) and spaced using the same carrier oil and surfactant mixture described above (FIG. 15, Panels A-B). The picoinjection fluid was contained in a BD Falcon tube. Through the cap of the Falcon tube was submerged a wire electrode into the fluid, as illustrated in FIG. 15, Panel A. Gaps in the cap were sealed with LocTite UV-cured epoxy. The picoinjection fluid was charged using a function generator outputting a 10 kHz sinusoidal signal ranging from 0 to 5 volts. This output was amplified 1000× by a Trek 609E-6 model HV amplifier. The positive output of the amplifier was attached via an alligator clip to the wire submerged in the picoinjection fluid. The ground electrode of the amplifier was attached to the metal needle of a syringe containing a 1 M solution of NaCl, introduced into the Faraday Mote (FIG. 15, Panel A). The two electrodes were never in electrical contact and the emulsions exiting the device were collected into separate, electrically isolated containers to avoid a closed circuit and prevent current flow.

The picoinjected reagent was infused into the device through PE-2 tubing (Scientific Commodities) using an air pressure pump (ControlAir Inc.) controlled by custom LabVIEW software. The injection fluid was pressurized such that the oil/water interface at the picoinjection orifice is in mechanical equilibrium with the droplet channel; the pressure difference across the interface is equal to the Laplace pressure, causing the injection fluid to bulge into the droplet channel without budding off and forming its own drops (FIG. 15, Panel C). For this device, drops and spacer oil were injected the at flow rates of 200 and 400 µL hr$^{-1}$, respectively. At these flow rates, the picoinjection fluid interface is in mechanical equilibrium for an applied pressure of ~13 psi. The lengths of the tubing carrying the injection fluid and solution serving as a Faraday mote was controlled, since longer tubes have higher electrical resistance and may attenuate the AC signal applied to trigger picoinjection.

To picoinject drops with reagent, the previously formed monodisperse emulsion was re-injected into the picoinjection device. The emulsion was introduced at a high volume-fraction such that there is little carrier oil and the drops are packed together. The packed drops traveled through a narrowing channel that forced them single file. Additional oil with surfactant is added from two perpendicular channels, spacing the drops evenly, as shown in FIG. 15, Panel B. A simple T-junction spacer was also found to work. The droplets then passed the picoinjector, a narrow channel containing the reagent to be added. To trigger picoinjection, the voltage signal was applied to the electrode submerged in the injection fluid, generating an electric field at the picoinjector as the drops pass the injection site. This caused the drops to coalesce with the injection fluid. As they traveled past, fluid was injected into them through a liquid bridge formed after the two fluids coalesce. The applied signal must have zero offset to prevent electrophoretic migration of charged particles in the solutions. Additionally, the frequency of the signal must be high enough to ensure that during the act of injecting, the sign of the field switches many times between positive and negative, so that the net charge of the fluid added to the droplets is approximately zero. This ensured that the droplets leaving the injector have zero net charge, which was important for ensuring that they remain stable. A 10 kHz signal was applied.

To analyze the behavior of the picoinjector, the injection site was observed under a microscope. In the absence of an electric field, a distinct boundary was observed between the droplet and the injection fluid, as shown in FIG. 16, Panel A. When a 250 V signal was applied to the picoinjector, the boundary vanishes and droplet coalescence is visible, as demonstrated in FIG. 16, Panel B. Thus, electrification of the injection fluid is adequate to trigger picoinjection, demonstrating that electrically-isolated electrodes are not needed.

To determine if it were possible to vary the injection volume using the applied voltage, voltage was varied between 0-5000V and the volume change of the resulting droplets was measured. Injection volume was quantified with an optical fluorescence detection setup. As the drops passed a 472 nm wavelength laser focused on the droplet channel ~1 cm downstream of the picoinjector, the emitted fluorescence signal from the dissolved fluorescein contained within the drops was amplified by a photomultiplier tube (PMT) and converted to a voltage signal analyzed with LabVIEW FPGA. As the drops passed the laser, their fluorescence signals resembled square waves as a function of time, with amplitudes and widths that corresponded to the drop intensity and length, respectively. The drops had a spherical diameter larger than the dimensions of the channel, causing them to be cylindrical in shape. Thus, the drop volume is approximately linear as a function of length. To calculate the volume fractional (Vf) increase, the ratio of the drop length before and after picoinjection was measured. These measurements were repeated for a range of applied voltages and molarities of NaCl in the injection fluid.

Figure 17:
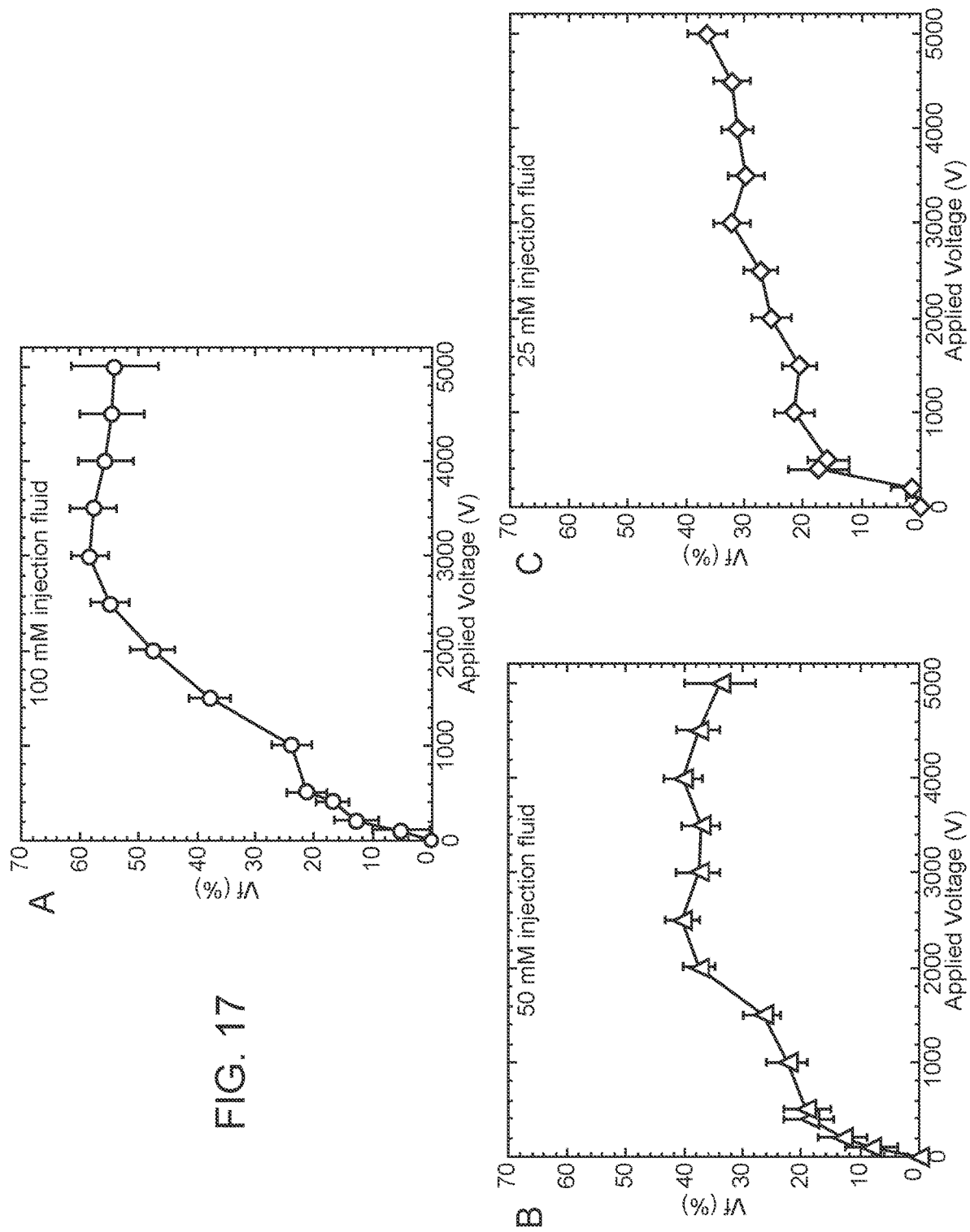
FIG. 17, Panels A-C show the volume fraction increase (Vf) of drop size after injection for (Panel A) 100 mM, (Panel B) 50 mM, and (Panel C) 25 mM injection fluids. A stronger electric field more readily ruptures the oil/water interfaces allowing injection over a larger length of the passing droplets, and larger injection volumes. Higher molarities of dissolved electrolytes produce stronger electric fields at the injection site for a given voltage, also increasing injection volume. The error bars represent 1 standard deviation in either direction for >1200 drops sampled at each point.

The increase in volume was plotted as a function of applied voltage for three representative molarities of injection fluid in FIG. 17, Panels A-C. In all cases the injection volume increased with the applied voltage, though this effect is most prominent for the 100 mM injection solution shown in FIG. 17, Panel A. The dependence of the droplet volume on the applied voltage may be attributed to the observation that the droplets are not perfect cylinders as they travel past the picoinjector; instead they have a "bullet" shape, with the leading edge having a smaller radius of curvature than the trailing edge. Consequently, as the drops pass the picoinjector, the thickness of the oil layer separating their interface from the bulge of the picoinjection fluid decreases. For an electrically-induced thin-film instability, the threshold voltage required to rupture the interface depends on the thickness of the film, decreasing as the film gets thinner. Hence, because the film thickness decreases as the drops pass the picoinjector, the moment of coalescence depends on electric field magnitude: for higher fields it is possible to rupture thicker films, leading to picoinjection at an earlier point; conversely, for lower fields thinner films are ruptured, causing picoinjection to start at a later point. Because the volume injected depends on the duration of picoinjection, it therefore also depends on applied voltage. This is supported by data which shows a dependence on applied voltage for all molarities (FIG. 17, Panels A-C). It was also observed that the curves relating volume injected to applied voltage are lower for lower molarities, as shown for the 50 mM and 25 mM data in FIG. 17, Panels B and C, respectively. This may be attributable to the fact that lower molarity solutions have a lower conductivity, and can thus attenuate the AC signals used to trigger injection, reducing the volume injected for a particular applied voltage.

Above 3000V and 100 mM, the injected volume begins to decrease and the variability in drop size increases. In images of these systems at these voltages, it was observed that the picoinjection fluid is no longer held at equilibrium in the picoinjection orifice, but instead wets the channel walls and buds off small drops into the flow channel.

Figure 18:
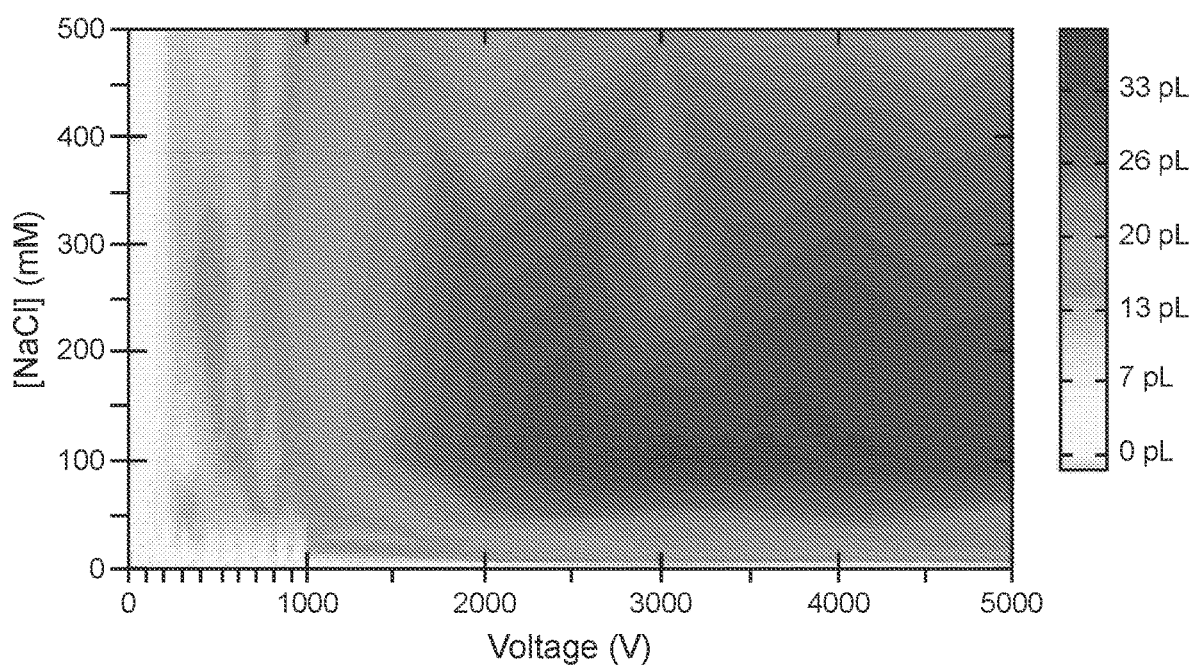
FIG. 18 is a heat map showing injection volume as a function of applied voltage and the molarity of dissolved NaCl in the injection fluid. Arrows/ticks indicate data points. The injection volume can be adjusted in the range of 0-36 pL with a resolution of ~2.6 pL 5 (4% Vf) with 100V increments of the applied signal. The largest injected volumes were 3000 V with the 100 mM fluid. Increasing electric field above this allows for electrowetting, causing drops to spontaneously form at the picoinjector, adversely affecting injection efficacy and consistency.
Figure 19:
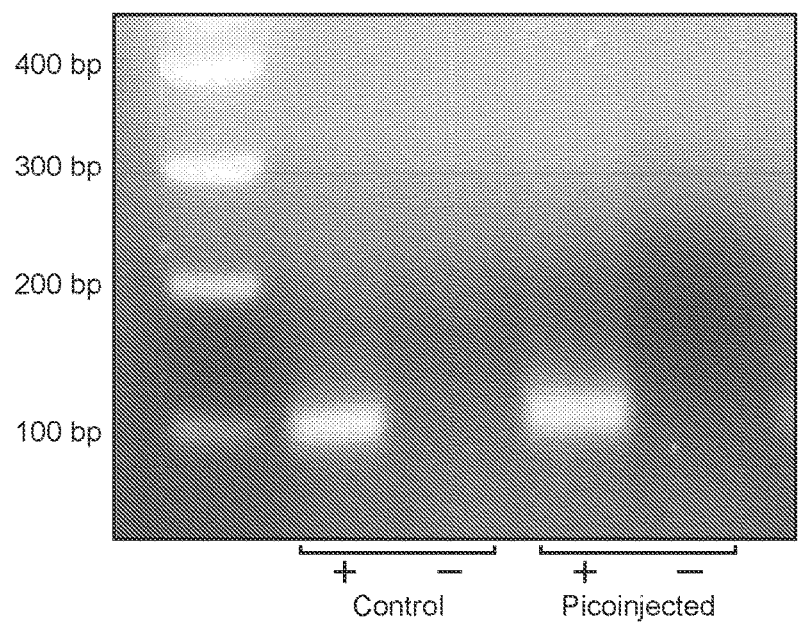
FIG. 19 shows ethidium bromide stained 2% agarose gel. Total RNA isolated from an MCF7 human cell line was encapsulated in drops and picoinjected with an RT-PCR reaction mixture either with (+) or without 50 (−) reverse transcriptase (RT) and Taq DNA polymerase. Non-emulsified control reactions were performed in parallel. Only reactions receiving enzyme generated the expected 100 bp amplicon. Both positive control and picoinjected reactions produced PCR products, demonstrating that the electric field generated during picoinjection is 55 biologically compatible with DNA, reverse transcriptase, and Taq.

To characterize the behavior of the electrode-free picoinjector for all parameters, injection volume was measured as a function of molarity and applied voltage and the resulting data was plotted on a 2D heat-map (FIG. 18). This data demonstrates that the technique should allow controlled picoinjection for most biological buffers, which commonly have molarities within the tested range.

To investigate whether the electric fields and currents generated by the high-voltage signal may disrupt biomolecules needed for downstream assays, the picoinjector was used to prepare droplets for an RT-PCR reaction. Drops containing total RNA isolated from an MCF7 human cell line were picoinjected with an RT-PCR reaction mixture containing the enzymes reverse transcriptase (RT) and Taq DNA polymerase. Negative-control drops were injected with a mixture containing no enzymes. Additional non-emulsified positive and negative control reactions were performed in parallel with the same RT-PCR mixture. Following thermocycling, the emulsions were broken and the amplification products visualized on an ethidium bromide-stained 2% agarose gel. The positive control and picoinjected drops showed PCR bands of comparable intensity for the expected 100 bp amplicon length, as visible in FIG. 19. In contrast, the negative controls showed no amplification, demonstrating that applying the triggering signal to the picoinjection fluid is sufficiently biocompatible so as to allow downstream RT-PCR reactions in drops.

Example 4: Coalescing Triple-Emulsions to Add Reagent to Droplets

One step, which may be important in running a droplet reaction, is the ability to add reagents to pre-existing drops. As an example, drop addition might be beneficial if a final drop reaction requires a reagent that could be denatured in a prior heating step. If no drop-stabilizing surfactants are used, adding reagent can be as simple as bringing a drop in contact with a second reagent-filled one. Standard drop processing and storage often require surfactant-stabilized drops, however, and localized electric fields have been utilized to selectively disrupt and merge pairs of drops. Merging involves timing the flow of original and reagent drops so that they pair up and are in contact. A second strategy uses electric fields to destabilize a passing drop so it can be injected with reagent from a side channel. This avoids the issue of synchronization, but has the disadvantage that each drop is potentially cross-contaminated when joined with the side channel. Furthermore, only a volume less than or equal to the passing drop can be injected.

Rather than merging or injecting reagents with a drop, presented here is a different scheme where the original drop is enveloped within a larger reagent droplet and then both are coalesced via application of an electric field. In some embodiments, this enveloping facilitates the pairing of one original drop with one reagent envelope. The contained nature of the mixing may also limit cross-contamination and facilitate the addition of arbitrary volumes as compared with a droplet injector.

The drop-envelope pairing is made possible with surface chemistry. To reduce interfacial energy, a hydrophilic channel encapsulates an oil-coated drop in aqueous reagent if available. A subsequent hydrophobic channel then encapsulates it in oil, creating a stable water-in-oil drop in a water-in-oil drop, or triple emulsion (E3). This technique of alternating channel hydrophobicity has each low-order emulsion triggering the formation of the next higher one, with reliable quintuple emulsions even possible. The triggering leads to the proper pairing of one original drop per envelope. Once there, the original drop surface is in maximal contact with the inner surface of the reagent envelope, facilitating later electro-coalescence. This contact means that any volume of reagent could be added to the original drop, from a thin-shelled reagent envelope of fractional volume to an envelope $10^2$, $10^3$, $10^4$ or more times larger.

Figure 23:
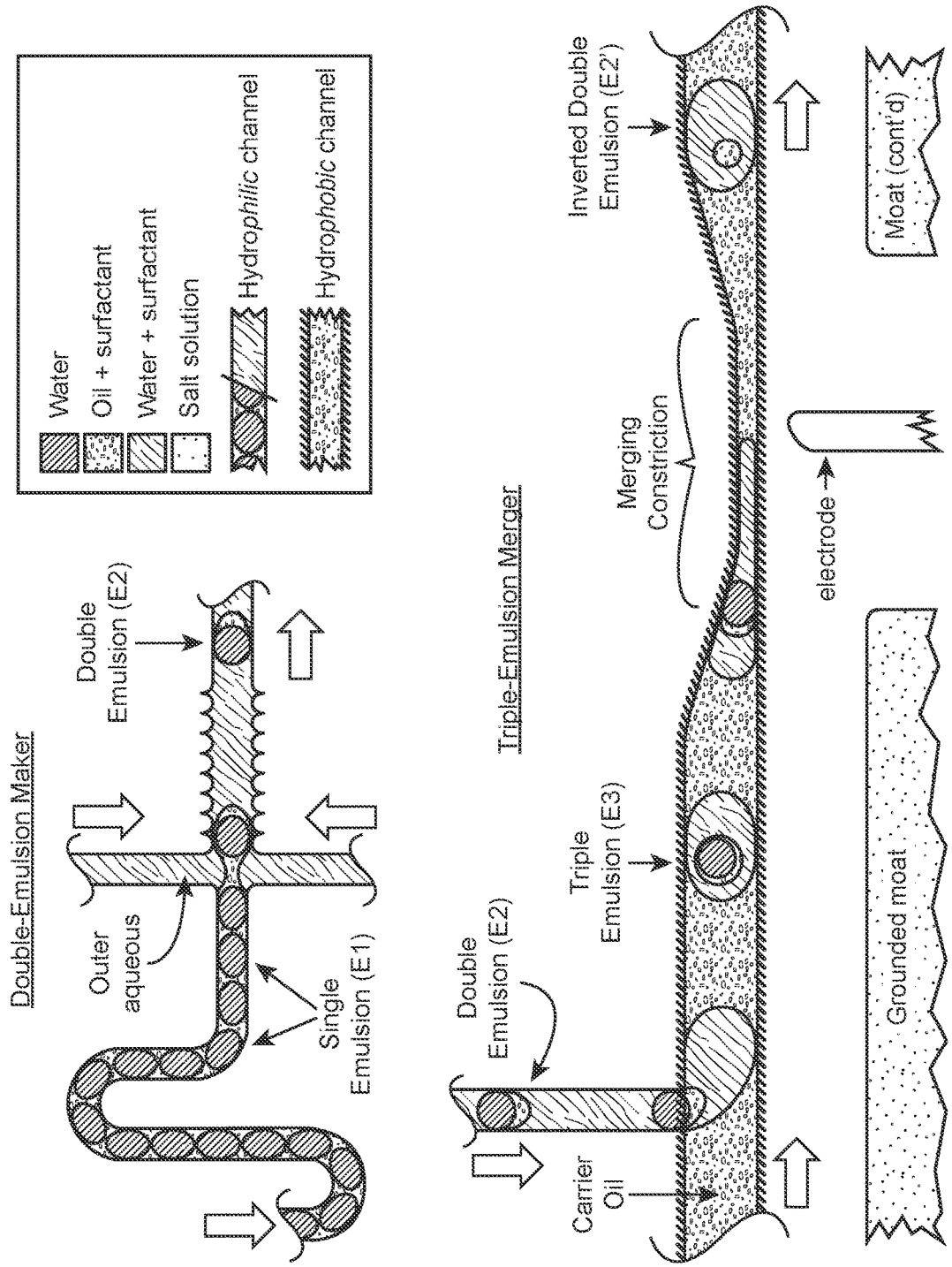
FIG. 23 shows a schematic of a coalescence process, starting with the formation of double emulsions (E2) from a reinjected single emulsion (E1) in a hydrophilic channel (top, left). These are turned into triple emulsions (E3) at a hydrophobic junction (bottom, left), which are then coalesced using an electric field into an inverted E2 (E2', bottom, right).

A detailed schematic of the E3 scheme is shown in FIG. 23. First, a premade, water-in-oil emulsion (E1) was reinjected into the device through a hydrophilic channel (FIG. 23, top left). The drops met a junction where co-flowing reagent pinched them off individually, surrounding them to reduce surface repulsion. The oil of the E1 formed thin, stable shells that housed each original drop. The channel immediately after the junction was designed to include ridges as described herein to traps pockets of aqueous fluid. This prevented oil from contacting the walls during budding and potentially altering their hydrophobicity. The water-in-oil-in water double emulsion (E2) then traveled to a second junction where it met a hydrophobic channel carrying oil (FIG. 23, bottom left) (Additional description and characterization of double emulsions and their formation are provided in the descriptions of FIGS. 38-51). Here, the aqueous reagents were repelled from the walls, and formed an E3 drop. In the figure, the E2 is shown in the process of seeding the E3 by weakening the adhesion of the reagent fluid to the hydrophilic channel. The volume ratio of reagent to the original E1 drops was determined by the flow rates at the first junction.

After formation, the E3 was passed into a narrow constriction and coalesced with an electric field. The electric field was generated between two salt-solution containing channels, an electrode carrying a high, alternating voltage and a grounded moat (FIG. 23, bottom). The constriction may have facilitated application of the electric field to the drops because the reagent envelope likely contained mobile ions that could screen the interior from the electric field. As seen in the figure, constricting the E3 forces the inner drop to the channel wall. After coalescing, the oil shell collapsed and became the innermost phase of an inverted oil-water-oil double emulsion (E2').

The device itself was constructed using conventional PDMS fabrication techniques. First, a master was made by spinning layers of SU-8 resist onto a silicon wafer and sequentially exposing them with UV light (Blakray) and a patterned mylar mask (Fineline Imaging). After developing in CD-30, the SU-8 master was covered in PDMS (PDMS manufacturer) with a 10:1 polymer to cross-linker mix, placed in vacuum to remove trapped air, and baked for 1 hour at 75° C. The device was then extricated and given access holes with a 0.75 mm biopsy punch. Next, the device was bonded to a 1 mm-thick glass slide by exposing both to 1 mbar $O_2$ in a 300 W plasma cleaner for 20 s, attaching, and then baking for 10 min at 75° C.

The final processing steps created the hydrophilic and hydrophobic channels. First, Aquapel® was flowed backwards through the device, into the drop outlet and out the carrier oil inlet. At the same time, the drop reinjector inlet was pressurized with 15 psi air to prevent the Aquapel® from entering the double-emulsion, hydrophilic section of the device. Next, the same inlets exposed to Aquapel® were plugged with PEEK tubing (Resolution Systems, TPK.515-5M) and the device was re-exposed to 1 mbar $O_2$ plasma in the same cleaner for 1 min. The plasma made exposed channels hydrophilic, while the plugs kept the hydrophobic channels as they were. This hydrophilic treatment was only semi-permanent, and other methods not used here are capable of creating robust hydrophilic channels.

To operate, syringes filled with the appropriate fluids were connected to the finished device via PE-2 tubing (Scientific Commodities, #BB31695) and the same PEEK tubing and pressurized using syringe pumps (New Era). The reinjected drops consisted of Milli-Q water in a fluorinated oil (Novec HFE 7500) with a 1% w/w biocompatiable surfactant. The drops were flowed at a relatively slow flow rate of 20 µL/hr, and a snaking channel was used (FIG. 23, top left) to add flow resistance and filter any pressure fluctuations. The test reagent was PBS buffer (model #) with 0.1% pluronic surfactant (model #), and the carrier oil was the same as with the reinjected drops. These were flowed at equal rates between 200 µL/hr and 1200 µL/hr. The electrodes and moat were filled with 3.0 NaCl solution. The electrode, which was a dead end, was pressurized with a solution-filled syringe until air in the channel was absorbed by the PDMS. It was connected to a 20 kHz high voltage oscillator (JKL Components Corp, BXA-12579) running at 500 V. Such large voltages applied to merge or inject drops have been shown to be biologically compatible.

Figure 24:
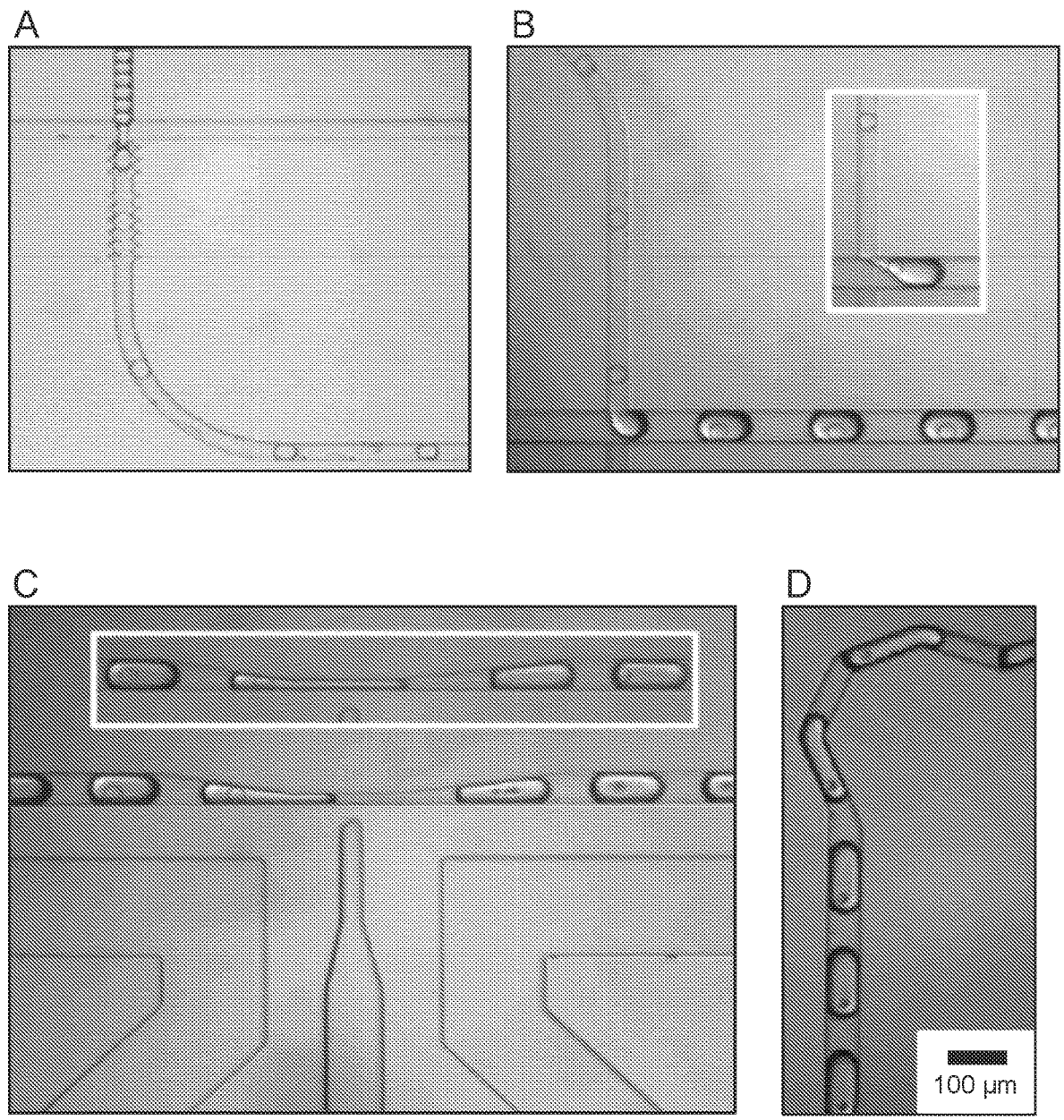
FIG. 24, Panels A-D show microscope images of (a) double emulsions (E2) formation, (b) triple emulsion (E3) formation, (c) E3 coalescence, and (d) the final inverted E2 (E2') products. The scale bar applies to all images.

FIG. 24 shows microscope images of the running E3 device. The reinjected E1 travelling from the top of FIG. 24, Panel A, are starkly outlined because the disparate oil and water indices of refraction bent the back lighting. After the E1 was encapsulated at the junction by reagent flowing from the sides and became an E2, the inner and outer indices of refraction matched and the borders became much fainter. This is an indication of the thinness of the oil shell, which did not appreciably refract. In FIG. 24, Panel A, the E1 consisted of 30 µm-diameter drops (15 pL), and all channels here were hydrophilic and square, 30 µm to a side.

At the next junction, seen in FIG. 24, Panel B, the E2 exited the hydrophilic channel as an E3 in a large square, hydrophobic channel, 60 µm to a side. As with the initial emulsion, the edges of these E3 drops were clearly visible due to refractive mismatch. Conceivably, this step could have caused timing issues because the inner E1 needed to synchronize with the large drop formation. However, this problem was avoided because the arrival of the E1 at the junction weakened the adhesion of the reagent phase to the hydrophilic channel and induced budding. The process is shown in the inset of FIG. 24, Panel B, and caused a very regular loading of E1 into the E3.

The coalescence of the E3 is shown in FIG. 24, Panel C. The 60 µm-wide channel narrowed to 15 µm, squeezing the E1 against the walls where the electric field from the electrode could penetrate. The new E2' product of coalescing can be seen on the right. The collapsed oil remnants appear in high contrast and have a volume of roughly 2 pL, corresponding to an original oil shell that was 1 µm thick. The remnants could conceivably have merged with the carrier oil during coalescence except for the fact that the E3 was squeezed against the channel wall where there is no oil. In the inset, the constriction is shown without electric field. No coalescence occurred and the constriction moved the inner phases to the rear. The regularity of coalescence is demonstrated in FIG. 24, Panel D, the top of which shows a mixing channel for homogenizing the aqueous contents of the drop.

Figure 25:
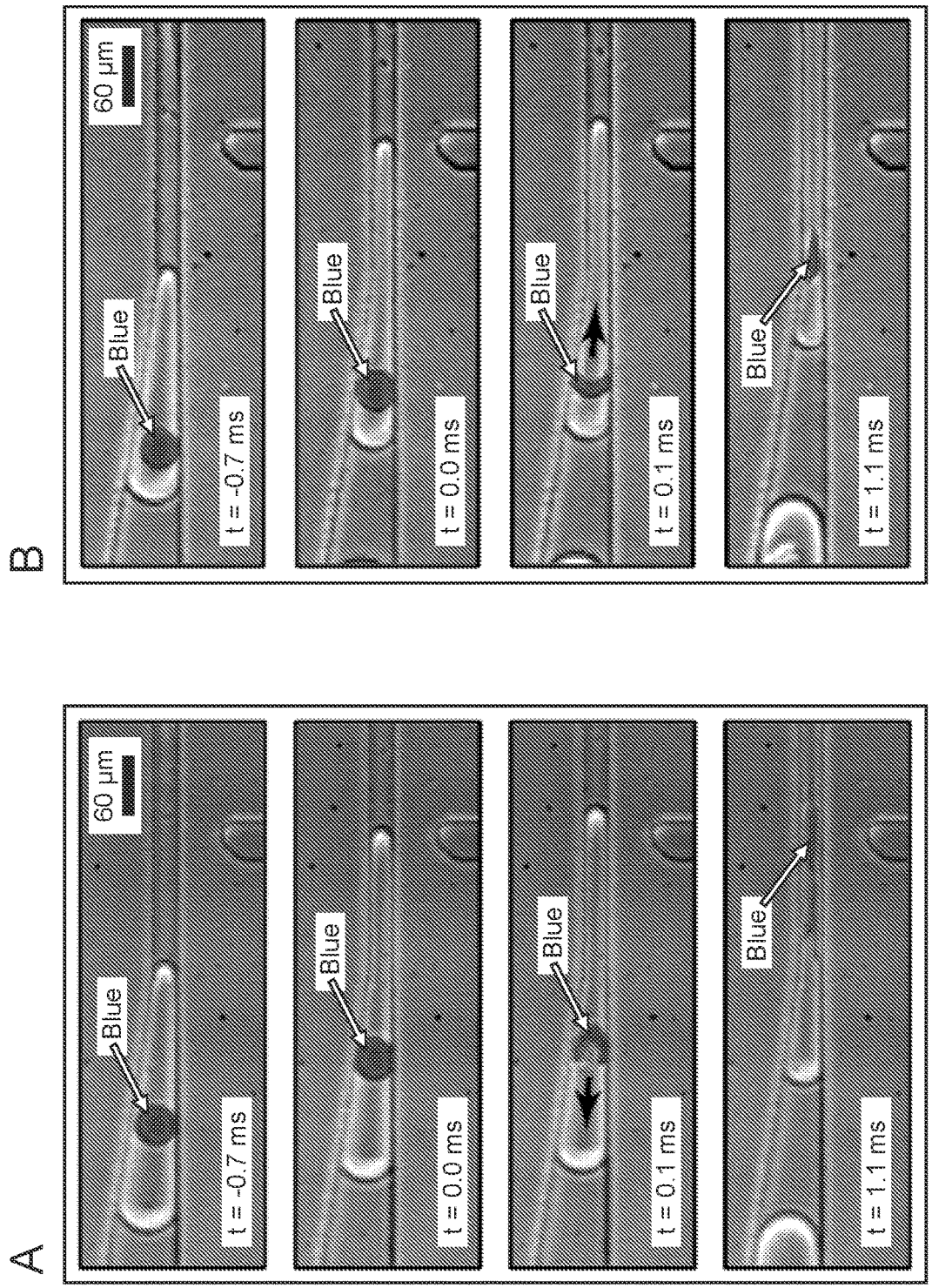
FIG. 25, Panels A-B show two fast-camera time series showing E3 coalescence into E2'. The oil shell of the inner E1 is false-colored blue.

The precise dynamics of E3 coalescing were determined using a fast camera. Two time series are shown in FIG. 25, with the oil shell of the inner E1 highlighted in blue (indicated by arrows in FIG. 25). Each starts out at a time t=−0.7 ms where the inner E1 was not yet constricted and was spherical. Time t=0.0 ms was set immediately before rupturing when the E1 was pinned against the constriction walls and slightly flattened. By next frame, t=0.1 ms, the E1 ruptured. In FIG. 25, Panel A, the rupturing ejected contents of the E1 to the back of the drop, whereas in FIG. 25, Panel B, the contents were ejected forward. In high-order emulsions, the unconstrained surface of an inner phase will be tangent somewhere with the surface of the next outermost phase to reduce interfacial energy (i.e. the phases are never perfectly concentric). This randomly positioned contact point helps merging and may determine where the drop ruptures. After rupturing, the oil shells collapsed as shown in the frame at t=1.1 ms.

The robustness of this process depends on the appropriate channels being hydrophilic or hydrophobic. If the first section of the device is not sufficiently hydrophilic, the oil of E1 may wet the channel walls immediately after the junction. Instead of travelling as spheres down the center of the channel as in FIG. 24, Panel A, they may travel as hemispheres down the side and slip into the carrier fluid at the next junction as a single emulsion rather than enveloped. If the second section of the device is not sufficiently hydrophobic, there may be electro-wetting at the constriction and small satellite drops will buff off at the tail of the passing E3. As is, this scheme produces aqueous drops with oil in them (E2') as opposed to the pure aqueous drops (E1) of the merger and injector strategies mentioned previously. Depending on the desired product, this might be acceptable; otherwise, various techniques like microfluidic centrifuges or drop splitting can be employed to remove the oil.

From the study described, a triple emulsion coalescence strategy was demonstrated to be a robust method for adding a reagent to a collection of drops. Such triple emulsion coalescence was carried out without loss of drops or drop mixing, owing to the surface chemistry of the channels rather than careful synchronization.

Example 5: Picoinjection Enables Digital Detection of RNA Molecules with Droplet RT-PCR Most biological assays require the stepwise addition of reagents at different times. For microfluidic techniques to be most widely useful, a robust procedure for adding reagents to drops is therefore important. One technique for accomplishing this is electrocoalescence of drops, in which the reagent is added by merging the drop with a drop of the reagent using an electric field. Another technique is picoinjection, which injects the reagent directly into the drops by flowing them past a pressurized channel and applying an electric field. An advantage of picoinjection is that it does not require the synchronization of two streams of drops, making it easier to implement and more robust in operation. However, variability in the volume injected from drop to drop and the potential degradation of reagents by the electric field may interfere with assays. In addition, during picoinjection, the drops temporarily merge with the reagent fluid, potentially allowing transfer of material between drops, and cross-contamination.

This study investigated the impact of picoinjection on biological assays performed in drops and the extent of material transfer between drops. Using sensitive digital RT-PCR assays, it is shown that picoinjection is a robust method for adding reagents to drops, allowing the detection of RNA transcripts at rates comparable to reactions not incorporating picoinjection. It was also determined that there is negligible transfer of material between drops. The benefit of workflows incorporating picoinjection over those that do not is that picoinjection allows reagents to be added in a stepwise fashion, opening up new possibilities for applying digital RT-PCR to the analysis of heterogeneous populations of nucleic acids, viruses, and cells.

Materials and Methods

Microfluidic Device Fabrication

The microfluidic devices consisted of polydimethylsiloxane (PDMS) channels bonded to a glass slide. To make the PDMS mold, a device master was first created by spinning a 30 mm-thick layer of photoresist (SU-8 3025) onto a silicon wafer, followed by a patterned UV exposure and resist development. Next, an uncured mix of polymer and crosslinker (10:1) was poured over the master and baked at 80° C. for 1 hour. After peeling off the cured mold, access holes were punched in the PDMS slab with a 0.75 mm biopsy coring needle. The device was washed with isopropanol, dried with air, and then bonded to a glass slide following a 20 s treatment of 1 mbar $O_2$ plasma in a 300 W plasma cleaner. To make the devices hydrophobic, the channels were flushed with Aquapel® and baked at 80° C. for 10 min RNA Isolation Human PC3 prostate cancer or Raji B-lymphocyte cell lines were cultured in appropriate growth medium supplemented with 10% FBS, penicillin and streptomycin at 37° C. with 5% $CO_2$. Prior to RNA isolation, Raji cells were pelleted and washed once in phosphate buffered saline (PBS). Confluent and adhered PC3 cells were first trypsinized prior to pelleting and washing. Total RNA was isolated from cell pellets using an RNeasy Mini Kit (Qiagen). Total RNA was quantified using a spectrophotometer and the indicated amounts (between 150 and 1000 ng) of RNA were used in subsequent 25 ml RT-PCR reactions.

TaqMan® RT-PCR Reactions

The sequence of amplification primers used for the RT-PCR reactions were as follows: EpCAM Forward 5'-CCTATGCATCTCACCCATCTC-3' (SEQ ID NO:1), EpCAM Reverse 5'-AGTTGTTGCTGGAATTGTTGTG-3' (SEQ ID NO:2); CD44 Forward 5'-ACGGTTAACAATAGTTATGGTAATTGG-3' (SEQ ID NO:3), CD44 Reverse 5'-CAACACCTCCCAGTATGACAC-3' (SEQ ID NO:4); PTPRC/CD45 Forward 5'-CCATATGTTTGCTTTCCTTCTCC-3' (SEQ ID NO:5), PTPRC/CD45 Reverse 5'-TGGTGACTTTTGGCAGATGA-3' (SEQ ID NO:6). All PCR primers were validated prior to use in microfluidic droplet experiments with tube-based RT-PCR reactions. Products from these reactions were run on agarose gels and single bands of the predicted amplicon size were observed for each primer set. The sequence of the TaqMan® probes was as follows: EpCAM 5'-/6-FAM/ATCTCAGCC/ZEN/TTCTCATACTTTGCCATTCTC/IABkFQ/-3' (SEQ ID NO:7); CD44 5'-/Cy5/TGCTTCAATGCTTCAGCTCCACCT/IAbRQSp/-3' (SEQ ID NO:8); PTPRC/CD45 5'-/HEX/CCTGGTCTC/ZEN/CATGTTTCAGTTCTGTCA/IABkFQ/-3' (SEQ ID NO:9). Pre-mixed amplification primers and TaqMan® probes were ordered as a PrimeTime Standard qPCR assay from Integrated DNA Technologies (IDT) and were used at the suggested 1× working concentration. Superscript III reverse transcriptase (Invitrogen) was added directly to PCR reactions to enable first stand cDNA synthesis. Following emulsification or picoinjection of RT-PCR reagents, drops were collected in PCR tubes and transferred to a T100 Thermal Cycler (BioRad). Reactions were incubated at 50° C. for 15 min followed by 93° C. for 2 min and 41 cycles of: 92° C., 15 s and 60° C., 1 min.

Emulsion Generation and Picoinjection

The reaction mixtures were loaded into 1 mL syringes and injected into microfluidic T junction drop makers using syringe pumps (New Era) controlled with custom LabVIEW software. The dimensions of the device and flow rates of the reagents were adjusted to obtain the desired 30 mm drop size. To apply the electric field for picoinjection, the electrode and surrounding moat channels were filled with a 3M NaCl solution, having a conductivity of ~0.1 S/cm. The electrode was energized using 20 kHz, 300 VAC signals generated by a fluorescent light inverter (JKL Components Corp) attached via an alligator clip to the syringe needle.

Immunofluorescence Imaging

To image the thermocycled droplets, 10 mL of emulsion were pipetted into Countess chambered coverglass slides (Invitrogen). The slides were imaged on a Nikon Eclipse Ti inverted microscope using conventional widefield epifluorescence and a 4× objective. Fluorescence filters were chosen to optimize the signal intensity and to mitigate background fluorescence due to spectral overlapping of the dyes used in the multiplexed reactions. The images were captured using NIS Elements imaging software from Nikon.

Data Analysis

The droplet images were analyzed using custom MATLAB software. For each field of view, brightfield and fluorescence images were captured. The software first located all drops in the brightfield image by fitting circles to the drop interfaces. Next, the light background in the fluorescence images was subtracted using a smooth polynomial surface constrained to vary over size scales much larger than the drops. The software then measured the average fluorescence intensity within each droplet's circular boundary. The resultant intensity values were offset so that the cluster of lowest intensity (empty) had an average of zero. Drops were determined to be "positive" or "negative" based on whether their intensity fell above or below, respectively, a defined threshold.

Results

Detection of RNA Transcripts in Picoinjected Drops.

Figure 26:
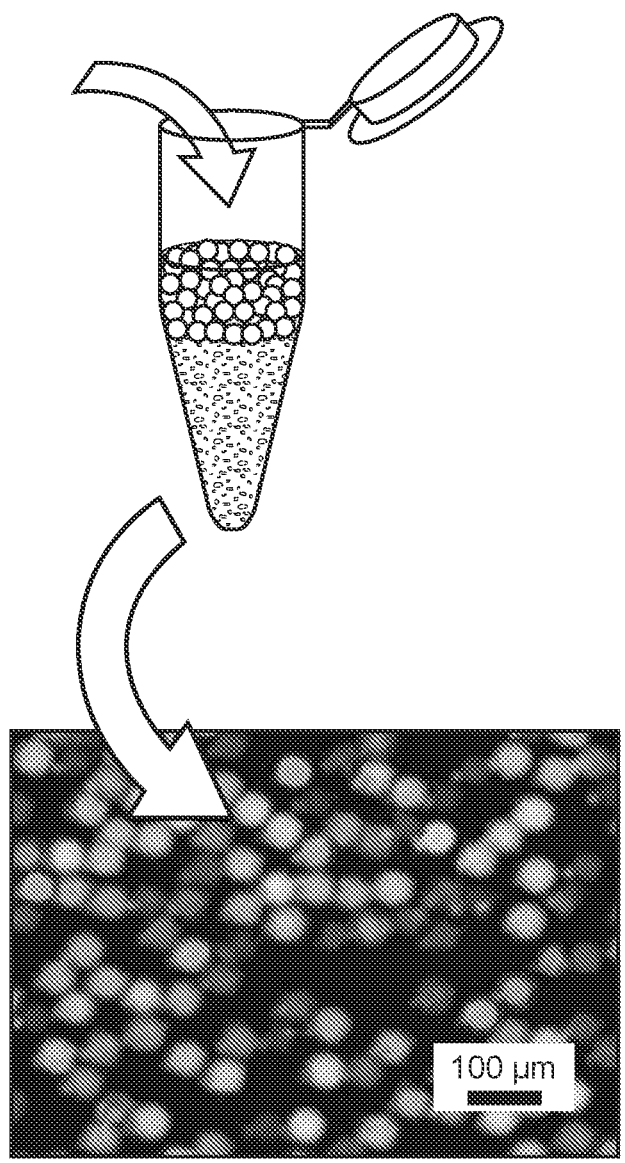
FIG. 26, Panels A-C show microfluidic devices and digital RT-PCR workflow used in the study of Example 5. (A) Drops containing RNA and RT-PCR reagents are created with a microfluidic T-junction and carrier oil. Brightfield microscopy images of the drop formation are shown below, the middle image showing the generation of one population of drops from a single reaction mixture, and the lower the generation of two populations from two mixtures. (B) After formation, the drops are picoinjected with reverse transcriptase using a picoinjection channel triggered by an electric field, applied by an electrode channel immediately opposite the picoinjector. (C) The picoinjected drops are collected into a tube, thermocycled, and imaged with a fluorescent microscope.

A potential concern when using picoinjection for RT-PCR assays is the possibility that it may interfere with reactions in the drops; for example, the process may result in variability in the amount of reagents between the drops or degradation of key components upon exposure to the electric field. To investigate these issues, the detection of two cancer-relevant human transcripts, EpCAM and CD44, was compared in picoinjected and non-picoinjected drops using TaqMan® RT-PCR, (FIG. 26). The TaqMan® probe for detecting EpCAM was conjugated to the fluorophore 6 carboxyfuoroscein (FAM) and the probe for CD44 to the dye Cy5. The probe mix also contained primers that flank the TaqMan® probes and yield ~150 base amplicons from these genes.

Figure 27:
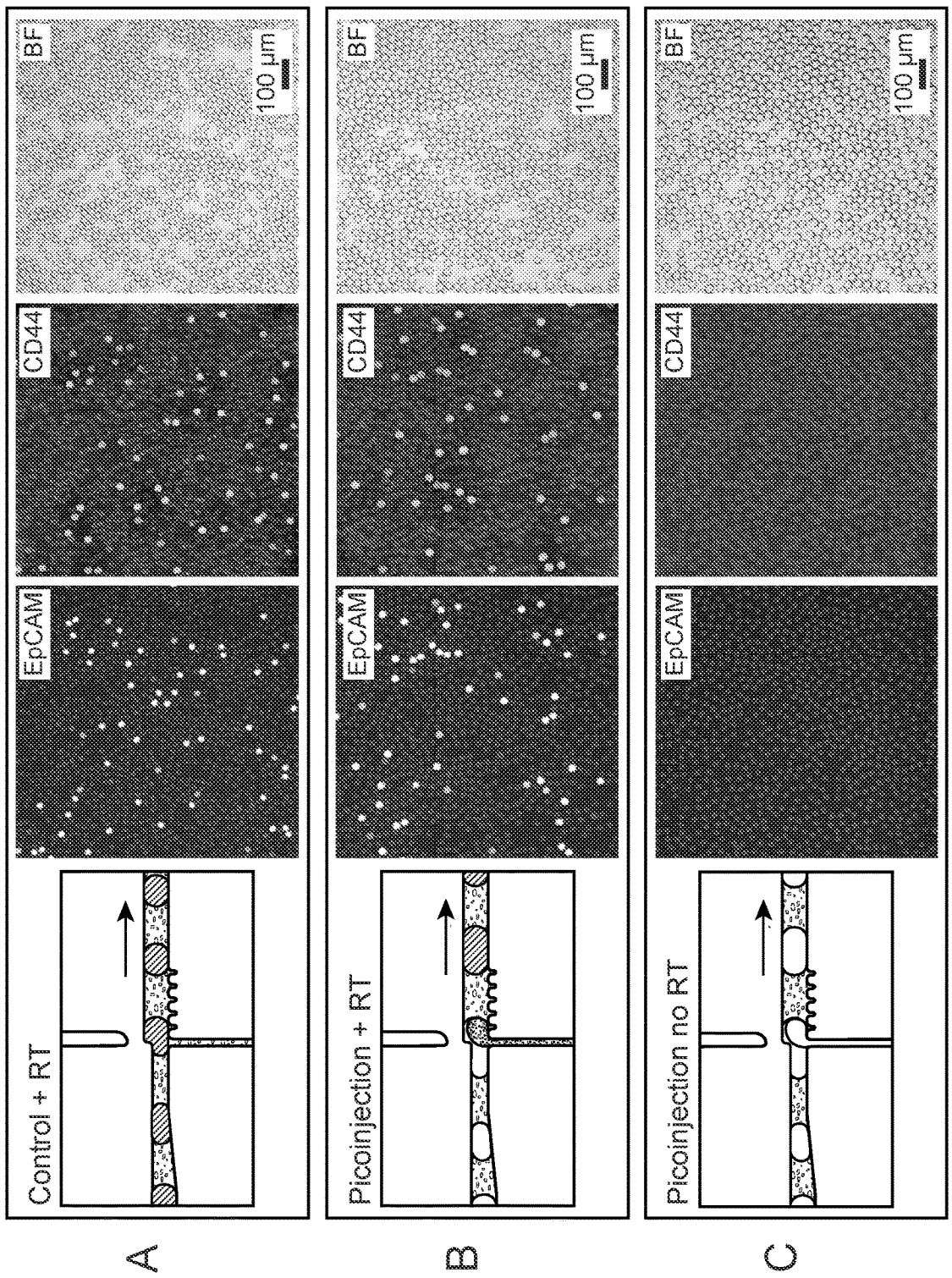
FIG. 27, Panels A-C show digital RT-PCR TaqMan® assays in microfluidic drops following picoinjection of reverse transcriptase. (A) Control RT-PCR reactions containing PC3 cell total RNA were emulsified on a T-junction drop maker, thermocycled, and imaged. FAM (green) fluorescence indicates TaqMan® detection of an EpCAM transcript and Cy5 (red) indicates detection of CD44 transcripts. Brightfield images (BF) of the same drops are shown in the image panel on the far right. (B) RT-PCR reactions lacking reverse transcriptase were emulsified on a T-junction drop maker and subsequently picoinjected with reverse transcriptase. Picoinjection fluid is pictured as dark gray in the schematic diagram on the left. Brightfield images demonstrate that the drops roughly doubled in size after picoinjection. (C) RT-PCR reactions subjected to picoinjection omitting the reverse transcriptase show no TaqMan® signal for EpCAM and CD44, demonstrating the specificity of the TaqMan® assay. The red arrows indicate the direction of emulsion flow in the illustrations. Scale bars=100 µm.

To prepare the non-picoinjected control drops, the probe mix was added to a 25 ml RT-PCR master mix reaction containing 150 ng of total RNA isolated from the human PC3 prostate cancer cell line. The RT-PCR solution was the emulsified into monodisperse 30 mm (14 pL) drops with a T-junction drop maker, and the drops were collected into PCR tubes and thermocycled (FIGS. 26, Panel A and 26, Panel C). During thermocycling, drops containing at least one EpCAM or CD44 transcript were amplified, becoming fluorescent at the wavelengths of the associated FAM and Cy5 dyes. By contrast, drops without a molecule did not undergo amplification and remained dim, as in standard TaqMan®-based digital droplet RT-PCR. Following thermocycling, the drops were pipetted into chambered slides and imaged with a fluorescence microscope. To measure the concentrations of EpCAM and CD44 in the original solution, the number of drops with FAM or Cy5 fluorescence were counted. The reactions showed a digital fluorescent signal for both the EpCAM and CD44 probes, indicating that these transcripts were present at limiting concentrations in the drops, as shown in FIG. 27, Panel A. Control reactions where reverse transcriptase was omitted failed to produce a fluorescent signal, indicating that the TaqMan® assays were specific and not the result of non-specific cleavage of TaqMan® probes caused by the emulsification process.

To test the impact of picoinjection on TaqMan® RT-PCR, a similar experiment as above was performed, but the RT-PCR reagents were separated into two solutions added at different times. Total RNA, RT-PCR buffer, primers, probes, and DNA polymerase were emulsified into 30 mm diameter drops; these drops were not capable of RT-PCR, since they lacked reverse transcriptase. Using picoinjection, an equal volume of 2× reverse transcriptase was introduced in PCR buffer and the drops were thermocycled. Just as with the non-picoinjected control, this emulsion showed a robust digital signal and had an equivalent ratio of fluorescent-to-non-fluorescent drops, as shown in FIG. 27, Panels A and B. To confirm that the fluorescence was not due to background hydrolysis of the TaqMan® probes, disruption of the probes by the electric field, or some other factor, additional reactions were performed where a picoinjection fluid lacking reverse transcriptase was added to RNA-containing drops. In these drops, no fluorescence was evident following thermocycling (FIG. 27, Panel C), demonstrating that the signal was indeed a result of digital detection of RNA molecules, and that these assays were specific.

Quantification of RT-PCR Detection Rates in Picoinjected Drops

Figure 28:
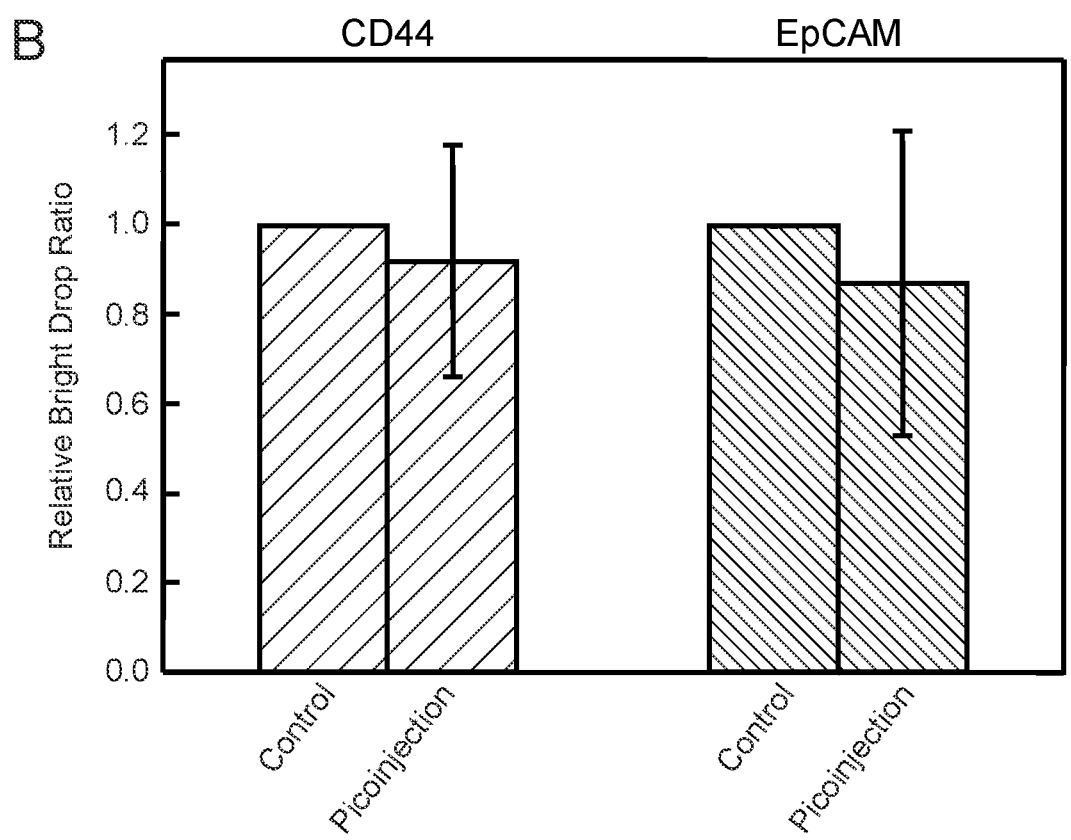
FIG. 28, Panels A-B show a comparison of digital RT-PCR detection rates between control drops and drops that were picoinjected with reverse transcriptase. (A) Scatter plots of FAM and Cy5 drop intensities for a control sample (left) and picoinjected sample (right). The gating thresholds used to label a drop as positive or negative for TaqMan® signal are demarcated by the lines, and divide the scatter plot into quadrants, (−,−), (−,+), (+,−), (+,+). (B) The bar graph shows the average TaqMan® positive drop count with picoinjection relative to the normalized count for CD44 and EpCAM TaqMan® assays for control populations. The data represent the average of four independent experimental replicates.

To precisely quantify the impact of picoinjection on TaqMan® RT-PCR transcript detection, four independent replicates of the picoinjected and non-picoinjected drops were collected. To automate data analysis, a custom MATLAB software was used to locate the drops in the images and measure their fluorescence intensities. For a particular channel (FAM or Cy5), the fluorescence intensity within each drop was averaged; all drop values were subsequently offset so that the cluster of empty drops had an average of zero (See Materials and Methods). Using one threshold for both channels, each drop was labeled as positive or negative for EpCAM and CD44 based on whether it was above or below the threshold, respectively, as shown in FIG. 28, Panel A. In total, 16,216 control drops and 14,254 picoinjected drops were analyzed from the four experimental replicates. To determine the TaqMan® detection rate of picoinjected drops relative to non-picoinjected controls, the total number of CD44 (Cy5) and EpCAM (FAM) positive control drops in each replicate was normalized. Following picoinjection of reverse transcriptase, 92% (+/−26%) of CD44 positive drops and 87% (+/−34%) of EpCAM positive drops were detected relative to the control drops (FIG. 28, Panel B). Although the average transcript detection rate for picoinjected drops was slightly lower than that of control drops for a given RNA concentration, the difference was not statistically significant, and some experimental replicates had detection rates for picoinjected drops higher than for the controls. Based on these results, it was conclude that picoinjection affords transcript detection rates equivalent to that of digital RT-PCR, with the benefit of allowing the reaction components to be added at different times.

Discrete Populations of Drops Can be Picoinjected with Minimal Cross-Contamination An important feature when adding reagents to drops is maintaining the unique contents of each drop and preventing the transfer of material between drops. Unlike the merger of two discrete drops, the contents of a picoinjected drop become momentarily connected with the fluid being added, as illustrated in FIG. 26, Panel B. After the drop disconnects from the fluid, it may leave material behind that, in turn, may be added to the drops that follow. This could lead to transfer of material between drops, and cross-contamination. To examine the extent to which picoinjection results in cross-contamination, TaqMan® RT-PCR reactions were again used because they are extremely sensitive and capable of detecting the transfer of just a single RNA molecule. A FAM-conjugated TaqMan® probe was used for targeting the EpCAM transcript and a hexachlorofluorescein (HEX) conjugated TaqMan® probe was used for recognizing the B-lymphocyte-specific transcript PTPRC. Total RNA was isolated from PC3 cells expressing EpCAM but not PTPRC, and a B-lymphocyte derived cell line (Raji) expressing PTPRC but not EpCAM. For a control set of drops, the RNA from both cell types was mixed, TaqMan® probes and RT-PCR reagents were added, and the solutions were emulsified into 30 mm drops. The drops were collected into a tube, thermocycled, and imaged, FIG. 29A. In the images, a large number of drops displayed FAM and HEX fluorescence, indicative of multiplexed TaqMan® detection of PTPRC and EpCAM transcripts. A smaller fraction had pure green or red fluorescence, indicating that they originally contained just one of these molecules, while even fewer were dim and were thus devoid of these transcripts.

Figure 29:
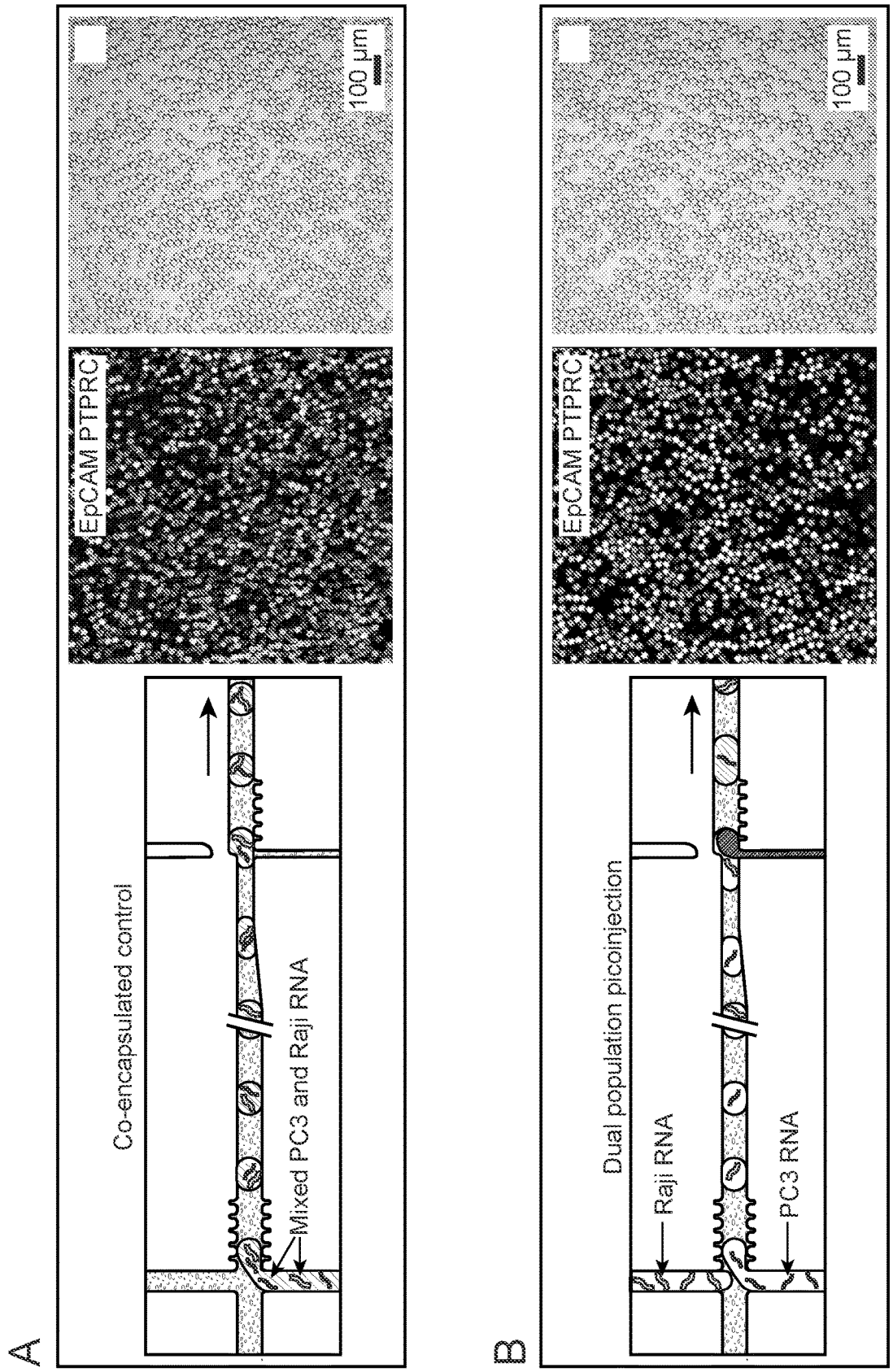
FIG. 29, Panels A-B shows that picoinjection enables analysis of discrete drop populations. (A) Non-picoinjected drops. Control RT-PCR reactions containing mixed PC3 cell total RNA and Raji cell total RNA were emulsified with a T-junction drop maker, thermocycled, and imaged. Merged FAM and HEX fluorescent images are shown with FAM (green) fluorescence indicating TaqMan® detection of an EpCAM transcript and HEX (red) indicating the presence of PTPRC transcripts. The yellow drops indicate the presence of multiplexed TaqMan® assays, where EpCAM and PTPRC transcripts were co-encapsulated in the same drop. The brightfield images (BF) are shown in the panel on the right. (B) Picoinjected drops. A double T-junction drop maker simultaneously created two populations of drops that were immediately picoinjected. One drop maker created drops containing only Raji cell RNA, and the other drops containing only PC3 cell RNA. Both drop types initially lack reverse transcriptase, which is added via picoinjection just downstream of the drop makers. The overwhelming majority of drops display no multiplexing, demonstrating that transfer of material during picoinjection is very rare. The red arrows indicate the direction of emulsion flow in the illustrations. Scale bars=100 µm.

To observe the rate of picoinjector cross-contamination, a microfluidic device was used that synchronously produced two populations of drops from opposing T-junctions, pictured in FIG. 29, Panel B. One population contained only Raji cell RNA and PTPRC transcripts; the other, only PC3 cell RNA and EpCAM transcripts, as illustrated in FIG. 29, Panel B. Both populations contained primers and TaqMan® probes for EpCAM and PTPRC and were therefore capable of signalling the presence of either transcript Immediately after formation, the drops were picoinjected with the 2× reverse transcriptase, thereby enabling first strand cDNA template synthesis for the TaqMan® assay, and an opportunity for contamination. If RNA was transferred between drops, some of the drops should have displayed a multiplexed TaqMan® signal, whereas in the absence of contamination, there should have been two distinct populations and no multiplexing. In the fluorescence images, two distinct populations were observed, one positive for EpCAM (FAM) and the other for PTPRC (HEX), with almost no yellow multiplexed drops that would be indicative of a multiplexed signal, as shown in FIG. 29, Panel B. This demonstrated that cross-contamination during picoinjection is rare.

Figure 30:
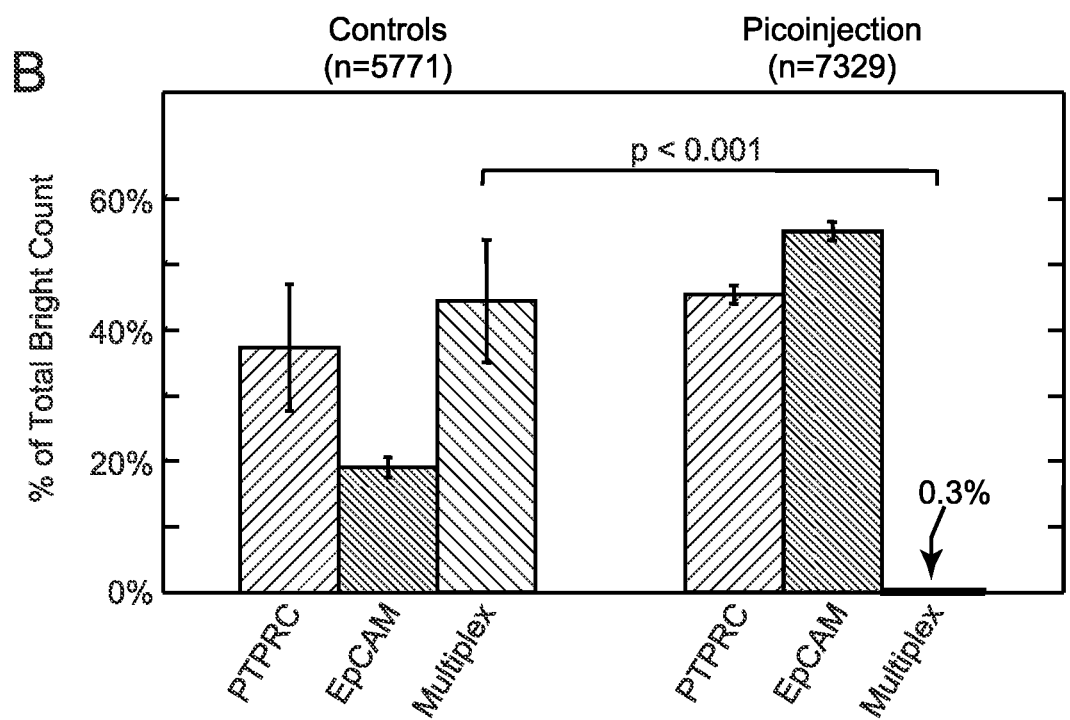
FIG. 30, Panels A-B shows a dual transcript detection analysis, indicating minimal cross-contamination during picoinjection. (A) Scatter plots of FAM and HEX drop intensities for a co-encapsulated control sample (left) and dual population picoinjected sample (right). Using this analysis, large numbers of TaqMan® multiplexed drops were identified in the co-encapsulated controls that were virtually absent in the dual population picoinjected drops (upper right quadrants of gated scatter plots). (B) A bar graph of different bright drop populations relative to the total bright count for co-encapsulation control and for dual population picoinjection. The data represent the average of three experimental replicates.

To measure the precise rate of cross-contamination, automated droplet detection software was used to analyze thousands of drops, FIG. 30, Panel A, and the results were plotted as a percentage of the total number of TaqMan® positive drops, FIG. 30, Panel B. A total of 5771 TaqMan® positive control drops and 7329 TaqMan® positive picoinjected drops were analyzed from three independent experimental replicates. For the control drops, in which the Raji and PC3 RNA were combined, a multiplexing rate 44% (+/−9.26) was observed. By contrast, for the picoinjected drops, only 0.31% (+/−0.14) multiplexed drops were observed, as shown in FIG. 30, Panel B. Hence, with picoinjection, there was some multiplexing, although the rate was so low it cannot be ruled out as resulting from other sources of RNA transfer, such as merger of drops during thermocycling or transport of RNA between droplet interfaces.

Figure 31:
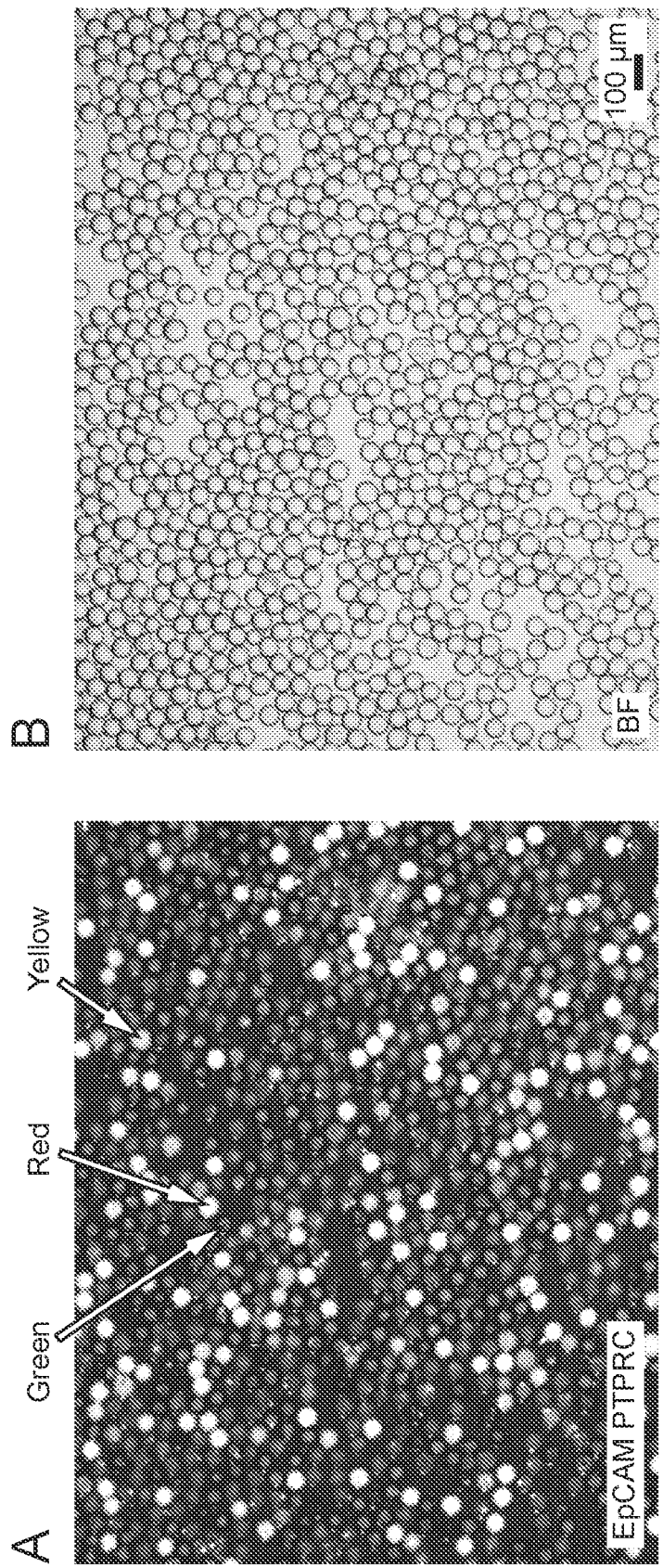
FIG. 31 Panels A-B shows that dual populations of RNA drops can be stored offline and picoinjected at a later time. (A) An emulsion was made consisting of two populations of drops, one containing RNA recovered from Raji cells, and the other from PC3 cells. The drops were collected into a syringe, incubated off chip, and then re-introduced into a microfluidic device to picoinject. The drops were then collected, thermocycled, and imaged. These drops are somewhat more polydisperse and displayed higher multiplexing rates (1%) than the drops picoinjected on the same device on which they were formed, which is most likely due to merger of some of the drops during incubation and reinjection. The ability to reinject emulsions following incubation to add reagents may be important for numerous droplet-based molecular biology assays. (B) Brightfield images of picoinjected emulsions. Scale bars=100 µm.

The dual population experiments in which the drops were picoinjected immediately after being formed allowed for the estimation of the precise amount of cross-contamination, but in most actual implementations of picoinjection for biological assays, the drops will be formed on one device, removed offline for incubation or thermocycling, and then reinjected into another device for picoinjection. To demonstrate that picoinjection is effective for digital RT-PCR reactions performed under these conditions, and to estimate the rate of cross contamination, a dual population of drops was again created, but this time the drops were pulled offline and stored in a 1 mL syringe before reinjecting and picoinjecting them. Just as before, it was observed that nearly all drops were pure green or red, indicating minimal cross contamination, as shown in FIG. 31. However, some drops with a multiplexed signal were also observed, as shown by the rare yellow drops in the image. In this experiment, the multiplexing rate was 1%, higher than with the drops that were picoinjected immediately after formation. While cross-contamination at the picoinjector cannot be ruled out, it is suspected that the higher multiplexing rate was the result of merger of drops during offline storage and reinjection, during which the drops may be subjected to dust, air, and shear forces that can increase the chances for merger. This is supported by the observation that during reinjection of the emulsion there were occasional large merged drops, and also that the picoinjected emulsion was somewhat polydisperse, as shown in FIG. 31. Nevertheless, even under these rough conditions, the vast majority of drops displayed no multiplexing, indicating that they retained their integrity as distinct reactors.

From these studies, it was demonstrated that picoinjection is compatible with droplet digital RT-PCR and affords single RNA molecule detection rates equivalent to workflows not incorporating picoinjection. This showed that picoinjection is compatible with reactions involving common biological components, like nucleic acids, enzymes, buffers, and dyes. It was also observed that there was negligible transfer of material between drops during picoinjection. These results support picoinjection as a powerful and robust technique for adding reagents to drops for ultrahigh-throughput biological assays.

Example 6: Single Cell RT-PCR Microfluidic Device

FIG. 32 shows one embodiment of a single cell RT-PCR microfluidic device as provided herein. The cells of interested were first encapsulated in drops with lysis reagent including proteases and detergents and incubated offline. These drops were then introduced into this device and spaced by oil using an input microchannel and a flow focus drop maker for introducing microdroplets (Panel A). In a pairing microchannel, the spaced drops were then paired with large drops containing a dilution buffer that were created by a dilution buffer drop maker in fluidic communication with the pairing microchannel (Panel B). The big and small drops were then merged in a merging microchannel with an electric field (Panel C), adding the contents of the small drop to the large drop. The merged drops passed through mixing microchannels and then a small portion was sampled from them by a drop sampler (Panel D). The small portion was then passed by a picoinjection microchannel where the small portion was then picoinjected with the RT-PCR reagent (Panel E). The drops were then thermocycled for the RT-PCR reaction.

This system facilitated single cell RT-PCR because it allowed for the performance of the cell lysis and protein digestion in one step (not shown) and subsequent dilution of the lysate in the drop prior to addition of the RT-PCR reagent. Without the dilution, the lysate could have inhibited the RT-PCR reaction.

The device worked robustly, at least in part, because the timing of each microfluidic component was set by the periodicity of the large drop maker making the dilution drops. Without this periodic drop formation, the device might operate less stably and potentially produce polydisperse drops.

Figure 33:
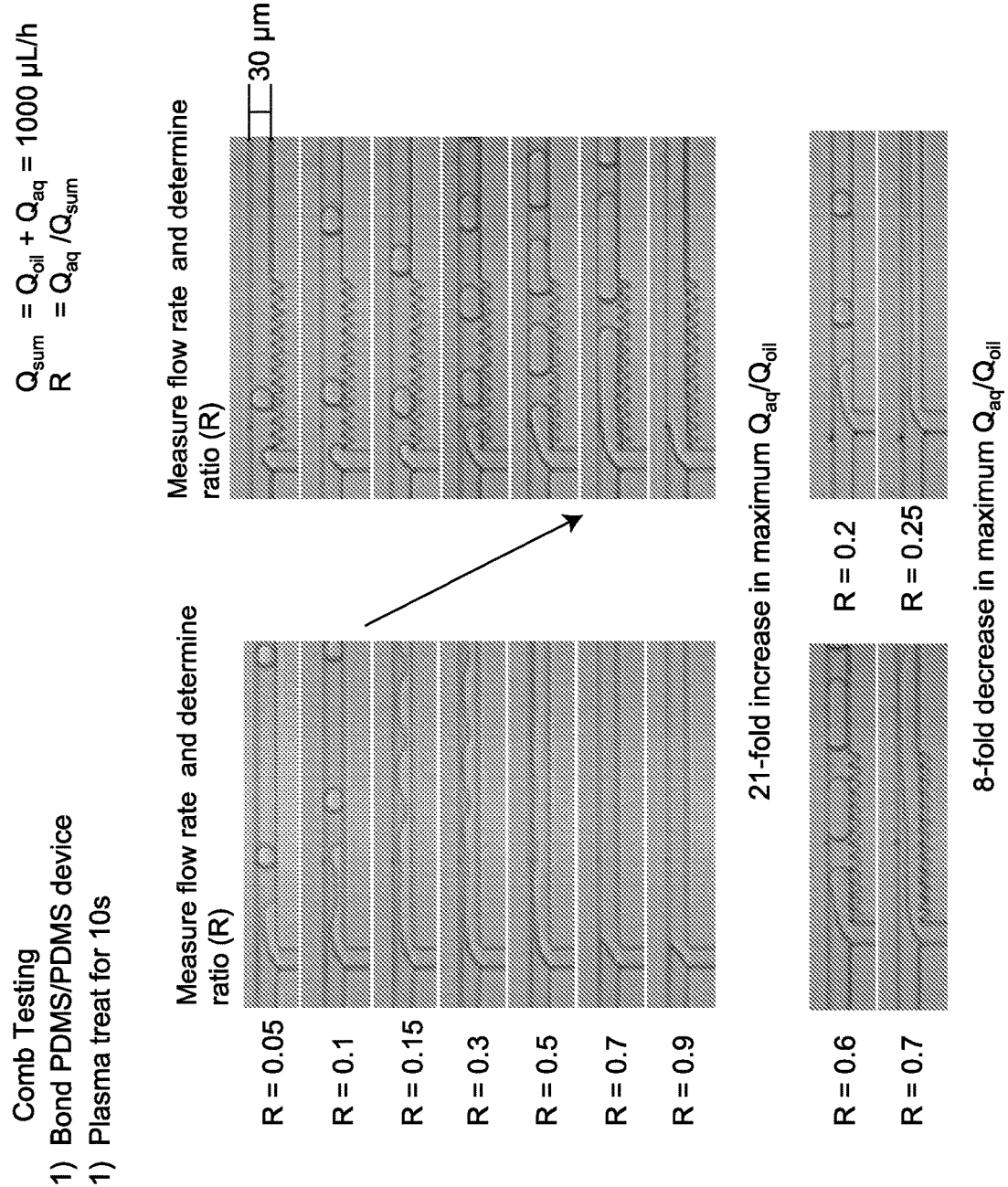
FIG. 33 shows the effect of including ridge structures in a microfluidic device channel downstream of a droplet forming junction. A T-junction drop maker without ridges is shown to the left. As the flow rate ratio is increased, the drop maker stops forming drops and instead forms a long jet. This is due to the jet wetting the channel walls and adhering, preventing the formation of drops. On the right, a similar T-junction is shown with ridge structures. The ridges trap a suitable phase, e.g., a hydrophobic oil phase, near the walls, making it difficult for the aqueous phase to wet. This allows the device to form drops at much higher flow rate ratios before it eventually wets at R=0.9. This shows that inclusion of the ridges allows the drop maker to function over a much wider range than if the ridges are omitted. The channel widths are 30 microns and the peaks of the ridges are about 5-10 microns. The top and bottom sets of images correspond to experiments performs with different microfluidic devices.

Example 7: Testing of Microfluidic Droplet Forming Devices Utilizing Channels Including Ridges T-junction drop makers with and without channel ridges positioned downstream of the T-junction were tested to determine the effect of including such ridges on droplet formation performance. The channel widths were about 30 microns and the width of the ridge peaks were from about 5 to about 10 microns. See FIG. 33.

PDMS microfluidic devices were prepared generally as described herein and plasma treated for 10 seconds. The flow rate ratio was monitored, wherein the sum ($Q_{sum}$) of individual flow rates ($Q_{oil}$)+($Q_{aq}$) was approximately 1000 μl/hr, and the ratio (R)=$Q_{aq}/Q_{sum}$, and droplet formation was visualized.

As the flow rate ratio was increased for the device lacking ridges, the drop maker stopped forming drops and instead formed a long jet. Without intending to be bound by any particular theory, it is believe that this was due to the jet wetting the channel walls and adhering, preventing the formation of drops. See FIG. 33, left side. For the device which included the ridges, the ridges successfully trapped oil near the walls, making it difficult for the aqueous phase to wet. This allowed the device to form drops at much higher flow rate ratios before it eventually wet at R=0.9. This demonstrated that the ridges allow the drop maker to function over a much wider range than would be possible without the ridges. The top and bottom sets of images in FIG. 33 correspond to experiments performs with different devices. When the experiment was performed with the first pair of devices, a 21-fold increase in maximum $Q_{aq}/Q_{oil}$ was achieved. When the same experiment was performed with a second set of devices, an 8-fold increase in maximum $Q_{aq}/Q_{oil}$ was achieved. This discrepancy may be attributed to experimental variability because the wetting properties that lead to jetting are somewhat unpredictable, hysteretic, and prone to variability.

Example 8: Fabrication and Testing of Liquid Electrodes

Many microfluidic devices utilize metal electrodes to create electric fields when such fields are called for in a particular microfluidic device application. However, there may be disadvantages to using such metal electrodes including an increased number of fabrication steps and the potential for failure of the electrodes.

Advantageously, the present disclosure describes the fabrication and use of liquid electrodes, which simplify the fabrication process and provide similar and/or improved capabilities relative to metal electrodes.

Figure 34:
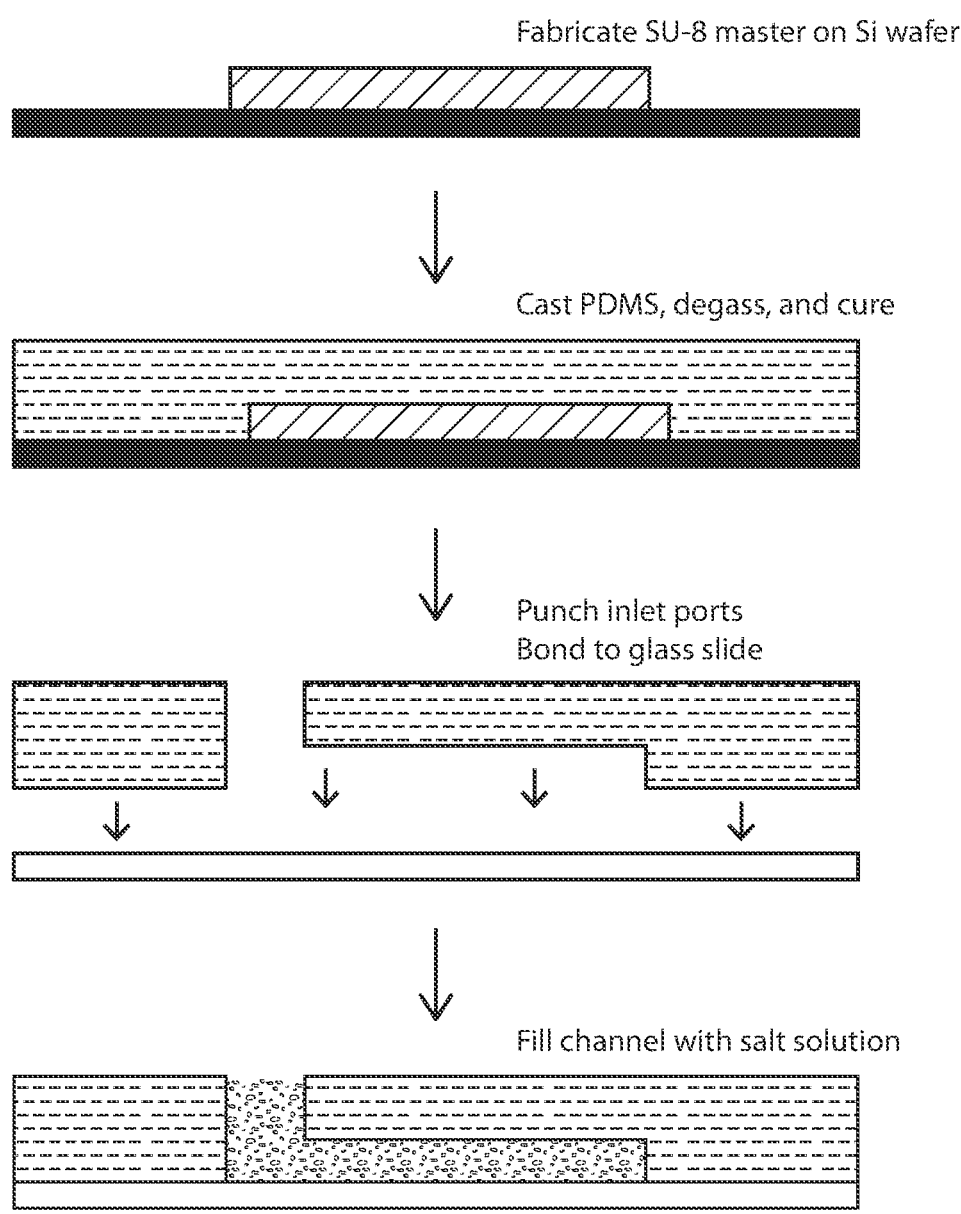
FIG. 34 provides a flow diagram showing a general fabrication scheme for an embodiment of a liquid electrode as described herein.
Figure 35:
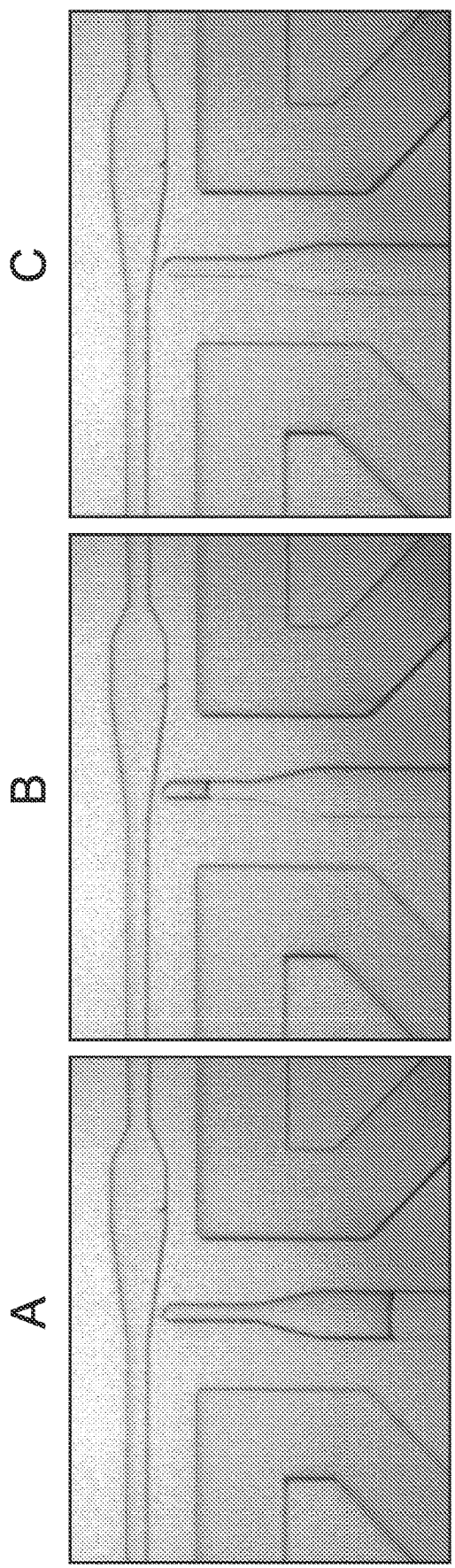
FIG. 35 provides a sequence of three images taken at different times as an electrode channel is being filled with salt water (time course proceeds from left to right; Panels A-C). The salt water is introduced into the inlet of the channel and pressurized, causing it to slowly fill the channel. The air that is originally in the channel is pushed into the PDMS so that, by the end, it is entirely filled with liquid.

FIG. 34 provides an overview of an exemplary liquid electrode fabrication method. Initially, an SU-8 photoresist master was fabricated on an Si wafer (A). PDMS was then cast, degassed and cured (B). Inlet ports were punched in the PDMS, and the PDMS was bonded to a glass slide (C). Finally, the channel was filled with a NaCl solution. FIG. 35 provides a sequence of three images taken at different times as an electrode channel was being filled with salt water (time course proceeds from left to right). The salt water was introduced into the inlet of the channel and pressurized, causing it to slowly fill the channel. The air that was originally in the channel was pushed into the PDMS so that, by the end, it was entirely filled with liquid.

Figure 36:
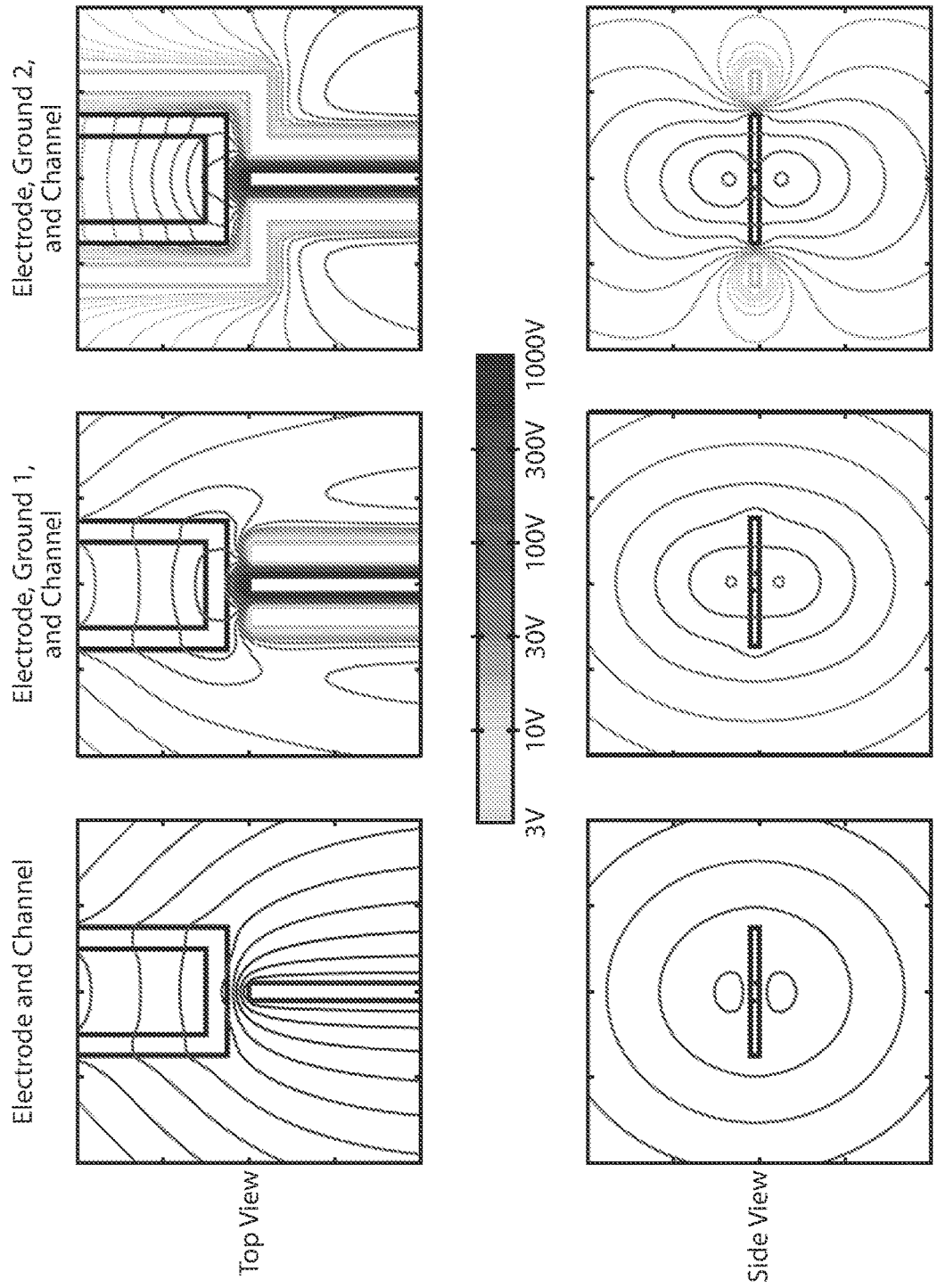
FIG. 36 shows electric field lines simulated for various liquid electrode configurations. The simulations are of positive and ground electrodes showing equipotential lines for three different geometries.

Electric field lines for various liquid electrode configurations were simulated as shown in FIG. 36. The simulations are of positive and ground electrodes showing equipotential lines for three different geometries.

Figure 37:
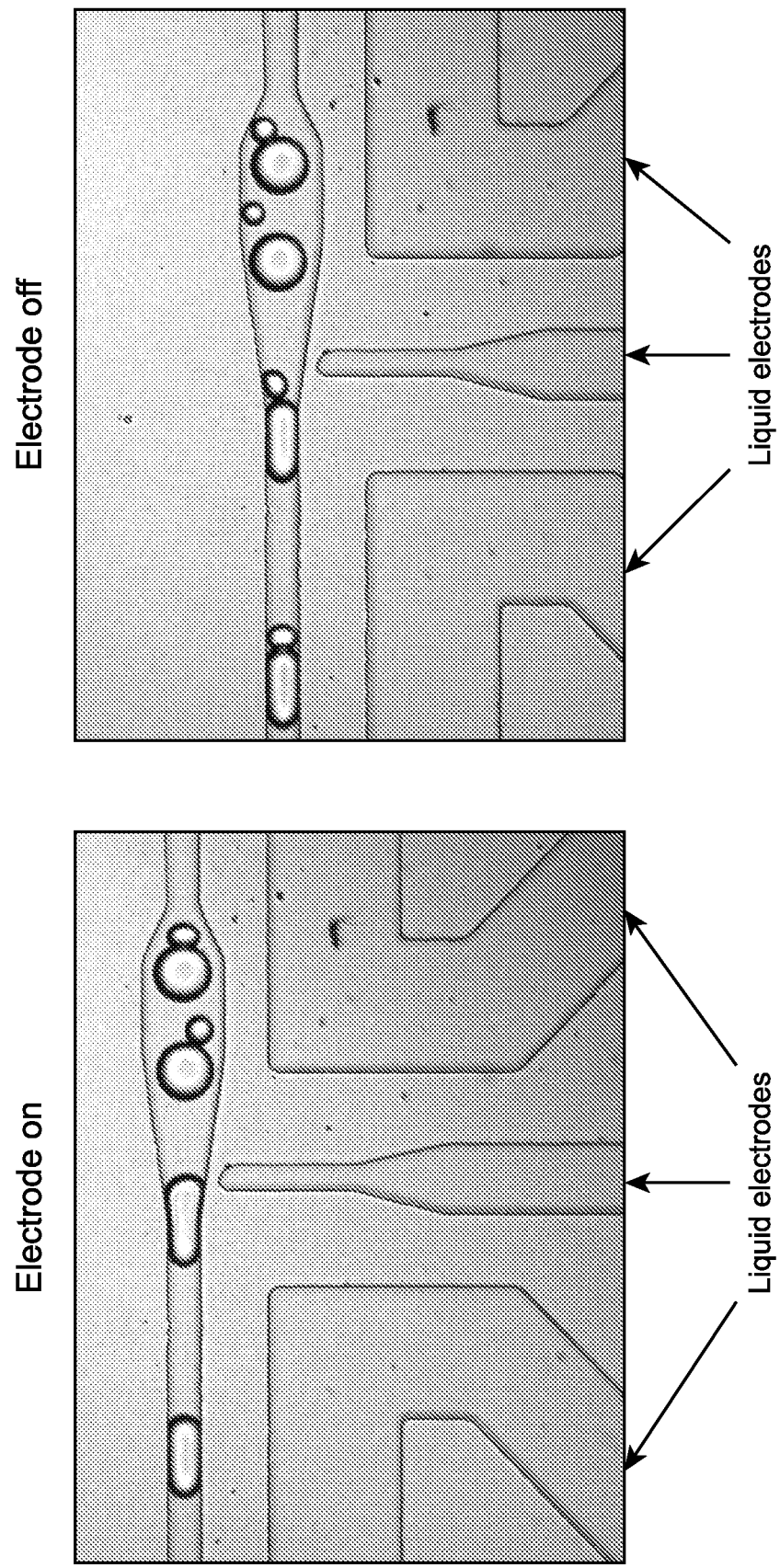
FIG. 37 provides two images of a droplet merger device that merges large drops with small drops utilizing liquid electrodes. To merge the drops, an electric field is applied using a salt-water electrode. When the field is off, no merger occurs (right) and when it is on, the drops merge (left).
Figure 38:
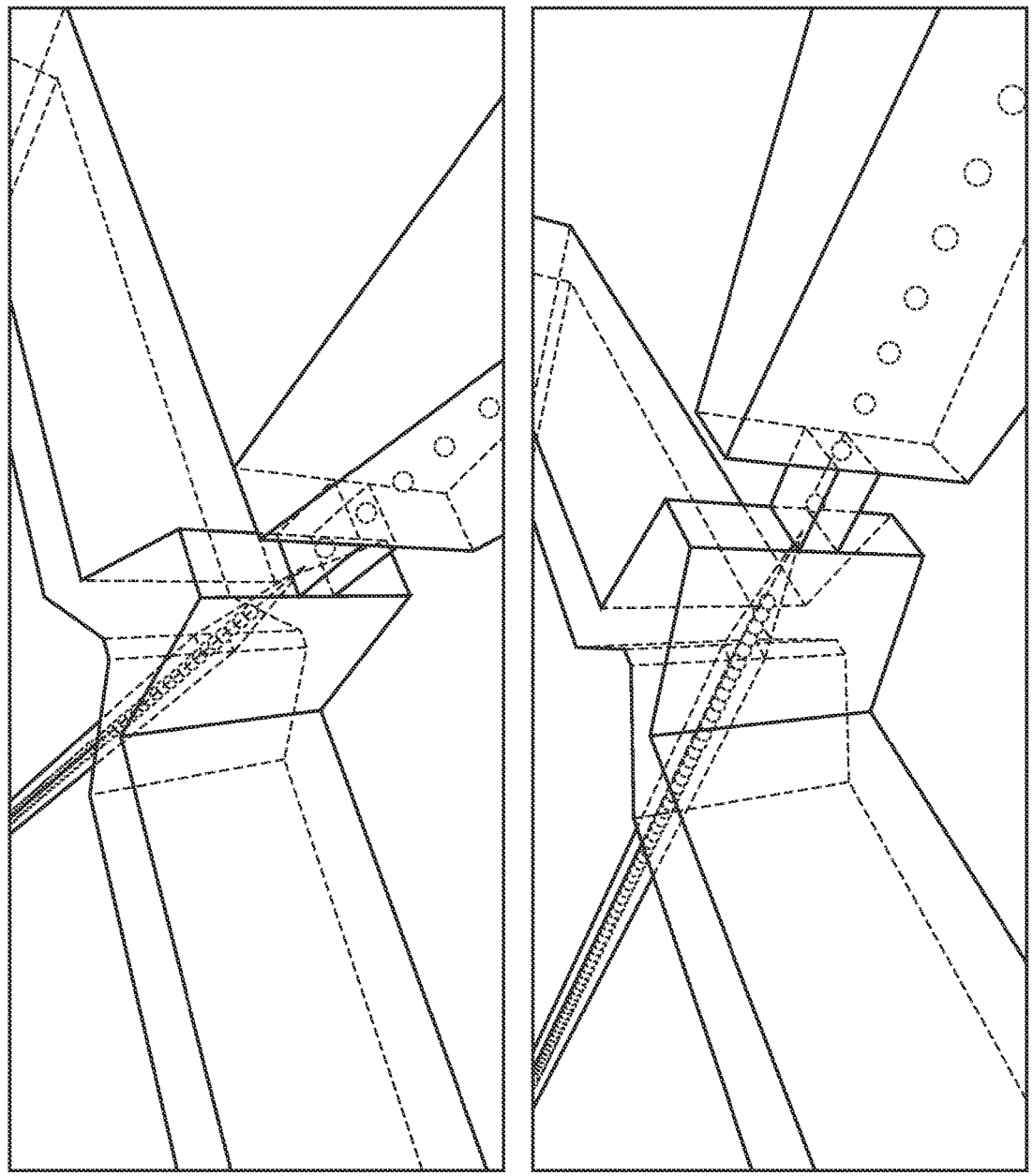
FIG. 38 provides two different views of a three dimensions schematic showing a device which may be used to encapsulate single emulsions in double emulsions. It includes a channel in which the single emulsions are introduced, which channel opens up into a large channel in which additional aqueous phase is added. This focuses the injected drops through an orifice, causing them to be encapsulated in oil drops and forming water-in-oil-in-water double emulsions.
Figure 39:
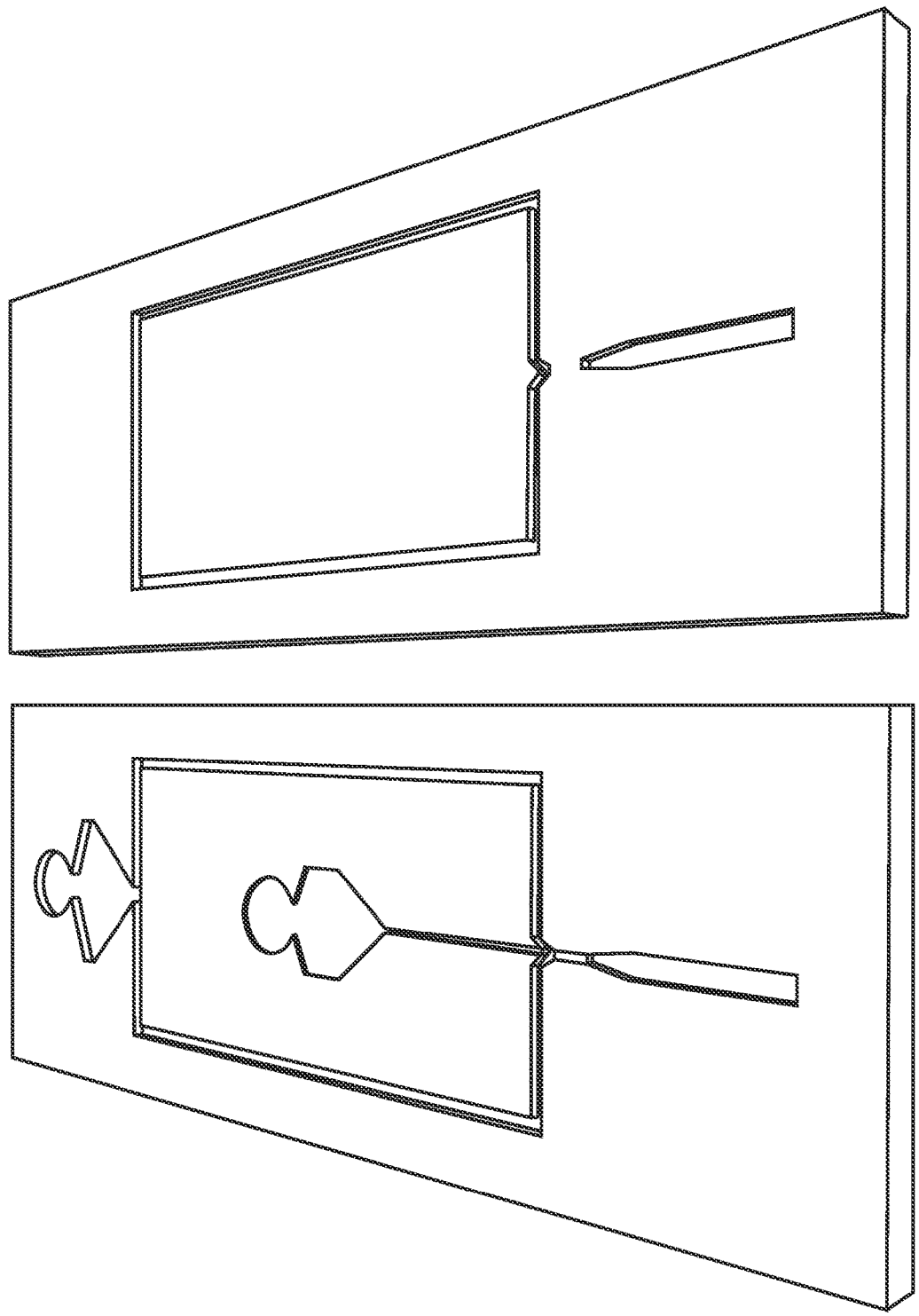
FIG. 39 provides two schematics of PDMS slabs that may be used to construct a double emulsification device. The slab on the left has channels with two heights—short channels for the droplet reinjection and constriction channels (see previous Figure) and tall channels for the aqueous phase and outlets. The slab on the right has only the tall channels. To complete the device, the slabs are aligned and sealed together so that the channels are facing. The devices are bonded using plasma oxidation.
Figure 40:
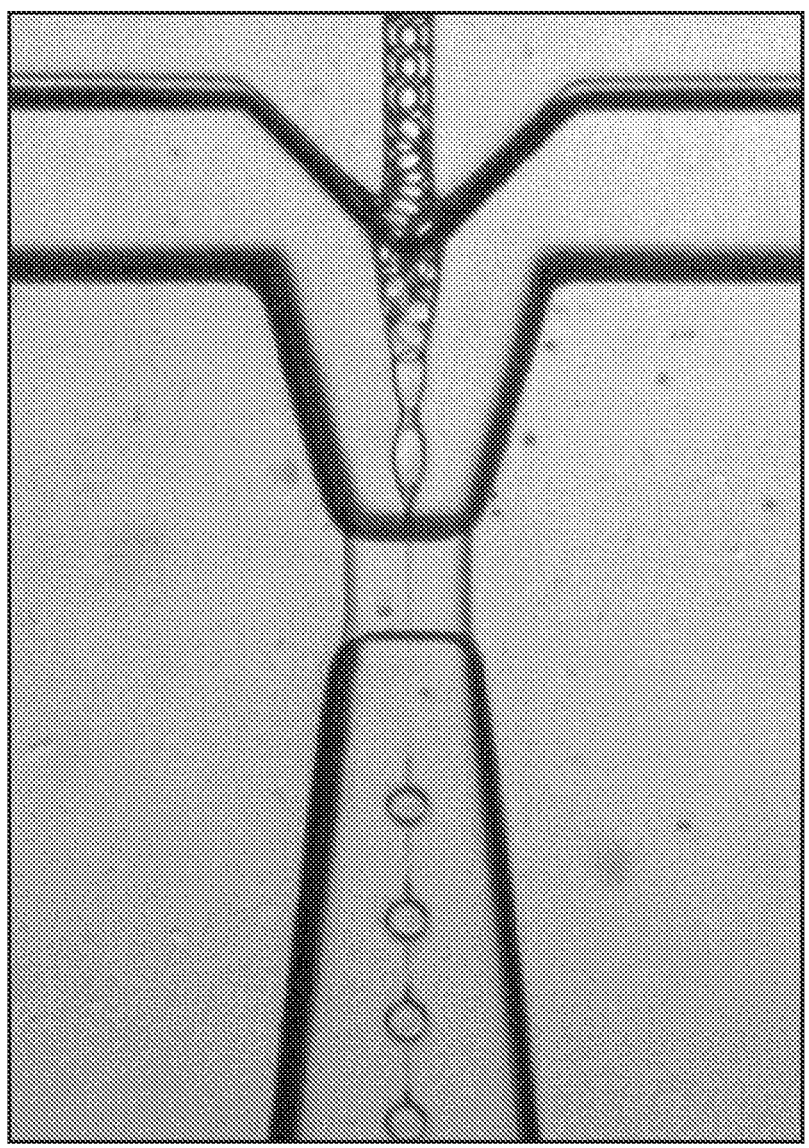
FIG. 40 provides a microscope image of a double emulsification device encapsulating a reinjected single emulsions in double emulsions. The reinjected single emulsions enter from above and are encapsulated in the constriction shown in the center of the device. They then exit as double emulsions, four of which are shown towards the bottom of the device.
Figure 42:
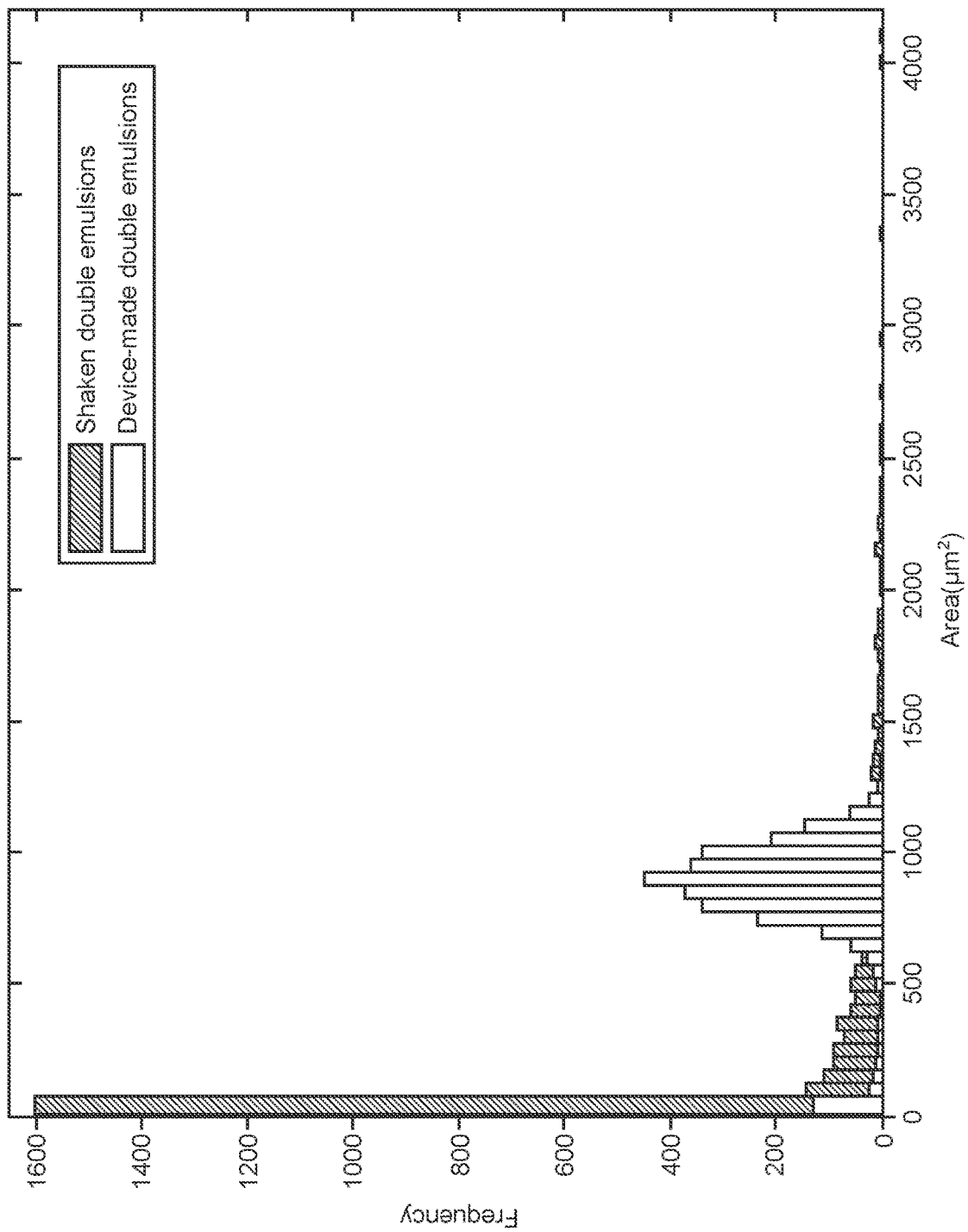
FIG. 42 provides a histogram of the drop areas for shaken vs. device-created double emulsions. The device-created double emulsions are much more monodisperse, as demonstrated by the peak.
Figure 43:
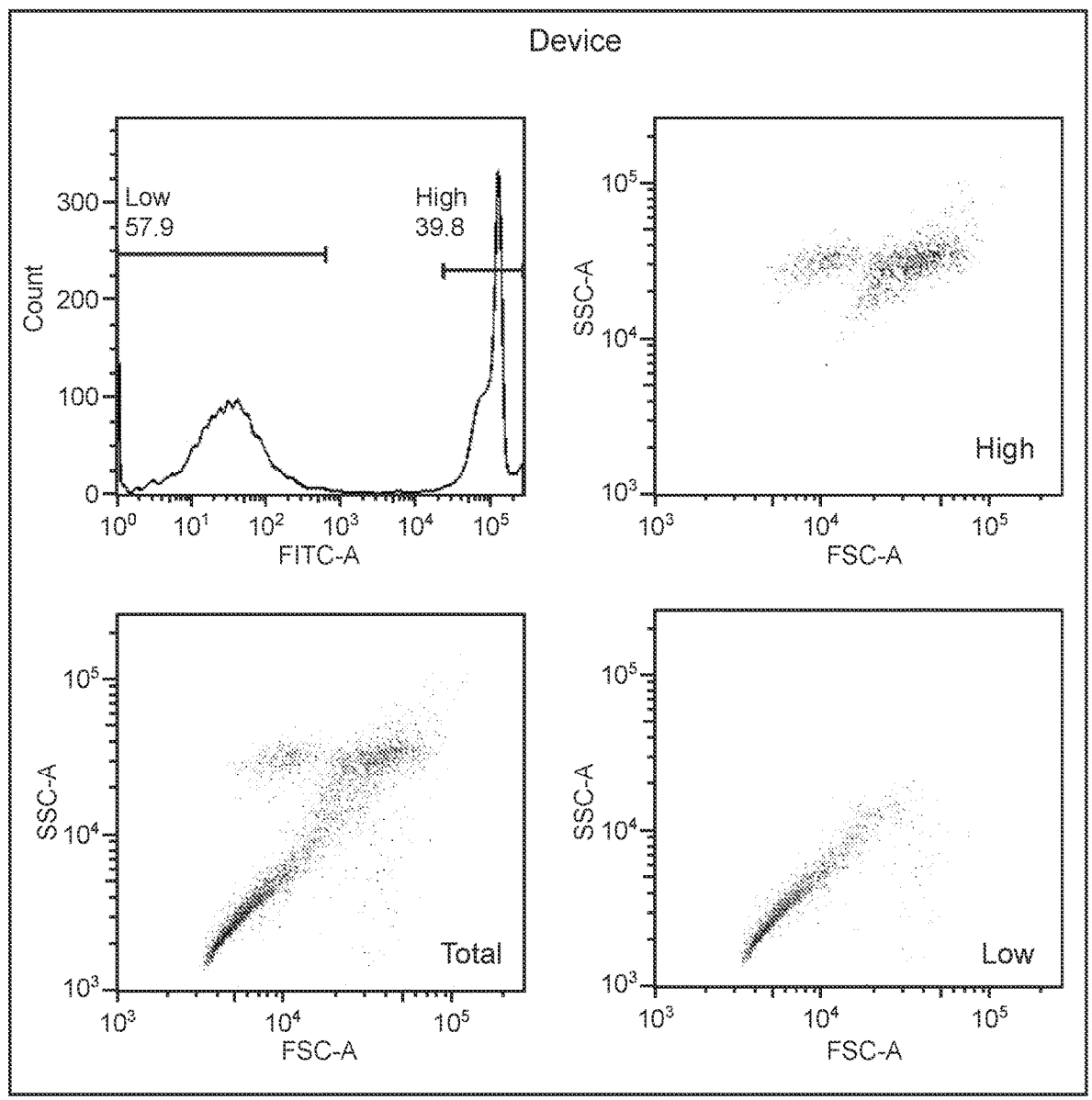
FIG. 43 shows FACS fluorescence and scattering data for microfluidic device generated double emulsions according to the present disclosure. The upper plot shows the intensity histogram of the population as measured with the FITC channel (~520 nm) of the FACS. The plots below show the forward and side scattering of the drops, gated according to FITC signal.
Figure 44:
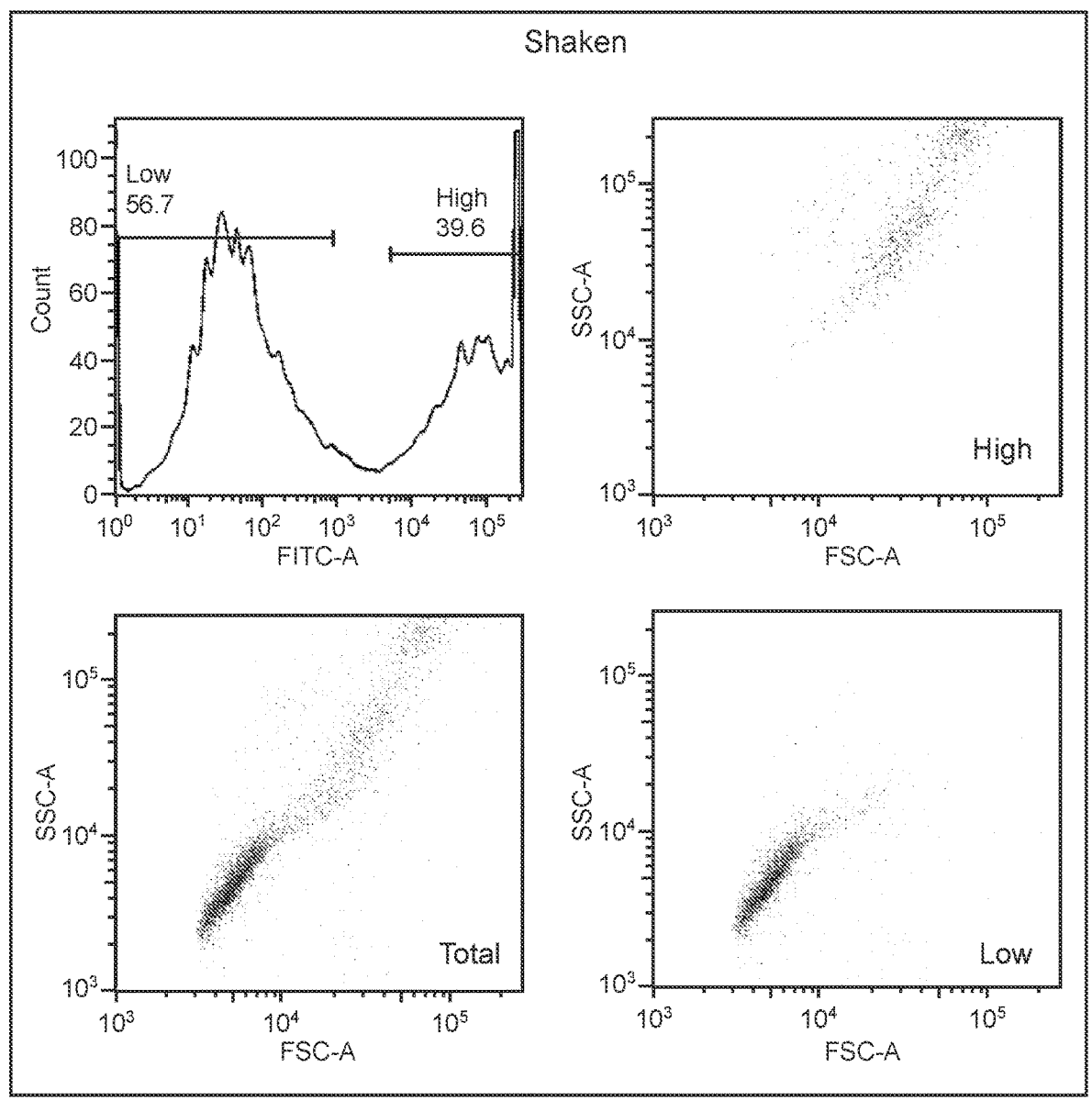
FIG. 44 shows FACS fluorescence and scattering data for shaken double emulsions. The upper plot shows the intensity histogram of the population as measured with the FITC channel (~520 nm) of the FACS. The plots below show the forward and side scattering of the drops, gated according to FITC signal.
Figure 45:
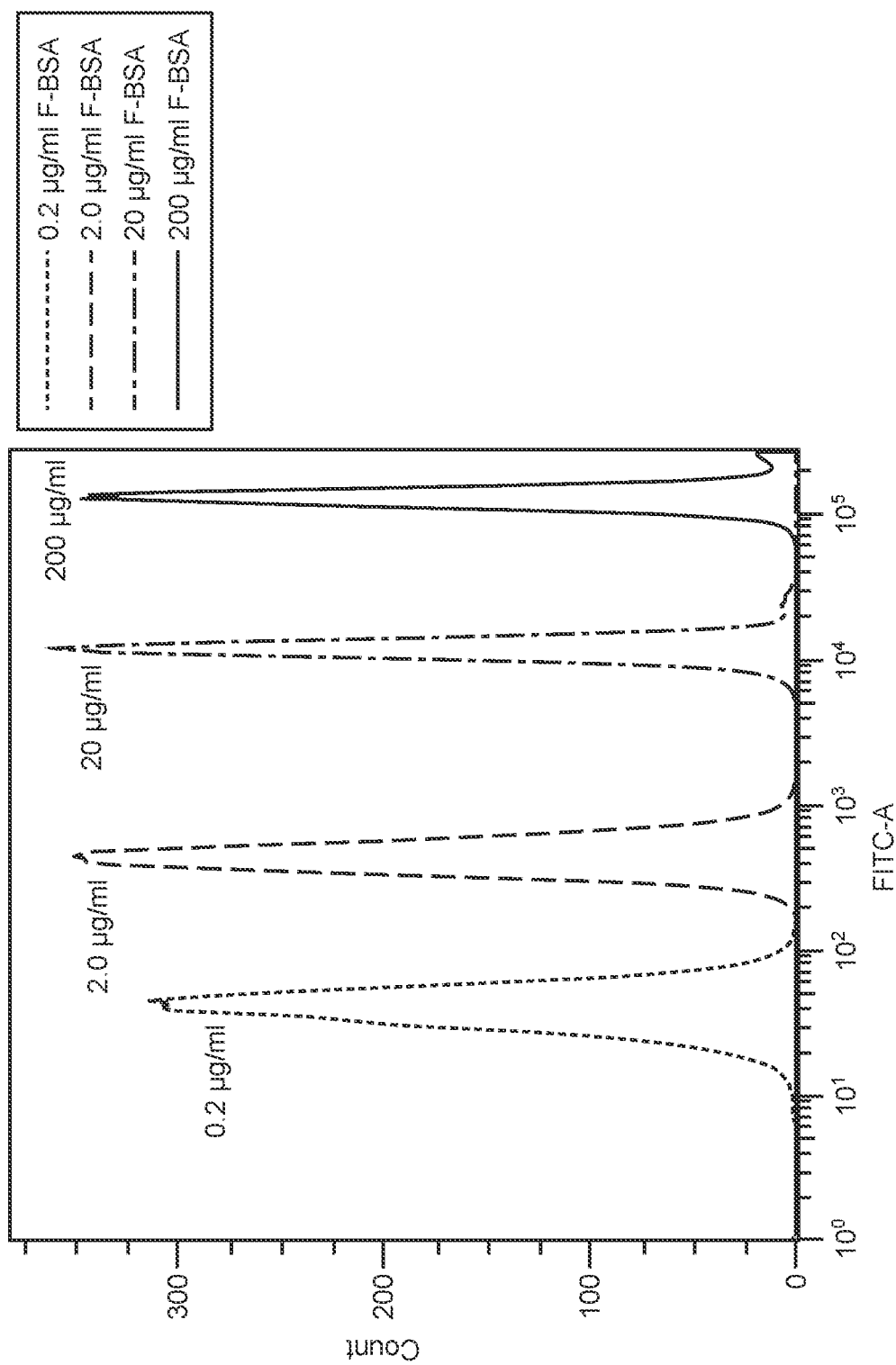
FIG. 45 provides a histogram of droplet intensity as read out with the FACS (FITC channel) for four different concentrations of encapsulated dye. The dye is composed of fluorescently-labeled BSA.
Figure 46:
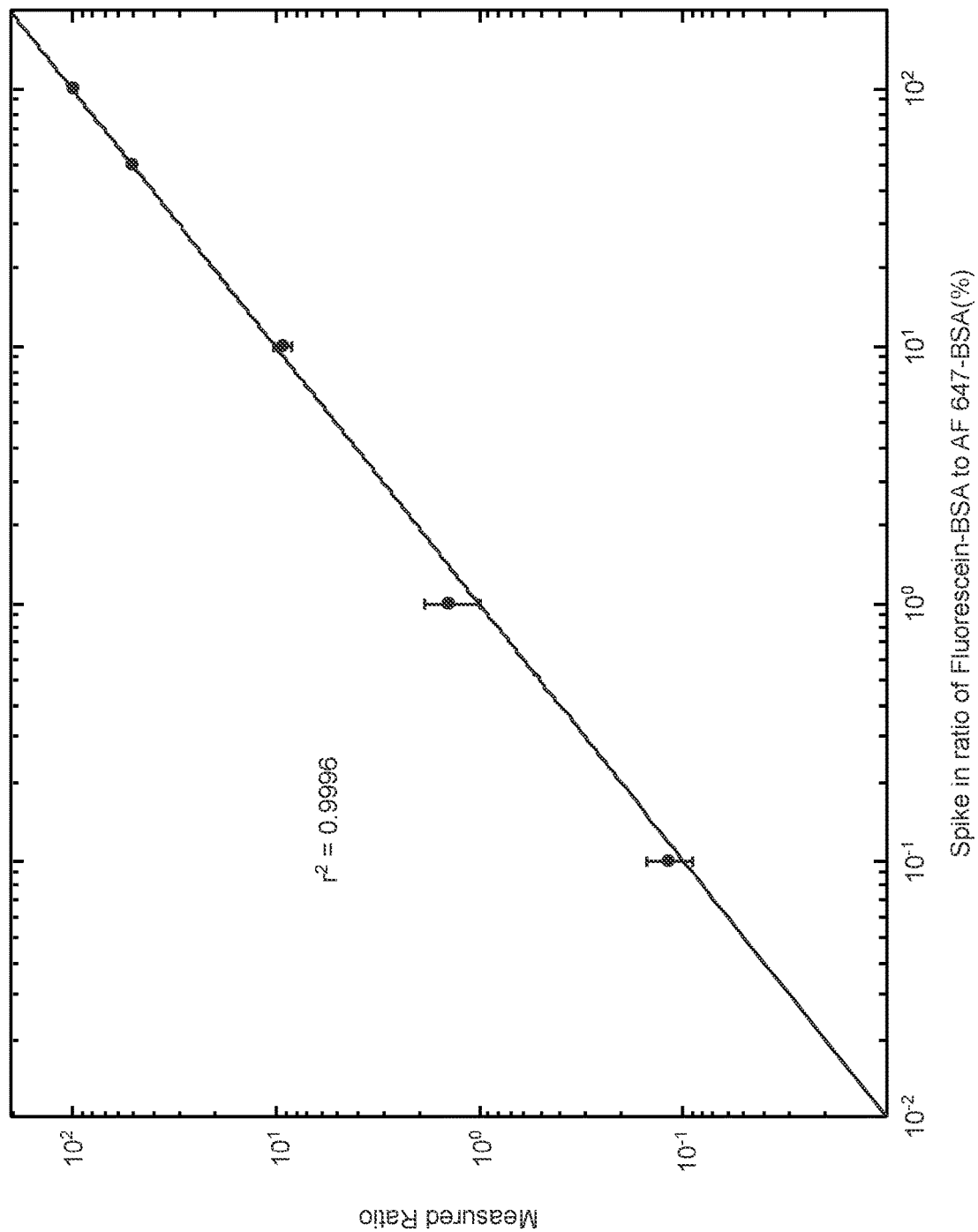
FIG. 46 shows the results of an experiment designed to test the detection rate of the FACS-run drops. Two populations of drops were created, one with labeled BSA fluorescent at 520 nm, and another with BSA fluorescent at 647 nm. The two populations were then mixed in defined ratios and the samples were run on FACS. The measured ratio was found to agree with the known ratio, demonstrating that the FACS measurements are accurate over this range.
Figure 50:
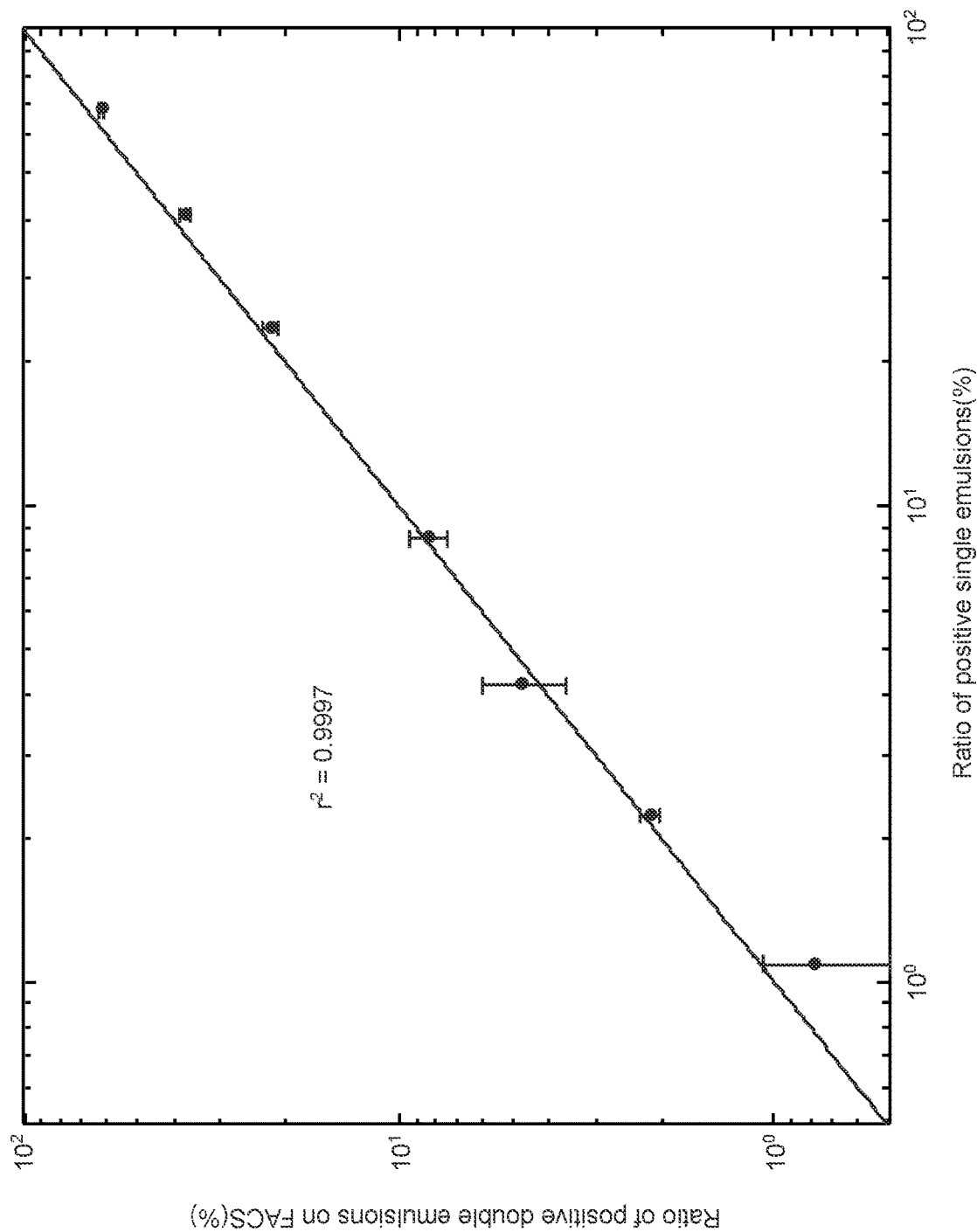
FIG. 50 shows a plot of the detected number of positives by FACS analysis of double emulsions plotted versus the number of positives detected by imaging the drops before double emulsification using a fluorescent microscope. The results agree with one another over the two decades tested.
Figure 51:
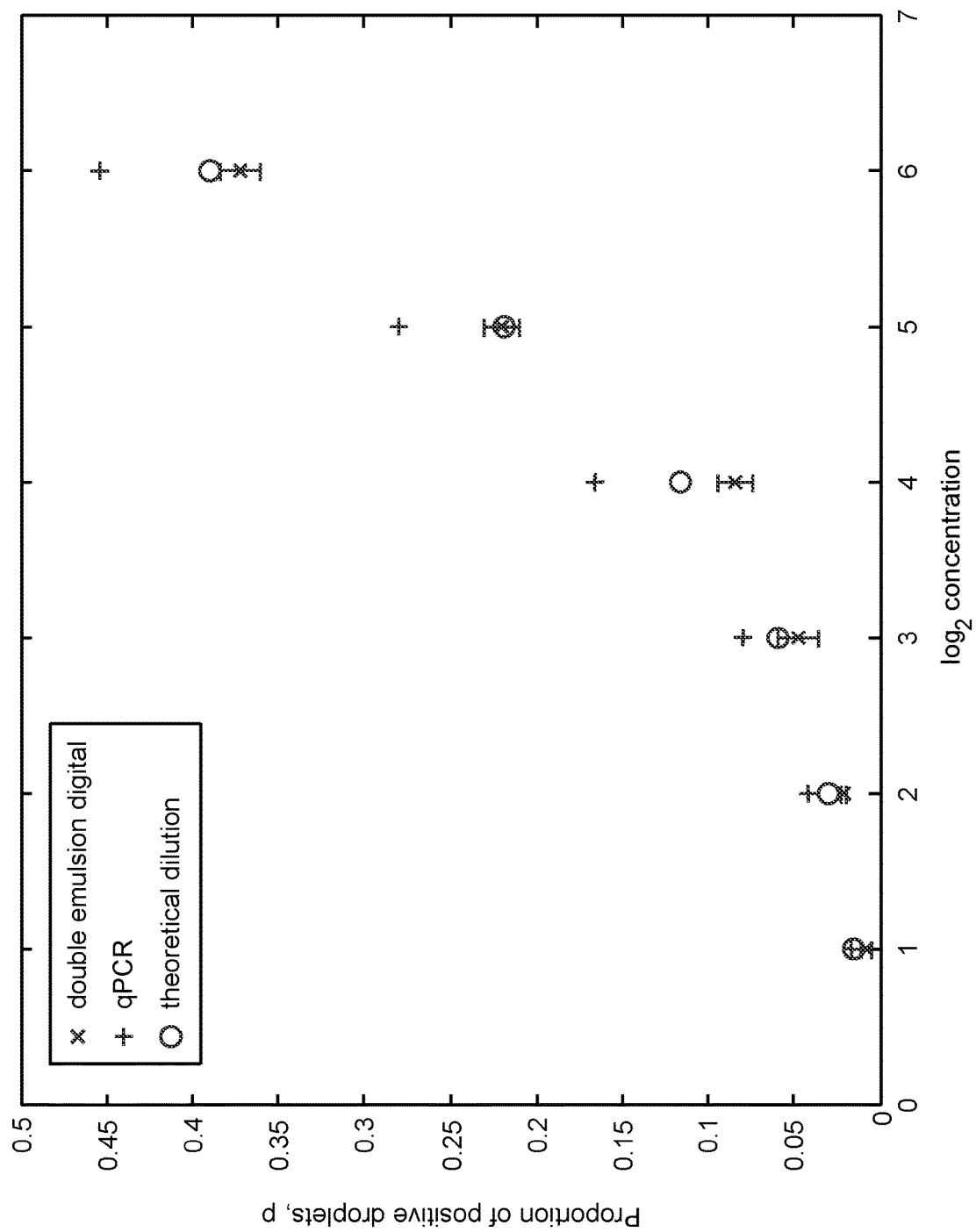
FIG. 51 provides a plot showing the fraction of drops that are positive as a function of the log-2 concentration. As the concentration of DNA goes up, more drops become fluorescent because more of them contain at least a single molecule.

The liquid electrodes were capable of merging drops through application of an electric field as shown in FIG. 37, which provides two images of a droplet merger device that merges large drops with small drops utilizing liquid electrodes. To merge the drops, an electric field was applied using a salt-water electrode. When the field was off, no merger occured (right) and when it was on, the drops merged (left).

Example 9: PCR Analysis and FACS Sorting of Azopira/E. coli Mixture

Figure 52:
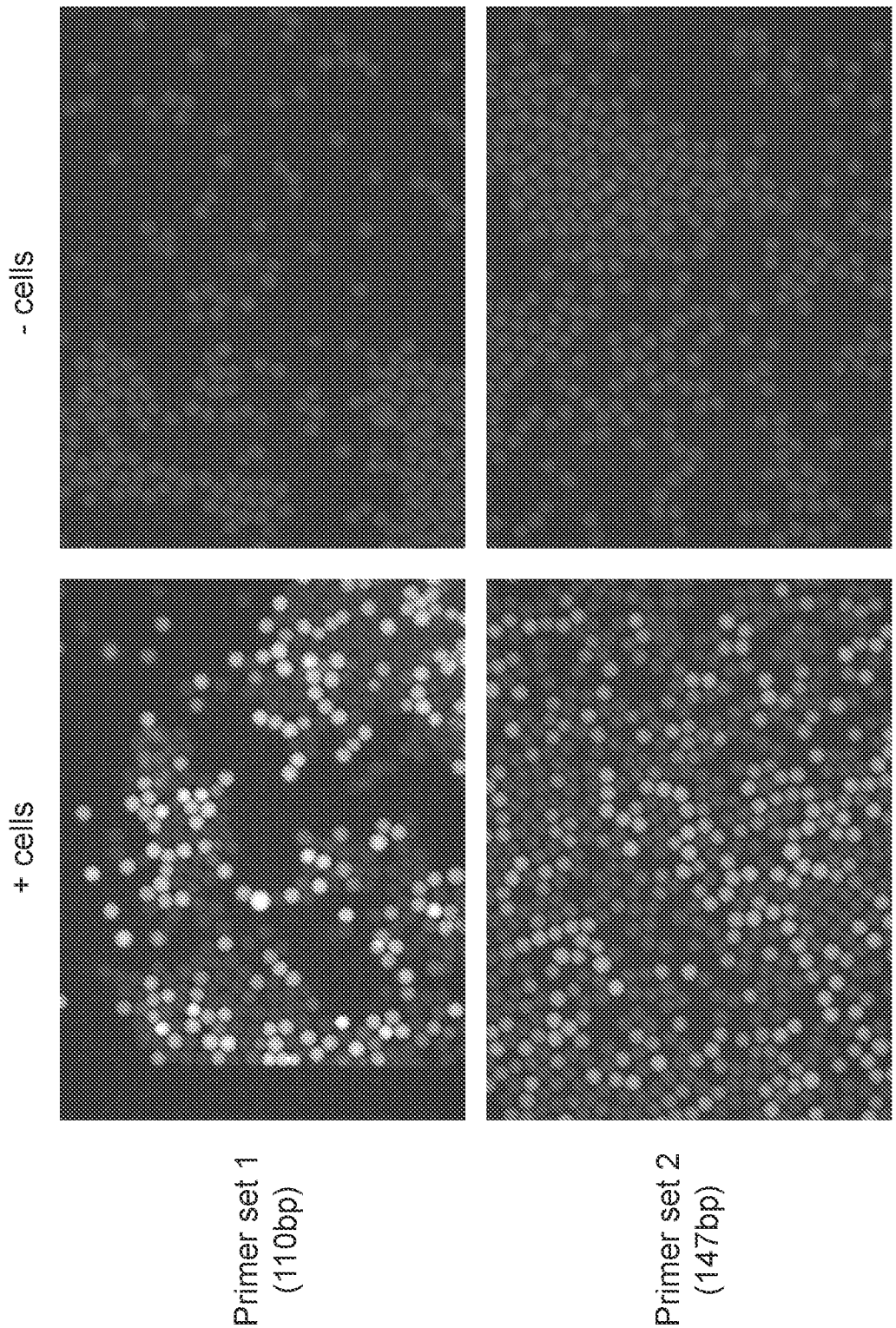
FIG. 52 provides images showing drops in which a TaqMan® PCR reaction has been performed with encapsulated Azospira. The upper images correspond to a reaction in which a 110 bp amplicon was produced, whereas the lower images correspond to a 147 bp amplicon.
Figure 53:
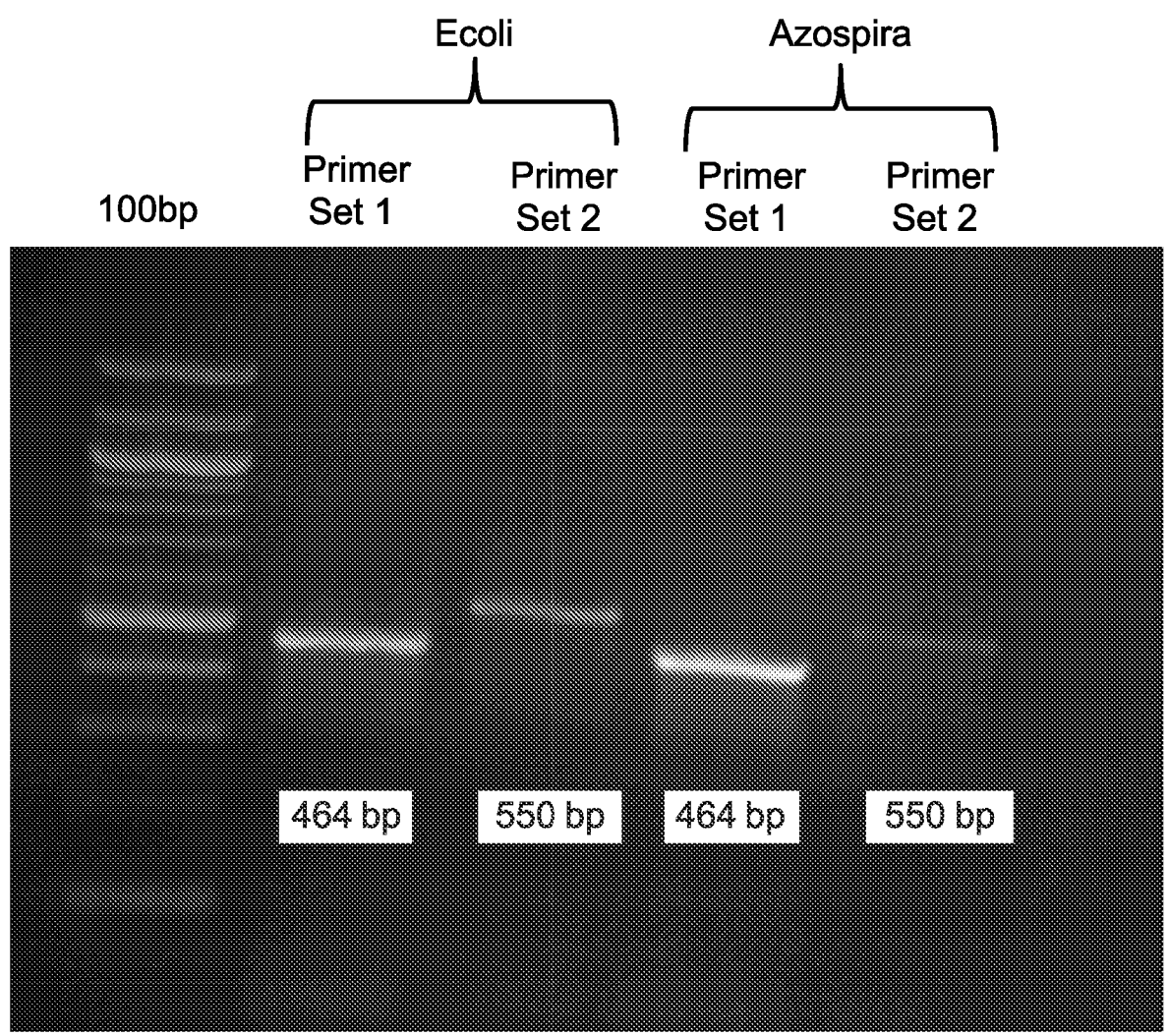
FIG. 53 shows a picture of a gel showing bands corresponding to the amplicons of two TaqMan® PCR reactions, one for a 464 bp amplicon and one for a 550 bp amplicon.
Figure 54:
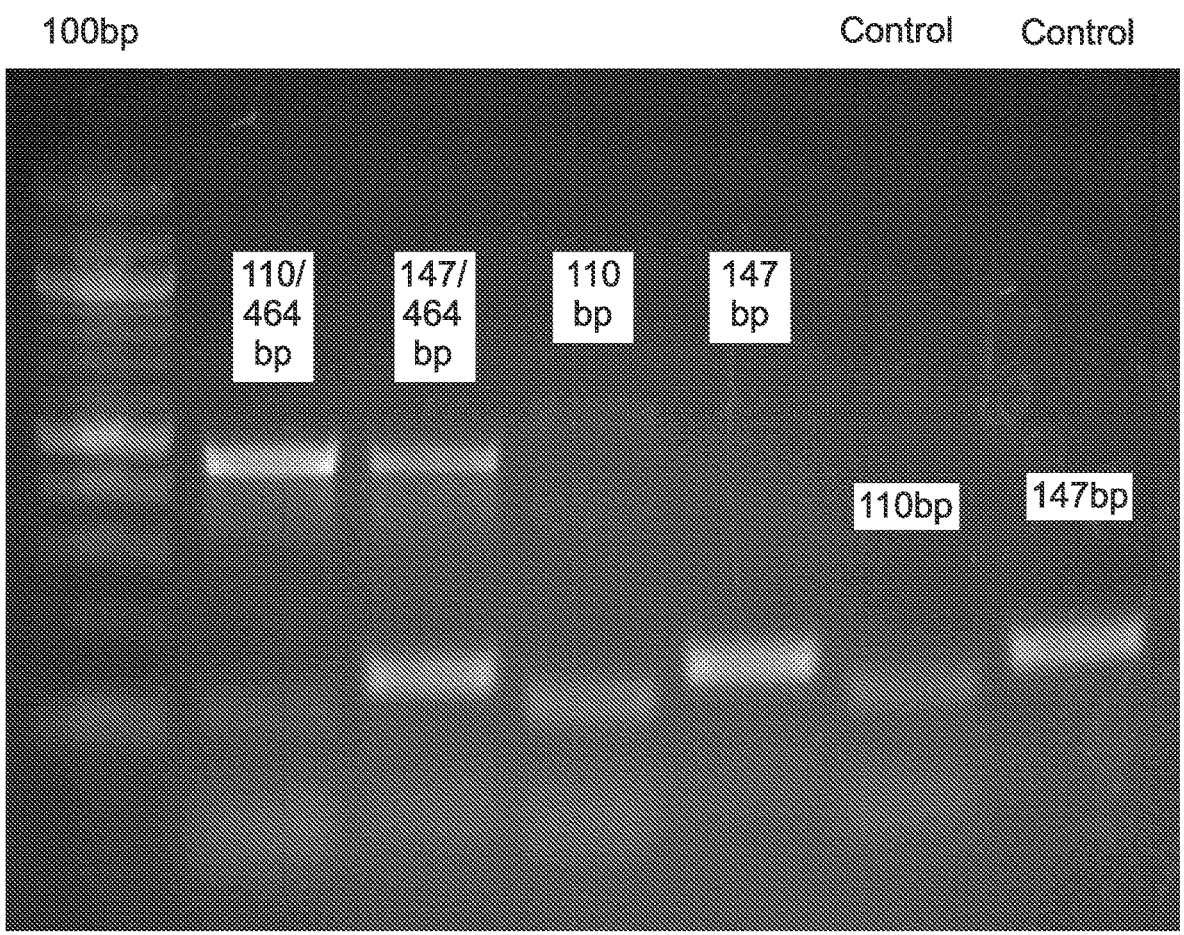
FIG. 54 shows a picture of a gel validating that PCR reactions can be multiplexed by adding multiple primer sets to a sample containing bacteria.

Two different species of microbes, *Azospira* and *E. coli*. Were encapsulated in microdrops. In-droplet PCR was performed using TaqMan® and primers for *Azospira* and/or *E. coli*. FIG. 52 provides images showing drops in which a TaqMan® PCR reaction was performed with encapsulated *Azospira*. The upper images correspond to a reaction in which a 110 bp amplicon was produced, whereas the lower images to a 147 bp amplicon. FIG. 53 shows a picture of a gel testing 16S primers for *Azospira* and *E. coli*. The gel shows the bands corresponding to the amplicons of two TaqMan® PCR reactions, one for a 464 bp amplicon and one for a 550 bp amplicon. FIG. 54 provides a picture of a gel validating that the in-droplet PCR reactions can be multiplexed by adding multiple primer sets to a sample containing bacteria. FIG. 55 shows results for an experiment where the TaqMan® reaction had primers and probes only for *Azospira*, so only the drops containing one of these microbes underwent amplification and became fluorescent, while the empty drops or the ones with *E. coli* remained dim. The emulsion was then encapsulated into double emulsions using a microfluidic device and sorted on FACS. The plots to the right in FIG. 55 show the FACS data. The upper plot shows the scattering cross section plotted as a function of the drop fluorescence. Based on this, a population was gated out by drawing boundaries (shown above), and this population was sorted based on the drop intensity. The gating allowed erroneous events due to small oil drops or dust to be discarded. When looking at only the double emulsions, the population had two distinct peaks which corresponded to the fluorescent and non-fluorescent drops, shown in the lower histogram. An attempt to re-amplify the amplicons created during the in-droplet PCRs was unsuccessful, potentially due to their chemical structure since they may contain analogue bases or due to an inhibitory effect of the carrier oil.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of synthesizing a target polynucleotide, the method comprising:
   contacting on a first device a polynucleotide-containing component from a sample with lysis reagents in a lysate droplet, the lysis reagents comprising an enzyme having protease activity, wherein the lysate droplet is encapsulated in an immiscible carrier fluid;
   moving the lysate droplet into a collection chamber of a second device;
   incubating the lysate droplet in the collection chamber for a first duration and at a temperature sufficient to inactivate the enzyme having protease activity;
   returning the lysate droplet to the first device;
   adding to the lysate droplet a nucleic acid synthesis reagent to form a nucleic acid synthesis droplet in the immiscible carrier fluid; and
   synthesizing the target polynucleotide within the nucleic acid synthesis droplet.

2. The method of claim 1, wherein the first device is a microfluidic device.

3. The method of claim 1, wherein the second device is a syringe.

4. The method of claim 1, wherein the first duration is a period longer than necessary for lysis.

5. The method of claim 1, wherein the step of adding to the lysate droplet a nucleic acid synthesis reagent further comprises adding a plurality of nucleic acid synthesis reagents.

6. The method of claim 1, wherein the nucleic acid synthesis droplet has a volume of 0.001 to 1000 picoliters.

7. The method of claim 1, wherein the nucleic acid synthesis droplet has a diameter of between 0.1 microns to 1000 microns.

8. The method of claim 1, wherein the step of adding to the lysate droplet a nucleic acid synthesis reagent further comprises:
   contacting the lysate droplet with a continuous stream of fluid comprising the nucleic acid synthesis reagent, and forming the nucleic acid synthesis droplet from a portion of the continuous stream of fluid and the lysate droplet.

9. The method of claim 1, further comprising detecting the target polynucleotide by determining a sequence of a nucleic acid synthesis product of the nucleic acid synthesis droplet or by forming a double-emulsion comprising the nucleic acid synthesis droplet within an outer droplet, and sorting the double-emulsion based on at least one of droplet size and fluorescence.

* * * * *

UNITED STATES PATENT AND TRADEMARK OFFICE
CERTIFICATE OF CORRECTION

PATENT NO. : 11,203,787 B2  
APPLICATION NO. : 16/164707  
DATED : December 21, 2021  
INVENTOR(S) : Adam R. Abate et al.

Page 1 of 1

It is certified that error appears in the above-identified patent and that said Letters Patent is hereby corrected as shown below:

In the Specification  
In Column 24, Line 51, "minor" should read --mirror--  
In Column 28, Line 25, "deteregents" should read --detergents--  
In Column 33, Line 57, "microchanel" should read --microchannel--  
In Column 33, Line 58, "pioinjection" should read --picoinjection--  
In Column 33, Line 62, after "50 microns or less," please insert --e.g.,--  
In Column 34, Line 1, "less." should read --less,--  
In Column 41, Line 36, "whereineach" should read --wherein each--

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*

```
                        SEQUENCE LISTING

<160> NUMBER OF SEQ ID NOS: 9

<210> SEQ ID NO 1
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 1
cctatgcatc tcacccatct c                                          21

<210> SEQ ID NO 2
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 2
agttgttgct ggaattgttg tg                                         22

<210> SEQ ID NO 3
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 3
acggttaaca atagttatgg taattgg                                    27

<210> SEQ ID NO 4
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 4
caacacctcc cagtatgaca c                                          21

<210> SEQ ID NO 5
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 5
ccatatgttt gctttccttc tcc                                        23

<210> SEQ ID NO 6
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 6
tggtgacttt tggcagatga                                            20

<210> SEQ ID NO 7
```

```
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 7
atctcagcct tctcatactt tgccattctc                                              30

<210> SEQ ID NO 8
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 8
tgcttcaatg cttcagctcc acct                                                    24

<210> SEQ ID NO 9
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 9
cctggtctcc atgtttcagt tctgtca                                                 27
```